United States Patent
Minond et al.

(10) Patent No.: US 11,149,028 B2
(45) Date of Patent: Oct. 19, 2021

(54) METHODS FOR TREATING MELANOMA USING SMALL MOLECULES

(71) Applicants: NOVA SOUTHEASTERN UNIVERSITY, Fort Lauderdale, FL (US); AUBURN UNIVERSITY, Auburn, AL (US); FLORIDA ATLANTIC UNIVERSITY BOARD OF TRUSTEES, Boca Raton, FL (US); TORREY PINES INSTITUTE FOR MOLECULAR STUDIES, Port St. Lucie, FL (US)

(72) Inventors: Dmitriy Minond, Fort Lauderdale, FL (US); Gregg B. Fields, Boca Raton, FL (US); Marcello Giulianotti, Port St. Lucie, FL (US)

(73) Assignees: Nova Southeastern University, Fort Lauderdale, FL (US); Auburn University, Auburn, AL (US); Florida Atantic University Board Of Trustees, Boca Raton, FL (US); Torrey Pines Institute for Molecular Studies, Port St. Lucie, FL (US)

( * ) Notice: Subject to any disclaimer, the term of this patent is extended or adjusted under 35 U.S.C. 154(b) by 0 days.

(21) Appl. No.: 16/469,865

(22) PCT Filed: Dec. 15, 2017

(86) PCT No.: PCT/US2017/066876
§ 371 (c)(1),
(2) Date: Jun. 14, 2019

(87) PCT Pub. No.: WO2018/112443
PCT Pub. Date: Jun. 21, 2018

(65) Prior Publication Data
US 2020/0062736 A1    Feb. 27, 2020

Related U.S. Application Data

(60) Provisional application No. 62/434,803, filed on Dec. 15, 2016.

(51) Int. Cl.
| | |
|---|---|
| A61K 31/495 | (2006.01) |
| C07D 403/14 | (2006.01) |
| A61P 35/02 | (2006.01) |
| G01N 33/50 | (2006.01) |
| G01N 33/564 | (2006.01) |
| G01N 33/566 | (2006.01) |

(52) U.S. Cl.
CPC .......... *C07D 403/14* (2013.01); *A61P 35/02* (2018.01); *G01N 33/5011* (2013.01); *G01N 33/564* (2013.01); *G01N 33/566* (2013.01)

(58) Field of Classification Search
CPC ............................ A61K 31/495; C07D 403/14
See application file for complete search history.

(56) References Cited

U.S. PATENT DOCUMENTS 10,048,272 B2 *    8/2018    Edwards ................. G16C 20/60
2016/0320402 A1 *  11/2016    Edwards ................. A61K 45/06

FOREIGN PATENT DOCUMENTS

WO    2013130882 A1    9/2013

OTHER PUBLICATIONS

Onwuhu-Ekpete et al., Journal of Medicinal Chemistry, 2014, 57(4): 1599-1608.*
ISR International Search Report and Written Opinion for PCT/US17/066876 dated Mar. 13, 2018.
Lilllian Ekpete et al., Novel Pyrrolidine Diketopiperazines Selectively Inhibit Melanoma Cells via Induction of Lae-onset Apoptosis; Joural of Medicinal Chemistry; 57 1599-1608; Published Jan. 28, 2014.
IPRP International Preliminary Report and Written Opinion for PCT/US17/066876 dated Jun. 28, 2019.
Vidwans, S. J. et al. A melanoma molecular disease model. PLoS One 6, e18257, doi:10.1371/journal.pone.0018257 2011.
Cohen, C. et al. Mitogen-actived protein kinase activation is an early event in melanoma progression. Clin Cancer Res 8, 3728-3733 2002.
Davies, H. et al. Mutations of the BRAF gene in human cancer. Nature 417, 949-954, doi:10.1038/nature00766 2002.
Tentori, L., Lacal, P. M. & Graziani, G. Challenging resistance mechanisms to therapies for metastatic melanoma. Trends Pharmacol Sci 34, 656-666, doi:10.1016/j.tips. 2013.
Menzies, A. M. & Long, G. V. Dabrafenib and Trametinib, Alone and in Combination for BRAF-Mutant Metastatic Melanoma. Clin Cancer Res 20, 2035-2043, doi:10.1158/1078-0432.CCR-13-2054, 1078-0432. 2014.
Spain, L., Julve, M. & Larkin, J. Combination dabrafenib and trametinib in the management of advanced melanoma with BRAFV600 mutations. Expert Opin Pharmacother 17, 1031-1038, doi:10.1517/14656566.2016.1168805 2016.

(Continued)

*Primary Examiner* — Rei Tsang Shiao
(74) *Attorney, Agent, or Firm* — Fleit Intellectual Property Law; Paul D. Bianco; Katharine Davis

(57) ABSTRACT

The invention provides methods for treating cancers, such as melanoma and/or metastatic melanoma, using compounds that interact with and/or inhibit cellular proteins lamin A/C, ATP-dependent RNA helicase DDX1 (DDX1), heterogeneous nuclear ribonuclear protein H1/H2 (hnRNP H2), and/or heterogeneous nuclear ribonuclear protein A2/B1 (hnRNP A2/B1). The invention additionally provides a method for identifying compounds active against melanoma cells.

15 Claims, 57 Drawing Sheets

Specification includes a Sequence Listing.

(56) References Cited

OTHER PUBLICATIONS

Rizos, H. et al. BRAF inhibitor resistance Clin Cancer Res 20, 1965-1977, doi:10.1158/1078-0432.CCR-13-3122 2014; and Long, G. V. et al. Increased MAPK reactivation in early resistance to dabrafenib/trametinib combination therapy of BRAF-mutant metastatic melanoma. Nat Commun 5, 5694, doi:10.1038/ncomms6694 2014.

Long, G. V. et al. Increased MAPK reactivation in early resistance to dabrafenib/trametinib combination therapy of BRAF-mutant metastatic melanoma. Nat Commun 5, 5694, doi:10.1038/ncomms6694 2014.

Xu, W. & McArthur, G. Cell Cycle Regulation and Melanoma. Curr Oncol Rep 18, 34, doi:10.1007/s11912-016-0524-y 2016.

Larkin, J. et al. Combined Nivolumab and Ipilimumab or Monotherapy in Untreated Melanoma. N Engl J Med 373, 23-34, doi:10.1056/NEJMoa1504030 2015.

Ascierto, P. A. et al. meeting report from the "Melanoma Bridge", Napoli, Dec. 5-8, 2013. J Transl Med 12, 277, doi:10.1186/s12967-014-0277-z 2014.

Houghten, R. A.; Pinilla, C.; Giulianotti, M. A.; Appel, J. R.; Dooley, C. T.; Nefzi, A.; Ostresh, J. M.; Yu, Y.; Vlaggiora, G. M.; Medina-Franco, J. L.; Brunner, D.; Schneider, J. Strategies for the use of mixture-based synthetic combinatorial libraries: scaffold ranking, direct testing in vivo, and enhanced deconvolution by computational methods. J Comb Chem 2008, 10, 3-19.

Lee, J. A.; Berg, E. L. Neoclassic Drug Discovery: The case for lead generation using phenotypic and functional approaches. Journal of Biomolecular Screening 2013, 18, 1143-1155.

Swinney, D. C.; Anthony, J. How were new medicines discovered? Nat Rev Drug Discov 2011, 10, 507-519.

Medina-Franco, J. L.; Giulianotti, M. A.; Welmaker, G. S.; Houghten, R. A. Shifting from the single to the multitarget paradigm in drug discovery. Drug Discov Today 2013, 18, 495-501.

Paolini, G. V.; Shapland, R. H.; van Hoorn, W. P.; Mason, J. S.; Hopkins, A. L. Global mapping of pharmacological space. Nat Biotechnol 2006, 24, 805-815.

Reifenberger, J.; Knobbe, C. B.; Sterzinger, A. A.; Blaschke, B.; Schulte, K. W; Ruzicka, T.; Reifenberger, G. Frequent alterations of Ras signaling pathway genes in sporadic malignant melanomas. Int J Cancer 2004, 109, 377-384.

Bennett, D. C.; Charest, J.; Sebolt, K.; Lehrman, M.; Rehemtulla, A.; Contessa, J. N. High-throughput screening identifies aclacinomycin as a radiosensitizer of EGFR-mutant non-small cell lung cancer. Transl Oncol 2013, 6, 382-391.

Rideout, M. C.; Boldt, J. L.; Vahi-Ferguson, G.; Salamon, P.; Nefzi, A.; Ostresh, J. M.; Giulianotti, M.; Pinilla, C.; Segall, A. M. Potent antimicrobial small molecules screened as inhibitors of tyrosine recombinases and Holliday function-resolving enzymes. Mol Divers 2011, 15, 989-1005.

Wu, J. W. Z., Y.; Maida, L. E.; Santos R. G.; Welmaker, G. S.; LaVoi, T. M.; Nefzi, A.; Yu, Y.; Houghten, R. A.; Toll, L.; Giulianotti, M. A. Scaffold ranking and positional scanning utilized in the discovery of nAChR-selective compounds suitable for optimization studies. J.Med.Chem 2013, 56, 10103-10117.

Ranjit, D. K.; Rideout, M. C.; Nefzi, A.; Ostresh, J. M.; Pinilla, C.; Segall, A. M. Small molecule functional analogs of peptides that inhibit lambda site-specific recombination and bind Holliday junctions. Bioorg Med Chem Lett 2010, 20, 4531-4544.

Minond, D.; Cudic, M.; Bionda, N.; Giulianotti, M.; Maida, L; Houghten, R. A.; Fields, G. B. Discovery of novel inhibitors of a disintegrin and metalloprotease 17 (ADAM17) using glycosylated and non-glycosylated substrates. J Biol Chem 2012, 287, 36473-36487.

Houghten, R. A.; Pinilla, C.; Appel, J. R.; Blondelle, S. E; Dooley, C. T.; Eichler, J.; Nefzi, A.; Ostresh, J. M. Mixture-based synthetic combinatorial libraries. J Med Chem 1999, 42, 3743-3778.

Pinilla, C.; Appel, J. R.; Blanc, P.; Houghten, R. A. Rapid identification of high affinity peptide ligands using positional scanning synthetic peptide combinatorial libraries. Biotechniques 1992, 13, 901-915.

Castle, J. C.; Kreiter, S.; Diekmann, J.; Lower, M.; van de Roemer, N.; de Graaf, J.; Selmi, A.; Diken, M.; Boegel, S.; Paret, C.; Koslowski, M.; Kuhn, A. N.; Britten, C. M.; Huber, C.; Tureci, O.; Sahin, U. Exploiting the mutanome for tumor vaccination. Cancer Res 2012, 72, 1081-1091.

Sondergaard, J. N.; Nazarian, R.; Wang, Q.; Guo, D.; Hsueh, T.; Mok, S.; Sazegar, H.; MacConaill, L. E.; Barretina, J. G.; Kehoe, S. M.; Attar, N.; von Euw, E.; Zuckerman, J. E.; Chmielowski, B.; Comin-Anduix, B.; Koya, R. C.; Mischel, P. S.; Lo, R. S.; Ribas, A. Differential sensitivity of melanoma cell lines with BRAFV600E mutation to the specific Raf inhibitor PLX4032. J Transl Med 2010, 8, 29-39.

Yadav, V.; Zhang, X.; Liu, J.; Estrem, S.; Li, S.; Gong, X. Q.; Buchanan, S.; Henry, J. R.; Starling, J. J.; Peng, S. B. Reactivation of mitogen-activated protein kinase (MAPK) pathway by FGF receptor 3 (FGFR3)/Ras mediates resistance to vemurafenib in human B-RAF V600E mutant melanoma. J Biol Chem 2012, 287, 28087-28098.

Sheppard, K. E.; McArthur, G. A. The cell-cycle regulator CDK4: an emerging therapeutic target in melanoma. Clin Cancer Res 2013, 19, 5320-5328.

Nicotera, P.; Leist, M.; Manzo, L. Neuronal cell death: a demise with different shapes. Trends Pharmacol Sci 1999, 20, 46-51.

Niles, A. L.; Moravec, R. A.; Riss, T. L. In vitro viability and cytotoxicity testing and same-well multi-parametric combinations for high throughput screening. Curr Chem Genomics 2009, 3, 33-41.

Atadja, P. Development of the pan-DAC inhibitor panobinostat (LBH589): successes and challenges. Cancer Lett 2009, 280, 233-241.

Houghten, R. A. General method for the rapid solid-phase synthesis of large numbers of peptides: specificity of antigen-antibody interaction at the level of individual amino acids. Proc Natl Acad Sci U S A 1985, 82, 5131-5135.

Pinilla, C.; Edwards, B. S.; Appel, J. R.; Yates-Gibbins, T.; Giulianotti, M. A.; Medina-Franco, J. L.; Young, S. M.; Santos, R. G.; Sklar, L. A.; Houghten, R. A. Selective agonists and antagonists of formylpeptide receptors: duplex flow cytometry and mixture-based positional scanning libraries. Mol Pharmacol 2013, 84, 314-324.

Reilley, K. J.; Giulianotti, M.; Dooley, C. T.; Nefzi, A.; McLaughlin, J. P.; Houghten, R. A. dentification of two novel, potent, low-liability antinociceptive compounds from the direct in vivo screening of a large mixture-based combinatorial library. AAPS J 2010, 12, 318-329.

Acharya, A. N.; Ostresh, J. M.; Houghten, R. A. Determination of isokinetic ratios necessary for equimolar incorporation of carboxylic acids in the solid-phase synthesis of mixture-based combinatorial libraries. Biopolymers 2002, 65, 32-39.

Ostresh, J. M.; Winkle, J. H.; Hamashin, V. T.; Houghten, R. A. Peptide libraries: determination of relative reaction rates of protected amino acids in competitive couplings. Biopolymers 1994, 34, 1681-1689).

Santos, R. G.; Appel, J. R.; Giulianotti, M. A.; Edwards, B. S.; Sklar, L. A.; Houghten, R. A.; Pinilla, C. The mathematics of a successful deconvolution: a quantitative assessment of mixture-based combinatorial libraries screened against two formylpeptide receptors. Molecules 2013, 18, 6408-6424.

Landegren, U. Measurement of cell numbers by means of the endogenous enzyme hexosaminidase. Applications to detection of lymphokines and cell surface antigens. J Immunol Methods 1984, 67, 379-388.

Onwuha-Ekpete, L. et al. Novel pyrrolidine diketopiperazines selectively inhibit melanoma cells via induction of late-onset apoptosis. Journal of medicinal chemistry 57, 1599-1608, doi:10.1021/jm4019542 2014.

Atefi, M. et al. Reversing melanoma cross-resistance to BRAF and MEK inhibitors by co-targeting the AKT/mTOR pathway. PLoS One 6, e28973, doi:10.1371/journal.pone.0028973 2011.

(56) References Cited

OTHER PUBLICATIONS

Barth, S., Glick, D. & Macleod, K. F. Autophagy: assays and artifacts. J Pathol 221, 117-124, doi:10.1002/path.2694 2010.
Yang, Y. P. et al. Application and interpretation of current autophagy inhibitors and activators. Acta Pharmacol Sin 34, 625-635, doi:10.1038/aps.2013.5 2013.
Wu, H. et al. Caspases: a molecular switch node in the crosstalk between autophagy and apoptosis. Int J Biol Sci 10, 1072-1083, doi:10.7150/ijbs.9719 2014.
You, M. et al. TRAIL induces autophagic protein cleavage through caspase activation in melanoma cell lines under arginine deprivation. Mol Cell Biochem 374, 181-190, doi:10.1007/s11010-012-1518-1 2013.
Tiwari, M. et al. A nonapoptotic role for CASP2/caspase 2: modulation of autophagy. Autophagy 10, 1054-1070, doi:10.4161/auto.28528 2014.
Tiwari, M., Lopez-Cruzan, M., Morgan, W. W. & Herman, B. Loss of caspase-2-dependent apoptosis induces autophagy after mitochondrial oxidative stress in primary cultures of young adult cortical neurons. J Biol Chem 286, 8493-8506, doi:10.1074/jbc.M110.163824 2011.
Yi, C. H. & Yuan, J. The Jekyll and Hyde functions of caspases. Dev Cell 16, 21-34, doi:10.1016/j.devcel.2008.12.012 2009.
Gafni, J., Cong, X., Chen, S. F., Gibson, B. W. & Ellerby, L. M. Calpain-1 cleaves and activates caspase-7. J Biol Chem 284, 25441-25449, doi:10.1074/jbc.M109.038174 2009.
Ruiz-Vela, A., Gonzalez de Buitrago, G. & Martinez, A. C. Implication of calpain in caspase activation during B cell clonal deletion. EMBO J 18, 4988-4998, doi:10.1093/emboj/18.18.4988 1999).
Lomenick, B. et al. Target identification using drug affinity responsive target stability (DARTS). Proc Natl Acad Sci U S A 106, 21984-21989, doi:10.1073/pnas.0910040106 2009.
Lomenick, B., Olsen, R. W. & Huang, J. Identification of direct protein targets of small molecules. ACS Chem Biol 6, 34-46, doi:10.1021/cb100294v 2011.
Liu, Y. & Levine, B. Autosis and autophagic cell death: the dark side of autophagy. Cell Death Differ 22, 367-376, doi:10.1038/cdd.2014.143 2015.
Liu, Y. et al. Autosis is a Na+,K+-ATPase-regulated form of cell death triggered by autophagy-inducing peptides, starvation, and hypoxia-ischemia. Proc Natl Acad Sci U S A 110, 20364-20371, doi:10.1073/pnas.1319661110 2013.
Kuga, T. et al. Lamin B2 prevents chromosome instability by ensuring proper mitotic chromosome segregation. Oncogenesis 3, e94, doi:10.1038/oncsis.2014.6 2014.
Chen, H. C., Lin, W. C., Tsay, Y. G., Lee, S. C. & Chang, C. J. An RNA helicase, DDX1, interacting with poly(A) RNA and heterogeneous nuclear ribonucleoprotein K. J Biol Chem 277, 40403-40409, doi:10.1074/jbc.M206981200 2002.
Popow, J., Jurkin, J., Schleiffer, A. & Martinez, J. Analysis of orthologous groups reveals archease and DDX1 as tRNA splicing factors. Nature 511, 104-107, doi:10.1038/nature13284 2014.
Sharma, S., Kohlstaedt, L. A., Damianov, A., Rio, D. C. & Black, D. L. Polypyrimidine tract binding protein controls the transition from exon definition to an intron defined spliceosome. Nat Struct Mol Biol 15, 183-191, doi:10.1038/nsmb.1375 2008.
Zhong, N., Radu, G., Ju, W. & Brown, W. T. Novel progerin-interactive partner proteins hnRNP E1, EGF, Mel 18, and UBC9 interact with lamin A/C. Biochem Biophys Res Commun 338, 855-861, doi:10.1016/j.bbrc.2005.10.020 2005.
Mitchell, M. J. et al. Lamin A/C deficiency reduces circulating tumor cell resistance to fluid shear stress. American journal of physiology. Cell physiology 309, C736-746, doi:10.1152/ajpcell.00050.2015 2015.
Suzuki, A. et al. Identification of melanoma antigens using a Serological Proteome Approach (SERPA). Cancer genomics & proteomics 7, 17-23 2010.
Stark, M., Bram, E. E., Akerman, M., Mandel-Gutfreund, Y. & Assaraf, Y. G. Heterogeneous nuclear ribonucleoprotein H1/H2-dependent unsplicing of thymidine phosphorylase results in anti-cancer drug resistance. J Biol Chem 286, 3741-3754, doi:10.1074/jbc.M110.163444 2011.
Jean-Philippe, J., Paz, S. & Caputi, M. hnRNP A1: the Swiss army knife of gene expression. International journal of molecular sciences 14, 18999-19024, doi:10.3390/ijms140918999 2013.
Chen, W. L., Pan, L., Kinghorn, A. D., Swanson, S. M. & Burdette, J. E. Silvestrol induces early autophagy and apoptosis in human melanoma cells. BMC cancer 16, 17, doi:10.1186/s12885-015-1988-0 2016.
Zhang, J. et al. HnRNP K contributes to drug resistance in acute myeloid leukemia through the regulation of autophagy. Experimental hematology 44, 850-856, doi:10.1016/j.exphem.2016.04.014 2016.
Nara, H. et al. Thieno[2,3-d]pyrimidine-2-carboxamides bearing a carboxybenzene group at 5-position: Highly potent, selective, and orally available MMP-13 inhibitors interacting with the S1" binding site. Bioorg. Med. Chem., in press 2014.
Li, H. et al. Nanoparticle-conjugated aptamer targeting hnRNP A2/B1 can recognize multiple tumor cells and inhibit their proliferation. Biomaterials 63, 168-176, doi:10.1016/j.biomaterials.2015.06.013 2015.
Chen, C. Y. et al. The antitumor agent PBT-1 directly targets HSP90 and hnRNP A2/B1 and inhibits lung adenocarcinoma growth and metastasis. Journal of medicinal chemistry 57, 677-685, doi:10.1021/jm401686b 2014.
Colunga, A., Bollino, D., Schech, A. & Aurelian, L. Calpain-dependent clearance of the autophagy protein p62/SQSTM1 is a contributor to DeltaPK oncolytic activity in melanoma. Gene therapy 21, 371-378, doi:10.1038/gt.2014.6 2014.
Wales, S. Q., Laing, J. M., Chen, L. & Aurelian, L. ICP10PK inhibits calpain-dependent release of apoptosis-inducing factor and programmed cell death in response to the toxin MPP+. Gene therapy 15, 1397-1409, doi:10.1038/gt.2008.88 2008.
Munoz-Pinedo, C. & Martin, S. J. Autosis: a new addition to the cell death Tower of Babel. Cell death & disease 5, e1319, doi:10.1038/cddis.2014.246 2014.
Lin, L. & Baehrecke, E. H. Autophagy, cell death, and cancer. Molecular & cellular oncology 2, e985913, doi:10.4161/23723556.2014.985913 2015.
Mintzer, R. et al. A whole cell assay to measure caspase-6 activity by detecting cleavage of lamin A/C. PLoS One 7, e30376, doi:10.1371/journal.pone.0030376 2012.
Pinilla, C. et al. Selective agonists and antagonists of formylpeptide receptors: duplex flow cytometry and mixture-based positional scanning libraries. Mol Pharmacol 84, 314-324, doi:10.1124/mol.113.086595 2013.
Weatherly, D. B. et al. A Heuristic method for assigning a false-discovery rate for protein identifications from Mascot database search results. Molecular & cellular proteomics: MCP 4, 762-772, doi:10.1074/mcp.M400215-MCP200 2005.
Old, W. M. et al. Comparison of label-free methods for quantifying human proteins by shotgun proteomics. Molecular & cellular proteomics : MCP 4, 1487-1502, doi:10.1074/mcp.M500084-MCP200 2005.
Beissbarth, T. et al. Statistical modeling of sequencing errors in SAGE libraries. Bioinformatics 20 Suppl 1, 31-39, doi:10.1093/bioinformatics/bth924 2004.
Ostresh, J. M., Dorner, B. & Houghten, R. A. Peralkylation. "Libraries from libraries": chemical transformation of synthetic combinatorial libraries. Methods in molecular biology 87, 41-49 1998.
Nefzi, A. O., J. M.; Houghten, R. A. . Parallel solid phase synthesis of tetrasubstituted diethylenetriamines via selective amide alkylation and exhaustive reduction of N-acylated dipeptides. Tetrahedron 55, 335-344 1999.

\* cited by examiner

| Sample # | Moiety in defined position | | | |
|---|---|---|---|---|
| | R1 | R2 | R3 | R4 |
| 2 | S-benzyl | mix | mix | mix |
| 9 | R-2-naphthylmethyl | mix | mix | mix |
| 17 | R-methyl | mix | mix | mix |
| 28 | mix | S-benzyl | mix | mix |
| 33 | mix | (R,R)-1-hydroxyethyl | mix | mix |
| 35 | mix | S-4-hydroxybenzyl | mix | mix |
| 40 | mix | S-hydroxymethyl | mix | mix |
| 41 | mix | (S,S)-1-hydroxyethyl | mix | mix |
| 43 | mix | R-4-hydroxybenzyl | mix | mix |
| 51 | mix | R-cyclohexyl | mix | mix |
| 55 | mix | mix | hydrogen | mix |
| 58 | mix | mix | R-hydroxymethyl | mix |
| 59 | mix | mix | (R,R)-1-hydroxyethyl | mix |
| 61 | mix | mix | S-4-hydroxybenzyl | mix |
| 66 | mix | mix | S-hydroxymethyl | mix |
| 67 | mix | mix | (S,S)-1-hydroxyethyl | mix |
| 69 | mix | mix | R-4-hydroxybenzyl | mix |
| 111 | mix | mix | mix | (2-methyl-cyclopropyl)-methyl |

FIG. 4

| Mixture Sample # | Structure | M14 | CHO-K1 | A549 |
|---|---|---|---|---|
| 35 | 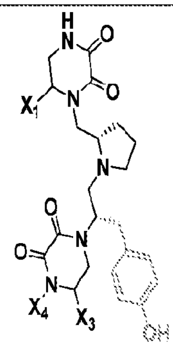 | 41 ± 5.3 | >100 | 6.0 ± 0.5 |
| 43 | 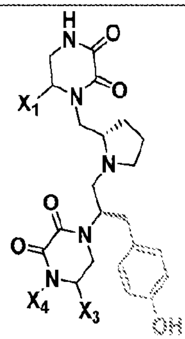 | 10 ± 1.3 | >100 | >100 |
| 61 | 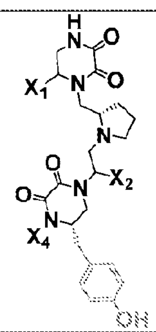 | 8.0 ± 0.9 | >100 | >50 |
| 69 | 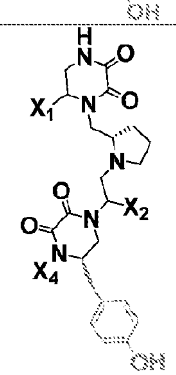 | 12 ± 1.5 | >100 | >50 |

FIG. 5

Table 3

| Compound # | R₁ | R₂ | R₃ | R₄ | Inhibition % @ 100 μM | | |
|---|---|---|---|---|---|---|---|
| | | | | | A549 | M14 | CHO-K1 |
| 1 | R-propyl | S-4-hydroxybenzyl | S-4-hydroxybenzyl | 2-phenylbutyl | 0 | 10±1 | 27±19 |
| 2 | R-propyl | S-4-hydroxybenzyl | R-4-hydroxybenzyl | 2-phenylbutyl | 0 | 14±3 | 0 |
| 3 | R-propyl | S-4-hydroxybenzyl | S-4-hydroxybenzyl | 2-adamantan-1-yl- | 19±4 | 7±1 | 3±97 |
| 4 | R-propyl | S-4-hydroxybenzyl | R-4-hydroxybenzyl | 2-adamantan-1-yl- | 0 | 11±3 | 23±55 |
| 5 | R-propyl | S-4-hydroxybenzyl | S-4-hydroxybenzyl | cyclopentyl-methyl | 0 | 15±6 | 7±5 |
| 6 | R-propyl | S-4-hydroxybenzyl | R-4-hydroxybenzyl | cyclopentyl-methyl | 5±7 | 3±21 | 7±12 |
| 7 | R-propyl | R-4-hydroxybenzyl | S-4-hydroxybenzyl | 2-phenylbutyl | 4±1 | 7±5 | 48±2 |
| 8 | R-propyl | R-4-hydroxybenzyl | R-4-hydroxybenzyl | 2-phenylbutyl | 8±4 | 14±21 | 59±1 |
| 9 | R-propyl | R-4-hydroxybenzyl | S-4-hydroxybenzyl | 2-adamantan-1-yl- | 2±4 | 12±3 | 8±9 |
| 10 | R-propyl | R-4-hydroxybenzyl | R-4-hydroxybenzyl | 2-adamantan-1-yl- | 38±5 | 35±1 | 77±6 |
| 11 | R-propyl | R-4-hydroxybenzyl | S-4-hydroxybenzyl | cyclopentyl-methyl | 16±16 | 23±14 | 19±1 |
| 12 | R-propyl | R-4-hydroxybenzyl | R-4-hydroxybenzyl | cyclopentyl-methyl | 14±2 | 25±16 | 11±9 |

FIG. 6

Table 4

| Compound # | M14 | SKMEL-28 | B16/F10 |
|---|---|---|---|
| 2155-14 | 3.6 ± 0.3 | 0.56 ± 0.04 | 2.7 ± 0.2 |
| 2155-18 | 0.89 ± 0.07 | 0.75 ± 0.06 | 1.15 ± 0.08 |

FIG. 8

Table 5

| Cell line | Mutation | Stage | Human melanoma subtype [3] |
|---|---|---|---|
| WM115 | $^{V600D}$BRAF/$^{-/-}$PTEN [63] | Primary | 1.2 |
| WM266-4 | $^{V600D}$BRAF/$^{-/-}$PTEN [63] | Metastatic | 1.2 |
| SK-MEL-28 | $^{V600E}$BRAF/$^{R24C}$CDK4 [15,63] | Primary | 1.4 |
| M14 | $^{G12C}$NRAS [64] | Metastatic | 4.1 |
| SK-MEL-2 | $^{Q12R}$NRAS [63] | Metastatic | 4.1 |
| B16F10 | p53/PTEN | Metastatic | N/A |

FIG. 14

Table 6

| ID | B16F10 | MEF | M14 | SKMEL28 | SKMEL2 | WM115 | WM266-4 | BJ | HEK 293 | CHO-K1 |
|---|---|---|---|---|---|---|---|---|---|---|
| 2155-14 | 3±0.2 | >100 | 4±0.3 | 0.6±0.4 | 4±0.6 | 7±1 | 4±0.5 | >100 | >100 | >100 |
| 2155-18 | 1±0.1 | 49±3 | 0.9±0.1 | 0.8±0.1 | 4±0.1 | 5±1 | 5±1 | 15±3 | 30±3 | >100 |
| Zelboraf | NT | NT | 25±2 | 1±0.2 | 4.6 | 1.4±0.7 | 5±0.9 | 3±0.4 | >100 | 45±5 |

FIG. 15

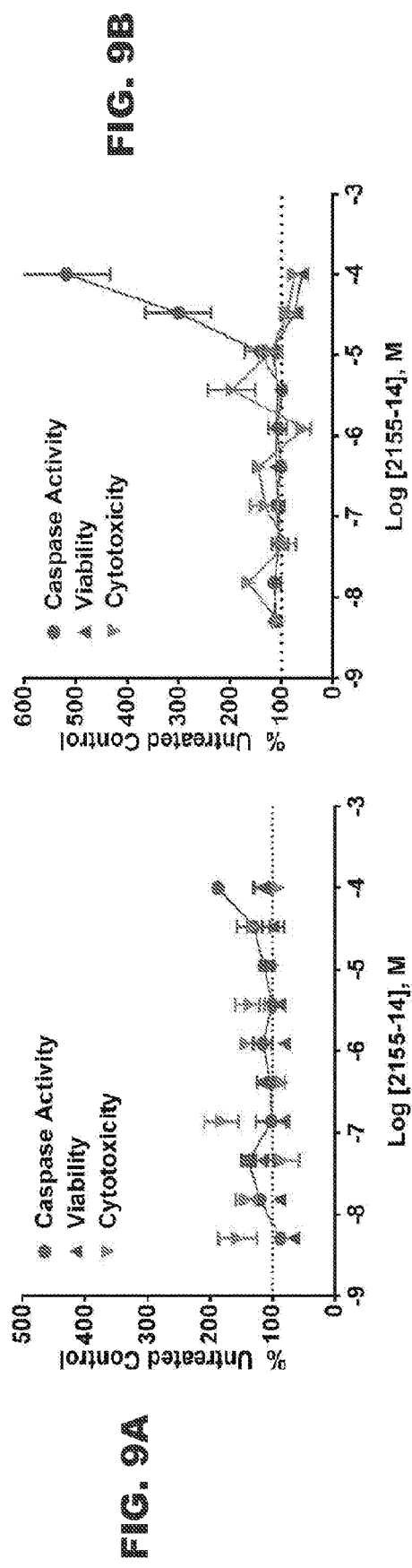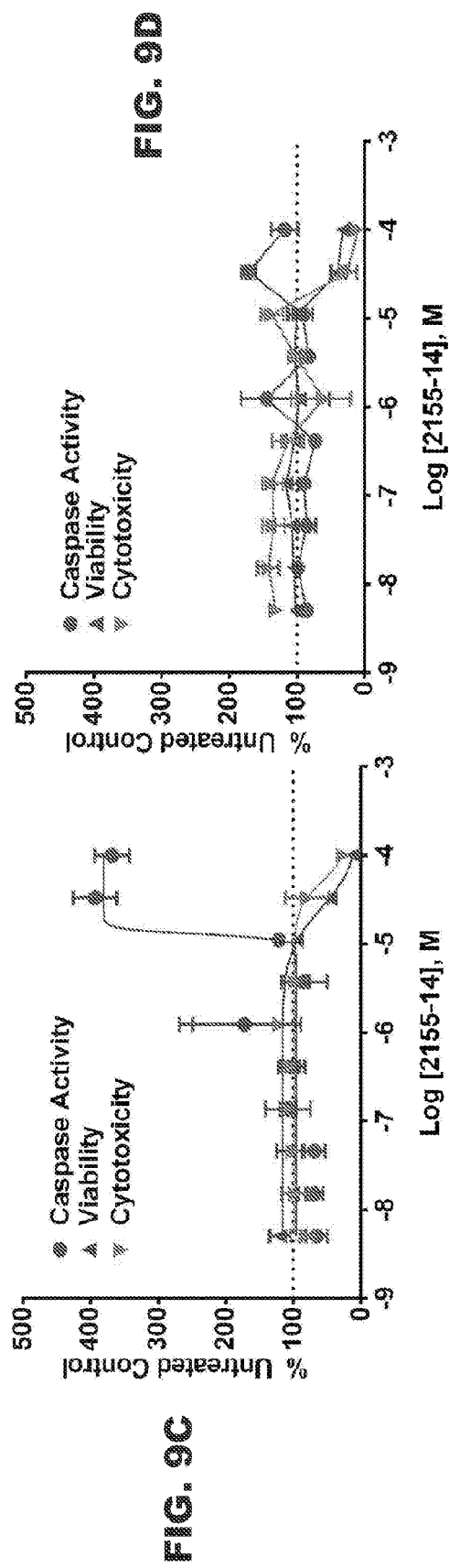
FIG. 9A  FIG. 9B  FIG. 9C  FIG. 9D

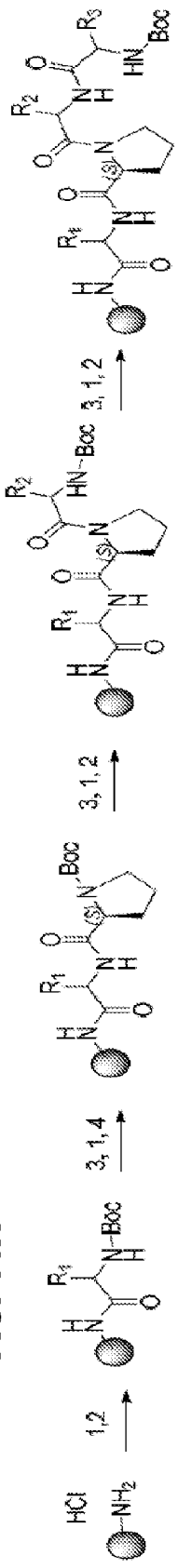
FIG. 11A — FIG. 11H

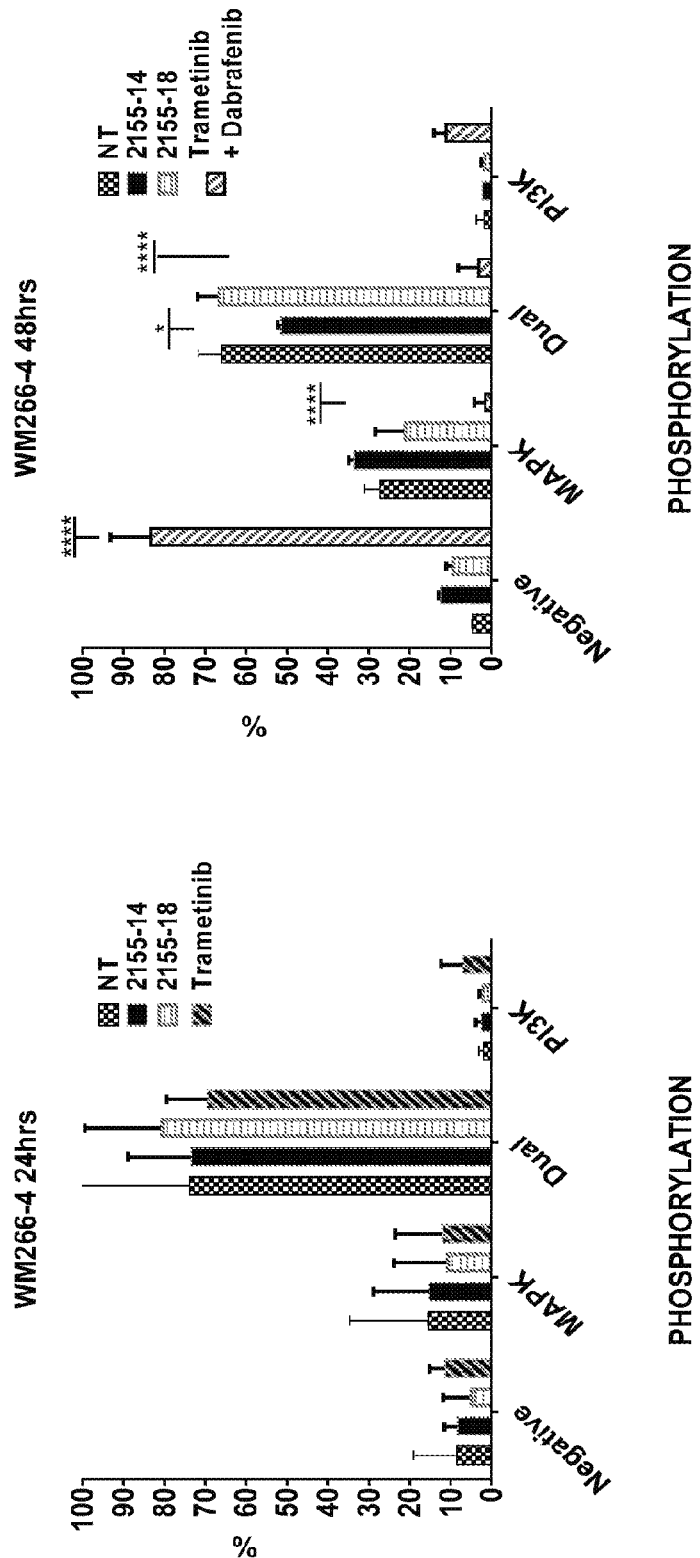

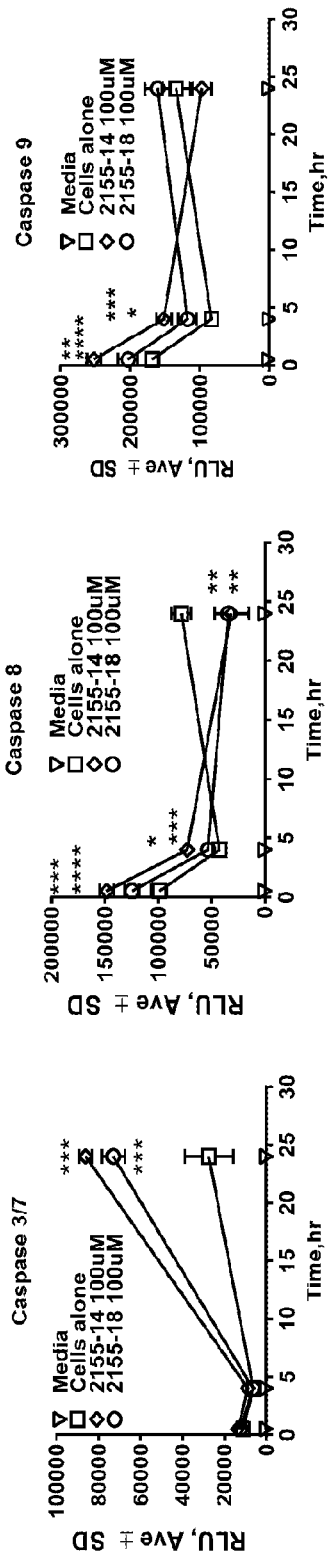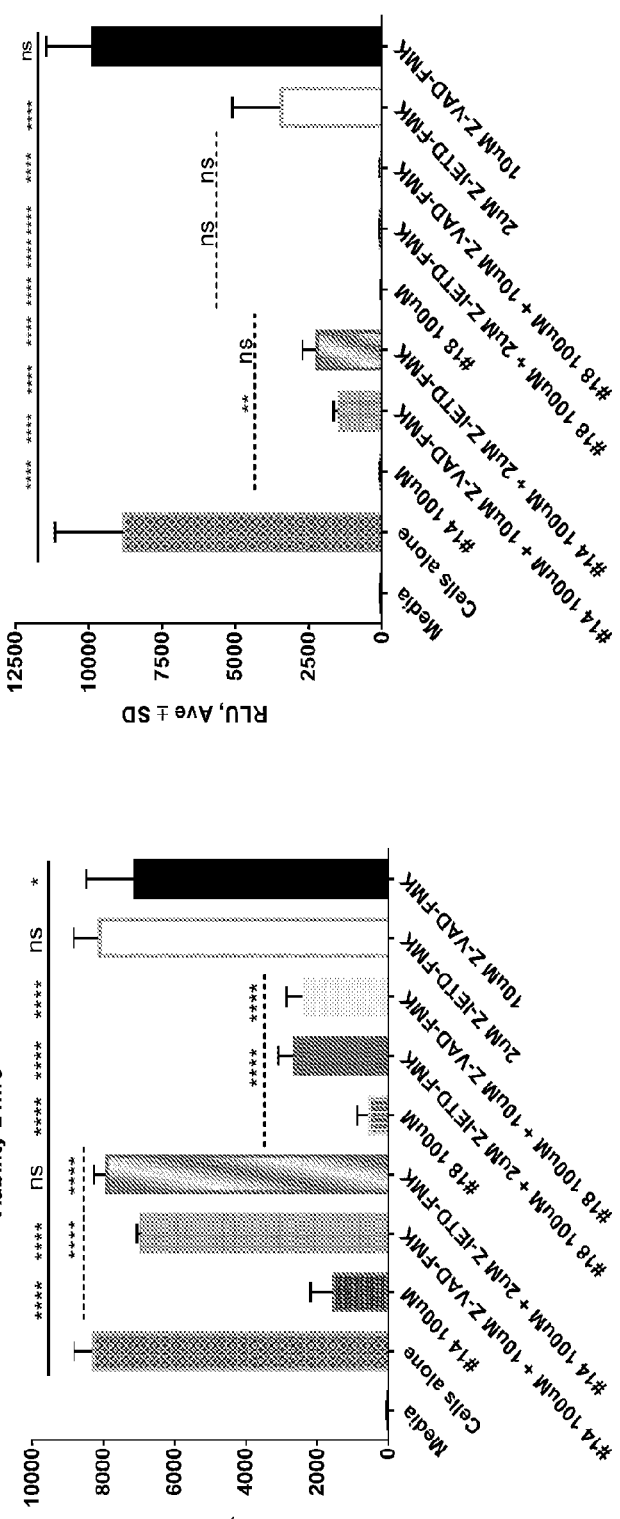

FIG. 19A 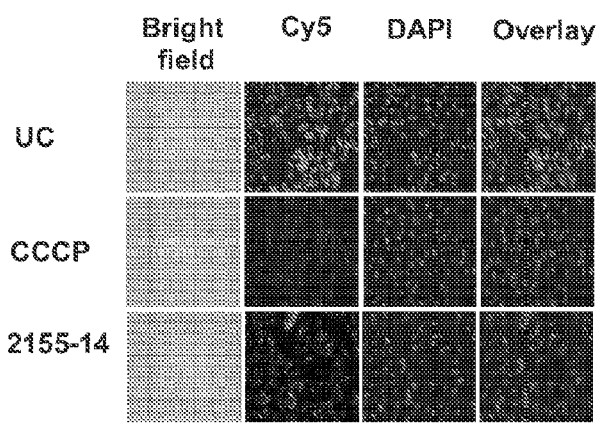 FIG. 19B 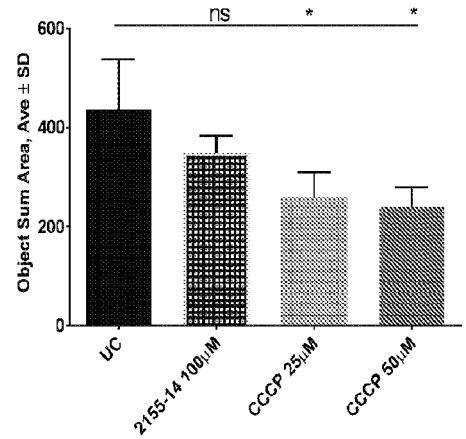
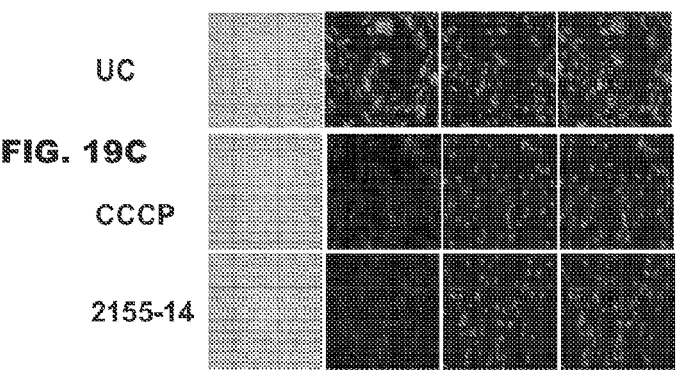
FIG. 19C
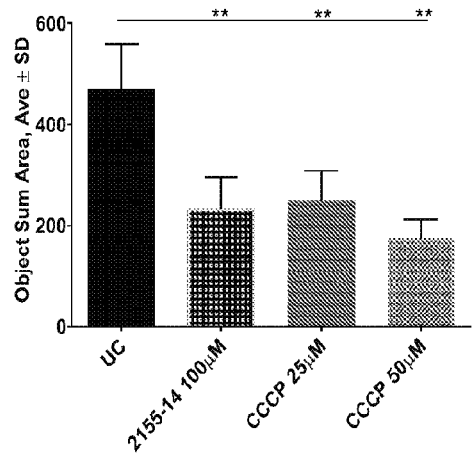
FIG. 19D
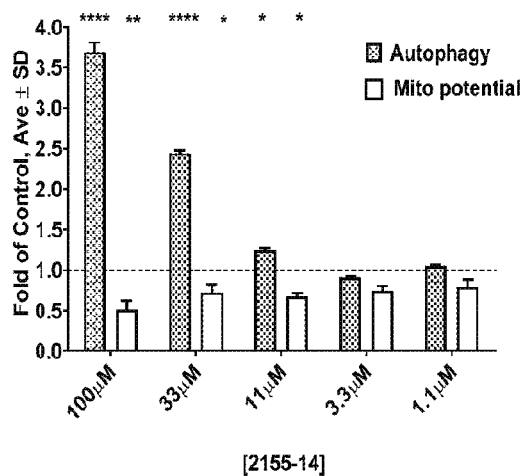
FIG. 19E

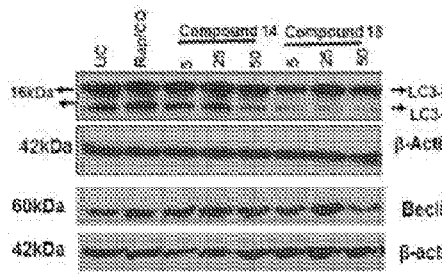
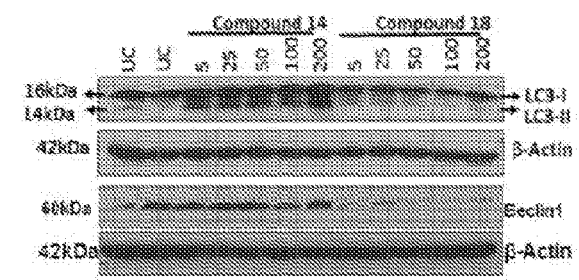
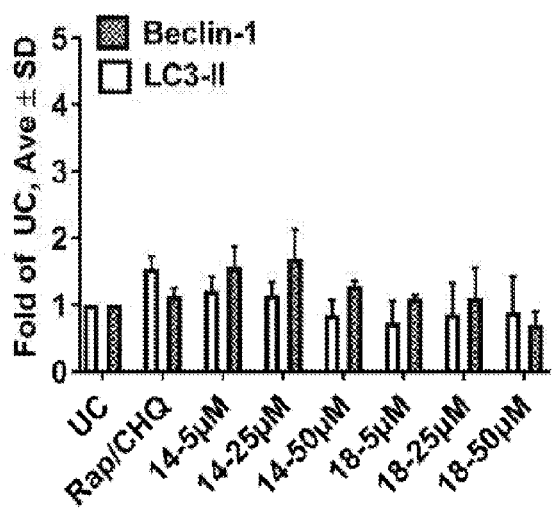
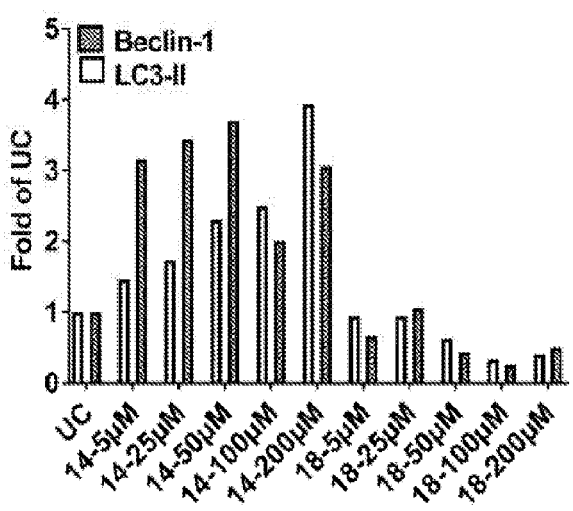
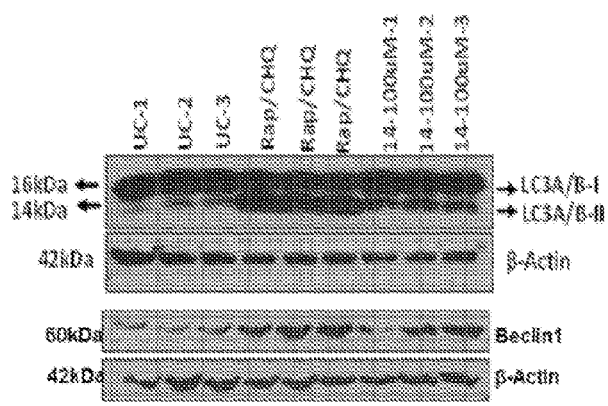
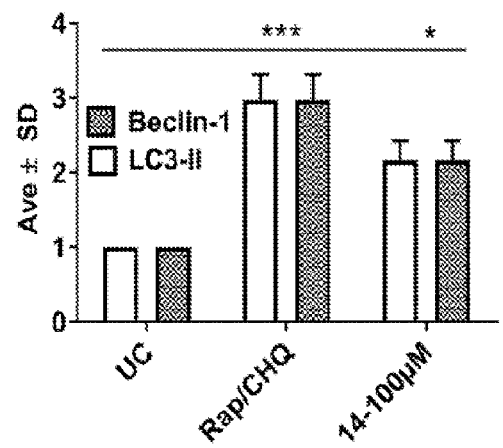

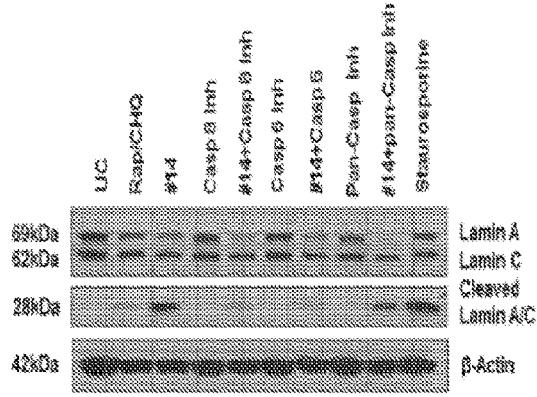
FIG. 22A
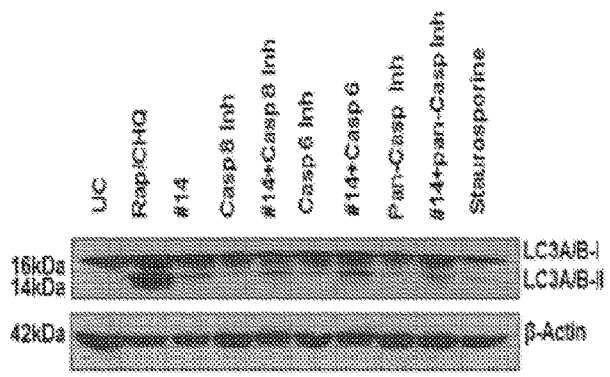
FIG. 22B
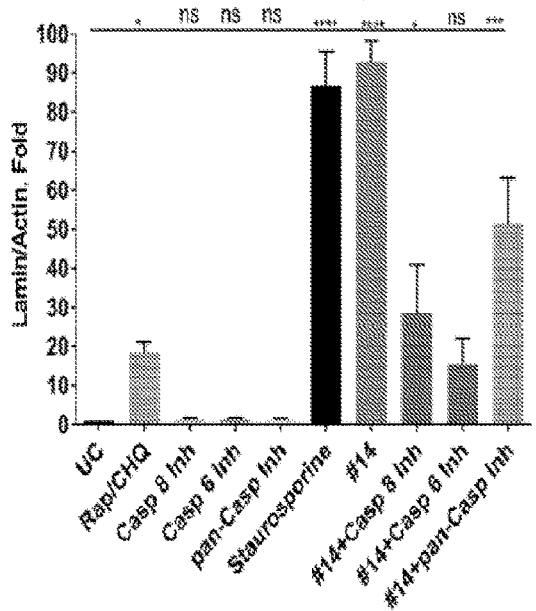
FIG. 22C
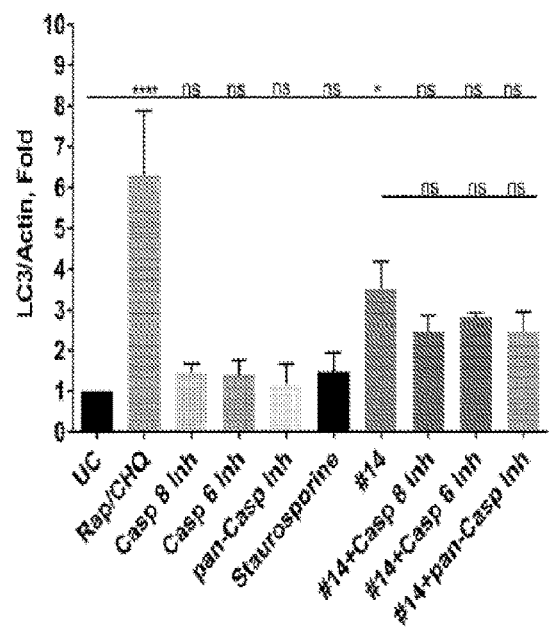
FIG. 22D
Table 7
| Protein | No pronase, no 2155-14 | No pronase, 100 μM 2155-14 | Pronase, no 2155-14 | Pronase, 100 μM 2155-14 |
|---|---|---|---|---|
| Lamin A/C | 33 | 38 | 4 | 12 |
| CAP4 | 17 | 20 | 5 | ND |
| Lamin B2 | 13 | 15 | ND | ND |
| Transketolase | 11 | 20 | 13 | 5 |
FIG. 27

FIG. 26B
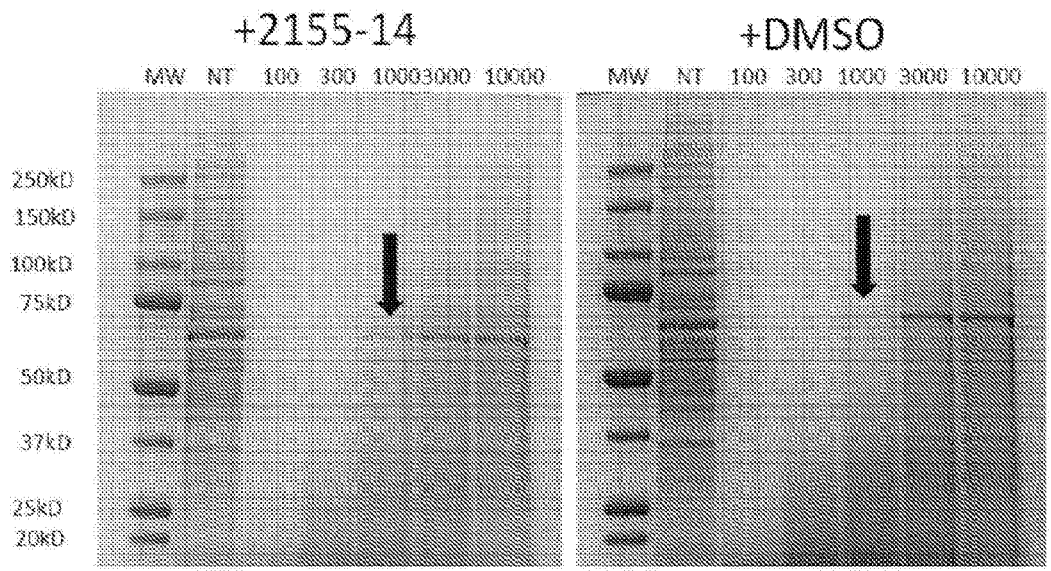
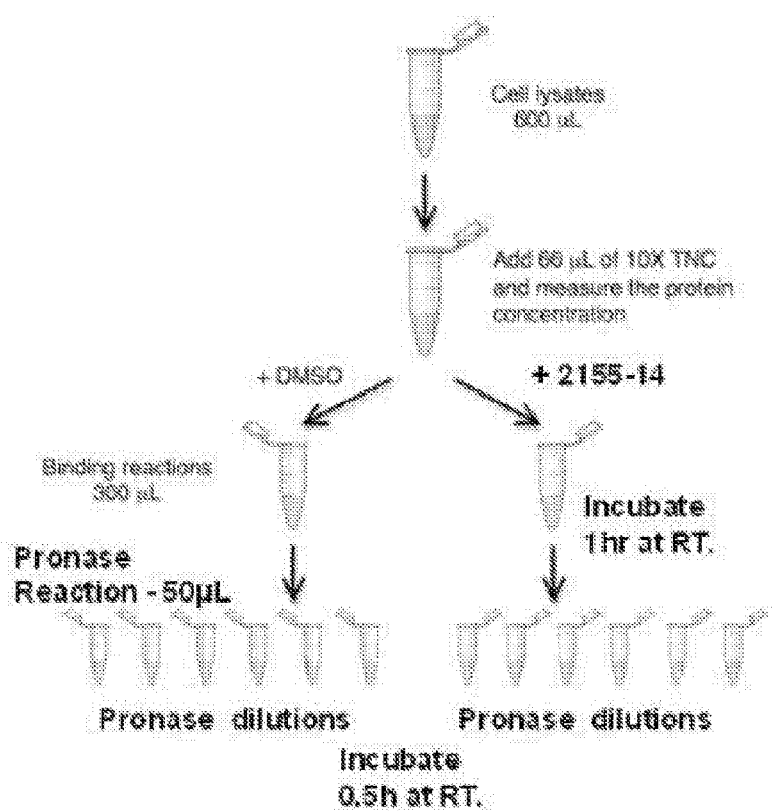
FIG. 26A

Table 8

| ID | Structure | R1 | R2 | R3 | R4 | IC$_{50}$, µM |
|---|---|---|---|---|---|---|
| 2155-14/2529-1 | 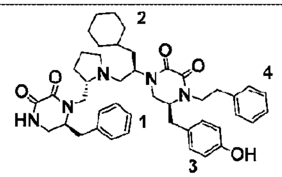 | | | | | 4.0/1.6 |
| 2476-65.2 | 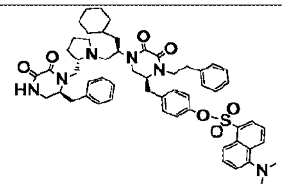 | | | Dansyl | | 7.2 |
| 2476-66 | 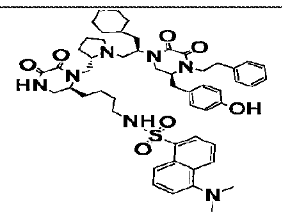 | Dansyl | | | | 5.8 |
| 2476-66.2 | 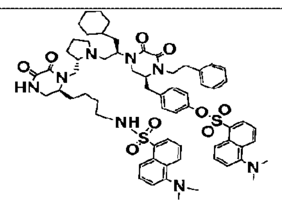 | Dansyl | | Dansyl | | 0.5 |
| 2476-67 | 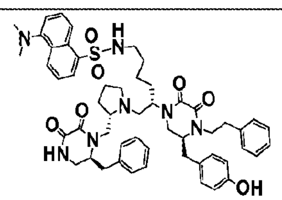 | | Dansyl | | | 1.4 |
| 2476-67.2 | 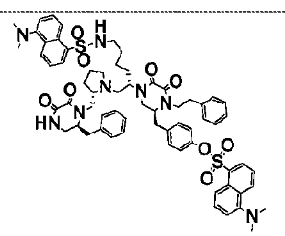 | | Dansyl | Dansyl | | 0.39 |

FIG. 28A

Table 8 (continued)

| ID | Structure | | | Label 1 | Label 2 | Value |
|---|---|---|---|---|---|---|
| 2476-68 | 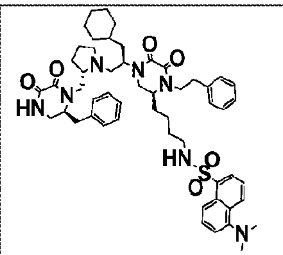 | | | Dansyl | | 0.8 |
| 2476-69 | 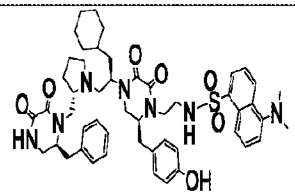 | | | Dansyl | | 13.1 |
| 2476-69.2 | 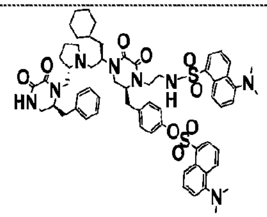 | | | Dansyl | Dansyl | >100 |
| 2529-3 | 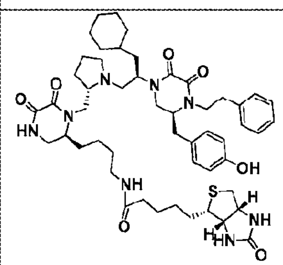 | Biotin | | | | >100 |
| 2529-5 | 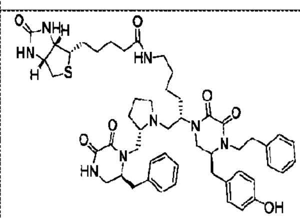 | | Biotin | | | >100 |
| 2529-7 | 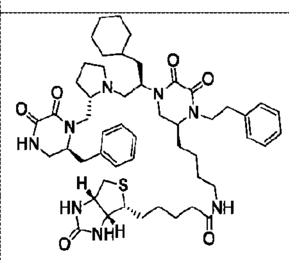 | | | Biotin | | 3.3 |

FIG. 28B

FIG. 29A
2155-14  2476-67.2  2476-69.2
WM266-4 IC₅₀ = 4μM  WM266-4 IC₅₀ = 300nM  WM266-4 IC₅₀ > 100μM
FIG. 29B
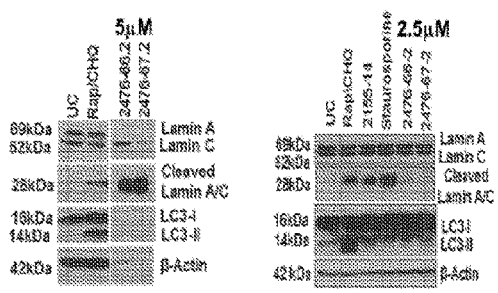
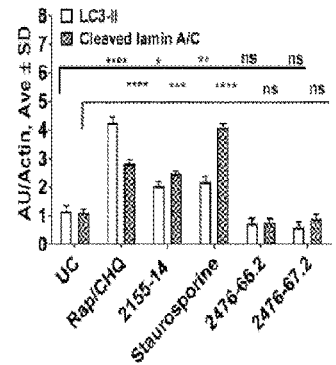
FIG. 29C
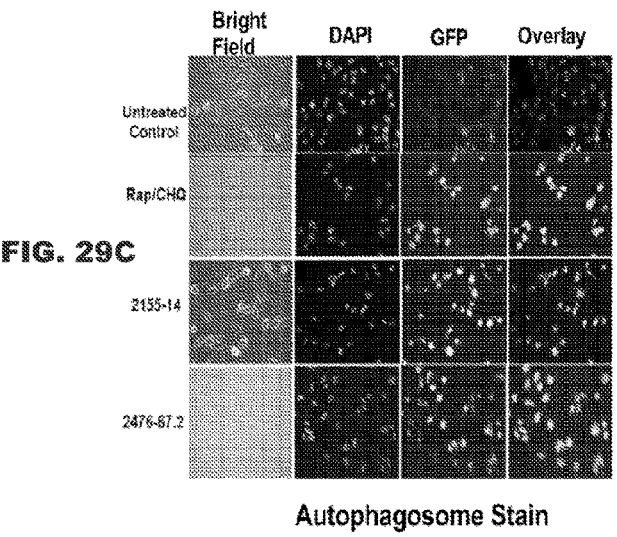
Autophagosome Stain
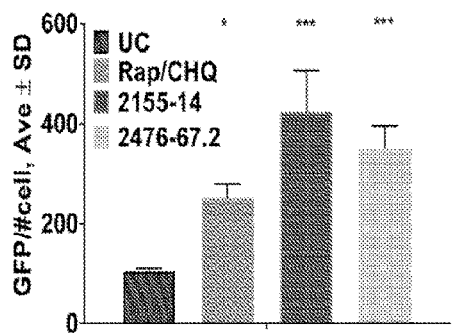
FIG. 29D
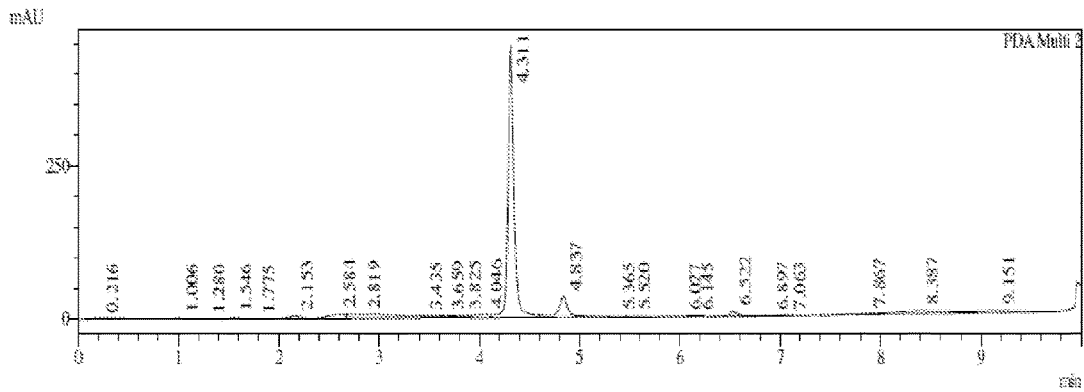
FIG. 50

FIG. 30A FIG. 30D FIG. 30G
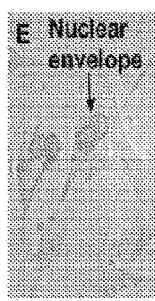
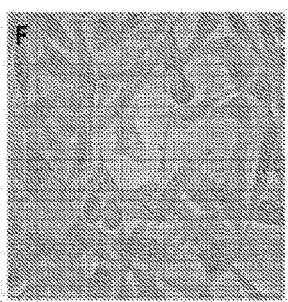
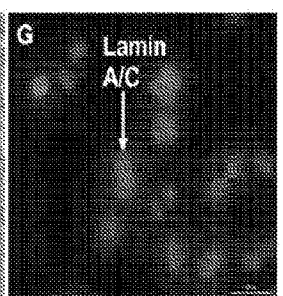
FIG. 30J
FIG. 30B
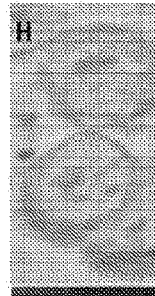
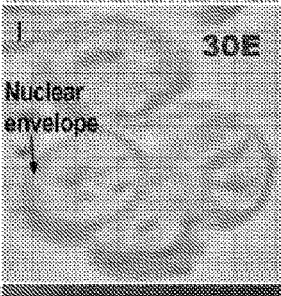
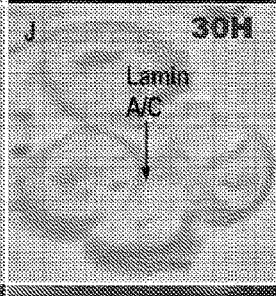
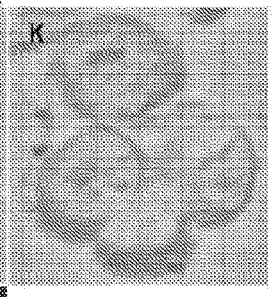
FIG. 30C
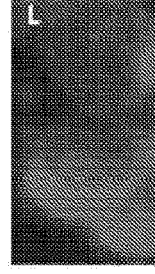
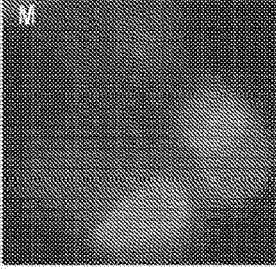
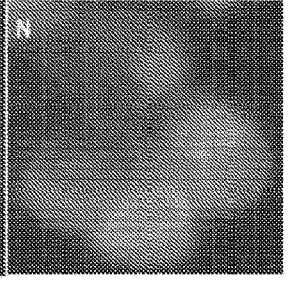
FIG. 30F   FIG. 30I

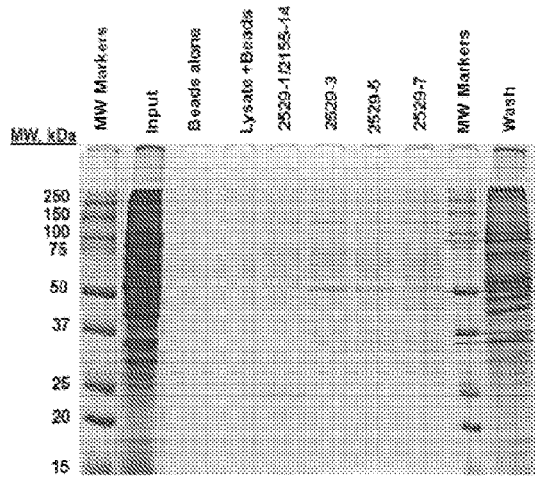
FIG. 32A
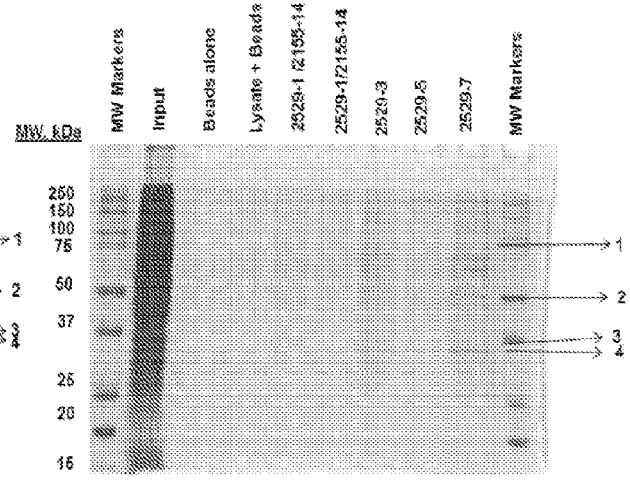
FIG. 32B
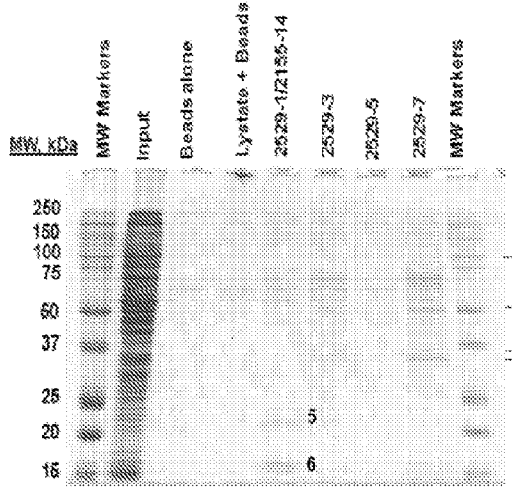
FIG. 32C
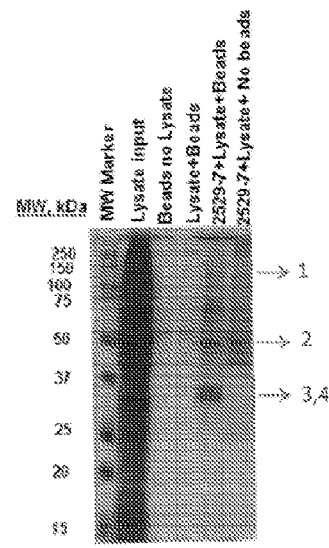
FIG. 32D
Table 9
| Band # | 1hr | 24hr | MW range, kDa | Protein ID | Accession # | Score |
|---|---|---|---|---|---|---|
| 1 | No | Yes | 100-75 | ATP-dependent RNA helicase DDX1 | Q92499 | 71.25 |
|   |   |   |   | hnRNP U-like protein 1 | Q9BUJ2 | 37.61 |
|   |   |   |   | ATP-dependent RNA helicase DDX3X | O00571 | 35.63 |
| 2 | Yes | Yes | 75-50 | hnRNP H2 | P55795 | 71.93 |
|   |   |   |   | hnRNP H1 | P31943 | 63.06 |
| 3 | Yes | Yes | 37-25 | hnRNP A2/B1 | P22626 | 85.5 |
| 4 | Yes | Yes | 37-25 | hnRNP A2/B1 | P22626 | 45.77 |
FIG. 33

FIG. 34A

P22626 (100%), 37,430.3 Da
Heterogeneous nuclear ribonucleoproteins A2/B1 n=12 Tax=Boreoeutheria RepID=ROA2_HUMAN
23 exclusive unique peptides, 30 exclusive unique spectra, 58 total spectra, 219/353 amino acids (62% coverage)

```
MEKTLETVPL  ERKKREKEQF  RKLFIGGLSF  ETTEESLRNY  YEQWGKLTDC
VVMRDPASKR  SRGFGFVTFS  SMAEVDAAMA  ARPHSIDGRV  VEPKRAVARE
ESGKPGAHVT  VKKLFVGGIK  EDTEEHHLRD  YFEEYGKIDT  IEIITDRQSG
KKRGFGFVTF  DDHDPVDKIV  LQKYHTINGH  NAEVRKALSR  QEMQEVQSSR
SGRGGNFGFG  DSRGGGGNFG  PGPGSNFRGG  SDGYGSGRGF  GDGYNGYGGG
PGGGNFGGSP  GYGGGRGGYG  GGGPGYGNQG  GGYGGGYDNY  GGGNYGSGNY
NDFGNYNQQP  SNYGPMKSGN  FGGSRNMGGP  YGGGNYGPGG  SGGSGGYGGR
SRY
```

P22626 (100%), 37,430.3 Da
Heterogeneous nuclear ribonucleoproteins A2/B1 n=12 Tax=Boreoeutheria RepID=ROA2_HUMAN
22 exclusive unique peptides, 34 exclusive unique spectra, 89 total spectra, 189/353 amino acids (54% coverage)

```
MEKTLETVPL  ERKKREKEQF  RKLFIGGLSF  ETTEESLRNY  YEQWGKLTDC
VVMRDPASKR  SRGFGFVTFS  SMAEVDAAMA  ARPHSIDGRV  VEPKRAVARE
ESGKPGAHVT  VKKLFVGGIK  EDTEEHHLRD  YFEEYGKIDT  IEIITDRQSG
KKRGFGFVTF  DDHDPVDKIV  LQKYHTINGH  NAEVRKALSR  QEMQEVQSSR
SGRGGNFGFG  DSRGGGGNFG  PGPGSNFRGG  SDGYGSGRGF  GDGYNGYGGG
PGGGNFGGSP  GYGGGRGGYG  GGGPGYGNQG  GGYGGGYDNY  GGGNYGSGNY
NDFGNYNQQP  SNYGPMKSGN  FGGSRNMGGP  YGGGNYGPGG  SGGSGGYGGR
SRY
```

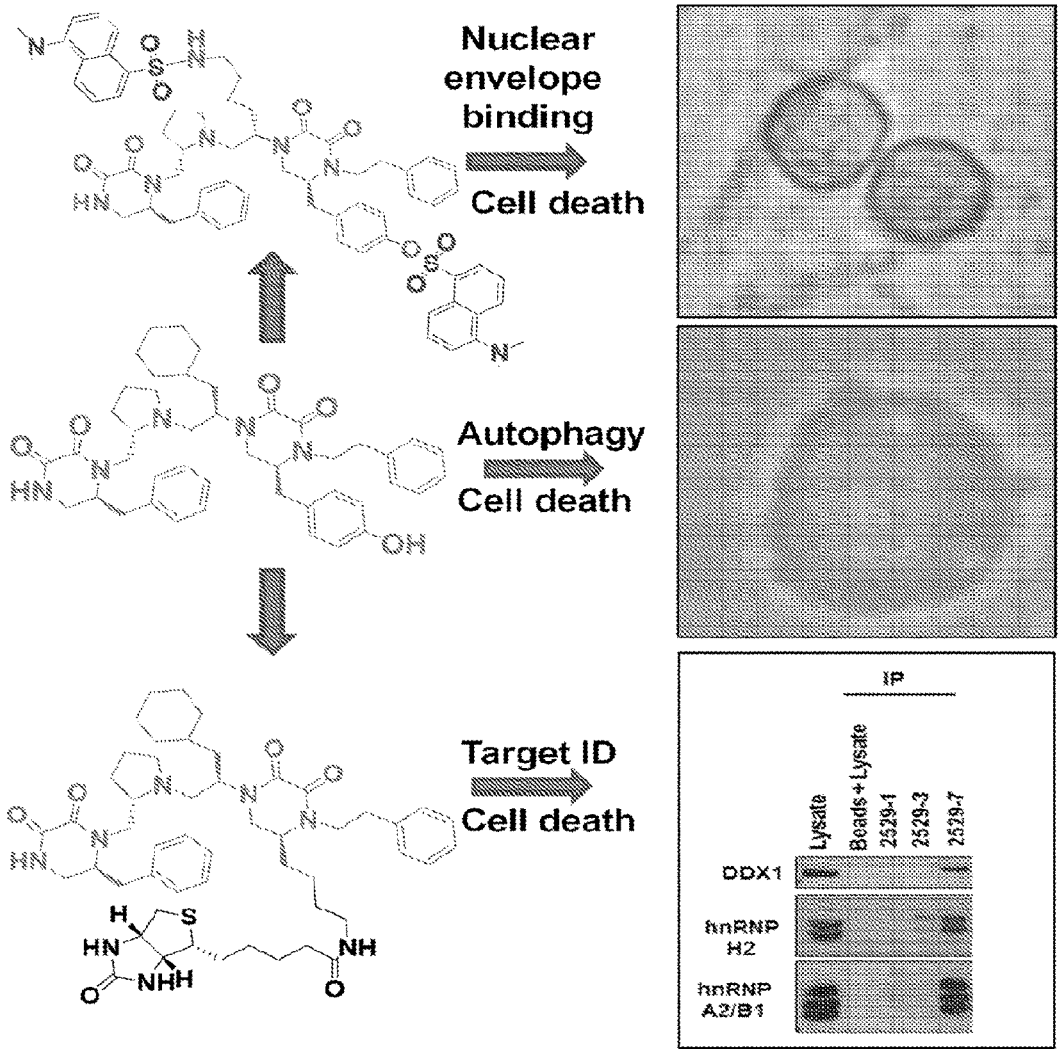

FIG. 34B

FIG. 43B
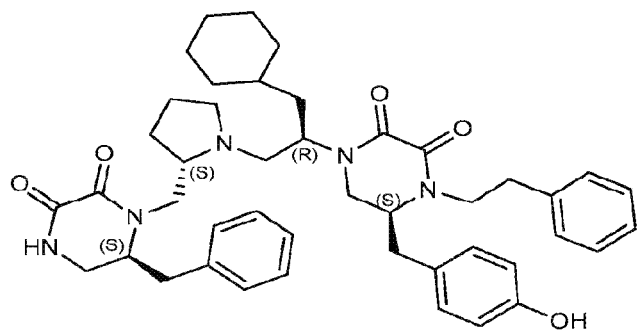
FIG. 43A
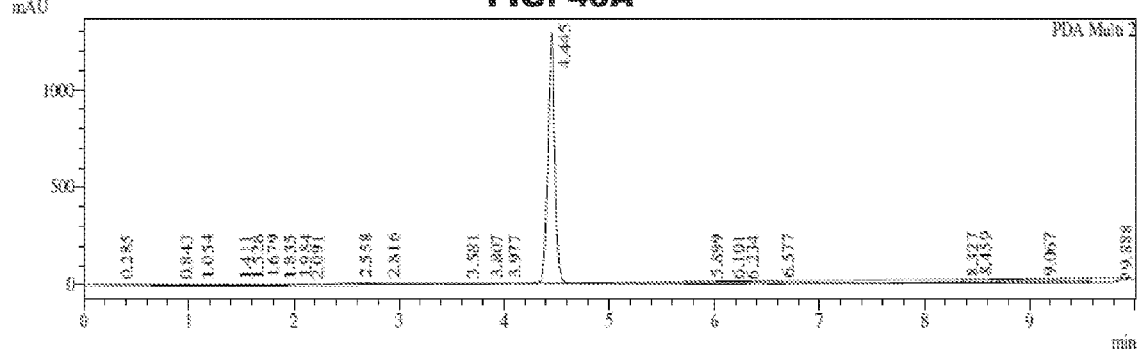
FIG. 45A
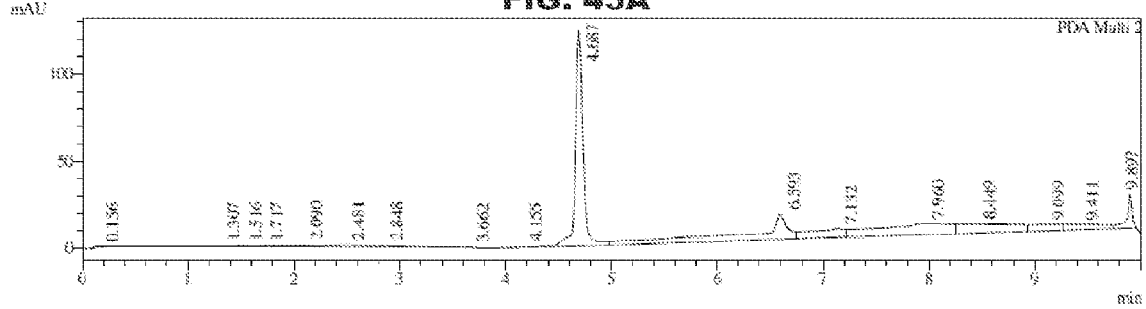
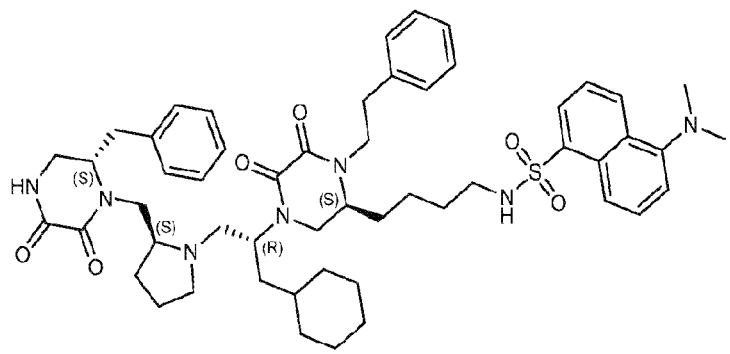
FIG. 45B

FIG. 46A
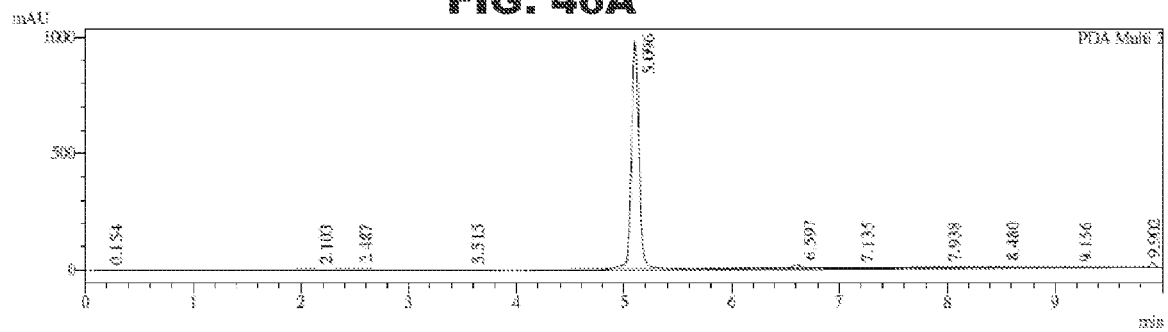
FIG. 46B
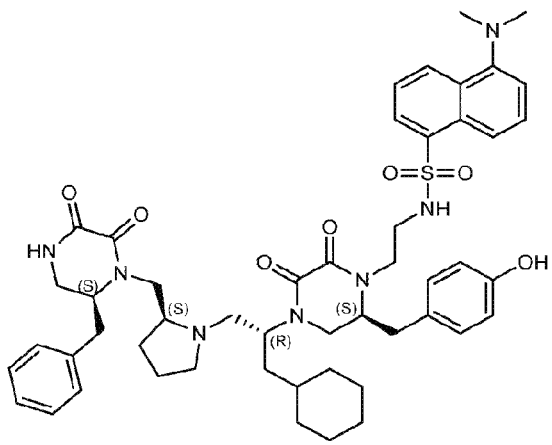
FIG. 47A
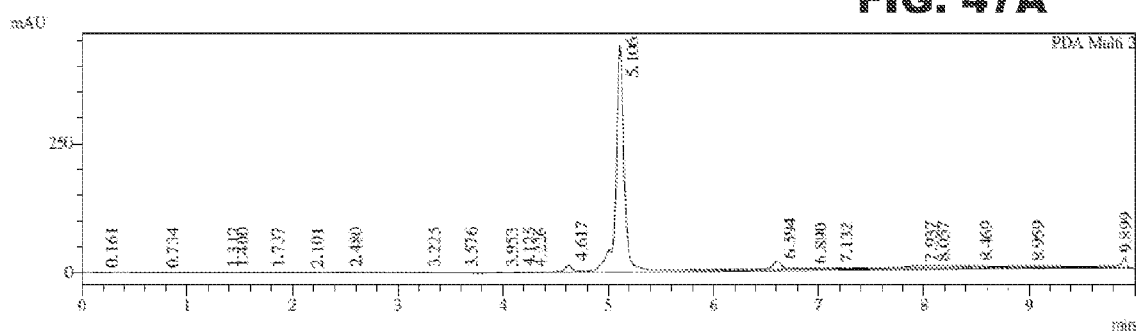
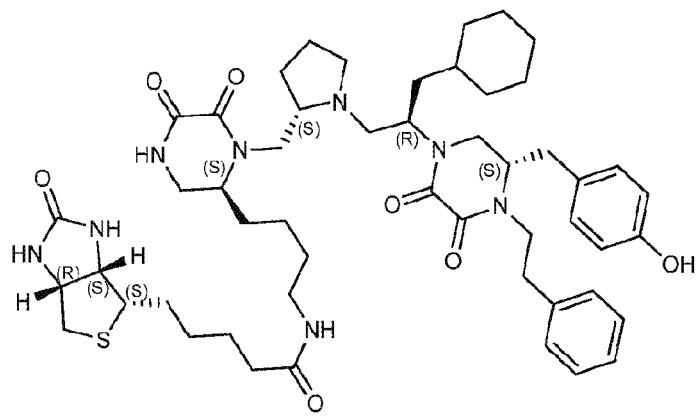
FIG. 47B

FIG. 48A
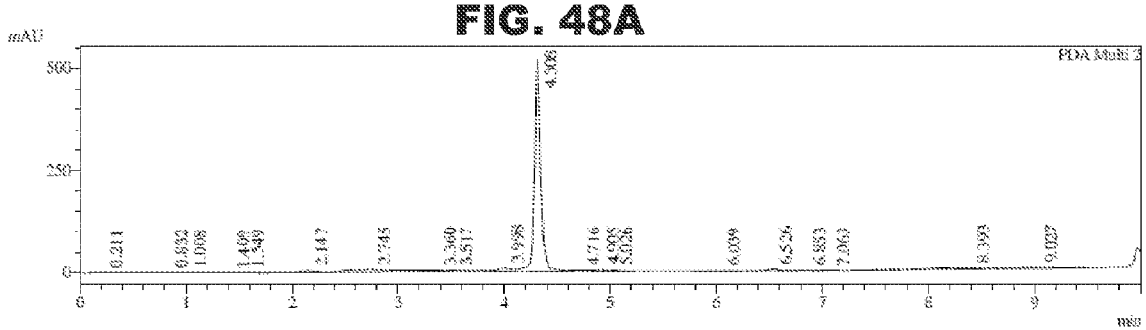
FIG. 48B
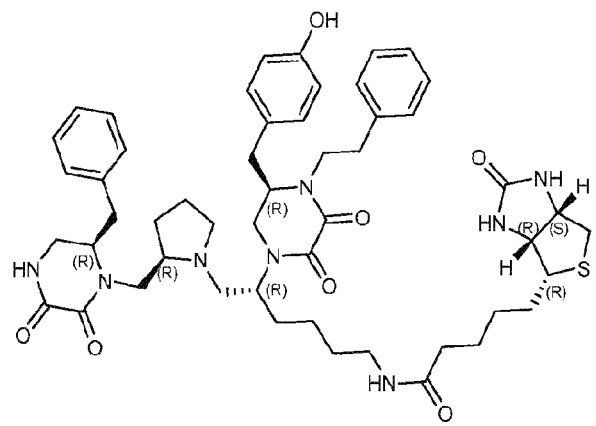
FIG. 49A
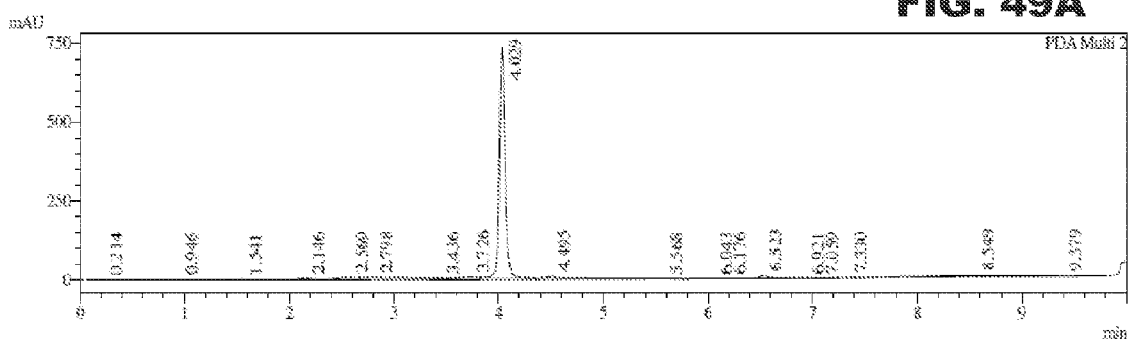
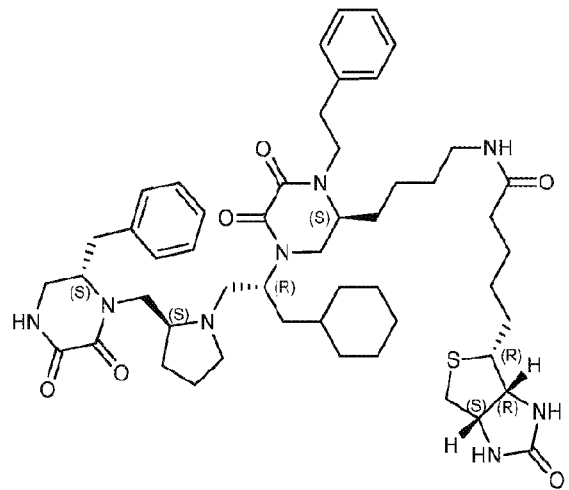
FIG. 49B

SEQUENCE LISTING

```
<160> NUMBER OF SEQ ID NOS: 2

<210> SEQ ID NO 1
<211> LENGTH: 353
<212> TYPE: PRT
<213> ORGANISM: Homo sapiens

<400> SEQUENCE: 1

Met Glu Lys Thr Leu Glu Thr Val Pro Leu Glu Arg Lys Lys Arg Glu
1               5                   10                  15

Lys Glu Gln Phe Arg Lys Leu Phe Ile Gly Gly Leu Ser Phe Glu Thr
            20                  25                  30

Thr Glu Glu Ser Leu Arg Asn Tyr Tyr Glu Gln Trp Gly Lys Leu Thr
        35                  40                  45

Asp Cys Val Val Met Arg Asp Pro Ala Ser Lys Arg Ser Arg Gly Phe
    50                  55                  60
```

```
Gly Phe Val Thr Phe Ser Ser Met Ala Glu Val Asp Ala Ala Met Ala
 65                  70                  75                  80

Ala Arg Pro His Ser Ile Asp Gly Arg Val Val Glu Pro Lys Arg Ala
                 85                  90                  95

Val Ala Arg Glu Glu Ser Gly Lys Pro Gly Ala His Val Thr Val Lys
            100                 105                 110

Lys Leu Phe Val Gly Gly Ile Lys Glu Asp Thr Glu Glu His His Leu
        115                 120                 125

Arg Asp Tyr Phe Glu Glu Tyr Gly Lys Ile Asp Thr Ile Glu Ile Ile
    130                 135                 140

Thr Asp Arg Gln Ser Gly Lys Lys Arg Gly Phe Gly Phe Val Thr Phe
145                 150                 155                 160

Asp Asp His Asp Pro Val Asp Lys Ile Val Leu Gln Lys Tyr His Thr
                165                 170                 175

Ile Asn Gly His Asn Ala Glu Val Arg Lys Ala Leu Ser Arg Gln Glu
            180                 185                 190

Met Gln Glu Val Gln Ser Ser Arg Ser Gly Arg Gly Gly Asn Phe Gly
        195                 200                 205

Phe Gly Asp Ser Arg Gly Gly Gly Asn Phe Gly Pro Gly Pro Gly
    210                 215                 220

Ser Asn Phe Arg Gly Gly Ser Asp Gly Tyr Gly Ser Gly Arg Gly Phe
225                 230                 235                 240

Gly Asp Gly Tyr Asn Gly Tyr Gly Gly Pro Gly Gly Gly Asn Phe
                245                 250                 255

Gly Gly Ser Pro Gly Tyr Gly Gly Arg Gly Gly Tyr Gly Gly Gly
            260                 265                 270

Gly Pro Gly Tyr Gly Asn Gln Gly Gly Tyr Gly Gly Gly Tyr Asp
        275                 280                 285

Asn Tyr Gly Gly Gly Asn Tyr Gly Ser Gly Asn Tyr Asn Asp Phe Gly
    290                 295                 300

Asn Tyr Asn Gln Gln Pro Ser Asn Tyr Gly Pro Met Lys Ser Gly Asn
305                 310                 315                 320

Phe Gly Gly Ser Arg Asn Met Gly Gly Pro Tyr Gly Gly Gly Asn Tyr
                325                 330                 335

Gly Pro Gly Gly Ser Gly Gly Ser Gly Gly Tyr Gly Gly Arg Ser Arg
            340                 345                 350

Tyr

<210> SEQ ID NO 2
<211> LENGTH: 341
<212> TYPE: PRT
<213> ORGANISM: Homo sapiens

<400> SEQUENCE: 2

Met Glu Arg Glu Lys Glu Gln Phe Arg Lys Leu Phe Ile Gly Gly Leu
 1               5                  10                  15

Ser Phe Glu Thr Thr Glu Glu Ser Leu Arg Asn Tyr Tyr Glu Gln Trp
                20                  25                  30

Gly Lys Leu Thr Asp Cys Val Val Met Arg Asp Pro Ala Ser Lys Arg
            35                  40                  45

Ser Arg Gly Phe Gly Phe Val Thr Phe Ser Ser Met Ala Glu Val Asp
        50                  55                  60

Ala Ala Met Ala Ala Arg Pro His Ser Ile Asp Gly Arg Val Val Glu
 65                  70                  75                  80
```

```
Pro Lys Arg Ala Val Ala Arg Glu Glu Ser Gly Lys Pro Gly Ala His
                85                  90                  95

Val Thr Val Lys Lys Leu Phe Val Gly Gly Ile Lys Glu Asp Thr Glu
            100                 105                 110

Glu His His Leu Arg Asp Tyr Phe Glu Glu Tyr Gly Lys Ile Asp Thr
        115                 120                 125

Ile Glu Ile Ile Thr Asp Arg Gln Ser Gly Lys Lys Arg Gly Phe Gly
    130                 135                 140

Phe Val Thr Phe Asp Asp His Asp Pro Val Asp Lys Ile Val Leu Gln
145                 150                 155                 160

Lys Tyr His Thr Ile Asn Gly His Asn Ala Glu Val Arg Lys Ala Leu
                165                 170                 175

Ser Arg Gln Glu Met Gln Glu Val Gln Ser Ser Arg Ser Gly Arg Gly
            180                 185                 190

Gly Asn Phe Gly Phe Gly Asp Ser Arg Gly Gly Gly Asn Phe Gly
        195                 200                 205

Pro Gly Pro Gly Ser Asn Phe Arg Gly Gly Ser Asp Gly Tyr Gly Ser
    210                 215                 220

Gly Arg Gly Phe Gly Asp Gly Tyr Asn Gly Tyr Gly Gly Pro Gly
225                 230                 235                 240

Gly Gly Asn Phe Gly Gly Ser Pro Gly Tyr Gly Gly Arg Gly Gly
                245                 250                 255

Tyr Gly Gly Gly Gly Pro Gly Tyr Gly Asn Gln Gly Gly Gly Tyr Gly
            260                 265                 270

Gly Gly Tyr Asp Asn Tyr Gly Gly Asn Tyr Gly Ser Gly Asn Tyr
        275                 280                 285

Asn Asp Phe Gly Asn Tyr Asn Gln Gln Pro Ser Asn Tyr Gly Pro Met
290                 295                 300

Lys Ser Gly Asn Phe Gly Gly Ser Arg Asn Met Gly Gly Pro Tyr Gly
305                 310                 315                 320

Gly Gly Asn Tyr Gly Pro Gly Gly Ser Gly Gly Ser Gly Gly Tyr Gly
            325                 330                 335

Gly Arg Ser Arg Tyr
            340
```

METHODS FOR TREATING MELANOMA USING SMALL MOLECULES

FIELD OF THE INVENTION

The invention generally relates to methods for using high-throughput screening for identification of targets for melanoma drug discovery; particularly to methods for treating melanoma using compounds that interact with cellular proteins; and most particularly to methods for treating melanoma using compounds that inhibit lamin A/C, ATP-dependent RNA helicase DDX1 (DDX1), heterogeneous nuclear ribonuclear protein H1/H2 (hnRNP H2), and/or heterogeneous nuclear ribonuclear protein A2/B1 (hnRNP A2/B1).

BACKGROUND OF THE INVENTION

As estimated by the National Cancer Institute (NIH/NCI), there are more than 900,000 people living with melanoma in the USA (NCI *Surveillance, Epidemiology, and End Results Program: Turning Cancer Data Into Discovery* 2014). The estimated number of new cases in 2016 is more than 76,000 with the number of deaths more than 10,000. If melanoma is resected before it metastasizes, the 5-year survival rate is 98%. However, if allowed to metastasize, the 5-year survival rate is only 10-15%. New therapies and approaches are urgently needed, and melanoma is one of the most active areas of oncological drug discovery with multiple active clinical trials (Active Melanoma Clinical Trials, website of NIH/NCI 2014). There are several molecular melanoma subtypes based on the molecular alterations present (Vidwans, S. J. et al. A melanoma molecular disease model. *PLoS One* 6, e18257, doi:10.1371/journal.pone.0018257 2011). Melanoma proliferation is mainly regulated by the Ras/Raf/MEK/ERK pathway. Most of molecular alterations (i.e. mutations, deletions, amplifications) that drive melanoma are concentrated in this pathway. ERK is hyperactivated in approximately 90% of human melanomas (Cohen, C. et al. Mitogen-activated protein kinase activation is an early event in melanoma progression. *Clin Cancer Res* 8, 3728-3733 2002). NRAS gain-of-function mutation Q61L occurs in 15-30% of cases and BRAF is mutated in 50-70% of melanomas (Davies, H. et al. Mutations of the BRAF gene in human cancer. *Nature* 417, 949-954, doi:10.1038/nature00766 2002). In most melanoma cases, more than one alteration is present which necessitates different therapeutic approaches to various molecular melanoma subtypes. An almost inevitable acquired resistance to therapy is another hallmark of melanoma. Chemo (dacarbazine, temolozomide), immuno (IL-2, ipilimumab), and targeted (vemurafenib, dabrafenib, trametinib) monotherapies usually result in resistance (Tentori, L., Lacal, P. M. & Graziani, G. Challenging resistance mechanisms to therapies for metastatic melanoma. *Trends Pharmacol Sci* 34, 656-666, doi: 10.1016/j.tips. 2013) which necessitates combination therapies using the aforementioned drugs. In January 2014, the FDA approved a BRAF/MEK inhibitor combination (dabrafenib/trametinib) for BRAF-mutant metastatic melanoma (Menzies, A. M. & Long, G. V. Dabrafenib and Trametinib, Alone and in Combination for BRAF-Mutant Metastatic Melanoma. *Clin Cancer Res* 20, 2035-2043, doi:10.1158/1078-0432.CCR-13-2054, 1078-0432. 2014), which demonstrated higher response rates (76% vs 59%) and slightly longer median progression-free survival (PFS) than dabrafenib or vemurafenib monotherapies (9.4 vs 6.9 months) with less toxicity. Some toxicity was reported, however, such that >50% of patients had to reduce the dosage and 9% discontinued the treatment. The resistance to this drug combination has already been reported (Spain, L., Julve, M. & Larkin, J. Combination dabrafenib and trametinib in the management of advanced melanoma with BRAFV600 mutations. *Expert Opin Pharmacother* 17, 1031-1038, doi: 10.1517/14656566.2016.1168805 2016; Rizos, H. et al. BRAF inhibitor resistance mechanisms in metastatic melanoma: spectrum and clinical impact. *Clin Cancer Res* 20, 1965-1977, doi:10.1158/1078-0432.CCR-13-3122 2014; and Long, G. V. et al. Increased MAPK reactivation in early resistance to dabrafenib/trametinib combination therapy of BRAF-mutant metastatic melanoma. *Nat Commun* 5, 5694, doi:10.1038/ncomms6694 2014) necessitating new approaches to melanoma drug discovery. Most recently, the FDA approved vemurafenib/cobimetinib. Overall survival (OS) in phase III trials was 25-26 months for dabrafenib/trametinib and 22 months for vemurafenib/cobimetinib (Spain, L., Julve, M. & Larkin, J. Combination dabrafenib and trametinib in the management of advanced melanoma with BRAFV600 mutations. *Expert Opin Pharmacother* 17, 1031-1038, doi:10.1517/14656566.2016.1168805 2016). Monotherapy using selective CDK 4/6 inhibitors (e.g., palbociclib, ribociclib, abemaciclib) has shown a limited response (~3% response rate) in melanoma clinical trials (Xu, W. & McArthur, G. Cell Cycle Regulation and Melanoma. *Curr Oncol Rep* 18, 34, doi:10.1007/s11912-016-0524-y 2016). CDK 4/6 inhibitors are currently being evaluated in combinations with BRAF and MEK inhibitors against BRAF- and NRAS-mutated melanomas. Combination of PD-1 and CTL-4 immunological checkpoint inhibitors nivolumab alone or combined with ipilimumab (Larkin, J. et al. Combined Nivolumab and Ipilimumab or Monotherapy in Untreated Melanoma. *N Engl J Med* 373, 23-34, doi:10.1056/NEJMoa1504030 2015 and Ascierto, P. A. et al. Future perspectives in melanoma research: meeting report from the "Melanoma Bridge", Napoli, Dec. 5-8 2013. *J Transl Med* 12, 277, doi:10.1186/s12967-014-0277-z 2014) exhibited overall response rate, PFS, and OS similar to dabrafenib/trametinib, but with a longer lasting effect after termination of therapy, likely due to the induced monitoring of cancer cells by immune cells.

Despite recent advances in melanoma drug discovery, the average overall survival of patients with late stage metastatic melanoma is ~3 years. Instances of complete response are very rare, therefore, more life-prolonging therapies are needed. This suggests a need for innovative approaches and targets for melanoma drug discovery.

SUMMARY OF THE INVENTION

The instant invention satisfies this need for innovative approaches and targets for melanoma drug discovery through identification of lamin A/C, ATP-dependent RNA helicase DDX1 (DDX1), heterogeneous nuclear ribonuclear protein H1/H2 (hnRNP H2), and/or heterogeneous nuclear ribonuclear protein A2/B1 (hnRNP A2/B1) as targets of selective anti-melanoma compound 2155-14. This is a first report suggesting that lamin A/C, DDX1, hnRNP H2, and A2/B1 could be targeted for melanoma drug discovery. Mechanistic investigations showed that 2155-14 potentiates basal autophagy and perturbs mitochondrial potential leading to melanoma cell death in BRAF and NRAS mutated melanoma cells. The approach utilized to identify 2155-14 may provide much needed broad-spectrum melanoma therapies.

Another significant discovery from the experiments described herein is the effect of hnRNPH2 modulation on autophagy. This discovery can lead to the deeper understanding of mechanisms regulating autophagy in melanoma and could explain the selectivity of 2155-14.

In a general embodiment, the invention provides a method for treating cancer, malignant tumors, and/or other conditions of unregulated cell growth.

In one aspect, the invention provides a method for treating cancer in a subject. The term "subject" includes any human being or animal exhibiting symptoms of cancer and/or unregulated cell growth and thus in need of treatment of the symptoms. The term "patient" is also used herein to refer to the subject. The method generally includes steps of (1) providing a composition including a pharmaceutically-acceptable carrier and a therapeutically-effective amount of a compound that interacts with a cellular protein selected from the group consisting of lamin A/C, ATP-dependent RNA helicase DDX1 (DDX1), heterogeneous nuclear ribonuclear protein H1/H2 (hnRNP H2), and heterogeneous nuclear ribonuclear protein A2/B1 (hnRNP A2/B1) and (2) administering the composition to the subject. The interaction of this composition with these cellular proteins is intended to inhibit primary and metastatic melanoma cells.

This method/composition can be applied alone or in combination with other cancer treatments.

The phrase "pharmaceutically-acceptable carrier" refers to an inactive and non-toxic substance used in association with an active substance, i.e. a compound that interacts with a cellular protein, especially for aiding in the application of the active substance. Non-limiting examples of pharmaceutically-acceptable carriers are diluents, binders, disintegrants, flavorings, fillers, and lubricants. Pharmaceutically-acceptable carriers can have more than one function, i.e. a filler can also be a disintegrant. Additionally, pharmaceutically-acceptable carriers may also be referred to as non-medicinal ingredients (HMIs).

The phrase "effective amount" refers to the amount of a composition necessary to achieve the composition's intended function.

The phase "therapeutically-effective amount" refers to the amount of a composition required to achieve the desired function, i.e. interaction with a cellular protein for treatment of the symptoms of cancer and/or unregulated cell growth.

The phrase "a compound that interacts with a cellular protein" refers to a compound that directly or indirectly acts on or with a protein. The term "compound" encompasses chemicals, proteins, peptides, antibodies, nucleic acids, and any combinations and/or mixtures thereof. The compound could be an antagonist and/or an inhibitor of the protein that can act to decrease or block an activity or function of the protein. A specific, yet non-limiting, example of such a compound is an antagonist of at least one of lamin A/C, DDX1, hnRNP H2, and hnRNP A2/B1. A preferred, nom-limiting example of the compound has a formula:

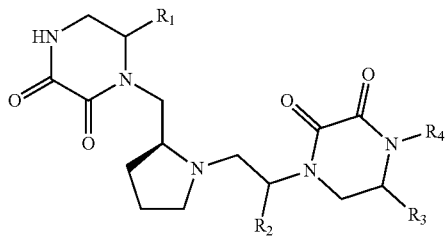

This formula can be substituted at multiple positions. A preferred, non-limiting, example is substitution at the third position.

In another aspect, the invention provides a method for treating melanoma and metastatic melanoma in a subject in need thereof. Melanoma is a deadly form of skin cancer resulting from a malignant neoplasm of melanocytes. Melanoma proliferation is mainly regulated by the Ras/Raf/MEK/ERK pathway. Most of molecular alterations (i.e. mutations, deletions, amplifications) that drive melanoma are concentrated in this pathway. In many cases, melanoma cells have a mutation in at least one of the BRAF and NRAS genetic pathways.

In yet another aspect, the invention provides a screening method for identifying compounds active against melanoma cells. The method includes steps of (1) selecting compounds for screening against the melanoma cells; (2) incubating the selected compounds in a screening reaction with at least one cellular protein selected from the group consisting of lamin A/C, ATP-dependent RNA helicase DDX1 (DDX1), heterogeneous nuclear ribonuclear protein H1/H2 (hnRNP H2), and heterogeneous nuclear ribonuclear protein A2/B1 (hnRNP A2/B1); (3) monitoring activity of lamin A/C, DDX1, hnRNP H2, and hnRNP A2/B1; and (4) identifying compounds having an effect on the melanoma cells. These studies were enabled by the probes which were derived from a combinatorial mixture-based library. Mixture-based compound libraries represent an important class of chemical biology tools for discovering novel targets.

In yet another aspect, any of the compounds described herein can be used in the manufacture of any of the above-described compositions.

Other objectives and advantages of this invention will become apparent from the following description taken in conjunction with the accompanying drawings, wherein are set forth, by way of illustration and example, certain embodiments of this invention. The drawings constitute a part of this specification and include exemplary embodiments of the present invention and illustrate various objects and features thereof.

BRIEF DESCRIPTION OF THE DRAWINGS

A more complete understanding of the present invention may be obtained by references to the accompanying drawings when considered in conjunction with the subsequent detailed description. The embodiments illustrated in the drawings are intended only to exemplify the invention and should not be construed as limiting the invention to the illustrated embodiments.

FIG. 3A is the $R_1$ scan.
FIG. 3B is the $R_2$ scan.
FIG. 3C is the $R_3$ scan.
FIG. 3D is the (D) $R_4$ scan.

FIG. 4 shows Table 1 which documents the most selective functionalities derived from the positional scan of library 1344.

FIG. 5 shows Table 2 which documents results of a dose response study of mixture samples that exhibited the most selectivity in the positional scanning study of library 1344. Data shown is a mean of three experiments, ±standard deviation, units in $IC_{50}$ in µm.

FIG. 6 shows Table 3 which documents results of a SAR study of individual compounds synthesized based on a positional scan of library 1344. % inhibition is a mean of three experiments, ±standard deviation.

FIG. 8 shows Table 4 which documents results from inhibition profiles of 2155-14 and 2155-18 with melanoma cell lines carrying different mutations. Data shown is a mean of three experiments, ±standard deviation, units in $IC_{50}$ in µm.

FIGS. 9A-D are graphs illustrating results of ApoTox time course assays.

FIG. 9A shows results from 4 hours.
FIG. 9B shows results from 24 hours.
FIG. 9C shows results from 48 hours.
FIG. 9D shows results from 72 hours.

FIGS. 10A, 10E, and 10I show results at 4 hours.
FIGS. 10B, 10F, and 10J show results at 24 hours.
FIGS. 10C, 10G, and 10K show results at 48 hours.
FIGS. 10D, 10H, and 10L show results at 72 hours.

FIGS. 11A-H is a schematic illustration of a general synthesis procedure for pyrrolidine-bis-diketopiperazines. 1.) 5% DIEA/95% DCM; 2.) Boc-AA, DIC, HOBt, DMF; 3.) 55% TFA/45% DCM; 4.) Boc-L-Pro-OH, DIC, HOBt, DMF; 5.) COOH, DIC, HOBt, DMF 6.) 40×BH3/THF (65° C., 72 hr) 7.) Piperdine (65° C., 18 hr); 8.) 10× (COlm)2 (18 hr); 9.) HF/Anisole, (0° C., 1.5 hr).

FIG. 11A represents a Boc-protected amino acid coupled to add $R_1$ to the resin.
FIG. 11B represents coupling of Boc-L-proline-OH.
FIG. 11C represents repetition of A and B to add $R_2$.
FIG. 11D represents repetition of A and B to add $R_3$.
FIG. 11E represented repetition of A and B with addition of carboxylic acid to add $R_4$.
FIG. 11F represents reductions of compounds.
FIG. 11G represents diketopiperazine cyclization.
FIG. 11H represents the compounds cleaved from the resin.

FIG. 12A shows 1H NMR spectra.
FIG. 12B shows 13C NMR spectra.

FIG. 13A shows 1H NMR spectra.
FIG. 13B shows 13C NMR spectra.

FIG. 14 shows Table 5 which documents cell lines used in the described experiments.

FIG. 15 shows Table 6 which documents the effect of 2155-14, 2155-18, and Zelboraf on viability of human and murine melanoma and non-malignant cells. All results are $IC_{50}$, (n=3). NT—not tested. % Inhibition data reported as a mean of three experiments±standard deviation. Values reported previously elsewhere are indicated by citation numbers.

FIGS. 16A-B are graphs showing results of a flow cytometry-based assay of MAPK/PI3K dual phosphorylation of WM266-4 cells in presence of 2155-14 and 2155-18.

FIG. 16A shows 24 h treatment with 2155-14 and 2155-18.
FIG. 16B shows 48 h treatment with 2155-14 and 2155-18.

One-way analysis of variance (ANOVA) was used followed by Dunnett post hoc test. The data shown are the mean±SD, n=3. ***—$p<0.0001$, *—$p<0.001$, **—$p<0.01$, *—$p<0.05$; 2155-14 and 2155-18 were tested at 25 µM. Trametinib/dabrafenib combination was tested at 25 µM of each compound. Negative—cell population with neither MAPK nor PI3K pathway activated; MAPK—cell population with just MAPK pathway activated; Dual—cell population with both MAPK and PI3K pathways activated; PI3K—cell population with just PI3K pathway activated.

FIGS. 17A-E are graphs showing the effect of 2155-14 and 2155-18 on caspase activity and viability of WM266-4 cells.

FIG. 17A shows caspase 3/7 activity assay results.
FIG. 17B shows caspase 8 activity assay results.
FIG. 17C shows caspase 9 activity assay results.
FIG. 17D shows cell viability after 24 h treatment with compounds.
FIG. 17E shows cell viability after 48 h treatment with compounds.

One-way analysis of variance (ANOVA) was used followed by Dunnett post hoc test. The data shown are the mean±SD, n=6. ***—$p<0.0001$, *—$p<0.001$, **—$p<0.01$, *—$p<0.05$; 2155-14 and 2155-18 were tested at 25 µM.

FIGS. 18A-D are micrographs showing autophagy detection in WM266-4 cells using autophagosome dye. Amount of cells present in each well was normalized using DAPI-stained nuclei. Scale bar=100 µm for all images with 20× magnification and 300 µm for all images with 4× magnification.

Figure 18A:
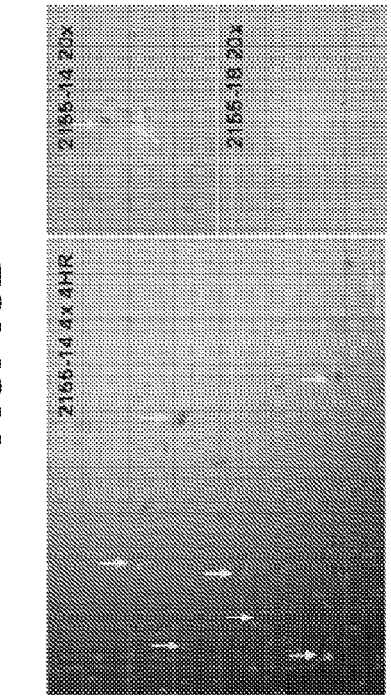

FIG. 18A shows bright field micrographs at 4× magnification of unstained WM266-4 cells in presence of 2155-14 and 2155-18 at 4 and 24 h after compound addition. Note differences in cell morphology as compared to untreated control (UTC).

Figure 18B:
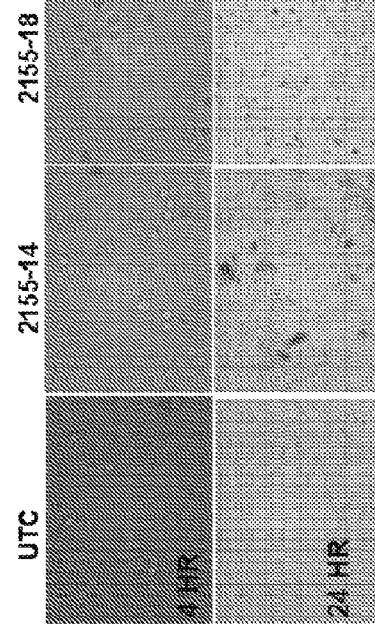

FIG. 18B illustrates that WM266-4 cells stain positive for autophagy at 4 h after addition of 2155-14, but not 2155-18. In a color micrograph, nuclei would be stained blue and yellow arrows would indicate green puncta signifying autophagosome formation.

Figure 18D:
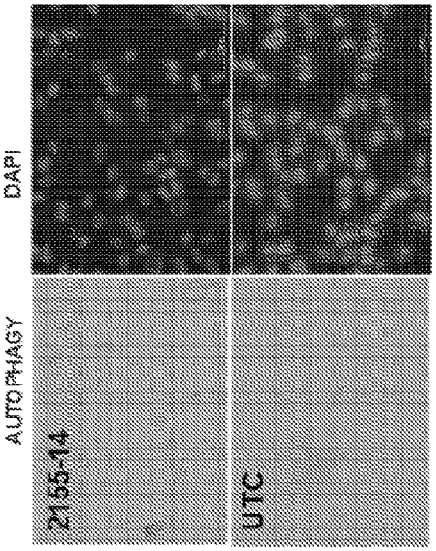
Figure 18C:
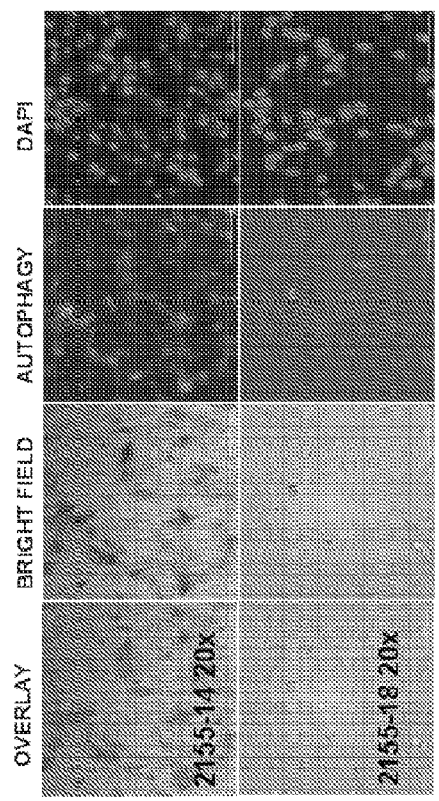

FIG. 18C illustrates that WM266-4 cells show increased autophagy staining at 24 h after addition of 2155-14, but not 2155-18. In a color micrograph, nuclei would be stained blue.

FIG. 18D shows that an Autophagy (GFP) channel was used to quantify positive WM266-4 cells.

FIGS. 19A-E include both micrographs and graphs showing the effect of 2155-14 on mitochondrial potential of WM266-4 cells.

FIG. 19A shows representative images of cells 1 h after addition of compounds.

FIG. 19B shows quantitation of effects of compounds on mitochondrial potential 1 h after compound addition. There is no significance between untreated control and cells treated with 2155-14. One-way analysis of variance (ANOVA) was used followed by Dunnett post hoc test. The data shown are the mean±SD, n=4. *—$p<0.05$.

FIG. 19 C shows representative images of cells 4 h after addition of compounds.

FIG. 19D shows quantitation of effects of compounds on mitochondrial potential 1 h after compound addition. One-way analysis of variance (ANOVA) was used followed by Dunnett post hoc test. The data shown are the mean±SD, n=4. **—$p<0.01$.

FIG. 19E shows dose response study of effect of 2155-14 on autophagy and mitochondrial potential of WM266-4 cells after 4 h treatment with 2155-14. One-way analysis of variance (ANOVA) was used followed by Dunnett post hoc test. The data shown are the mean±SD, n=4. **—$p<0.001$, —$p<0.01$, *—$p<0.05$. UC—untreated control, CCCP—carbonyl cyanide m-chlorophenyl hydrazine.

FIGS. 20A-C include both western blots and graphs showing western blot analysis of WM266-4 and M14 cells confirming that autophagy is induced by 2155-14, but not 2155-18.

FIG. 20 A shows LC3 and beclin-1 representative blots and quantification 30 min after addition of 5-50 µM 2155-14 and 2155-18 to WM266-4 cells. No statistical significance between untreated control and test conditions was observed.

FIG. 20B shows LC3 and beclin-1 representative blots and quantification 24 h after addition of 5-200 µM 2155-14 and 2155-18 to WM266-4 cells. Dose dependent increase of LC3 and beclin-1 was observed in the case of 2155-14, but not 2155-18.

FIG. 20C shows LC3 and beclin-1 representative blots and quantification 24 h after addition of 100 µM 2155-14 to M14 cells. UC—untreated control. Rapamycin/chloroquine (Rap/CHQ) mixture used as a control. One-way analysis of variance (ANOVA) was used followed by Dunnett post hoc test. The data shown are the mean±SD, n=3. ***—$p<0.0001$, *—$p<0.001$, **—$p<0.01$, *—$p<0.05$.

FIGS. 21A-E include both western blots and graphs showing the effect of pre-treatment of WM266-4 cells with autophagy inhibitors on viability and levels of LC3-II and lamin A/C cleavage in the presence of 2155-14.

Figure 21A:
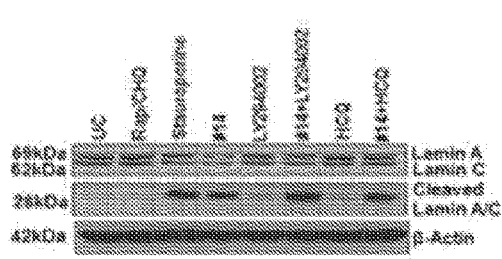

FIG. 21A shows a representative western blot of lamin A/C.

Figure 21B:
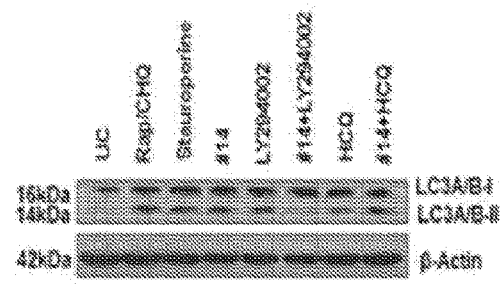

FIG. 21B shows a representative western blot of LC3.

Figure 21C:
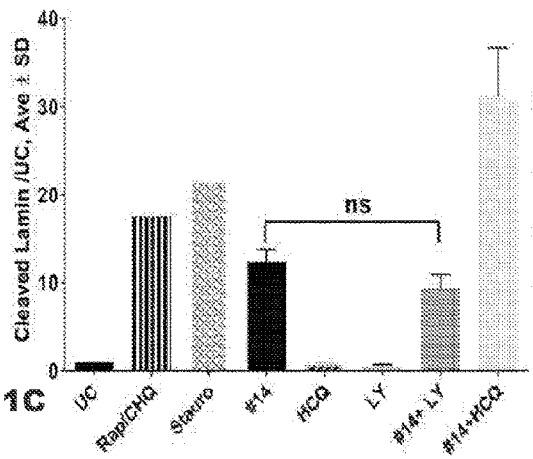

FIG. 21C shows quantification of western blot of lamin A/C. One-way analysis of variance (ANOVA) was used followed by Dunnett post hoc test. The data shown are the mean±SD, n=3. ns=not significant. 2155-14 was tested at 100 µM, LY and hydroxychloroquine (HCQ) were tested at 10 µM.

Figure 21D:
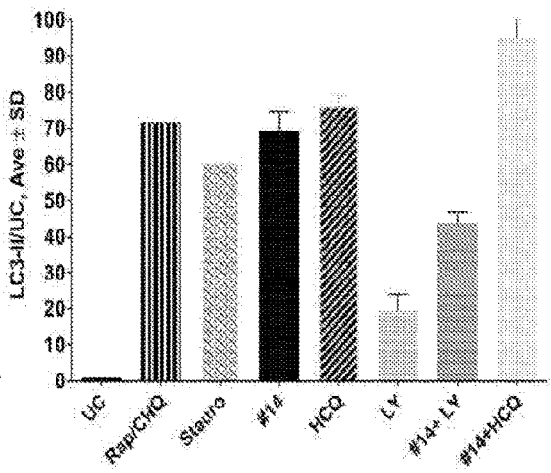

FIG. 21D shows quantification of western blot of LC3. The data shown are the mean±SD, n=3.

Figure 21E:
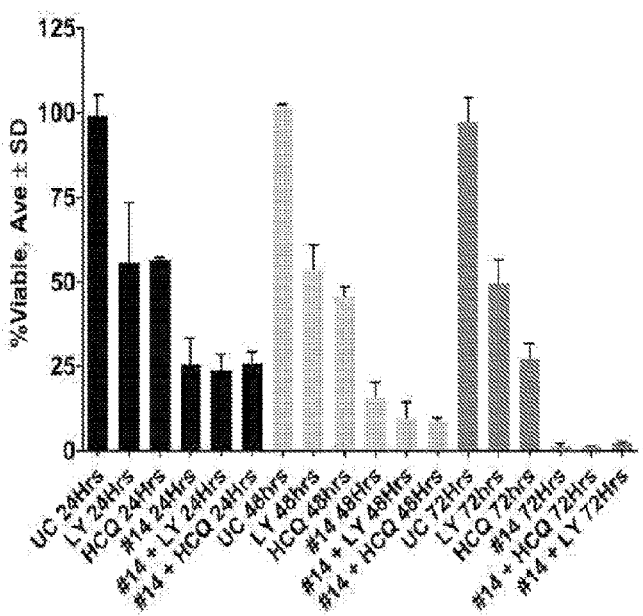

FIG. 21E shows viability of WM266-4 cells after pre-treatment with autophagy inhibitors in the presence of 2155-14. The data shown are the mean±SD, n=6.

FIGS. 22A-D include both western blots and graphs showing the effect of pre-treatment of WM266-4 cells with 10 µM caspase inhibitors on levels of LC3-II and lamin A/C cleavage in the presence of 2155-14.

FIG. 22A shows a representative western blot of lamin A/C in presence of 10 µM caspase inhibitors.

FIG. 22B shows a representative western blot of LC3 in presence of 10 µM caspase inhibitors.

FIG. 22C shows quantification of western blot of cleaved lamin A/C in presence of 10 µM caspase inhibitors.

FIG. 22D shows quantification of western blot of LC3-II in presence of 10 µM caspase inhibitors; One-way analysis of variance (ANOVA) was used followed by Dunnett post hoc test. The data shown are the mean±SD, n=3. ***—$p<0.0001$, *—$p<0.001$, **—$p<0.01$, *—$p<0.05$, ns—not significant. 2155-14 was tested at 100 µM. Rap/CHQ=Rapamycin (5 µM)/Chloroquine (10 Caspase 6 inh=Z-VEID-FMK, Caspase 8 inh=Z-IETD-FMK, pan-Caspase inh=Z-VAD-FMK.

FIGS. 23A-D include both western blots and graphs showing the effect of pre-treatment of WM266-4 cells with 50 µM caspase inhibitors on levels of LC3-II and lamin A/C cleavage in the presence of 2155-14.

Figure 23A:
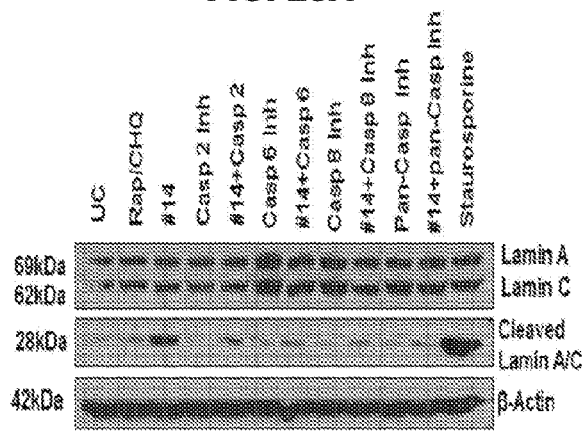

FIG. 23A shows a representative western blot of lamin A/C in presence of 50 caspase inhibitors.

Figure 23B:
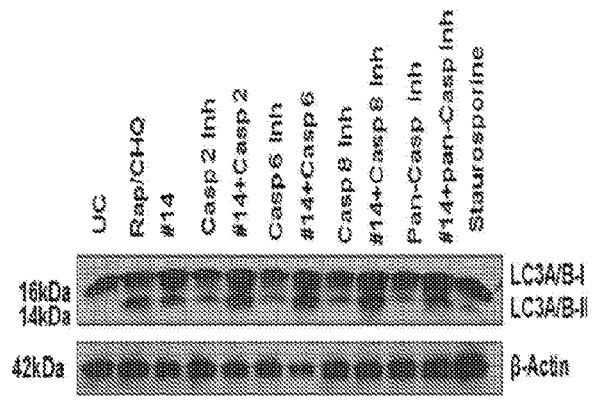

FIG. 23B shows a representative western blot of LC3 in presence of 50 µM caspase inhibitors.

Figure 23C:
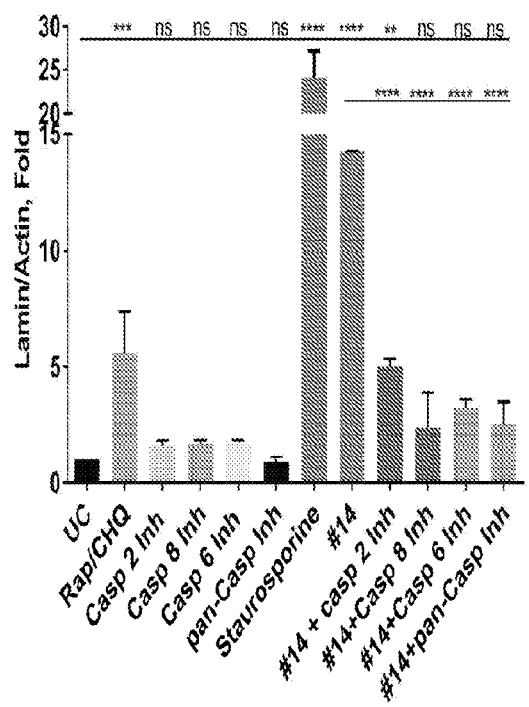

FIG. 23C shows quantification of western blot of cleaved lamin A/C in presence of 50 caspase inhibitors.

Figure 23D:
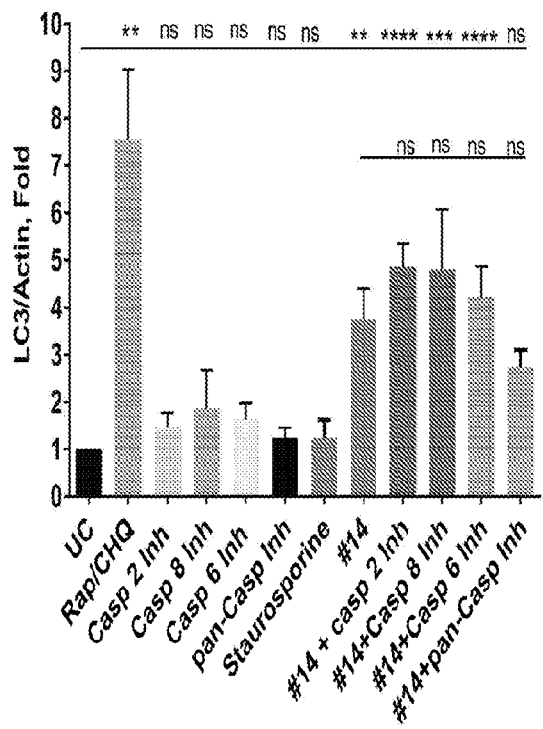

FIG. 23D shows quantification of western blot of LC3-II in presence of 50 µM caspase inhibitors. One-way analysis of variance (ANOVA) was used followed by Dunnett post hoc test. The data shown are the mean±SD, n=3. ***—$p<0.0001$, *—$p<0.001$, **—$p<0.01$, *—$p<0.05$, ns—not significant. 2155-14 was tested at 100 µM. Rap/CHQ=Rapamycin (5 µM)/Chloroquine (10 Caspase 2 inh=Z-VDVAD-FMK, Caspase 6 inh=Z-VEID-FMK, Caspase 8 inh=Z-IETD-FMK, pan-Caspase inh=Z-VAD-FMK.

FIGS. 24A-D include graphs showing results of an Annexin V assay confirming late apoptosis as one of the mechanisms of 2155-14-induced cell death.

Figure 24A:
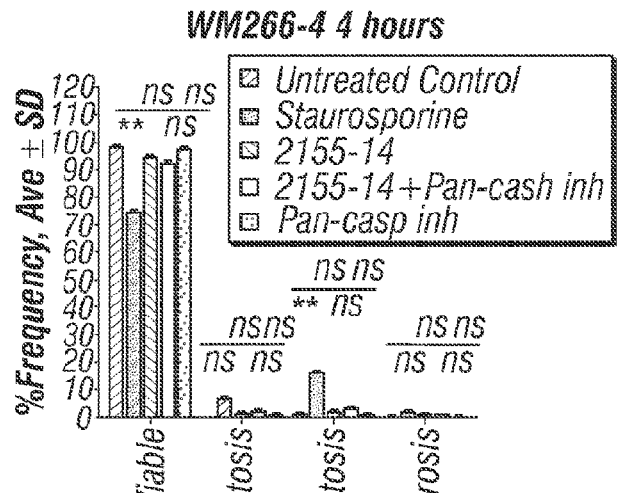

FIG. 24A shows results at 4 hours.

Figure 24B:
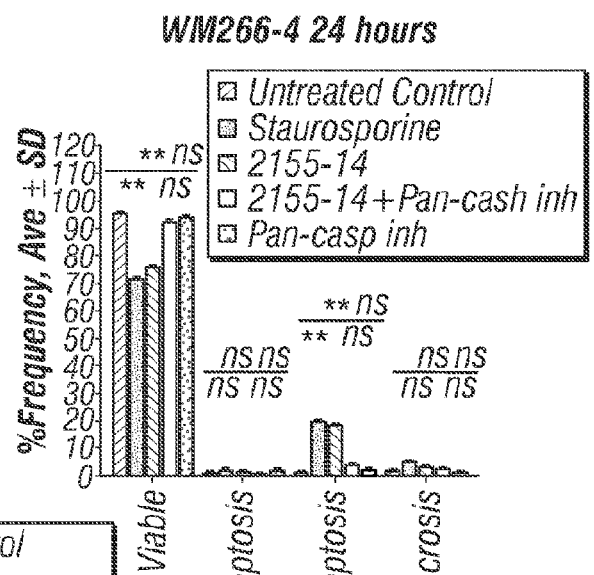

FIG. 24B shows results at 24 hours.

Figure 24C:
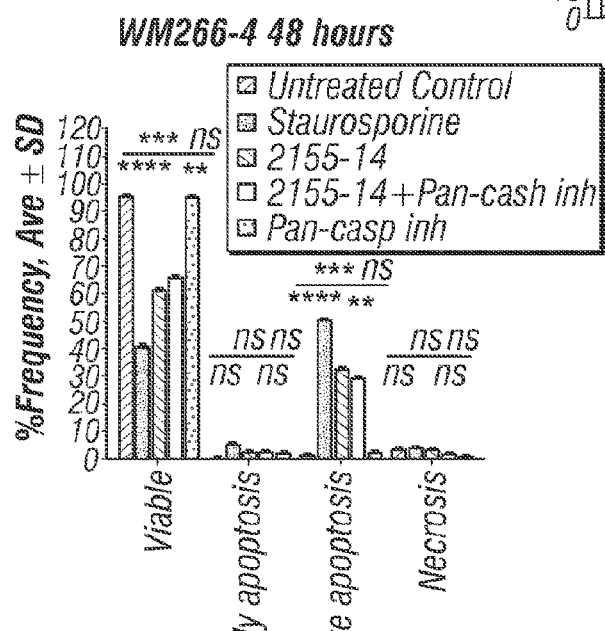

FIG. 24C shows (C) results at 48 hours.

Pan-caspase inhibitor—Z-VAD-FMK. Staurosporine was used at 2155-14 was used at 100 µM, Z-VAD-FMK was used at 10 µM. Cells treated with 2155-14 and 2155-14+pan-caspase inhibitor have similar distribution of cell populations suggesting lack of effect of pan-caspase inhibitor on biological effects of 2155-14 application. Two-way analysis of variance (ANOVA) was used followed by Dunnett post hoc test. The data shown are the mean±SD, n=3. ***—$p<0.0001$, *—$p<0.001$, **—$p<0.01$, *—$p<0.05$, ns—no significance.

Figure 24D:
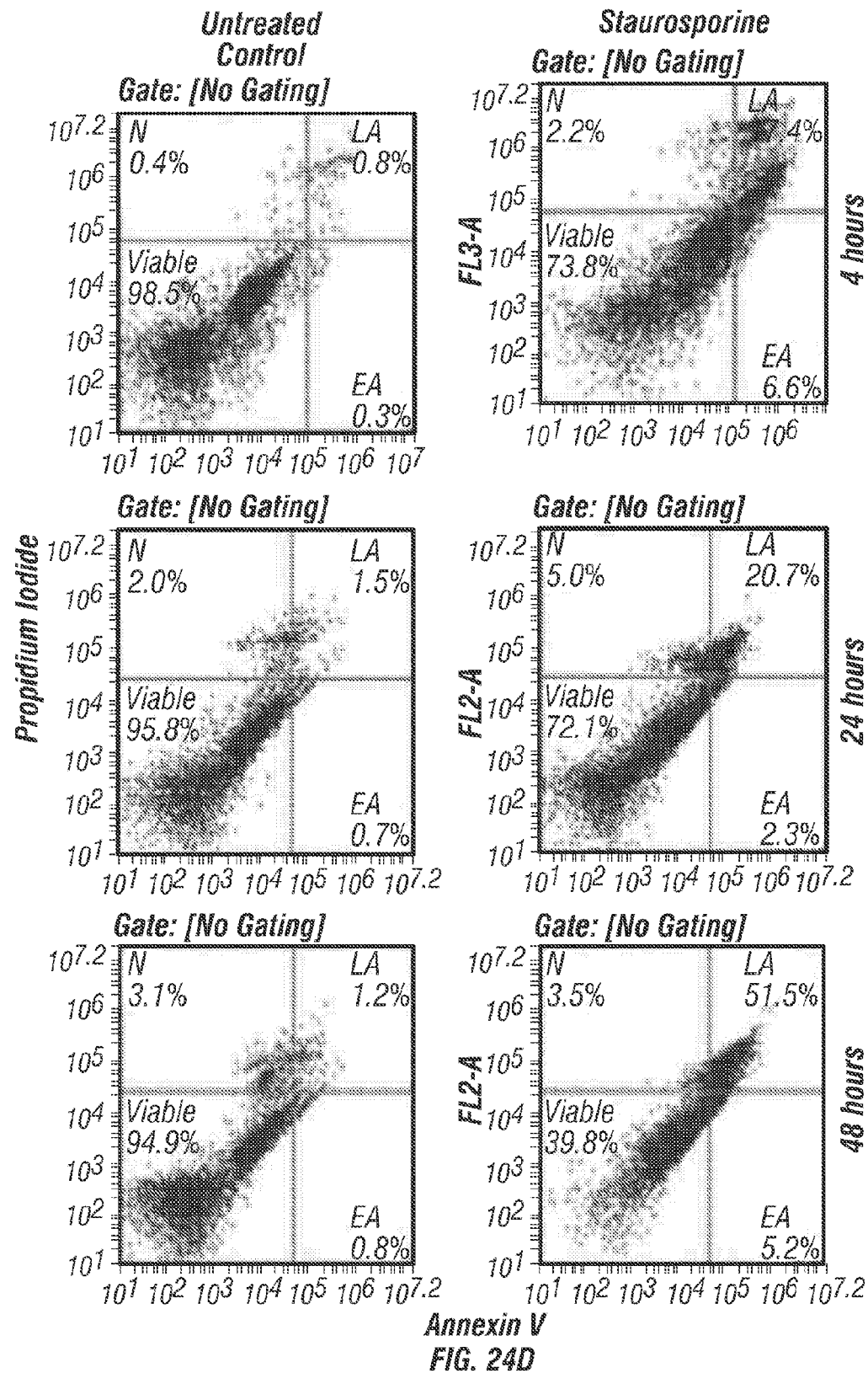
Figure 24D:
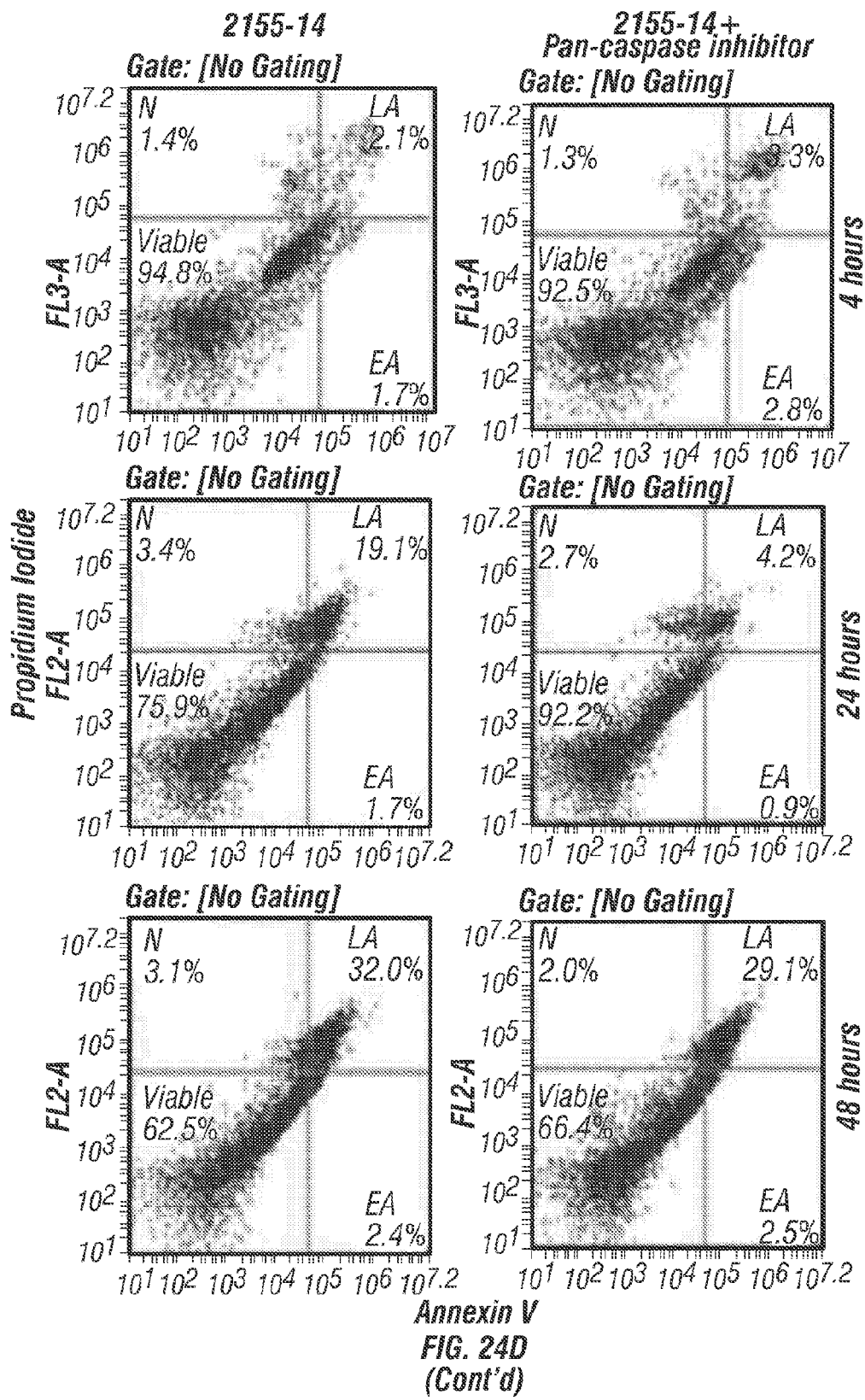
Figure 24D:
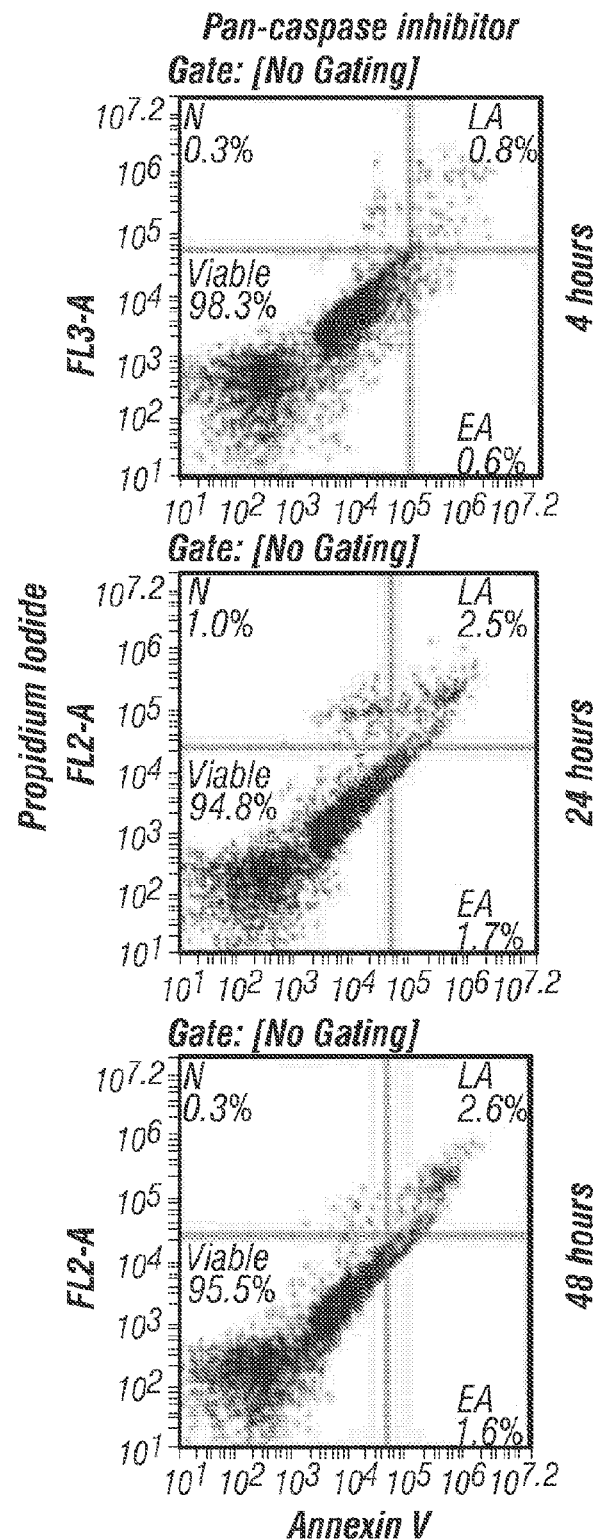

FIG. 24D shows results from pan-caspase inhibitor—Z-VAD-FMK. Staurosporine was used at 2155-14 was used at 100 µM, Z-VAD-FMK was used at 10 µM. Each cytogram is dived into 4 quadrants representing different cell populations: bottom left—viable, top left—necrotic (N), bottom right—early apoptotoc (EA) and top right—late apoptotic (LA). Cells treated with 2155-14 and 2155-14+pan-caspase inhibitor have similar distribution of cell populations suggesting lack of effect of pan-caspase inhibitor on biological effects of 2155-14 application.

FIGS. 25A-D include graphs showing the effect of pre-treatment of WM266-4 cells with calpain and cathepsin B inhibitors on viability and calpain activity in the presence of 2155-14.

FIG. 25 A shows calpain activity in presence of 2155-14 with and without 25 µM calpain inhibitors PD 151746 and MDL 28170 pre-treatment. Cells were pretreated with calpain inhibitors for 3 h before addition of 2155-14.

Figure 25B:
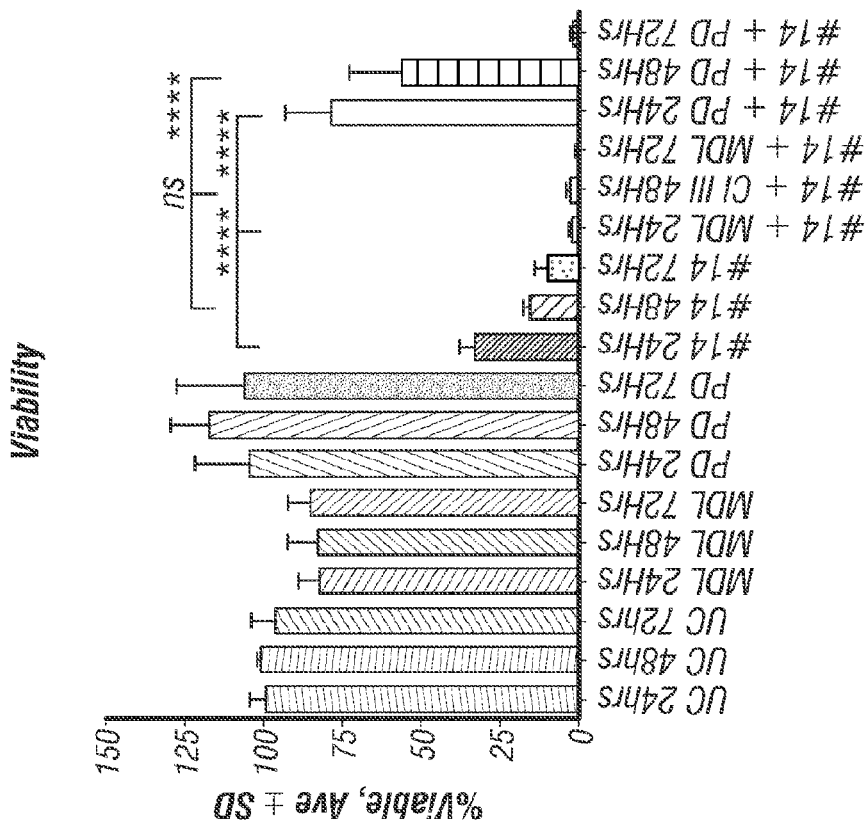

FIG. 25B shows viability of WM266-4 cells in presence of 2155-14 with and without 25 calpain inhibitors PD 151746 and MDL 28170 pre-treatment. Cells were pre-treated with calpain inhibitors for 3 h before addition of 2155-14.

Figure 25A:
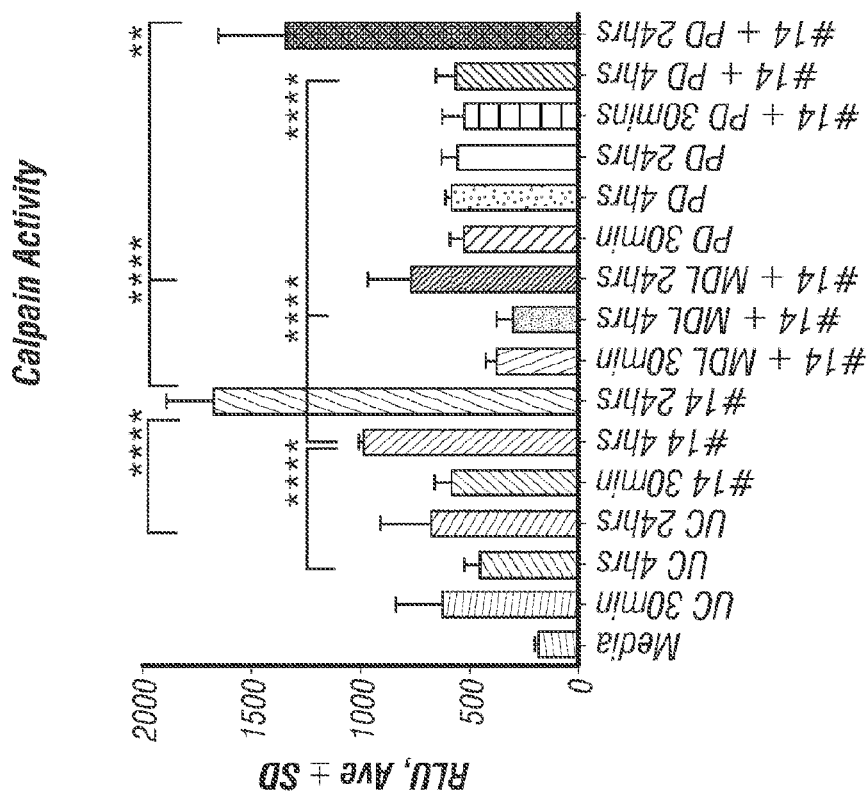
Figure 25D:
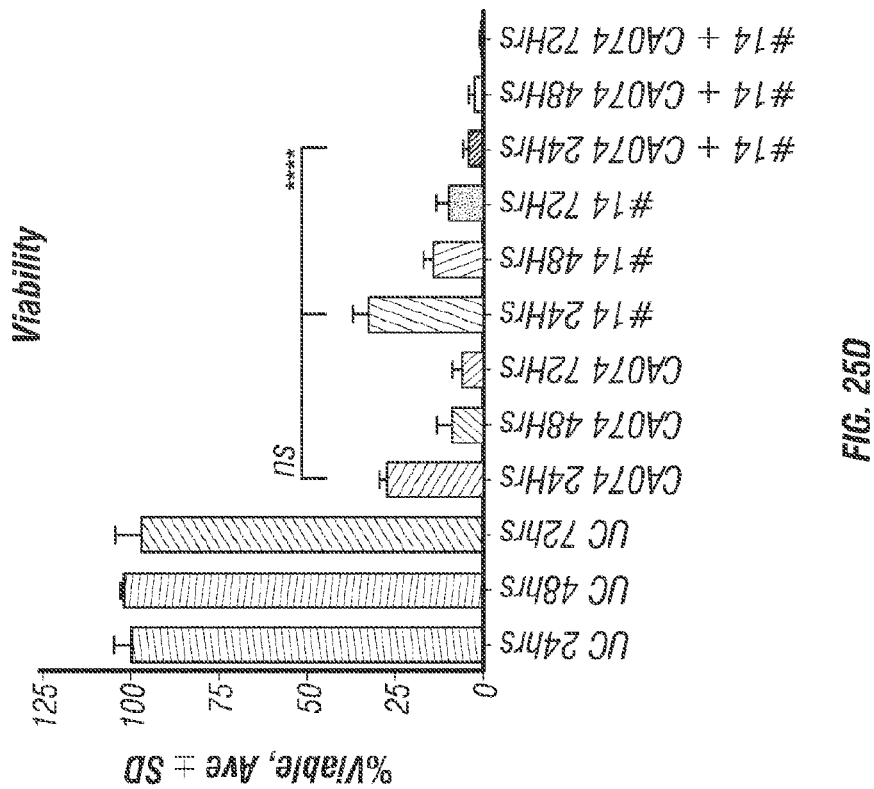
Figure 25C:
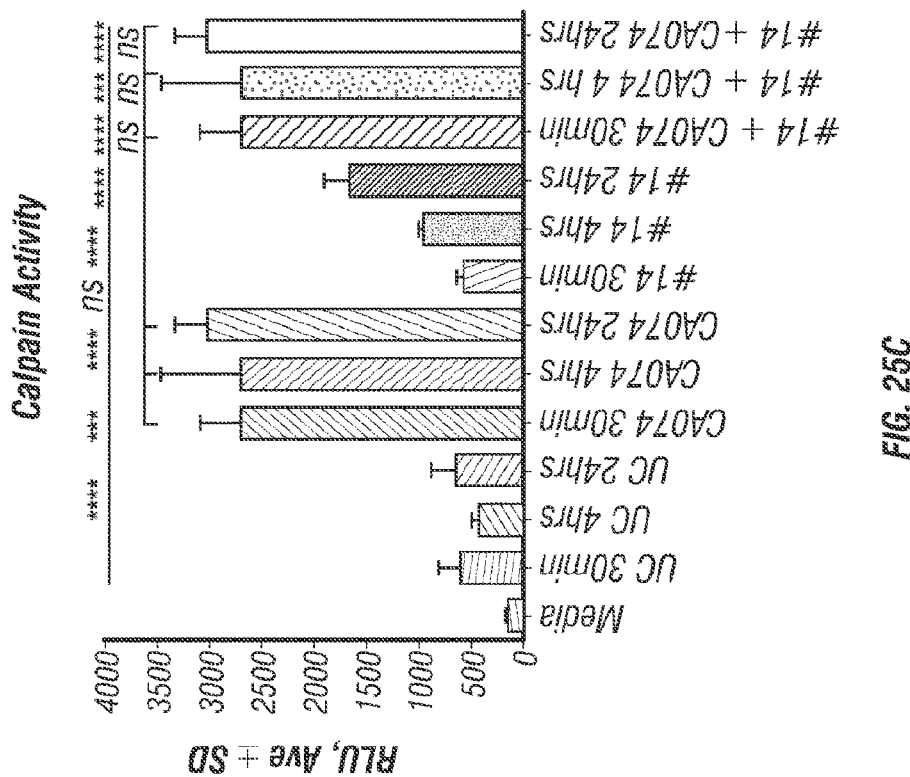

FIG. 25C shows calpain activity in presence of 2155-14 with and without 20 µM cathepsin B inhibitor CA074 pretreatment. Cells were pretreated with cathepsin B inhibitor for 3 h before addition of 2155-14.

FIG. 25D shows viability of WM266-4 cells in presence of 2155-14 with and without 20 µM cathepsin B inhibitor CA074 pretreatment. Cells were pretreated with 20 µM cathepsin B inhibitor CA074 for 3 h before addition of 2155-14. One-way analysis of variance (ANOVA) was used followed by Dunnett post hoc test. The data shown are the mean±SD, n=3. ***—$p<0.0001$, *—$p<0.001$, **—$p<0.01$, *—$p<0.05$, ns—no significance. 2155-14 was tested at 100 µM. MDL=MDL 28170.

FIGS. 26A-B show results from the Drug Affinity Responsive Target Stability (DARTS) protocol. Lomenick, B et al. *Proc Natl Acad Sci USA* 106:21981-21989 2009.

FIG. 26A is a schematic illustration of experimental workflow for 2155-14 target identification in WM266-4 cells using the DARTS protocol.

FIG. 26B illustrates 2155-14 target identification in WM266-4 cells using DARTS approach. This figures shows results of SDS-PAGE of pronase digests of WW226-4 lysates with and without 100 µM 2155-14. Vertical arrows point to differentially protected band that was identified as pre-lamin A/C. Pronase dilution factor is shown at the top of the gels.

FIG. 27 shows Table 7 which documents results of the DARTS-LC-MS/MS experiment. All units are unique peptide counts. ND=not detected. CAP4=cytoskeleton-associated protein 4. Pronase treatment results are from 1:1,000 pronase dilution condition.

FIGS. 28A-B show Table 8 which documents viability testing of dansylated and biotinylated analogs of compound 2155-14 with WM266-4 cells. All units are $IC_{50}$. µM (n=3). Numbers in 2155-14 structure positions indicate positions of substitution of the basic scaffold.

FIGS. 29A-D include chemical structures, micrographs, and graphs showing results indicating that dansylated 2155-14 (2476-67.2) induces autophagy.

FIG. 29A shows structures of 2155-14 and dansylated analogs. Dansyl moieties would be shown in blue in a color micrograph.

FIG. 29B shows a western blot of WM266-4 cell lysates after 24 hr treatment with 2476-66.2 and 2476-66.2. Left blot—5 µM dansylated compounds, right blot—2.5 µM dansylated compounds. Graph shows quantification of 2.5 µM blot.

FIG. 29C shows WM266-4 cells autophagosome dye assay microscopy images.

FIG. 29 D shows quantification of autophagosome dye assay.

FIGS. 30A-K include micrographs and graphs indicating that dansylated 2155-14 (2476-67.2) stains nuclear envelope and sub-nuclear structures.

FIGS. 31A-E show the effect of 2155-14 and its biotinylated analog on cell viability, levels of LC3 and cleaved lamin A/C in WM266-4 cells.

Figure 31A:
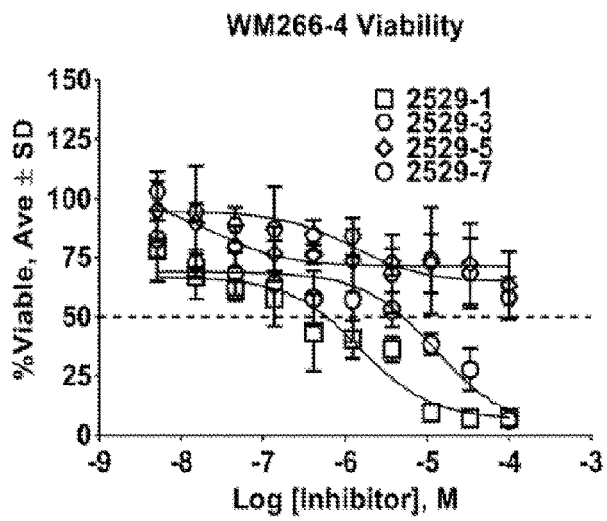

FIG. 31A shows results of cell viability study.

Figure 31B:
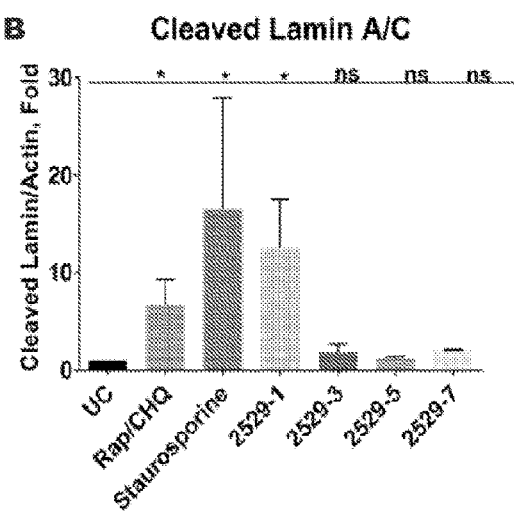

FIG. 31B shows quantification of western blot of cleaved lamin A/C in presence of 100 µM 2155-14/2529-1, 2529-3, 2529-5, and 2529-7.

Figure 31C:
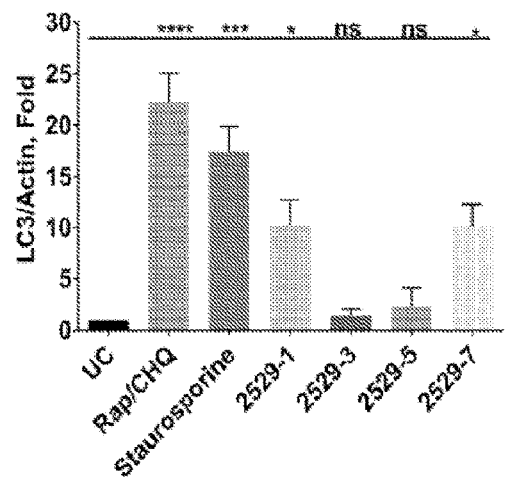

FIG. 31C shows quantification of western blot of LC3-II in presence of 100 µM 2155-14/2529-1, 2529-3, 2529-5, and 2529-7.

Figure 31D:
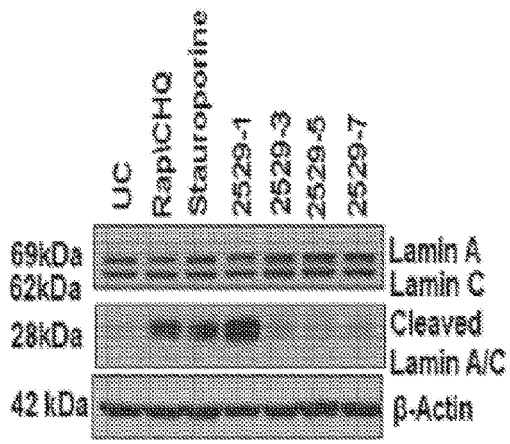

FIG. 31D shows a representative western blot of lamin A/C in presence of 100 µM 2155-14/2529-1, 2529-3, 2529-5, and 2529-7.

Figure 31E:
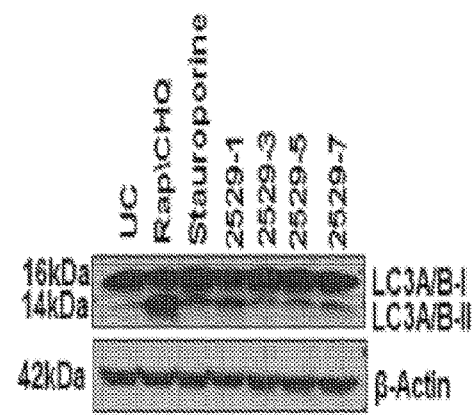

FIG. 31E shows a representative western blot of LC3 in presence of 100 µM 2155-14/2529-1, 2529-3, 2529-5, and 2529-7.

One-way analysis of variance (ANOVA) was used followed by Dunnett post hoc test. The data shown are the mean±SD, n=3. ***—$p<0.0001$, *—$p<0.001$, **—$p<0.01$, *—$p<0.05$, ns—not significant. Rap/CHQ=Rapamycin (5 µM)/Chloroquine (10 µM). Staurosporine was used at 1 µM. Note that 2529-3 and 2529-5 did not significantly increase levels of cleaved lamin A/C and LC3-II explaining their lower potency against WM266-4 cells. 2529-7 increased LC3-II to the levels of 2155-14/2529-1, while failing to increase levels of cleaved lamin A/C.

FIGS. 32A-D show results of SDS-PAGE of pulldown of WM266-4 cell lysates incubated with biotinylated analogs of 2155-14 pre-complexed with streptavidin beads.

FIG. 32 A shows WM266-4 cell lysates incubated for 24 h.

FIG. 32B shows M14 cell lysates incubated for 24 h.

FIG. 32C shows WM266-4 cell lysates incubated for 1 h. Note that 1 h incubation is missing band 1 present in 24 h incubation experiments in either WM266-4 or M14 cells. Note that bands 1-4 appear in both tested melanoma cell lines suggesting a common target for 2155-14.

FIG. 32D shows a repeat pulldown experiment with 2529-7 confirms bands 1-4, but not bands 5-6. Bands 1-4 were excised and sent for identification. Pulldown experiment was repeated three times. Protein identification was performed twice on bands from two independent pulldown experiments.

FIG. 33 shows Table 9 which documents results of proteomic analysis of pulldown of lysates of WM266-4 cells with compound 2155-14 and its biotinylated analogs. All units are scores based on unique peptide counts. Top hits for each band are listed. Protein with highest score in each band is in bold font.

FIGS. 34A-B characterize cellular proteins heterogeneous nuclear ribonuclear protein A2/B1 (hnRNP A2/B1) SEQ ID NO:1 and heterogeneous nuclear ribonuclear protein H1/H2 (hnRNP H2) SEQ ID NO:2 as targets for compound 2155-14.

FIG. 34A shows a comparison of sequence coverage of bands 3 and 4 of hnRNP A2/B1. Top=coverage of band 4, bottom=coverage of band 3. Note that there is a difference in coverage of amino acids 3-14 between band 3 and 4 suggesting that band 3 is hnRNP B1 and band 4 is hnRNP A2. In a color photo, Yellow=identified peptides and green=modified amino acids.

FIG. 34B illustrates targeting of hnRNPs, nuclear envelope binding, and cell death by autophagy.

FIGS. 35A-F show both gels and graphs illustrating genomic confirmation of DDX1, hnRNP H2, and hnRNP A2/B1 as targets of 2155-14.

Figure 35A:
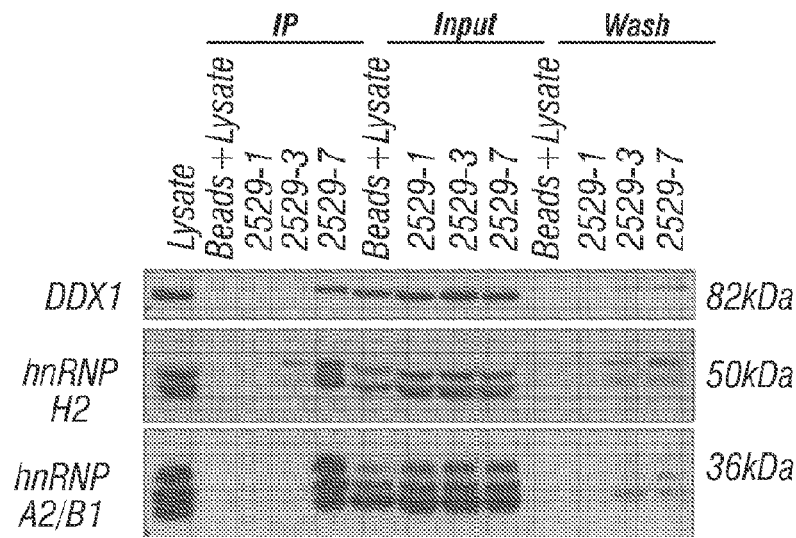

FIG. 35A is a western blot of WM266-4 lysates validates DDX1, hnRNP H2, and hnRNP A2/B1 as binding targets of biotinylated analog of 2155-14, 2529-7.

Figure 35B:
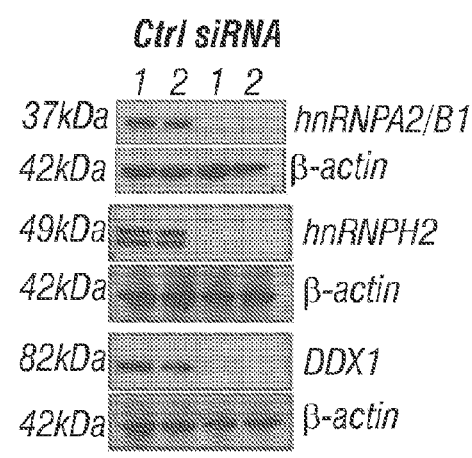

FIG. 35B shows DDX1, hnRNP H2, and hnRNP A2/B1 expression is knocked down by the corresponding siRNAs.

Figure 35C:
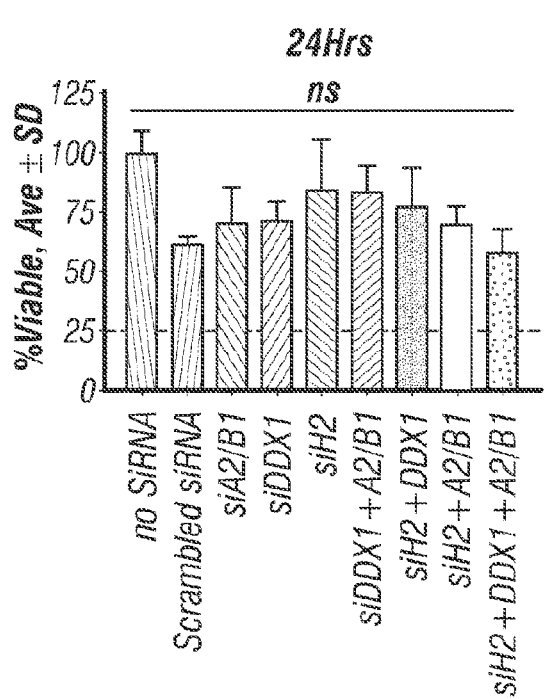
Figure 35D:
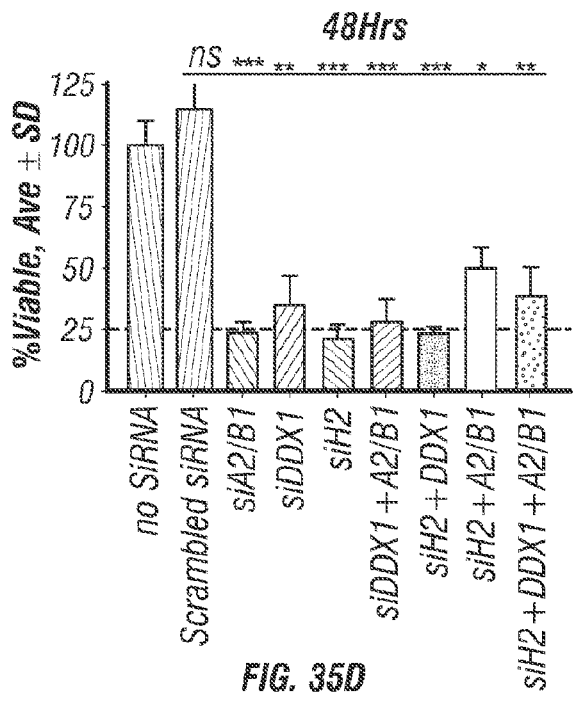
Figure 35E:
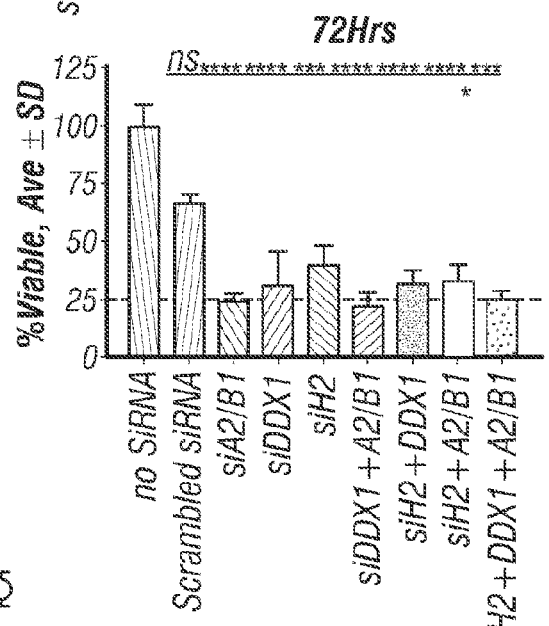

FIGS. 35C, 35D, and 35E show WM266-4 cell viability after treatment with DDX1, hnRNP H2, and hnRNP A2/B1 siRNAs and combinations thereof at concentrations which produced complete knockdown of respective proteins as shown in FIG. 35B. One-way analysis of variance (ANOVA) was used followed by Dunnett post hoc test. The data shown are the mean±SD, n=6. ***=$p<0.0001$, *—$p<0.001$, **—$p<0.01$, *—$p<0.05$, ns=no significance.

Figure 35F:
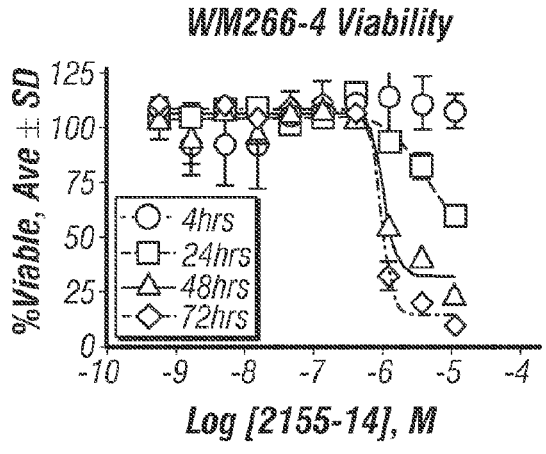

FIG. 35F shows WM266-4 viability time course assay in the presence of dose response of 2155-14. Note similarity of time dependent loss of viability of WM266-4 starting at 48 h in the presence of siRNAs and 2155-14.

Figure 36:
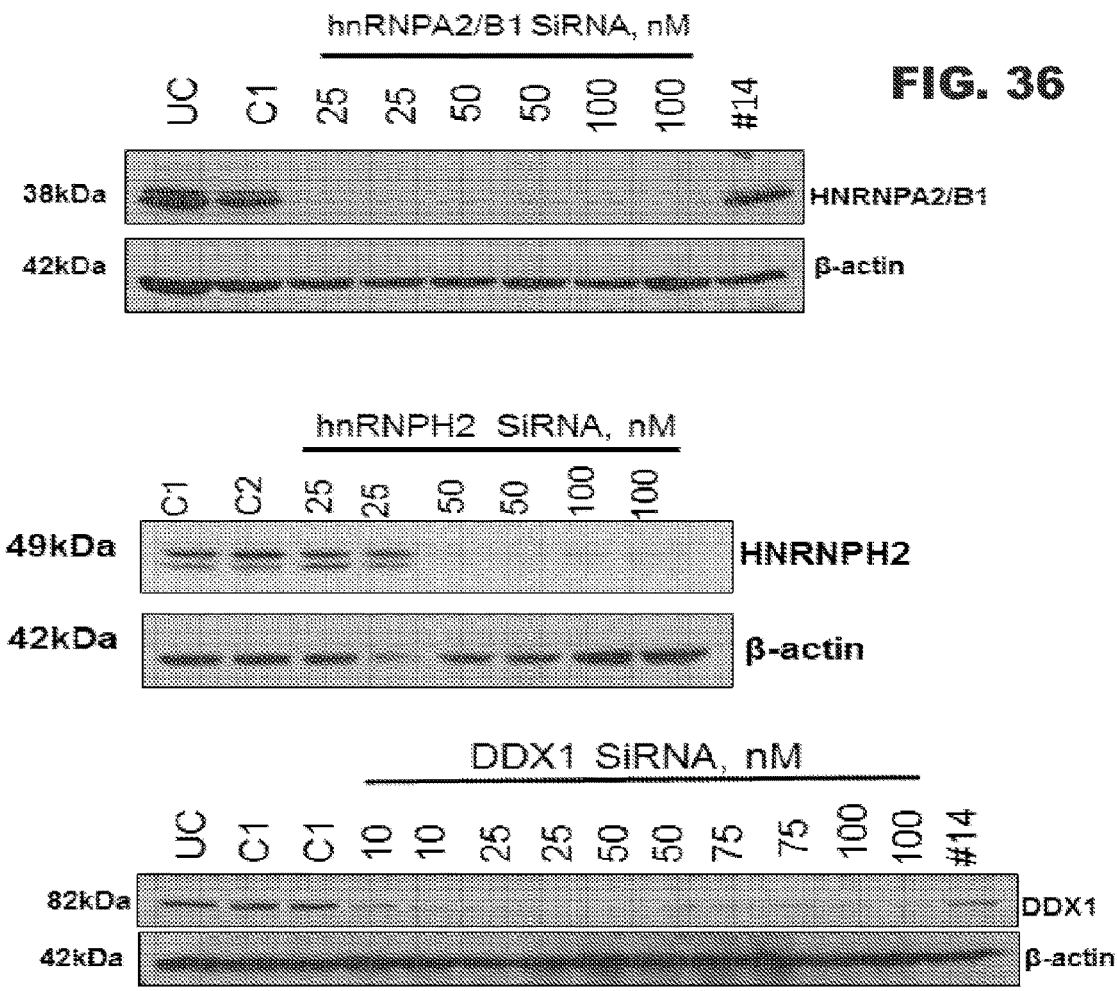

FIG. 36 shows optimization of DDX1, hnRNP H2, and hnRNP A2/B1 siRNA knockdown conditions. Encircled concentrations of respective siRNAs were chosen for downstream experiments. C1=scrambled siRNA control at 100 nM.

FIGS. 37A-F show the effect of siRNA knockdown on LC3-II and lamin A/C levels.

Figure 37A:
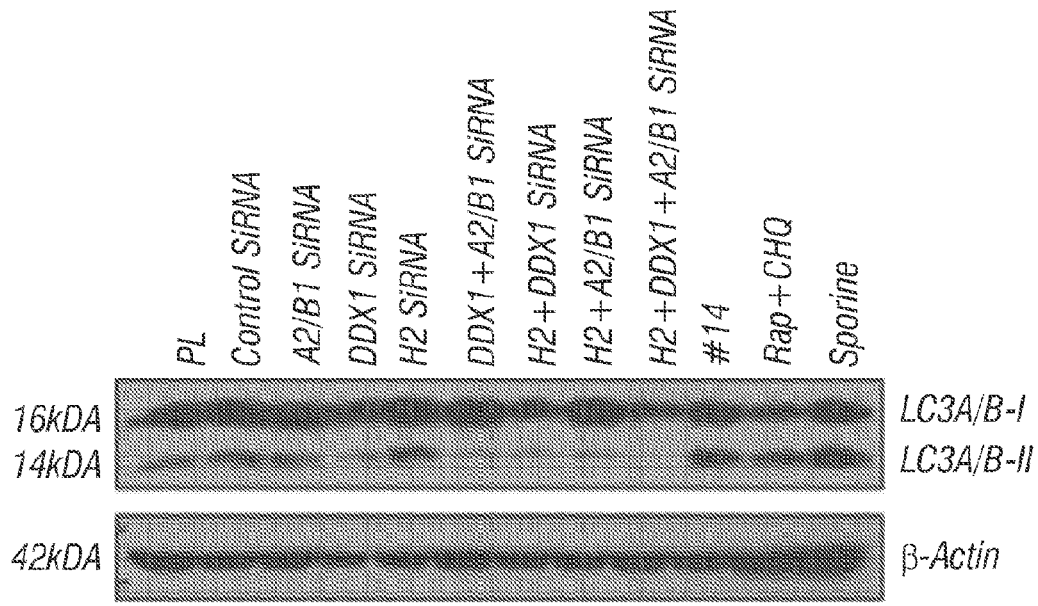

FIG. 37A shows a representative western blot of LC3-II in WM266-4 lysates in response to siRNA treatment.

Figure 37B:
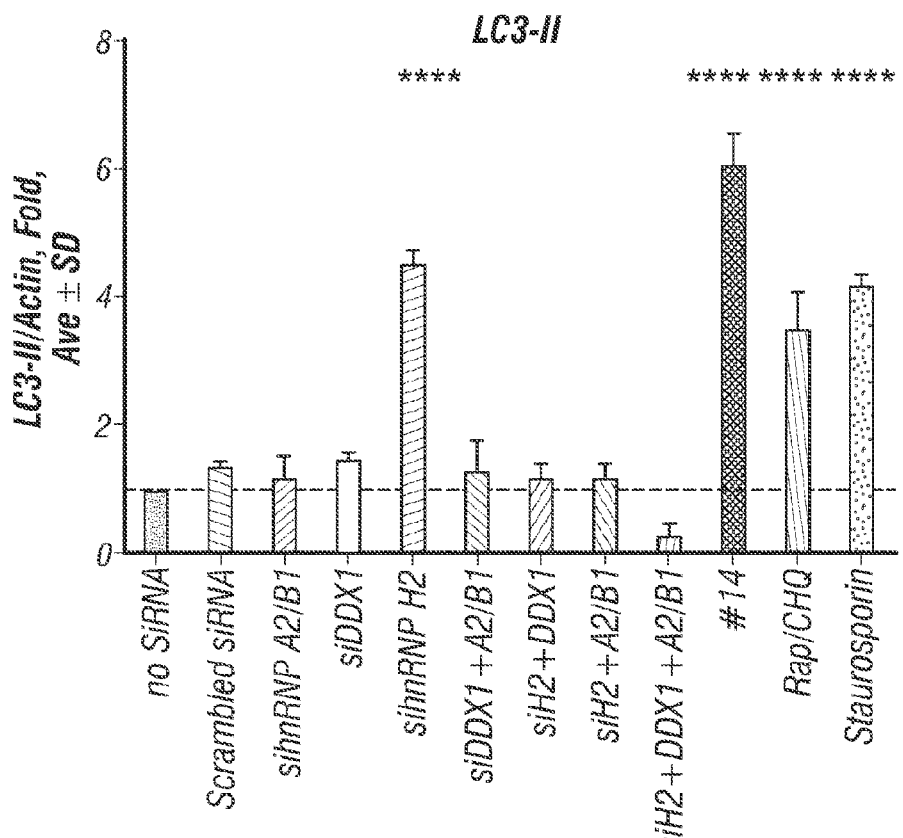

FIG. 37B shows quantification of FIG. 37A.

Figure 37C:
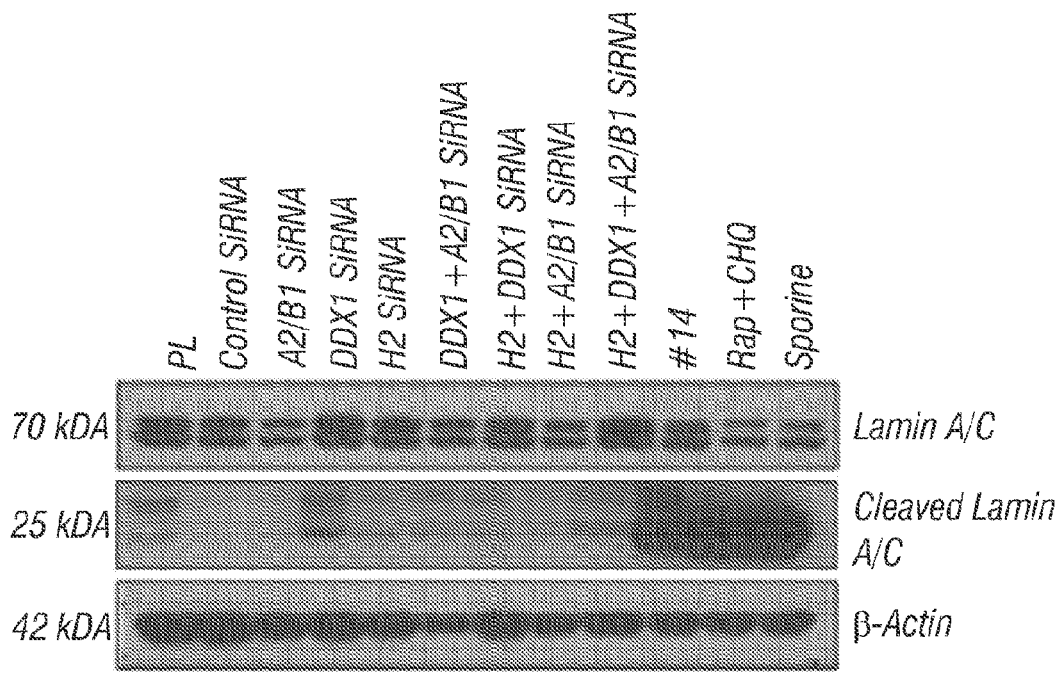

FIG. 37C shows a representative western blot of lamin A/C in WM266-4 lysates in response to siRNA treatment.

Figure 37D:
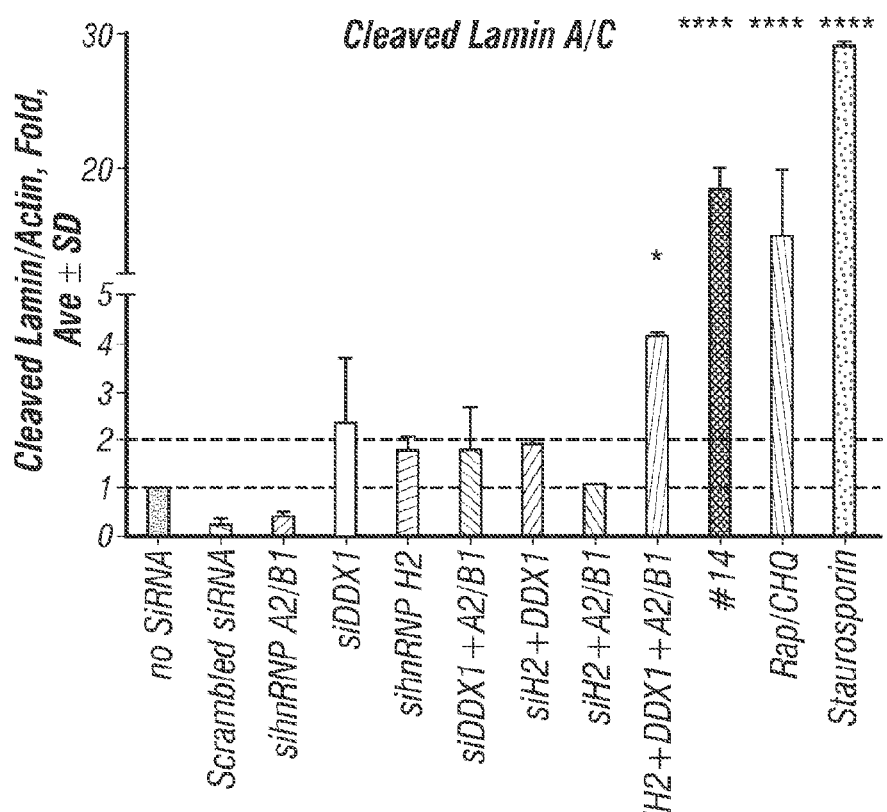

FIG. 37D shows quantification of FIG. 37C.

Figure 37E:
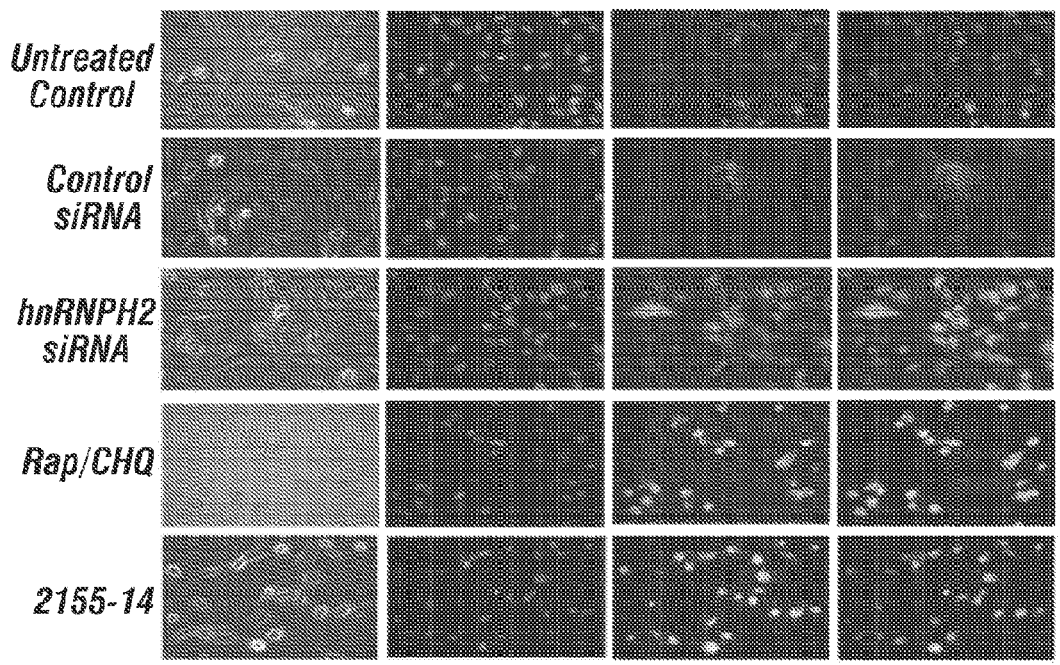

FIG. 37E shows WM266-4 cells illustrate increased autophagosome staining at 24 h after addition of hnRNPH2 siRNA and 2155-14. In color photo, nuclei would be stained blue.

Figure 37F:
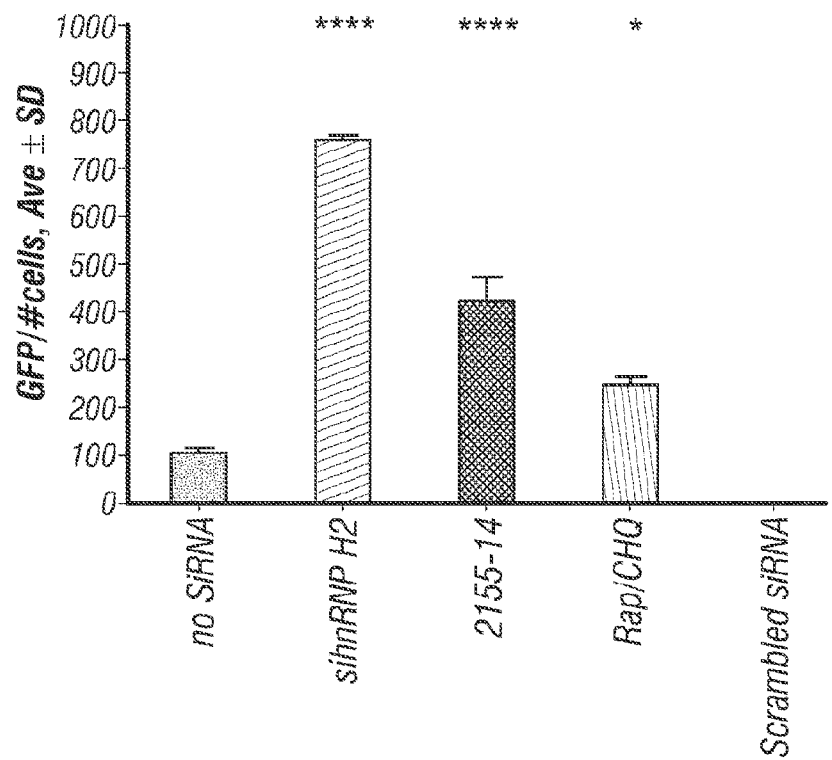

FIG. 37F shows an autophagy (GFP) channel used to quantify positive WM266-4 cells. Amount of cells present in each well was normalized using DAPI-stained nuclei. One-way analysis of variance (ANOVA) was used followed by Sidak multiple comparisons test. The data shown are the mean±SD, n=3. ***—$p<0.0001$, *—$p<0.001$, **—$p<0.01$, *—$p<0.05$, rest=no significance.

FIGS. 38A-F show confirmation of lamin A/C, DDX1, hnRNP H2, and hnRNP A2/B1 as targets of 2155-14 by DARTS approach.

Figure 38A:
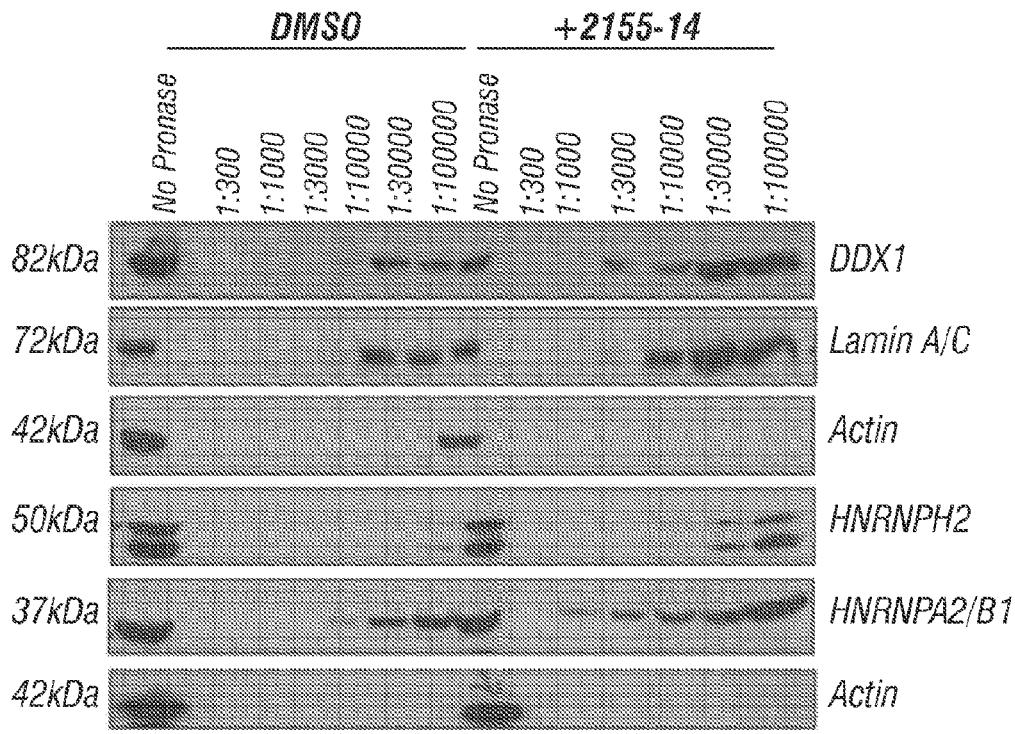

FIG. 38A shows a Western blot of lamin A/C, DDX1, hnRNP H2, and hnRNP A2/B1 after digestion with pronase in the presence and absence of 2155-14.

Figure 38B:
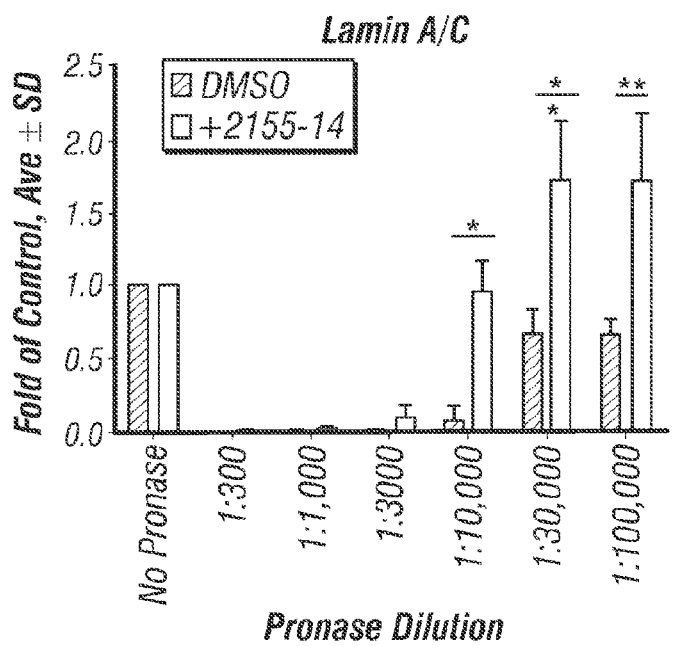

FIG. 38B shows quantification of western blots for lamin A/C.*

Figure 38C:
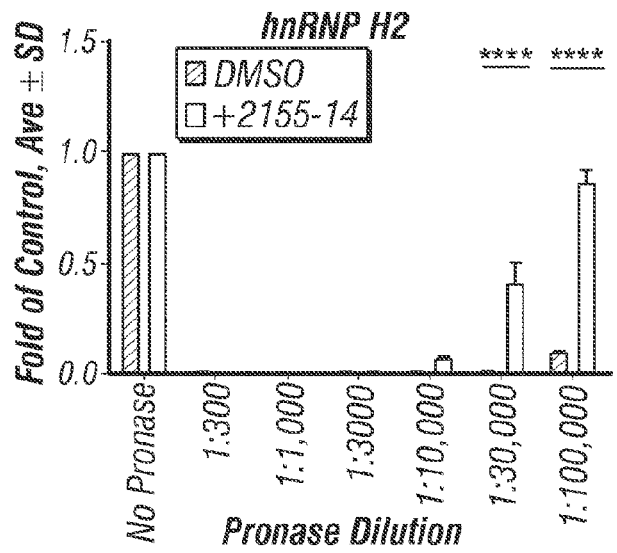

FIG. 38C shows quantification of western blots for hnRNP H2.*

Figure 38D:
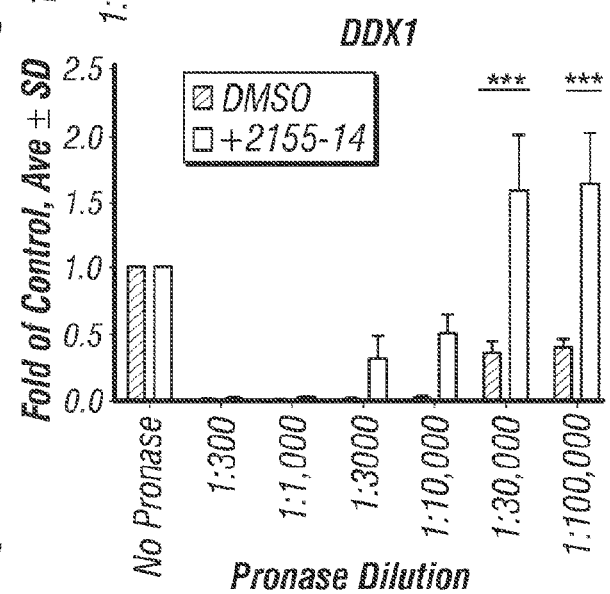

FIG. 38D shows quantification of western blots for DDX1.*

Figure 38E:
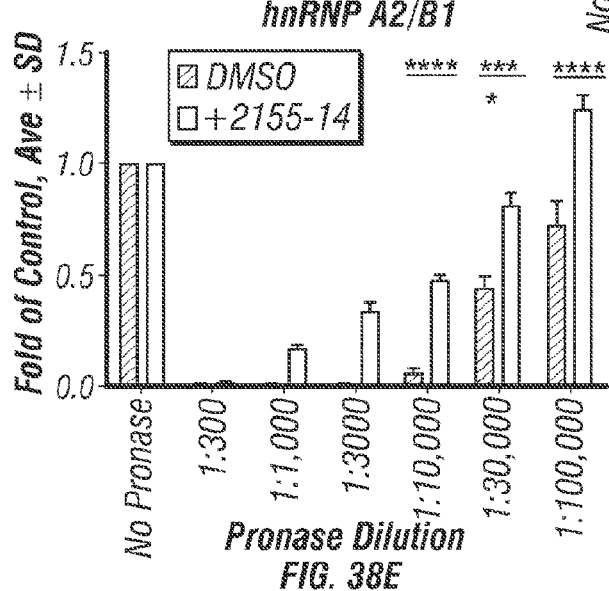

FIG. 38E shows quantification of western blots for hnRNP A2/B1.*

*in presence of various dilutions of pronase

One-way analysis of variance (ANOVA) was used followed by Dunnett post hoc test. The data shown are the mean±SD, n=3. ***—$p<0.0001$, *—$p<0.001$, **—$p<0.01$, *—$p<0.05$, rest=no significance.

Figure 39:
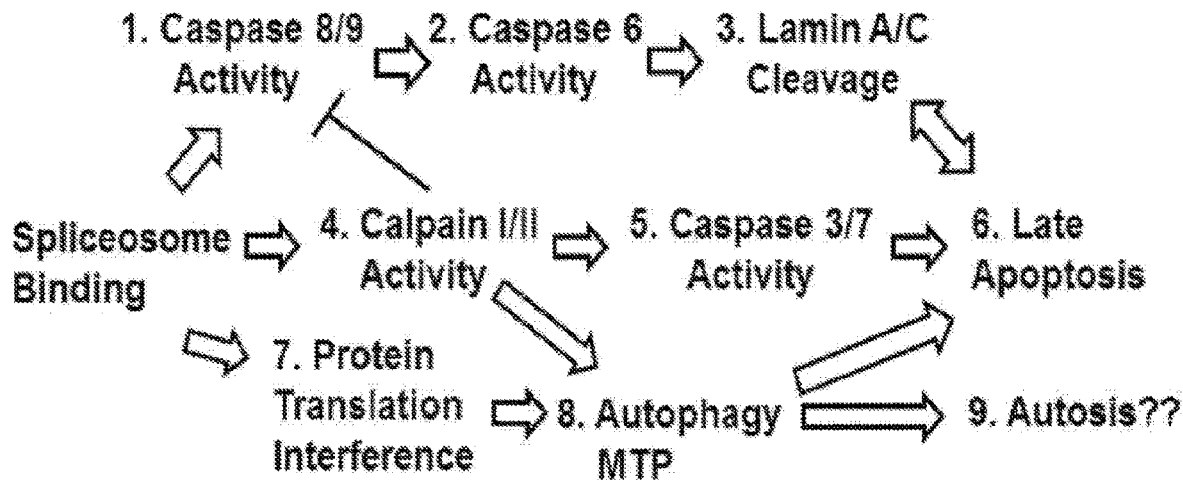

FIG. 39 is a schematic illustration of the proposed mechanism of action of compound 2155-14.

Figure 40:
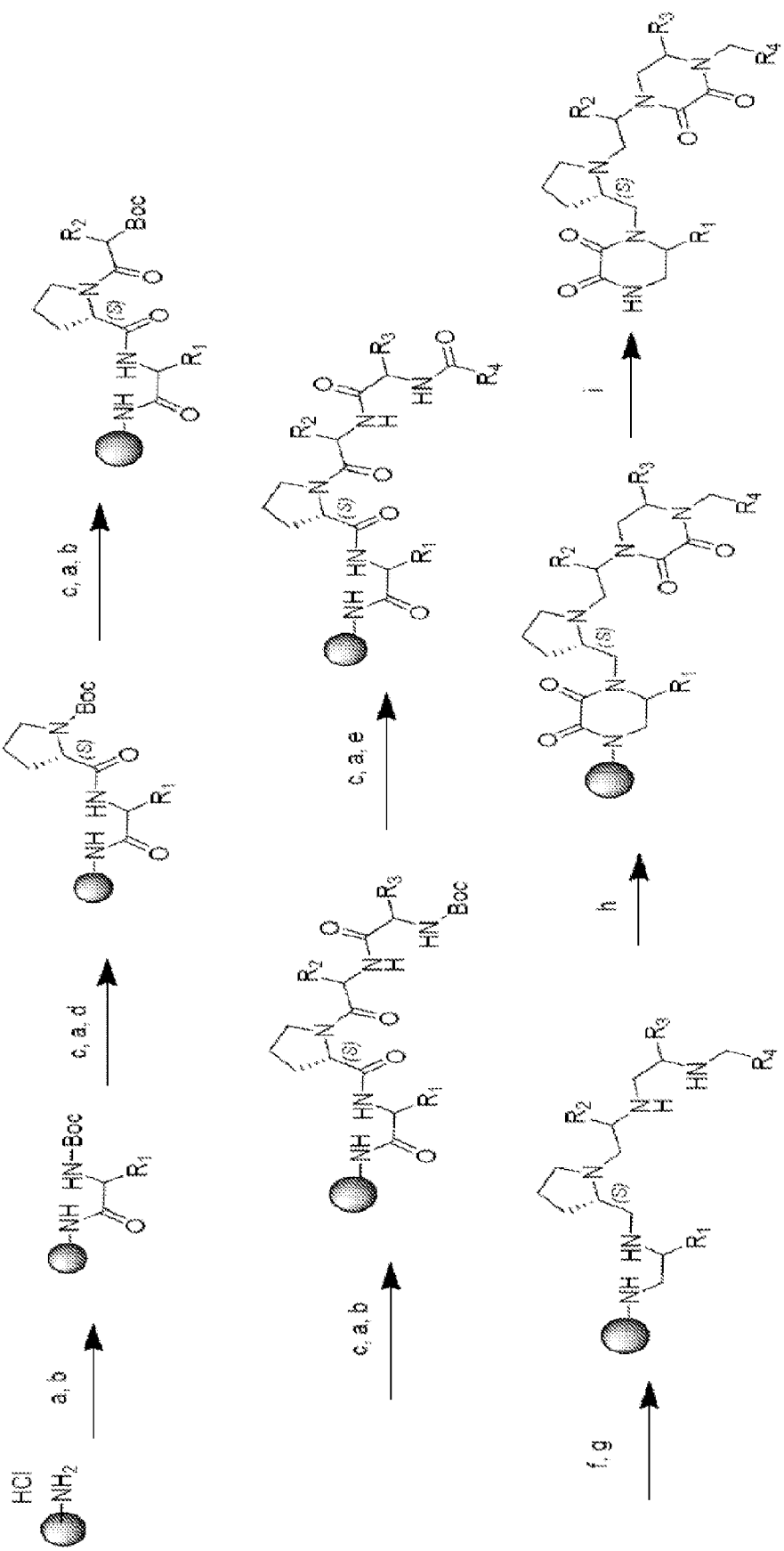
Figure 41:
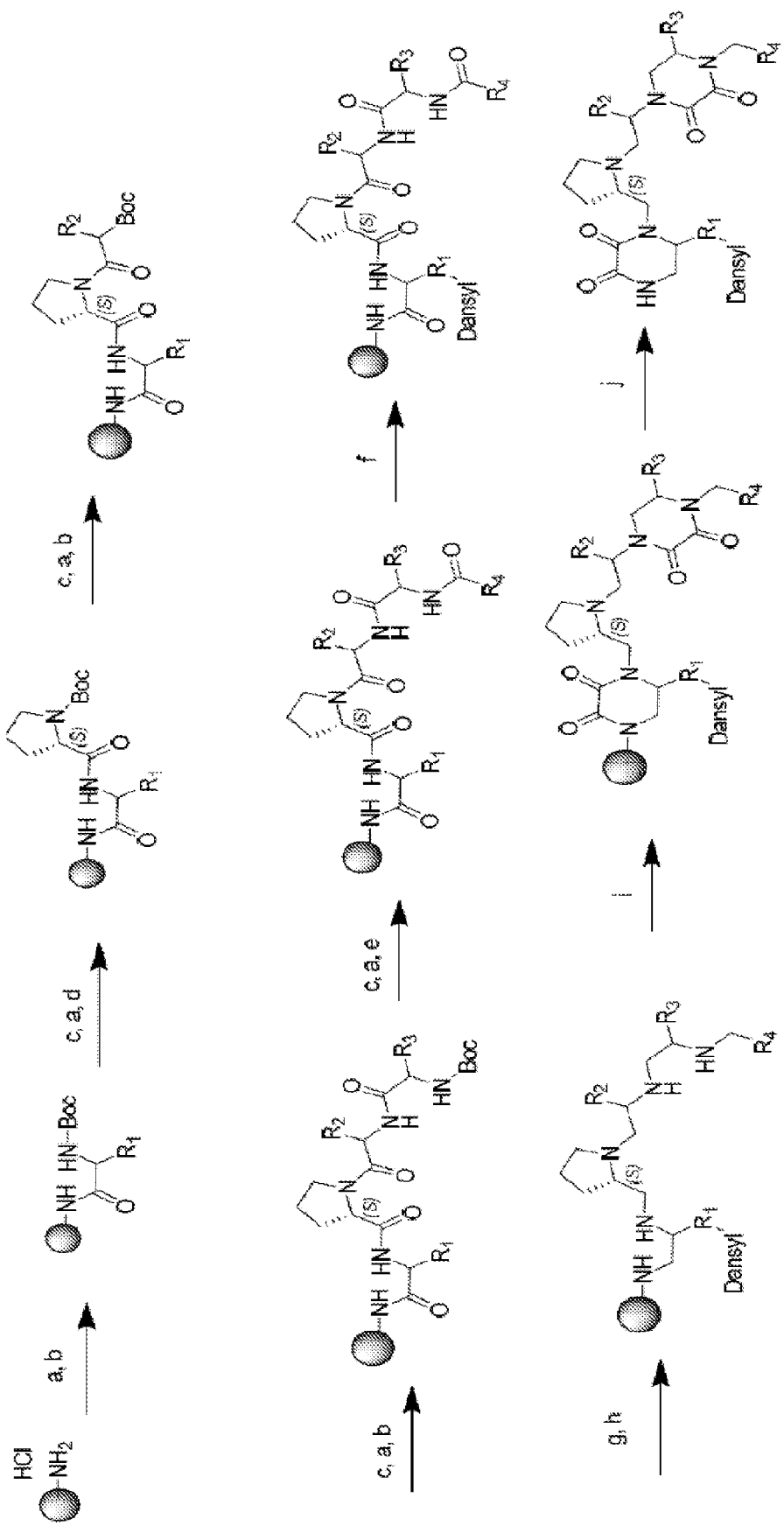
Figure 42:
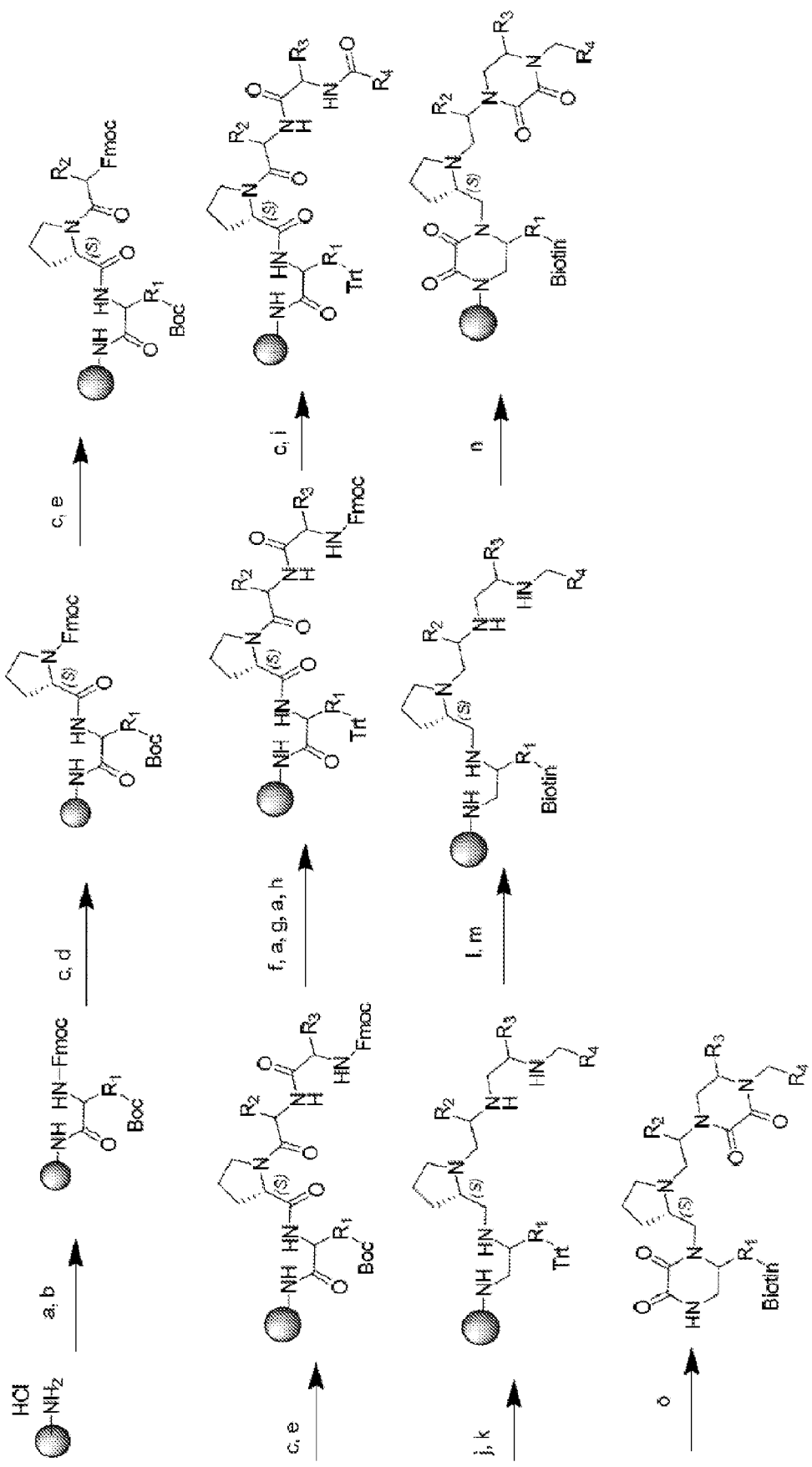

FIG. 40 is a schematic illustration of a synthesis procedure for (S)-1((R)-1((S)-2-(((S)-6-benzyl-2,3-dioxopiperazin-1-yl)methyl)pyrrolidin-1-yl)-3-cyclohexylpropan-2-yl)-5-(4-hydroxybenzyl)-4-phenethylpiperazine-2,3-dione. (a) 5% DIEA/95% DCM, 3×2 min; (b) Boc-AA (6 eq), DIC (6 eq), HOBt (6 eq), DMF, 2 hr; (c) 55% TFA/45% DCM, 30 min; (d) Boc-L-Pro-OH (6 eq), DIC (6 eq), HOBt (6 eq), DMF (6 eq), 2 hr; (e) RCOOH (10 eq), DIC (10 eq), HOBt (10 eq), DMF, 2 hr; (f) BH3/THF (40 eq), 65 C, 96 hr; (g) Piperidine, 65 C, 18 hr; (h) (COIm)$^2$ (10 eq), Anhydrous Atmosphere, 18 hr; (i) HF/Anisole, 0 C, 1.5 hr FIG. 41 is a schematic illustration of a synthesis procedure for Dansyl tagged pyrrollidine-bis-diketopiperazines. (a) 5% DIEA/95% DCM, 3×2 min; (b) Boc-AA (6 eq), DIC (6 eq), HOBt (6 eq), DMF, 2 hr; (c) 55% TFA/45% DCM, 30 min; (d)Boc-L-Pro-OH (6 eq), DIC (6 eq), HOBt (6 eq), DMF (6 eq), 2 hr; (e) RCOOH (10 eq), DIC (10 eq), HOBt (10 eq), DMF, 2 hr; (f) Dansyl Chloride (10 eq), DIEA (10 eq), DMF, 2 hr; (g) BH3/THF (40 eq), 65 C, 96 hr; (g) Piperidine, 65 C, 18 hr; (h) (COIm)$^2$ (10 eq), Anhydrous Atmosphere, 18 hr; (i) HF/Anisole, 0 C, 1.5 hr FIG. 42 is a schematic illustration of a synthesis procedure for Biotin tagged pyrrollidine-bis-diketopiperazines. (a) 5% DIEA/95% DCM, 3×2 min; (b) Fmoc-AA(Boc) (6 eq), DIC (6 eq), HOBt (6 eq), DMF, 2 hr; (c) 20% Piperidine/80% DMF, 2×30 min; (d) Fmoc-L-Pro-OH (6 eq), DIC (6 eq), HOBt (6 eq), DMF (6 eq), 2 hr; (e) Fmoc-AA (6 eq), DIC (6 eq), HOBt (6 eq), DMF, 2 hr; (f) 55% TFA/45% DCM, 30 min; (g) Trt-Cl (5 eq), DIEA (10 eq), 10% DMF/90% DMF, 2 hr; (h) Trt-Cl (5 eq), DIEA (10 eq), 10% DMF/90% DCM, 2 hr; (i) RCOOH (10 eq), DIC (10 eq), HOBt (10 eq), DMF, 2 hr; (j) BH3/THF (40 eq), 65 C, 96 hr); (k) piperidine, 65 C, 18 hr); (l) 2% TFA/5% TRIS, 95% DCM, 3×2 min; (m) biotin (10 eq), DIC (10 eq), DMF, 2 hr; (n) (COIm)$^2$ (10 eq), Anhydrous Atmosphere, 18 hr; (o) HF/Anisole, 0 C, 1.5 hr FIGS. 43A-B show compound purification and characterization of (S)-1-((R)-1-((S)-2-(((S)-6-benzyl-2,3-dioxopiperazin-1-yl)methyl)pyrrolidin-1-yl)-3-cyclohexylpropan-2-yl)-5-(4-hydroxybenzyl)-4-phenethylpiperazine-2,3-dione.

FIG. 43A shows the NMR result.

FIG. 43B illustrates compound structure.

Figure 44A:
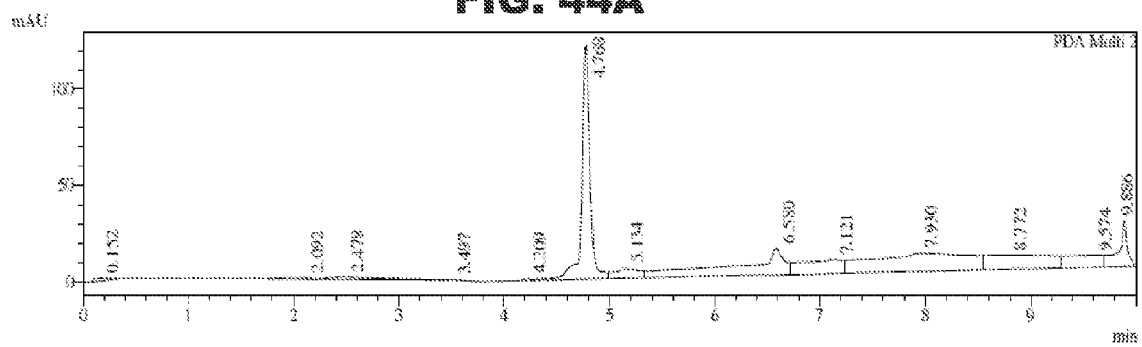
Figure 44B:
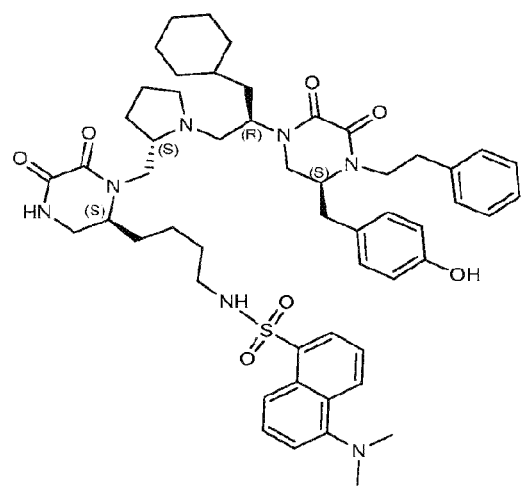
Figure 44C:
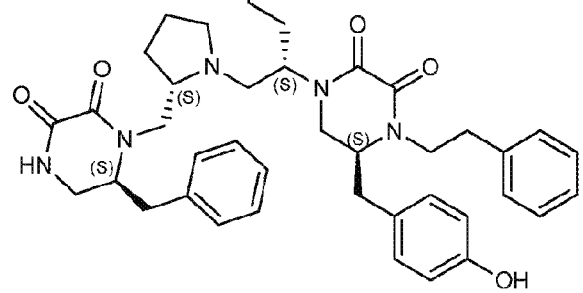

FIGS. 44A-C show compound purification and characterization of N-(4-((S)-1-(((S)-1-((R)-3-cyclohexyl-2-((S)-5-(4-hydroxybenzyl)-2,3-dioxo-4-phenethylpiperazin-1-yl)propyl)pyrrolidin-2-yl)methyl)-5,6-dioxopiperazin-2-yl)butyl)-5-(dimethylamino)naphthalene-1-sulfonamide.

FIG. 44A shows the NMR result.

FIG. 44B illustrates compound structure.

FIG. 44C illustrates compound structure.

FIGS. 45A-B show compound purification and characterization of N—((S)-6-((S)-2-(((S)-6-benzyl-2,3-dioxopiperazin-1-yl)methyl)pyrrolidin-1-yl)-5-((S)-5-(4-hydroxybenzyl)-2,3-dioxo-4-phenethylpiperazin-1-yl)hexyl)-5-(dimethylamino)naphthalene-1-sulfonamide.

FIG. 45A shows the NMR result.

FIG. 45B illustrates compound structure.

FIGS. 46A-B show compound purification and characterization of N-(4-((S)-4-((R)-1-((S)-2-((S)-6-benzyl-2,3-dioxopiperazin-1-yl)methyl)pyrrolidin-1-yl)-3-cyclohexylpropan-2-yl)-5,6-dioxo-1-phenethylpiperazin-2-yl)butyl)-5-(dimethylamino)naphthalene-1-sulfonamide.

FIG. 46A shows the NMR result.

FIG. 46B illustrates compound structure.

FIGS. 47A-B show compound purification and characterization of N-(2-((S)-4-((R)-1-((S)-2-(((S)-6-benzyl-2,3-dioxopiperazin-1-yl)methyl)pyrrolidin-1-yl)-3-cyclohexylpropan-2-yl)-6-(4-hydroxybenzyl)-2,3-dioxopiperazin-1-yl)ethyl)-5-(dimethylamino)naphthalene-1-sulfonamide.

FIG. 47A shows the NMR result.

FIG. 47B illustrates compound structure.

FIGS. 48A-B show compound purification and characterization of N-(4-((S)-1-(((S)-1-((R)-3-cyclohexyl-2-((S)-5-(4-hydroxybenzyl)-2,3-dioxo-4-phenethylpiperazin-1-yl)propyl)pyrrolidin-2-yl)methyl)-5,6-dioxopiperazin-2-yl)butyl)-5-((3aS,4S,6aR)-2-oxohexahydro-1H-thieno[3,4-d]imidazol-4-yl)pentanamide.

FIG. 48A shows the NMR result.

FIG. 48B illustrates compound structure.

FIGS. 49A-B show compound purification and characterization of N—((S)-6-((S)-2-(((S)-6-benzyl-2,3-dioxopiperazin-1-yl)methyl)pyrrolidin-1-yl)-54S)-5-(4-hydroxybenzyl)-2,3-dioxo-4-phenethylpiperazin-1-yl)hexyl)-5-((3aS,4S,6aR)-2-oxohexahydro-1H-thieno[3,4-d]imidazol-4-yl)pentanamide.

FIG. 49A shows the NMR result.

FIG. 49B illustrates compound structure.

FIG. 50 shows compound purification and characterization of N-(4-((S)-4-((R)-1-((S)-2-(((S)-6-benzyl-2,3-dioxopiperazin-1-yl)methyl)pyrrolidin-1-yl)-3-cyclohexylpropan-2-yl)-5,6-dioxo-1-phenethylpiperazin-2-yl)butyl)-5-((3aR,4R,6aS)-2-oxohexahydro-1H-thieno[3,4-d]imidazol-4-yl)pentanamide; NMR result.

DETAILED DESCRIPTION OF THE INVENTION

For the purpose of promoting an understanding of the principles of the invention, reference will now be made to embodiments illustrated herein and specific language will be used to describe the same. It will nevertheless be understood that no limitation of the scope of the invention is thereby intended. Any alterations and further modification in the described methods and compositions and any further application of the principles of the invention, as described herein, are contemplated as would normally occur to one skilled in the art to which the invention relates.

Pyrrolidine Diketopiperzine Compounds Inhibit Melanoma Cells

One of the most common liabilities of cancer drugs/drug candidates is toxicity to non-cancerous cells. Thus, molecules are needed that are potent towards cancer cells and spare healthy cells. Cell-based high-throughput screening (HTS) approaches can be used to discover such molecules. Unfortunately, the cost of HTS limits the amount and number of cell lines that can be screened in parallel in order to discover molecules with desired activity/toxicity profiles. The cost of traditional cell-based HTS is dictated by the HTS library size, which is typically in the hundreds of thousands or millions of individual compounds. This means that hundreds of thousands of wells need to be screened against at least 2 different cell lines (one cancerous and one healthy) to assess diverse chemical space in order to find potential leads.

Mixture-based combinatorial libraries offer a cost-effective alternative to single compound libraries (Houghten, R. A.; Pinilla, C.; Giulianotti, M. A.; Appel, J. R.; Dooley, C. T.; Nefzi, A.; Ostresh, J. M.; Yu, Y.; Maggiora, G. M.; Medina-Franco, J. L.; Brunner, D.; Schneider, J. Strategies for the use of mixture-based synthetic combinatorial libraries: scaffold ranking, direct testing in vivo, and enhanced deconvolution by computational methods. *J Comb Chem* 2008, 10, 3-19) especially when it comes to parallel screening of multiple targets/cell lines. The significantly reduced sample numbers utilized with a mixture-based combinatorial library screening approach eliminates the need for the molecular target validation typically needed prior to large scale HTS campaigns and rather allows one to directly probe cancer cells in an agnostic, target-unbiased fashion (Lee, J. A.; Berg, E. L. Neoclassic Drug Discovery: The case for lead generation using phenotypic and functional approaches. *Journal of Biomolecular Screening* 2013, 18, 1143-1155). A recent review by Swinney and Anthony (Swinney, D. C.; Anthony, J. How were new medicines discovered? *Nat Rev Drug Discov* 2011, 10, 507-519) showed that more "first-in-class" drugs came from phenotypic screening (i.e., cell- or organism-based) than from target-based screening.

Drug resistance is a major challenge of cancer drug discovery. Cancer can be de novo resistant to a particular drug or acquire resistance to it after a prolonged therapy. Monotherapy using drugs derived from target-based drug discovery has been shown to result in acquired resistance by cancer cells. For example, the recently approved inhibitor of $^{V600E}$BRAF, vemurafenib, while offering increased survival of patients of metastatic melanoma, became resistant after 6-8 months of therapy (Tentori, L.; Lacal, P. M.; Graziani, G. Challenging resistance mechanisms to therapies for metastatic melanoma. *Trends Pharmacol Sci* 2013, 34, 656-666). Given the propensity of single target-based compounds to cause resistance, a potential of phenotypic screening to discover compounds that favorably interact with multiple targets (i.e. polypharmacology) (Medina-Franco, J. L.; Giulianotti, M. A.; Welmaker, G. S.; Houghten, R. A. Shifting from the single to the multitarget paradigm in drug discovery. *Drug Discov Today* 2013, 18, 495-501 and Paolini, G. V.; Shapland, R. H.; van Hoorn, W. P.; Mason, J. S.; Hopkins, A. L. Global mapping of pharmacological space. *Nat Biotechnol* 2006, 24, 805-815), thus avoiding or diminishing the chances for resistance, represents an additional benefit as compared to the target-based screening.

The above considerations prompted the inventors to screen an in-house mixture-based drug-like library (Houghten, R. A.; Pinilla, C.; Giulianotti, M. A.; Appel, J. R.; Dooley, C. T.; Nefzi, A.; Ostresh, J. M.; Yu, Y.; Maggiora, G. M.; Medina-Franco, J. L.; Brunner, D.; Schneider, J. Strategies for the use of mixture-based synthetic combinatorial libraries: scaffold ranking, direct testing in vivo, and enhanced deconvolution by computational methods. *J Comb Chem* 2008, 10, 3-19) in order to potentially discover "first-in-class" selective inhibitors of various cancers to demonstrate the utility of mixture-based libraries. Two of the most lethal cancer types: lung cancer and melanoma, were selected to assess the library for inhibition of growth of drug-resistant cancer cells. NRAS mutation is one of the most common mutations exhibited in melanoma and is present in 95% of patients of familial melanoma. Therefore, the M14 melanoma cell line was selected as a representative of cutaneous malignant melanoma carrying NRAS but not BRAF mutation (Reifenberger, J.; Knobbe, C. B.; Sterzinger, A. A.; Blaschke, B.; Schulte, K. W.; Ruzicka, T.; Reifenberger, G. Frequent alterations of Ras signaling pathway genes in sporadic malignant melanomas. *Int J Cancer* 2004, 109, 377-384). Additionally, the library was screened against an A549 non-small cell lung cancer cell line harboring KRAS mutation (Bennett, D. C.; Charest, J.; Sebolt, K.; Lehrman, M.; Rehemtulla, A.; Contessa, J. N. High-throughput screening identifies aclacinomycin as a radiosensitizer of EGFR-mutant non-small cell lung cancer. *Transl Oncol* 2013, 6, 382-391) and a healthy control CHO-K1 cell line.

TPIMS Mixture Library Screen.

Figure 1:
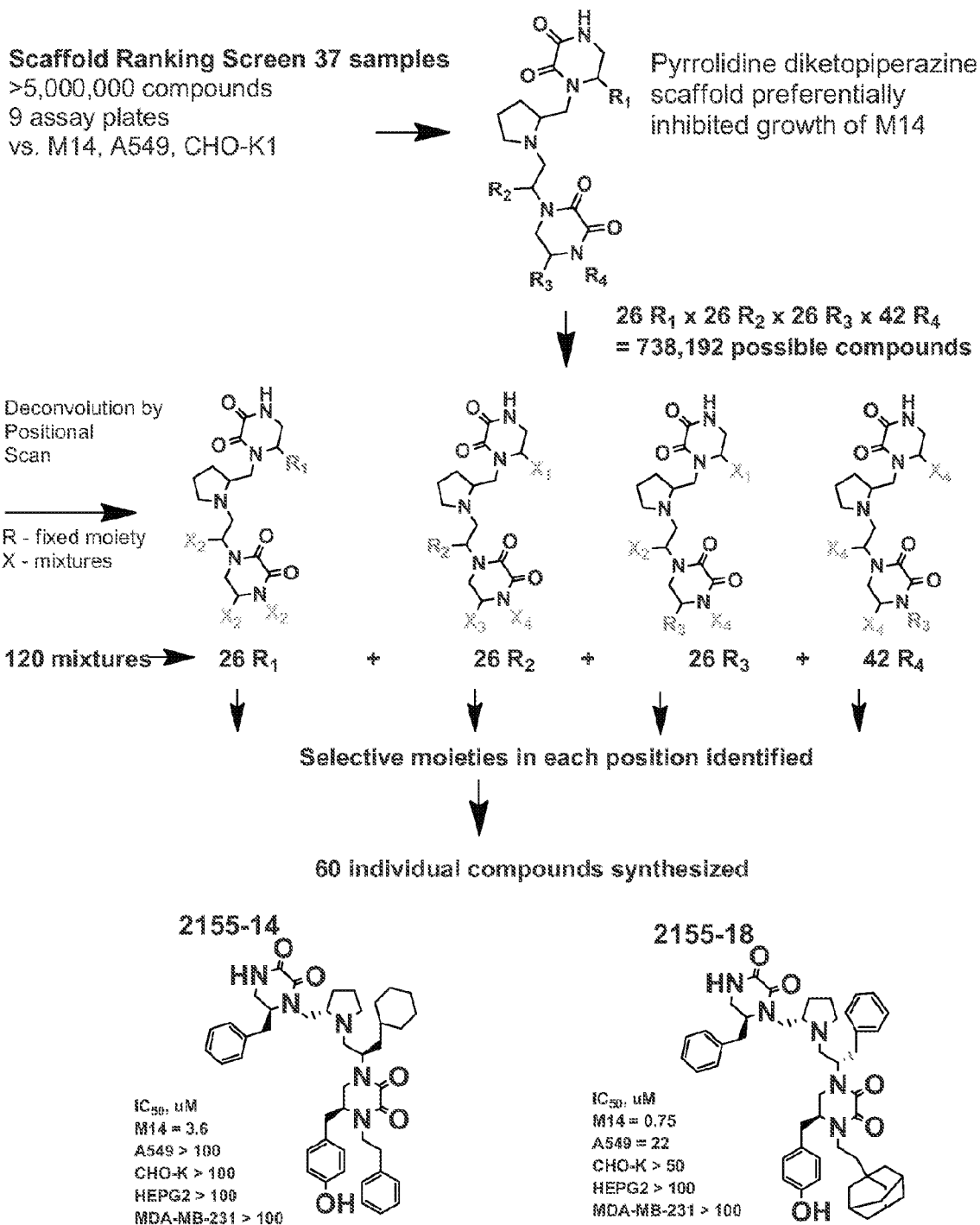
FIG. 1 is a schematic illustration of the deconvolution of the pyrrolidine diketopiperazine library.
Figure 2A:
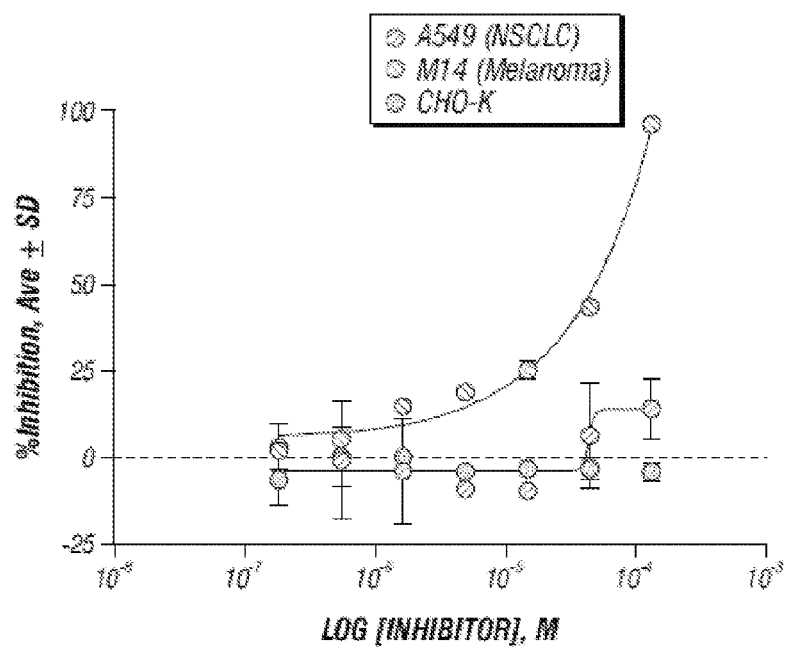
FIG. 2A is a graph showing results of a primary screen (scaffold ranking) of TPIMS mixture libraries. Dose response of TPI1344 versus A549, M14, and CHO-K cell lines
Figure 2B:
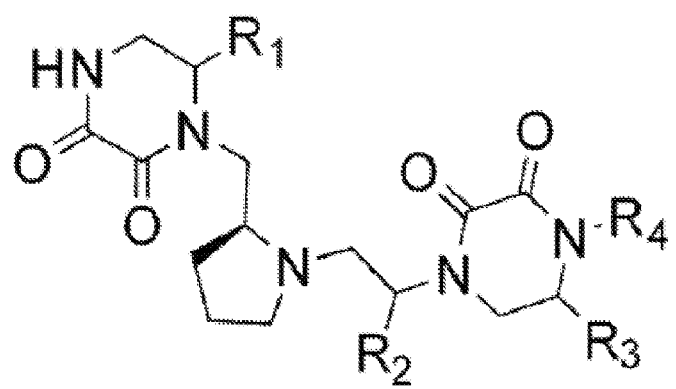
FIG. 2B is a chemical structure of the core scaffold of the TPI1344 mixture library.

The mixture based library screening work flow employed in these experiments for the identification of novel ligands of various targets (Rideout, M. C.; Boldt, J. L.; Vahi-Ferguson, G.; Salamon, P.; Nefzi, A.; Ostresh, J. M.; Giulianotti, M.; Pinilla, C.; Segall, A. M. Potent antimicrobial small molecules screened as inhibitors of tyrosine recombinases and Holliday junction-resolving enzymes. *Mol Divers* 2011, 15, 989-1005; Reilley, K. J.; Giulianotti, M.; Dooley, C. T.; Nefzi, A.; McLaughlin, J. P.; Houghten, R. A. Identification of two novel, potent, low-liability antinociceptive compounds from the direct in vivo screening of a large mixture-based combinatorial library. *AAPS J* 2010, 12, 318-329; Wu, J.; Zhang, Y.; Maida, L. E.; Santos, R. G.; Welmaker, G. S.; Lavoi, T. M.; Nefzi, A.; Yu, Y.; Houghten, R. A.; Toll, L.; Giulianotti, M. A. Scaffold ranking and positional scanning utilized in the discovery of nAChR-selective compounds suitable for optimization studies. *J Med Chem* 2013, 56, 10103-10117;

Ranjit, D. K.; Rideout, M. C.; Nefzi, A.; Ostresh, J. M.; Pinilla, C.; Segall, A. M. Small molecule functional analogs of peptides that inhibit lambda site-specific recombination and bind Holliday junctions. *Bioorg Med Chem Lett* 2010, 20, 4531-4544; and Minond, D.; Cudic, M.; Bionda, N.; Giulianotti, M.; Maida, L.; Houghten, R. A.; Fields, G. B. Discovery of novel inhibitors of a disintegrin and metalloprotease 17 (ADAM17) using glycosylated and non-glycosylated substrates. *J Biol Chem* 2012, 287, 36473-36487) was previously described and is summarized in FIG. 1 as Scheme 1:Deconvolution of Pyrrolidine Diketopiperzine Library. The approach allows for systematic assessment of >5,000,000 compounds through the use of approximately 200 samples in order to identify lead individual compounds all the while accumulating valuable SAR at each step. The first step in the process involved the screening of the 37 mixture samples contained in the scaffold ranking library (Houghten, R. A.; Pinilla, C.; Giulianotti, M. A.; Appel, J. R.; Dooley, C. T.; Nefzi, A.; Ostresh, J. M.; Yu, Y.; Maggiora, G. M.; Medina-Franco, J. L.; Brunner, D.; Schneider, J. Strategies for the use of mixture-based synthetic combinatorial libraries: scaffold ranking, direct testing in vivo, and enhanced deconvolution by computational methods. *J Comb Chem* 2008, 10, 3-19; Ranjit, D. K.; Rideout, M. C.; Nefzi, A.; Ostresh, J. M.; Pinilla, C.; Segall, A. M. Small molecule functional analogs of peptides that inhibit lambda site-specific recombination and bind Holliday junctions. *Bioorg Med Chem Lett* 2010, 20, 4531-4544; Minond, D.; Cudic, M.; Bionda, N.; Giulianotti, M.; Maida, L.; Houghten, R. A.; Fields, G. B. Discovery of novel inhibitors of a disintegrin and metalloprotease 17 (ADAM17) using glycosylated and non-glycosylated substrates. *J Biol Chem* 2012, 287, 36473-36487; Wu, J. W. Z., Y.; Maida, L. E.; Santos R. G.; Welmaker, G. S.; LaVoi, T. M.; Nefzi, A.; Yu, Y.; Houghten, R. A.; Toll, L.; Giulianotti, M. A. Scaffold ranking and positional scanning utilized in the discovery of nAChR-selective compounds suitable for optimization studies. *J. Med. Chem* 2013, 56, 10103-10117). As a result of this screen one mixture library (TPI1344) exhibited selective inhibition of M14 cell line viability (FIG. 2A) while no effect was seen on viability of A549 and CHO-K1 cells. The basic scaffold of mixture library 1344 consists of two diketopiperazine moieties connected via central pyrrolidine (FIG. 2B). In order to identify individual selective inhibitors from mixture library 1344, a structure-activity relationship study was conducted using a positional scan approach. A positional scan is a screen of a systematically formatted collection of compounds that allows for the rapid identification of the active functionalities around a core scaffold (Houghten, R. A.; Pinilla, C.; Giulianotti, M. A.; Appel, J. R.; Dooley, C. T.; Nefzi, A.; Ostresh, J. M.; Yu, Y.; Maggiora, G. M.; Medina-Franco, J. L.; Brunner, D.; Schneider, J. Strategies for the use of mixture-based synthetic combinatorial libraries: scaffold ranking, direct testing in vivo, and enhanced deconvolution by computational methods. *J Comb Chem* 2008, 10, 3-19; Houghten, R. A.; Pinilla, C.; Appel, J. R.; Blondelle, S. E.; Dooley, C. T.; Eichler, J.; Nefzi, A.; Ostresh, J. M. Mixture-based synthetic combinatorial libraries. *J Med Chem* 1999, 42, 3743-3778; and Pinilla, C.; Appel, J. R.; Blanc, P.; Houghten, R. A. Rapid identification of high affinity peptide ligands using positional scanning synthetic peptide combinatorial libraries. *Biotechniques* 1992, 13, 901-915). The basic scaffold of library 1344 (FIG. 2B), comprised of 738,192 (26×26×26×42) members, has four sites of diversity (R1, R2, R3, and R4) and, therefore, is made up of four separate sub-libraries, each having a single defined position (R) and three mixture positions (X).

Screening the four sets of mixtures, totaling 120 mixtures (26+26+26+42) against chosen cell lines provided information leading to the identification of individual compounds in library 1344 that are active and selective (Houghten, R. A.; Pinilla, C.; Giulianotti, M. A.; Appel, J. R.; Dooley, C. T.; Nefzi, A.; Ostresh, J. M.; Yu, Y.; Maggiora, G. M.; Medina-Franco, J. L.; Brunner, D.; Schneider, J. Strategies for the use of mixture-based synthetic combinatorial libraries: scaffold ranking, direct testing in vivo, and enhanced deconvolution by computational methods. *J Comb Chem* 2008, 10, 3-19. Each mixture was screened at a final assay concentration of 0.1 mg/mL (13.3 µM) in triplicate.

Figure 3A:
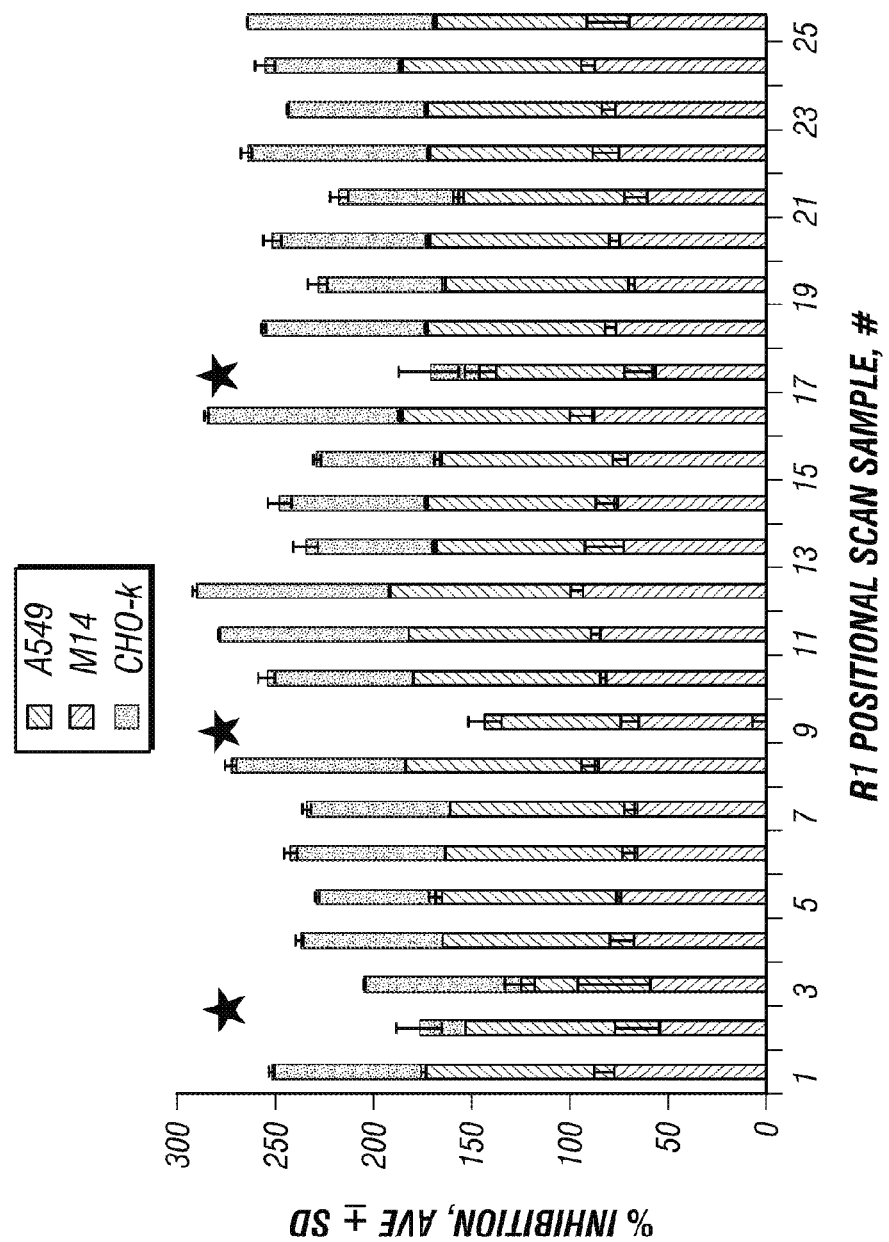
FIGS. 3A-D are graphs of the positional scan of mixture samples to deconvolute scaffold 1344. Stars indicate mixtures that are selective for CHO-K.

Eighteen moieties were identified (FIGS. 3A-D and Table 1 shown in FIG. 4) that did not significantly inhibit growth of the healthy cell line (CHO-K1). In position R1 mixture samples 2 (S-benzyl), 9 (R-2-naphthylmethyl), and 17 (R-methyl) inhibited growth of M14 and A549 cells in the range of 80-98% (FIG. 3A). Their stereoisomers (19, 10, and 7, R-benzyl, S-2-naphthylmethyl, and S-methyl, respectively) inhibited all three cell lines equipotently.

Figure 3B:
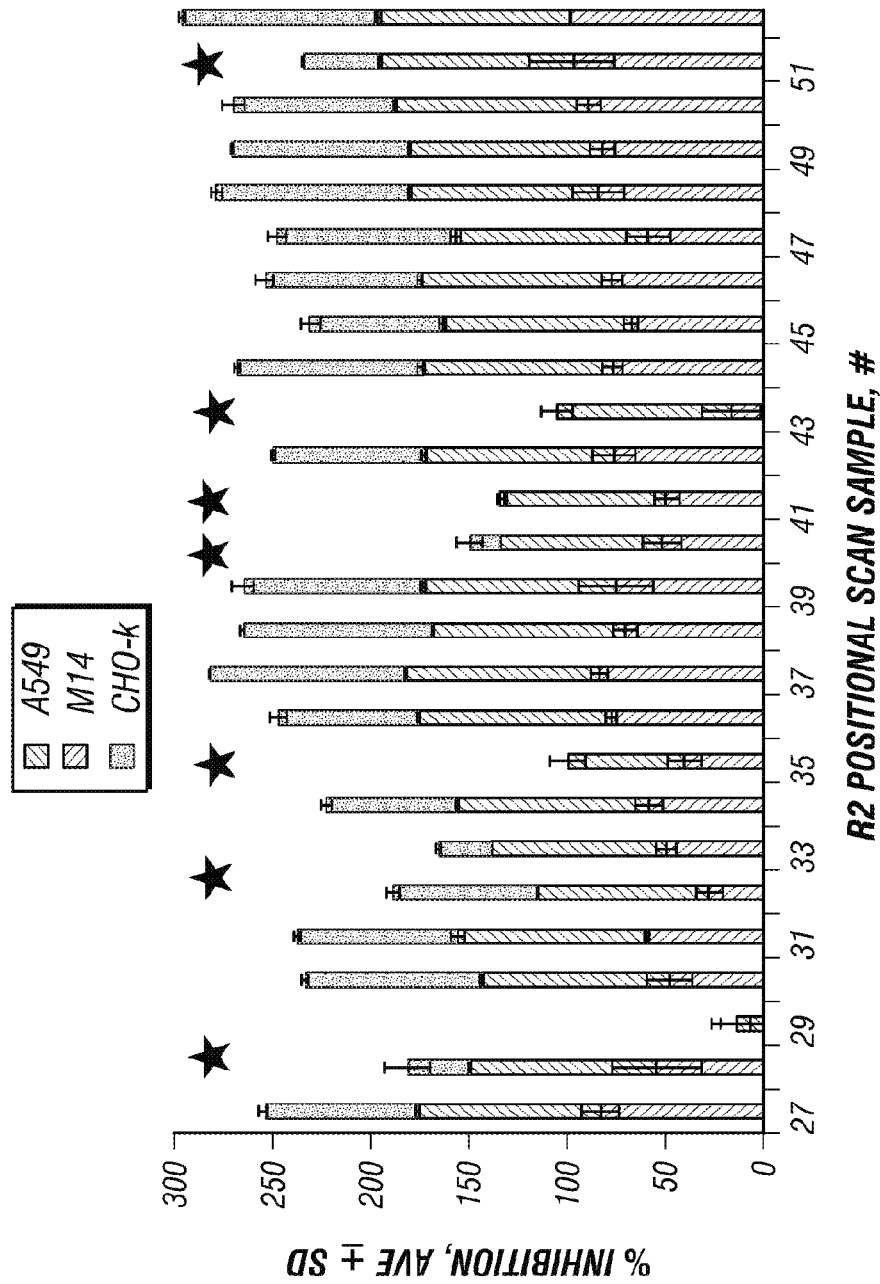

In position R2, 28 (S-benzyl), 33 ((R,R)-1-hydroxyethyl), 35 (S-4-hydroxybenzyl), 40 (S-hydroxymethyl), 41 ((S,S)-1-hydroxyethyl), 43 (R-4-hydroxybenzyl), and 51 (R-cyclohexyl) did not inhibit CHO-K1 cells while being active against both A549 and M14 cell lines. Sample 43 inhibited only M14 cells. Interestingly, samples 33 and 41 ((R,R)- and (S,S)-1-hydroxyethyl, respectively), 35 and 43 (S-4- and R-4-hydroxybenzylethyl), respectively) were stereoisomers. Stereochemistry did not appear to affect CHO-K1 viability. However, in the case of a hydroxybenzyl moiety in the R2 position (35 and 43), the R-isomer was much more potent against M14 cells and also the most selective for M14 cells. Interestingly, S-hydroxymethyl (40) was much more selective for CHO-K1 than R-hydroxymethyl (32) (FIG. 3B).

In position R3 seven residues were selective for CHO-K1 cells (FIG. 4C). Similarly to R2, they were mostly stereoisomers with the exception of 55 (R3=hydrogen), 58 and 66 (R- and S-hydroxymethyl, respectively), 59 and 67 ((R,R)- and (S,S)-1-hydroxyethyl, respectively), 61 and 69 (S-4- and R-4-hydroxybenzyl, respectively). This suggested that position R3 is the least sensitive to substitutions as far as retaining selectivity for CHO-K1 cells. Only one mixture sample exhibited selectivity towards CHO-K1 cells in position R4, sample 111 (2-methyl-cyclopropyl)-methyl).

To confirm the selective nature of these 18 mixture samples and estimate the potency, dose response experiments were performed using 10 point 3-fold serial dilutions. Mixtures with hydroxybenzyl in positions R2 (35 and 43) and R3 (61 and 69) exhibited the most selectivity against CHO-K1 cells (Table 2 shown in FIG. 5). Interestingly, 35 (S-4-hydroxybenzyl) was not selective against A549 cells, while its isomer (43, R-4-hydroxybenzyl) was significantly less potent against A549 than M14 cells. Sample 111 ((2-methyl-cyclopropyl)-methyl in the R4 position) did not confirm selectivity in the dose response assay.

Synthesis and Evaluation of Individual Compounds.

Figure 3C:
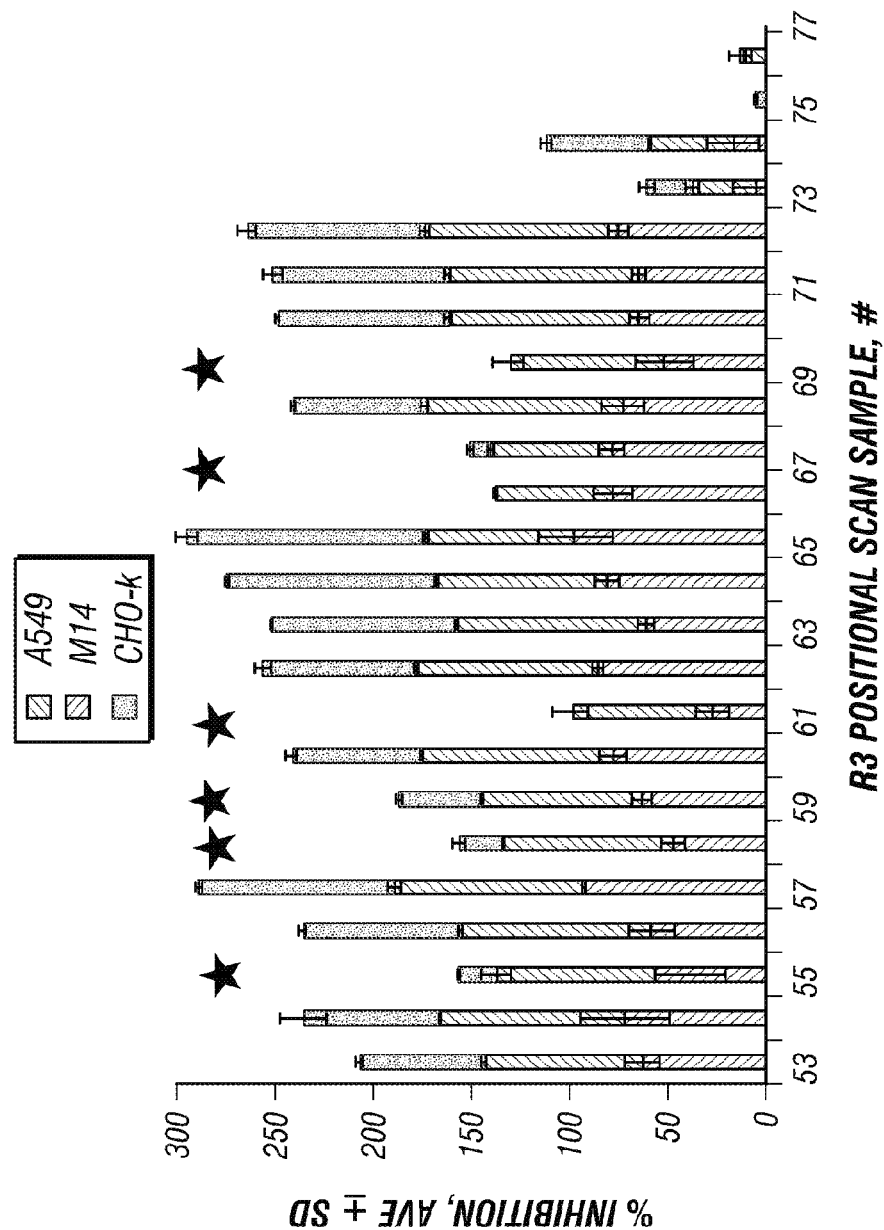
Figure 3D:
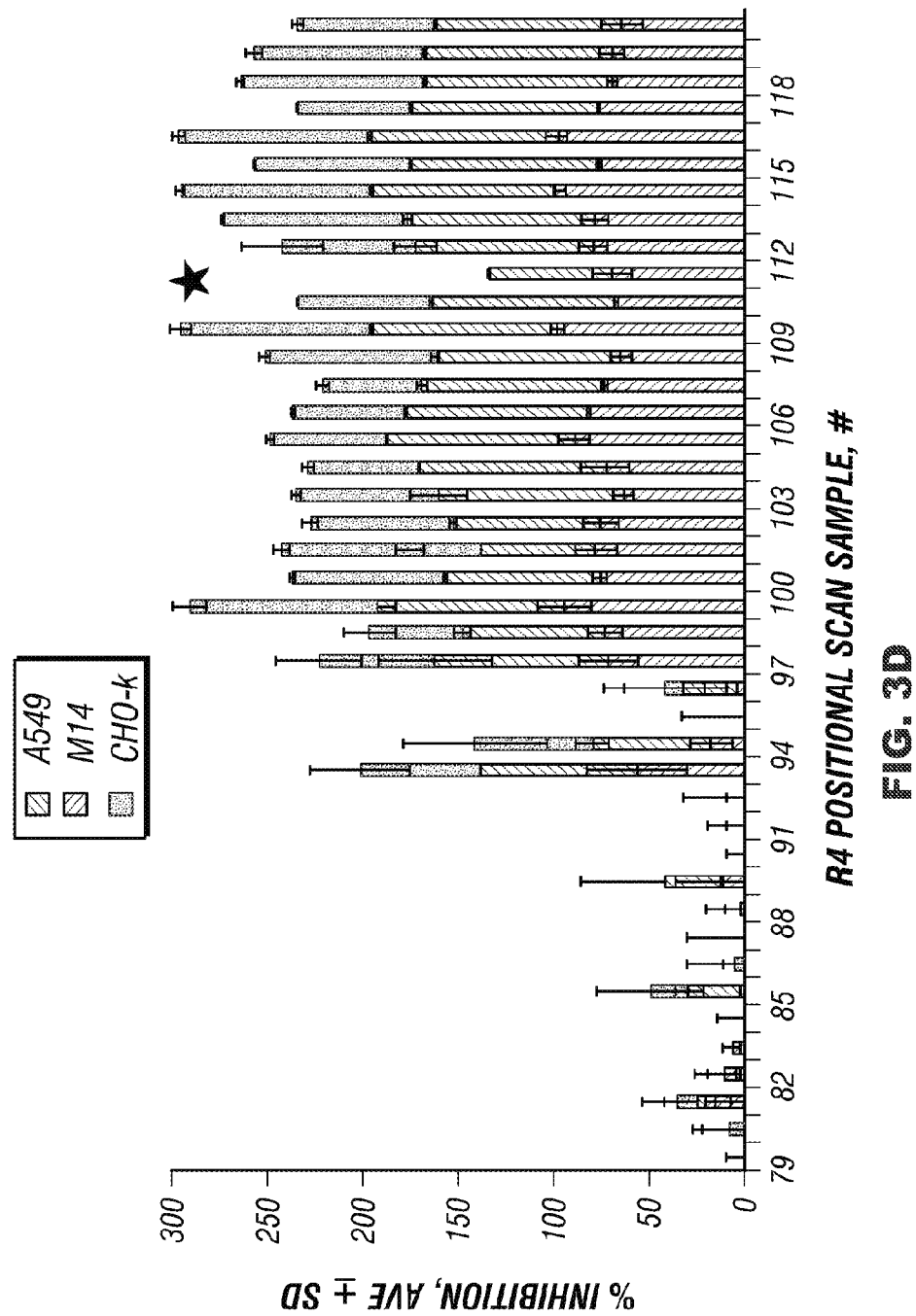
Figure 7:
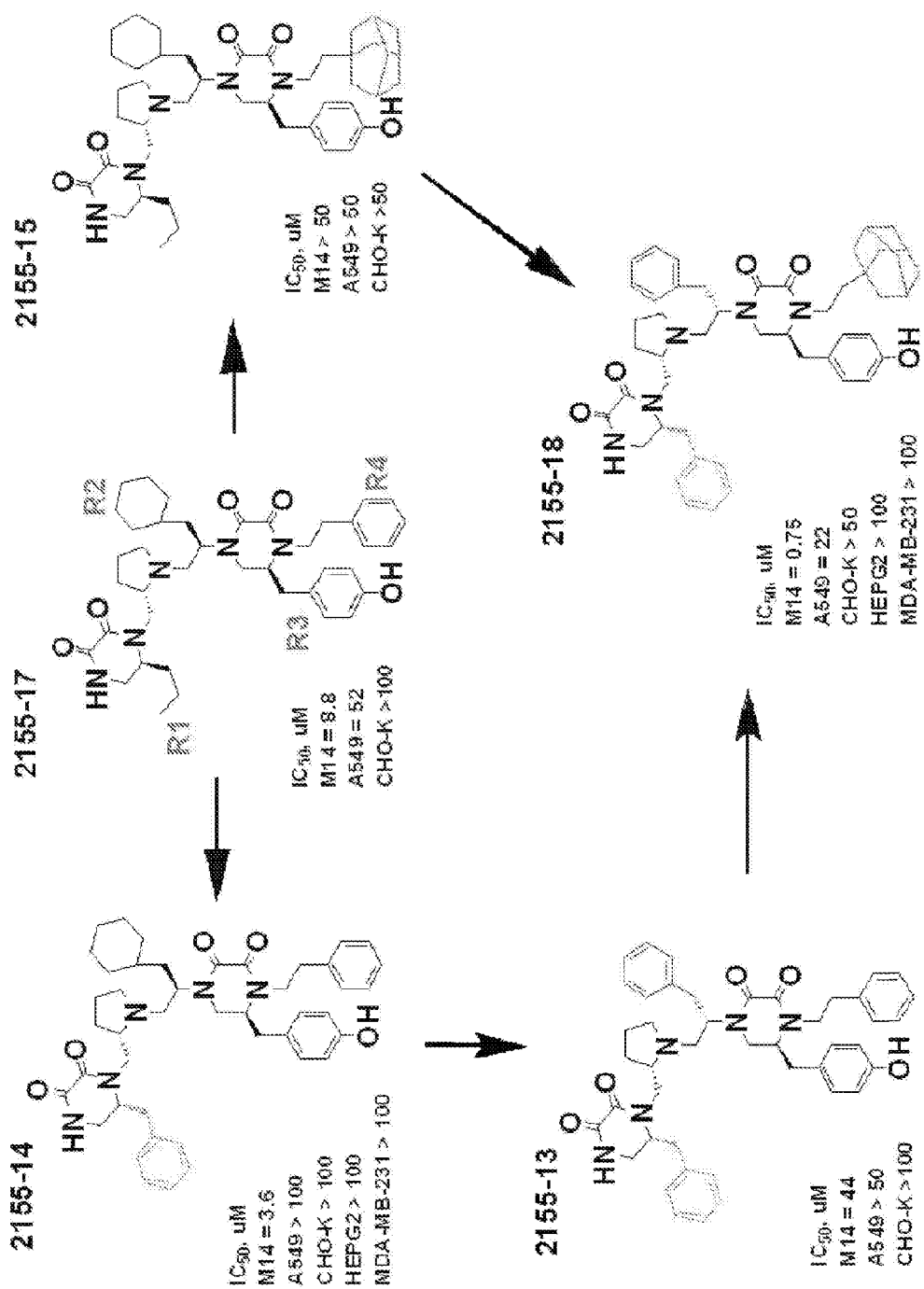
FIG. 7 is a schematic illustration of reaction pathways for optimization of pyrrolidine-bis-diketopiperazines.

Based on the dose response experiments with the mixture samples, individual compounds containing residues that exhibited selectivity against CHO-K1 cells were synthesized. Individual compounds with R-2-naphthylmethyl (9) and R-methyl (17) that were selective as mixtures in the positional scan (FIG. 3A) were not selective when present in combination with S-4 and R-4-hydroxybenzyl in R2 and R3 positions (FIGS. 3B-C). Therefore, several different moieties were examined in their place. First, individual compounds with R-propyl in R1 were tested. While similar to R-methyl in most properties, R-propyl is bigger which allows probing for the effect of size in the R1 position. Also, since the positional scan did not reveal clear preferences for a particular moiety in position R4, several different functionalities: 2-phenylbutyl, phenyl-ethyl, cyclopentyl-methyl, and 2-adamantan-1-yl-methyl (FIG. 3D, samples 80, 86, 106, and 118, respectively) were utilized. Samples 80 and 86 were completely inactive against all three cell lines, whereas 106 and 118 inhibited all three cell lines equipotently which allowed assessment of the importance of R4 for selectivity. None of individual compounds from this series exhibited good activity or selectivity towards M14 or A549 cells (Table 3 shown in FIG. 6). R-cyclohexyl in the R2 position in place of hydroxybenzyl was also tried. R-cyclohexyl exhibited selectivity for CHO-K1 in the positional scan (FIG. 3B, sample 51). Compound 2155-17 exhibited approximately 5-fold selectivity for M14 over A549 cells and more than 10-fold selectivity over CHO-K1 cells (FIG. 7, $IC_{50}$=8.8±1.2 µM, 52±8.3 µM, and >100 µM for M14, A549, and CHO-K1 cells, respectively). Substitution for 2-adamantan-1-yl-methyl in the R4 position to produce compound 2155-15 resulted in loss of activity towards all three cell lines ($IC_{50}$>50 µM). Additionally, S-benzyl in position R1, which showed some selectivity for CHO-K1 in the positional scan, was explored (FIG. 3A, sample 2). 2155-14 showed improvement of selectivity for M14 cells (FIG. 7, $IC_{50}$=3.6±0.3 µM for M14 and >100 µM for A549 and CHO-K1 cells). This suggested a preference for bulky aromatic functionalities in R1. However, a further increase of bulk in R1 by substituting benzyl for naphtylmethyl resulted in a loss of selectivity, as all 3 cell lines were inhibited close to 100% at 100 µM (data not shown). Combination of aromatic residues in R1 and R2 (S-benzyl) resulted in loss of activity towards M14 cells ($IC_{50}$=44 However, introduction of 2-adamantan-1-yl-methyl into position R4 to obtain 2155-18 resulted in improved activity towards M14 and A549 cells while maintaining selectivity for CHO-K1 cells. 2155-14 and 2155-18 also were selective against HEPG2 and MDA-MB-231 cell lines (liver and breast cancer cell lines, respectively). Interestingly, truncation of compounds of the 2155 series at each of the R1-4 positions resulted in complete loss of activity against all 3 cell lines (data not shown).

Next, whether or not 2155-14 and 2155-18 could also inhibit melanoma cells carrying different mutations was tested. Therefore, 2155-14 and 2155-18 against the SKMEL-28 melanoma cell line containing $^{V600E}$BRAF mutation (Xing, F.; Persaud, Y.; Pratilas, C. A.; Taylor, B. S.; Janakiraman, M.; She, Q. B.; Gallardo, H.; Liu, C.; Merghoub, T.; Hefter, B.; Dolgalev, I.; Viale, A.; Heguy, A.; De Stanchina, E.; Cobrinik, D.; Bollag, G.; Wolchok, J.; Houghton, A.; Solit, D. B. Concurrent loss of the PTEN and RB1 tumor suppressors attenuates RAF dependence in melanomas harboring (V600E)BRAF. Oncogene 2012, 31, 446-457) and B16/F10 murine metastatic melanoma containing p53 mutation (Castle, J. C.; Kreiter, S.; Diekmann, J.; Lower, M.; van de Roemer, N.; de Graaf, J.; Selmi, A.; Diken, M.; Boegel, S.; Paret, C.; Koslowski, M.; Kuhn, A. N.; Britten, C. M.; Huber, C.; Tureci, O.; Sahin, U. Exploiting the mutanome for tumor vaccination. Cancer Res 2012, 72, 1081-1091) were tested. Both 2155-14 and 2155-18 exhibited dose dependent inhibition of viability of all 3 cell lines (Table 4 shown in FIG. 8). 2155-14 was the most efficient against SKMEL-28 cell line ($IC_{50}$=563±40 nM, 3.6±0.3 and 2.7±0.2 µM for SKMEL-28, M14, and B16/F10, respectively) while 2155-18 inhibited all 3 lines equipotently ($IC_{50}$=890±70 nM, 745±60 nM, and 1,149±80 nM for SKMEL-28, M14, and B16/F10 cells, respectively). Of note, 2155-14 was not able to fully inhibit M14 cell viability at the highest tested concentration (100 µM) while the 2 other cell lines were ~100% inhibited starting at 10 µM of 2155-14. This suggests that 2155-14 may potentially act via inhibition of the MAPK pathway which is constitutively activated in melanomas carrying $^{V600E}$BRAF and NRAS mutations (Jang, S.; Atkins, M. B. Which drug, and when, for patients with BRAF-mutant melanoma? Lancet Oncol 2013, 14, e60-69 and Banerji, U.; Affolter, A.; Judson, I.; Marais, R.; Workman, P. BRAF and NRAS mutations in melanoma: potential relationships to clinical response to HSP90 inhibitors. Mol Cancer Ther 2008, 7, 737-749). 2155-14 could potentially be a better inhibitor of mutant $^{V600E}$BRAF than the wild type BRAF, which could explain the difference in potency towards M14 and SKMEL-28 cells. Another possibility is that 2155-14 could be acting on the HSP90 chaperone that has multiple client proteins in the MAPK pathway. Inhibition of HSP90 by small molecule (17-AAG) resulted in melanoma stabilization in patients carrying BRAF or NRAS mutation.

The potency exhibited by 2155-14 and 2155-18 against above mentioned melanoma cell lines is comparable to vemurafenib (Zelboraf, RG7204; PLX4032; RO5185426), which is a first-in-class, specific small molecule inhibitor of $^{V600E}$BRAF. Vemurafenib has been approved by the Food and Drug Administration for the treatment of late stage (metastatic) or unresectable melanoma in patients whose tumors express $^{V600E}$BRAF. Vemurafenib inhibited $^{V600E}$BRAF positive melanoma cell lines (i.e. M263, M321, SKMEL28, M229, M238, M249, and M262) with $IC_{50}$ values in 0.1-10 µM range (Sondergaard, J. N.; Nazarian, R.; Wang, Q.; Guo, D.; Hsueh, T.; Mok, S.; Sazegar, H.; MacConaill, L. E.; Barretina, J. G.; Kehoe, S. M.; Attar, N.; von Euw, E.; Zuckerman, J. E.; Chmielowski, B.; Comin-Anduix, B.; Koya, R. C.; Mischel, P. S.; Lo, R. S.; Ribas, A. Differential sensitivity of melanoma cell lines with BRAFV600E mutation to the specific Raf inhibitor PLX4032. J Transl Med 2010, 8, 29-39), but was inactive up to 10 µM against melanoma cells with mutated $Q^{61L}$NRAS and wild type BRAF (i.e., M202 and M207). M14 ($^{G12C}$NRAS) cell line was inhibited by vemurafenib with 150 nM $IC_{50}$ (Yadav, V.; Zhang, X.; Liu, J.; Estrem, S.; Li, S.; Gong, X. Q.; Buchanan, S.; Henry, J. R.; Starling, J. J.; Peng, S. B. Reactivation of mitogen-activated protein kinase (MAPK) pathway by FGF receptor 3 (FGFR3)/Ras mediates resistance to vemurafenib in human B-RAF V600E mutant melanoma. J Biol Chem 2012, 287, 28087-28098). Knowledge of the mechanism of cell death caused by a lead compound can help predict potential compound liabilities and allow prioritization of compounds. For example, compounds that cause primary necrosis usually do not make good drug candidates due to their general toxicity whereas cell-cycle inhibitors have proven to be very selective and well tolerated in melanoma clinical trials (Sheppard, K. E.; McArthur, G. A. The cell-cycle regulator CDK4: an emerging therapeutic target in melanoma. Clin Cancer Res 2013, 19, 5320-5328). The lead compounds were discovered as a result of a phenotypic assay; therefore, in order to exclude the possibility of necrosis as a mechanism of death a time course study using CellTiter-Glo® viability assay was performed. Primary necrosis is characterized by rapid loss of cell viability which can be detected as early as 3 h after compound addition (Nicotera, P.; Leist, M.; Manzo, L. Neuronal cell death: a demise with different shapes. Trends Pharmacol Sci 1999, 20, 46-51). The effect of lead compound application on the viability of M14 cells at 4, 24, 48, and 72 h was determined. The test and control compounds (gefitinib (fast apoptosis inducer), doxorubicin (late apoptosis inducer), and ionomycin (primary necrosis inducer)) were screened in 10-point, 1:3 serial dilution dose response format starting at 100 µM. None of the lead compounds exhibited signs of cell viability loss at any concentration at the 4 h time point and only slight loss of viability at the 24 h time point. All compounds reached their full potency at 48 h (data not shown). These data suggested that lead compounds (2155-14 and 2155-18) are unlikely to cause primary necrosis in M14 cells.

Once primary necrosis was excluded as a cell death mechanism a more detailed characterization of the cellular target for the lead compounds was started. ApoTox-Glo™ Triplex Assay which allows one to simultaneously assess the effect of small molecules on cell viability, toxicity, caspase activity, and cell cycle all in the same well (Niles, A. L.; Moravec, R. A.; Riss, T. L. In vitro viability and cytotoxicity testing and same-well multi-parametric combinations for high throughput screening. *Curr Chem Genomics* 2009, 3, 33-41) was utilized. First, a mixture of 2 fluorogenic substrates was added to cells. GF-AFC substrate is cell-permeant and non-lytic to cells, allowing the measurement of active protease inside live cells. The second substrate (bis-AAF-R110 Substrate) is not cell-permeable and is only cleaved when proteases are released from cells due to the loss of membrane integrity typical of cell death. This step generates an inversely correlated measurement of cell viability and toxicity.

The second addition is luminogenic DEVD-peptide substrate for caspase-3/7 and Ultra-Glo™ Recombinant Thermostable Luciferase. Caspase-3/7 cleavage of the substrate generates a luminescent signal which correlates with caspase-3/7 activation as a key indicator of apoptosis. As markers for cytotoxicity and apoptosis are transient, the assay was conducted in time course format with time points at 4, 24, 48, and 72 h.

Consistent with the CellTiter-Glo® viability time course experiment, compound 2155-14 exhibited no effect on cell viability as measured by live cell protease at the 4 h time point (FIGS. 9A-D). Additionally, there were no markers for apoptosis and cytotoxicity. This suggested a lack of effect on cell health at early time points. The 24 h time point was characterized by a significant spike in caspase activity suggesting activation of apoptotic machinery (FIG. 9B).

At 48 h the caspase signal was decreased as compared to the 24 h time point (FIG. 9C, 400% of untreated control versus 550% of untreated control for 48 and 24 h, respectively). Viability and cytotoxicity showed dose dependent response at 48 h, suggesting loss of cell membrane integrity. By 72 h the caspase signal has decayed suggesting that cells had completed the apoptotic process (FIG. 9D).

Figure 10A:
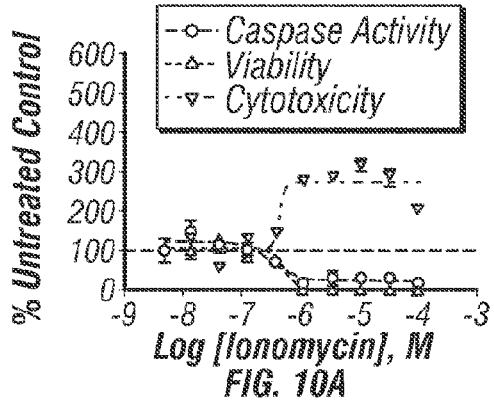
FIGS. 10A-L are graphs illustrating results of ApoTox time course assays for lonomycin (top row), terfenadine (middle row), and panobinostat (bottom row).
Figure 10B:
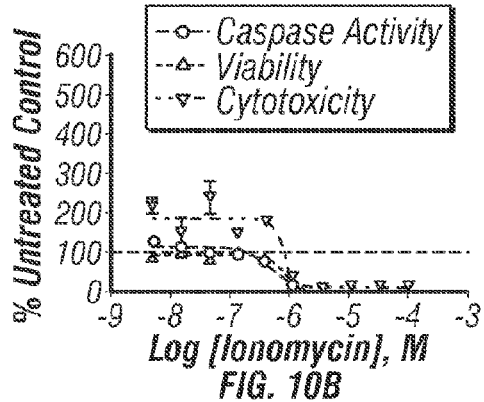
Figure 10C:
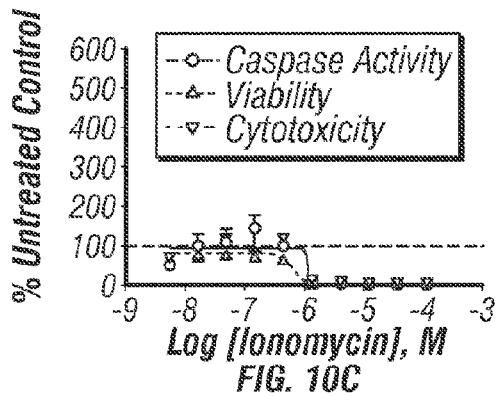
Figure 10D:
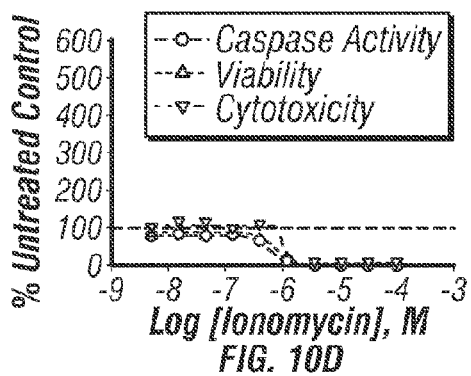
Figure 10E:
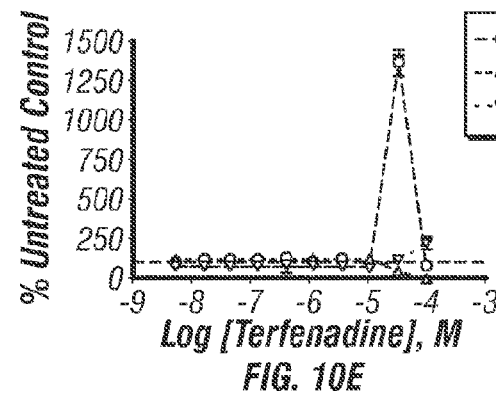
Figure 10F:
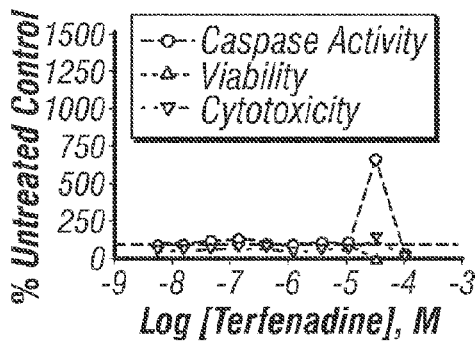
Figure 10G:
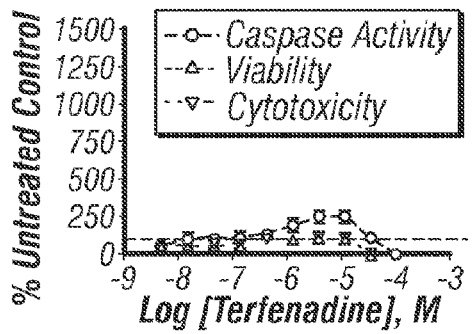
Figure 10H:
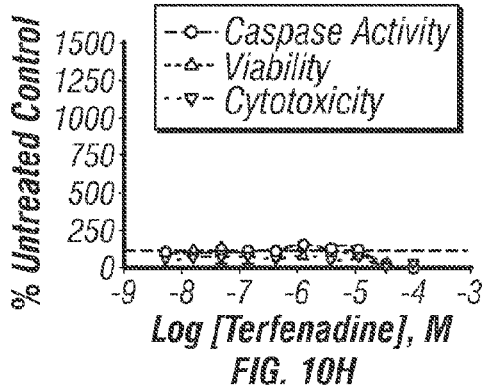

The ApoTox profile of 2155-14 with profiles of ionomycin (primary necrosis inducer), terfenadine (fast apoptosis inducer), and panobinostat (late apoptosis inducer) were compared (FIGS. 10A-L). Ionomycin induced a strong cytotoxicity response and dose dependent loss of viability as early as 4 h after addition to M14 cells, consistent with its mechanism of action (membrane disruption) (FIG. 10A). Also, ionomycin did not induce a spike in caspase activity at any of the time points as compared to the untreated control.

Figure 10I:
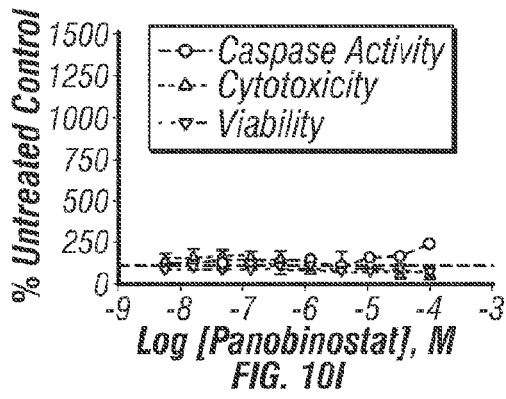
Figure 10J:
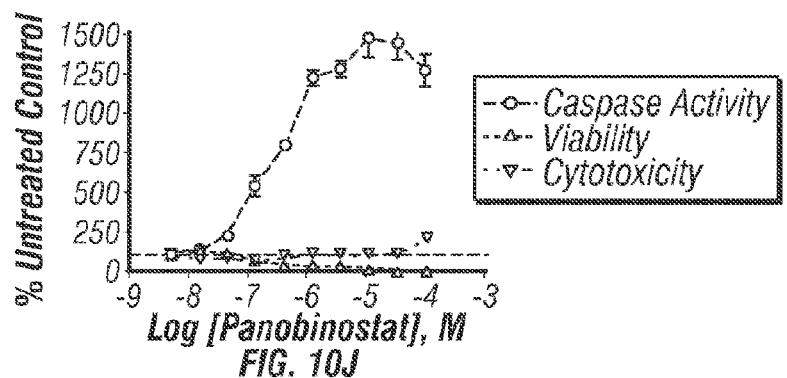
Figure 10K:
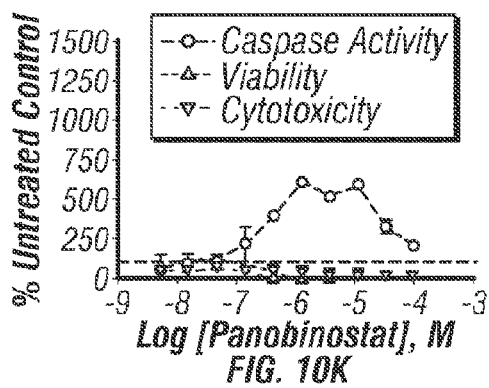
Figure 10L:
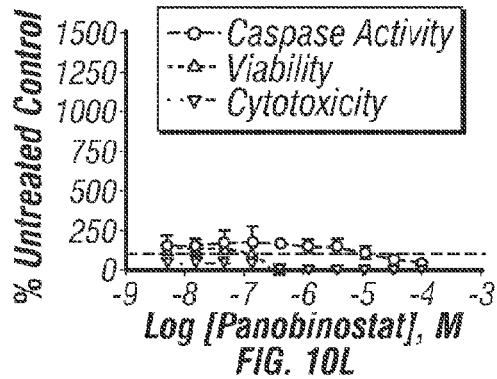

Terfenadine induced early loss of cell viability and a cytotoxicity spike similar to ionomycin. However, it also exhibited an early caspase activity spike (4-24 h) characteristic of early apoptosis (FIGS. 10I-J).

Panobinostat had no effect on viability, cytotoxicity, or caspase activity at the 4 h time point (FIG. 10M). Panobinostat has to penetrate the cell nucleus to inhibit HDACs, which results in the longer dose-to-effect time (late onset apoptosis). Caspase activity spiked at 24-48 h accompanied by dose dependent loss of viability (FIGS. 10N-O). Cytotoxicity spiked transiently at 24 h (FIG. 10N). This is consistent with what is known about panobinostat's mechanism of action which is based on pan-HDAC inhibition (Atadja, P. Development of the pan-DAC inhibitor panobinostat (LBH589): successes and challenges. *Cancer Lett* 2009, 280, 233-241). Since 2155-14 exhibited a profile most similar to panobinostat it was hypothesized that 2155-14 and 2155-18 could potentially act via HDAC inhibition. However, testing of 2155-14 and 2155-18 with representative HDACs from class I (HDAC1 and 2) and II (HDAC6) revealed a lack of HDAC inhibition up to 100 µM (data not shown). This suggests that 2155-14 and 2155-18 either act by selectively inhibiting other members of HDAC family or via an entirely different mechanism. Despite the fact that 2155-14 and 2155-18 do not appear to act by HDAC inhibition they inhibited M14 cells via inducing late stage apoptosis, which suggests the possibility of a novel intracellular target. Lack of a cytotoxicity signal over the time course of the assay also suggested possible cell cycle arrest.

As evident from results of these experiments, the instant inventors discovered and conducted initial characterization of a novel class of compounds that inhibit melanoma cell lines carrying NRAS and BRAF mutations while sparing healthy cells. The lead of the series, 2155-18, exhibited cell-based potency comparable to the FDA-approved melanoma therapy. Mechanism of death analysis suggests that these compounds act by inducing late onset apoptosis possibly due to the intracellular or intra-nuclear location of target(s). The following experiments further characterize this novel chemotype in order to determine the identity of target(s) and the possibility of utilizing this novel pyrrolidine diketopiperazine scaffold for oncological drug discovery.

It is also important to note that the screening campaign (i.e., scaffold ranking, deconvolution by positional scanning, testing of individual compounds, all done in triplicate) required only ~30 384 well plates for each cell type (CHO-K1, M14, and A549). This level of throughput requires only minimal laboratory automation while having allowed assessment of 738,192 members of the pyrrolidine diketopiperazine scaffold and greater than 5,000,000 small molecules in the scaffold ranking plate. For comparison, to screen 738,192 individual compounds in conventional HTS using the 1,536 well plate format would require approximately 500-600 plates per cell line, integrated robotics, and multiple scientific and engineering staff. Overall, mixture-based phenotypic HTS can significantly reduce cost and "hit-to-lead" time while yielding novel compounds with promising pharmacology.

Experimental Procedures: Pyrrolidine Diketopiperzine Compounds Inhibit Melanoma Cells General Synthesis Procedure for Pyrrolidine-Bis-Diketopiperazine.

All compounds were synthesized via solid-phase methodology (Scheme 2 shown in FIGS. 11A-H) on 4-methyl-benzhydrylamine hydrochloride resin (MBHA) (1.1 mmol/g, 100-200 mesh) using the "tea-bag" approach (Houghten, R. A. General method for the rapid solid-phase synthesis of large numbers of peptides: specificity of antigen-antibody interaction at the level of individual amino acids. *Proc Natl Acad Sci USA* 1985, 82, 5131-5135) as previously described elsewhere (Pinilla, C.; Edwards, B. S.; Appel, J. R.; Yates-Gibbins, T.; Giulianotti, M. A.; Medina-Franco, J. L.;

Young, S. M.; Santos, R. G.; Sklar, L. A.; Houghten, R. A. Selective agonists and antagonists of formylpeptide receptors: duplex flow cytometry and mixture-based positional scanning libraries. *Mol Pharmacol* 2013, 84, 314-324). Boc-amino acids were coupled utilizing standard coupling procedures (6 equiv) with hydroxybenzotriazole hydrate (HOBt, 6 equiv), and N,N'-diisopropylcarbodiimide (DIC, 6 equiv) in dimethylformamide (DMF, 0.1 M) for 120 min. Boc protecting groups were removed with 55% trifluoroacetic acid (TFA)/45% dichloromethane (DCM) (1×, 30 min) and subsequently neutralized with 5% diisopropylethylamine (DIEA)/95% DCM (3×, 2 min). Carboxylic acids (10 equiv) were coupled utilizing standard coupling procedures with HOBt (10 equiv) and DIC (10 equiv) in DMF (0.1 M) for 120 min. Completion of all couplings was monitored with a ninhydrin test. Initially, 100 mg of MBHA resin was placed inside a mesh "tea-bag" and washed with DCM (2×, 1 min), then neutralized with 5% DIEA/95% DCM (3×, 2 min), then rinsed with DCM (2×, 1 min). A Boc-protected amino acid was coupled utilizing the above procedure to add R1 to the resin (FIG. 11A). Once complete, the solution was poured off and the bags were rinsed with DMF (3×, 1 min) and DCM (3×, 1 min). The Boc protecting group was removed, and the bags were rinsed with DCM (2×, 1 min), isopropyl alcohol (IPA) (2×, 1 min), and DCM (2×, 1 min), and then neutralized. Boc-L-proline-OH was then coupled utilizing the above procedure (FIG. 11B). The process was repeated to add R2 (FIG. 11C) and R3 (FIG. 11D), then a carboxylic acid was coupled utilizing the above procedure to add R4 (FIG. 11E). Compounds were reduced to F (FIG. 11F) using a 40× excess of borane (1.0 M in tetrahydrofuran (THF)) over each amide bond in a glass vessel under nitrogen at 65° C. for 72 h. The solution was then poured off, the reaction was quenched with methanol (MeOH), and the bags were washed with THF (1×, 1 min) and MeOH (4×, 1 min) and allowed to air dry. Once dry, the bags were treated with piperidine overnight at 65° C. in a glass vessel. The solution was poured off, and the bags were washed with DMF (2×, 1 min), DCM (2×, 1 min), MeOH (1×, 1 min), DMF (2×, 1 min), DCM (2×, 1 min), and MeOH (1×, 1 min), and allowed to air dry. Completion of reduction was checked by cleaving a control sample and analyzing using LCMS. Diketopiperazine cyclization (FIG. 11G) was performed under anhydrous conditions (<22% humidity). The dry bags were washed with anhydrous DMF (2×, 1 min), then added to a solution of 1,1'-oxalyldiimidazole (5 fold excess for each cyclization site) in anhydrous DMF (0.1 M) and shaken at room temperature overnight. The solution was poured off and the bags were rinsed with DMF (3×, 1 min) and DCM (3×, 1 min). Completion of cyclization was checked by cleaving a control sample and analyzing by LCMS. The compounds were then cleaved from the resin with hydrofluoric acid (HF) in the presence of anisole in an ice bath at 0° C. for 90 min (FIG. S, structure H) and extracted using 95% acetic acid (AcOH)/5% $H_2O$ (2×, 5 mL). Final crude products were purified using HPLC as described above. All chirality was generated from the corresponding amino acids. Under the reaction conditions described, no epimerization was observed and, for those compounds with multiple chiral centers, a single diastereomer was obtained.

Compound Purification and Characterization.

Figure 12A:
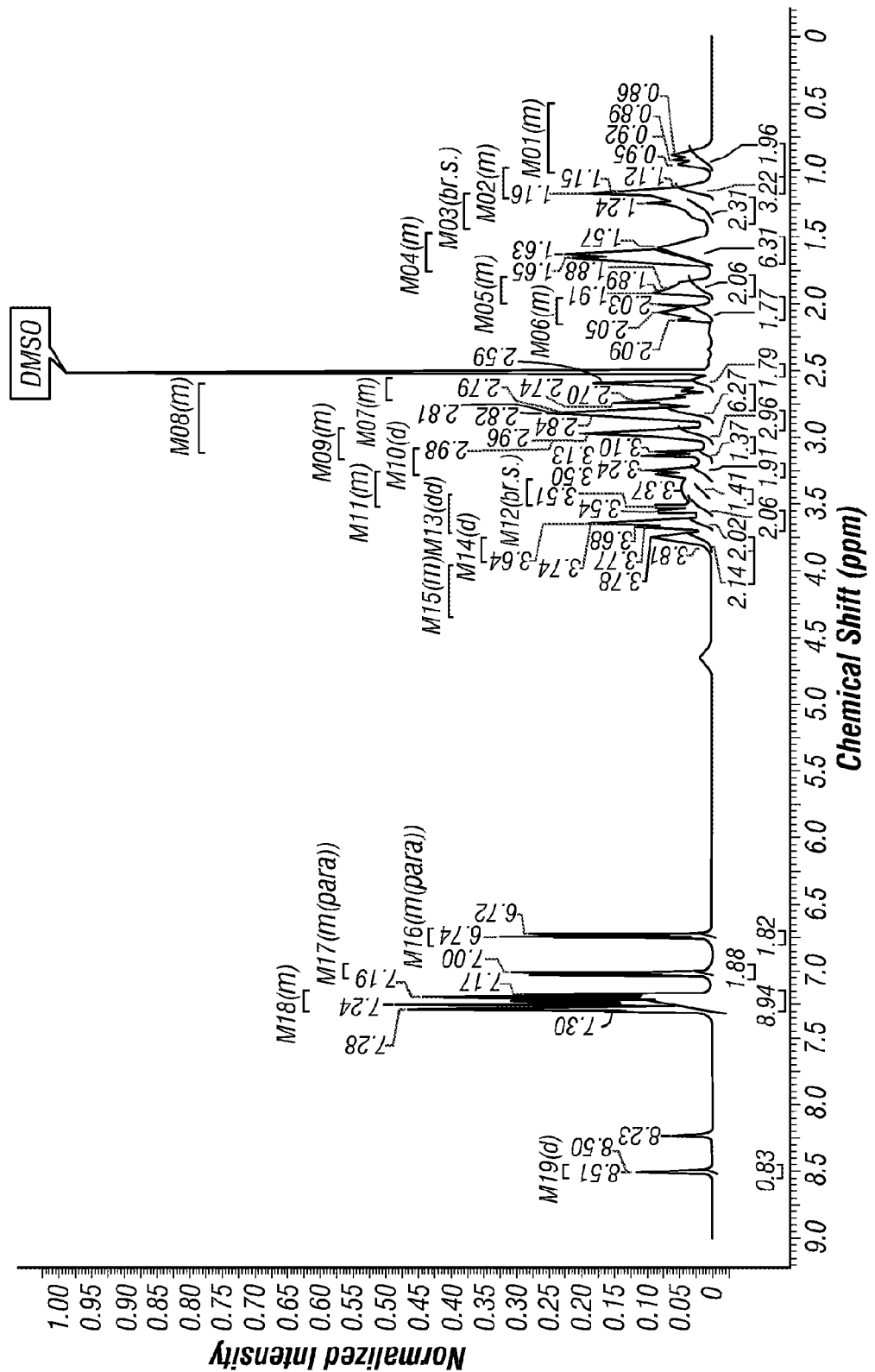
FIGS. 12A-B are graphs illustrating NMR characterization of compound 2155-14.
Figure 12B:
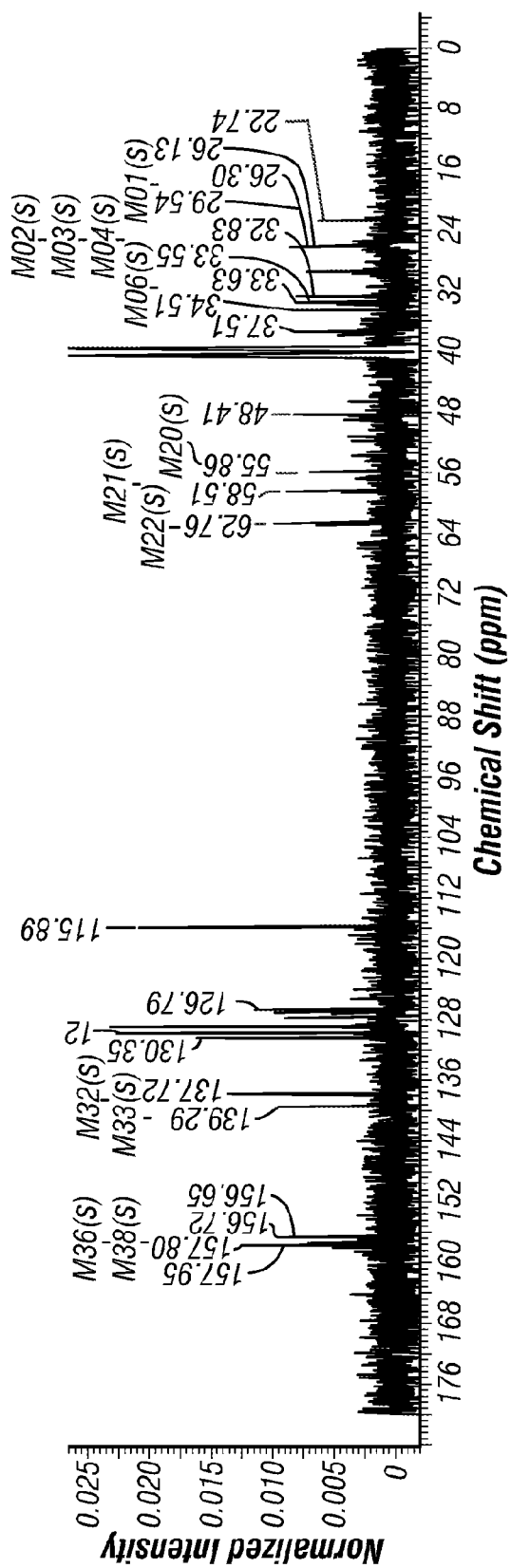
Figure 13A:
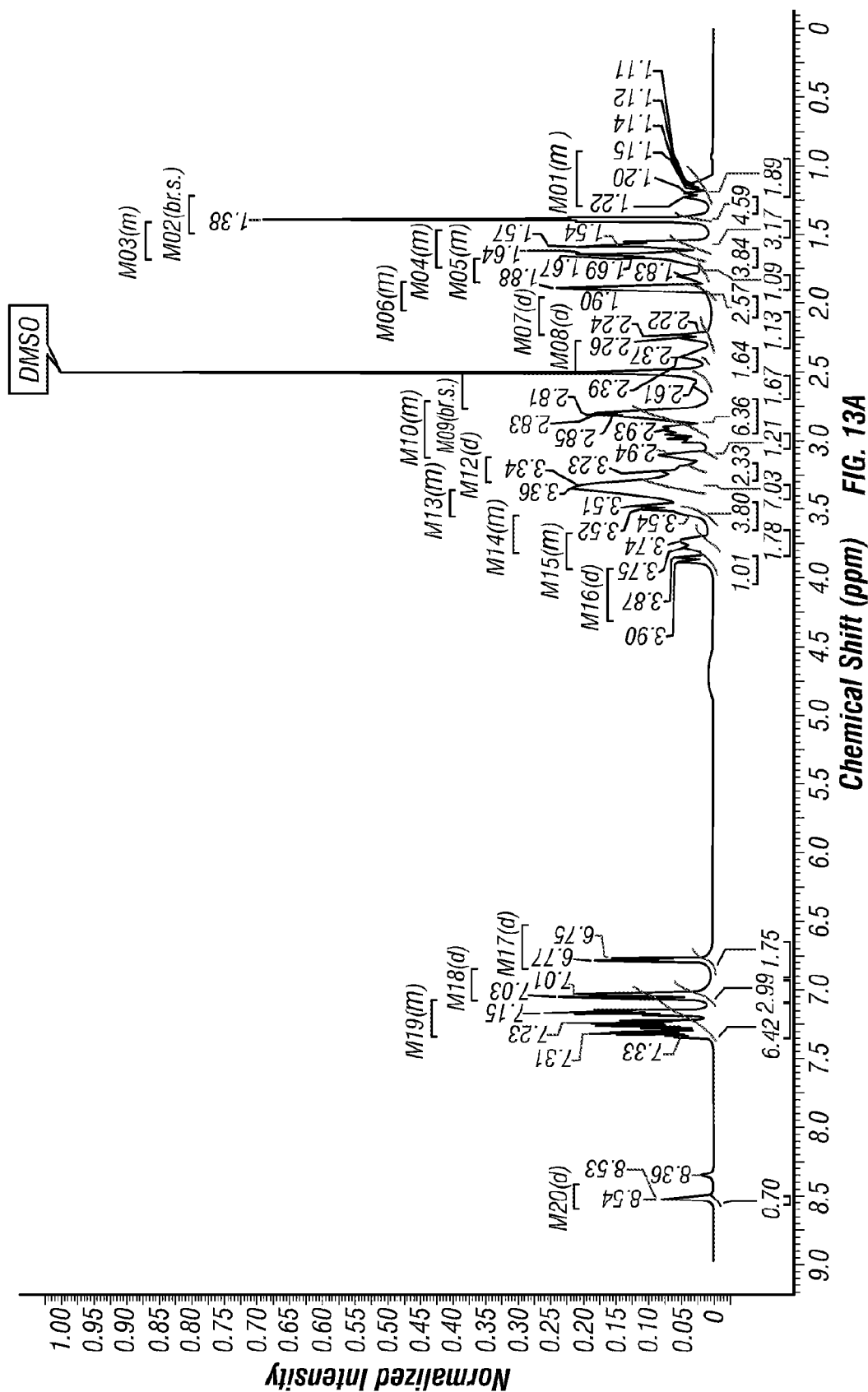
FIGS. 13A-B are graphs illustrating NMR characterization of compound 2155-18.
Figure 13B:
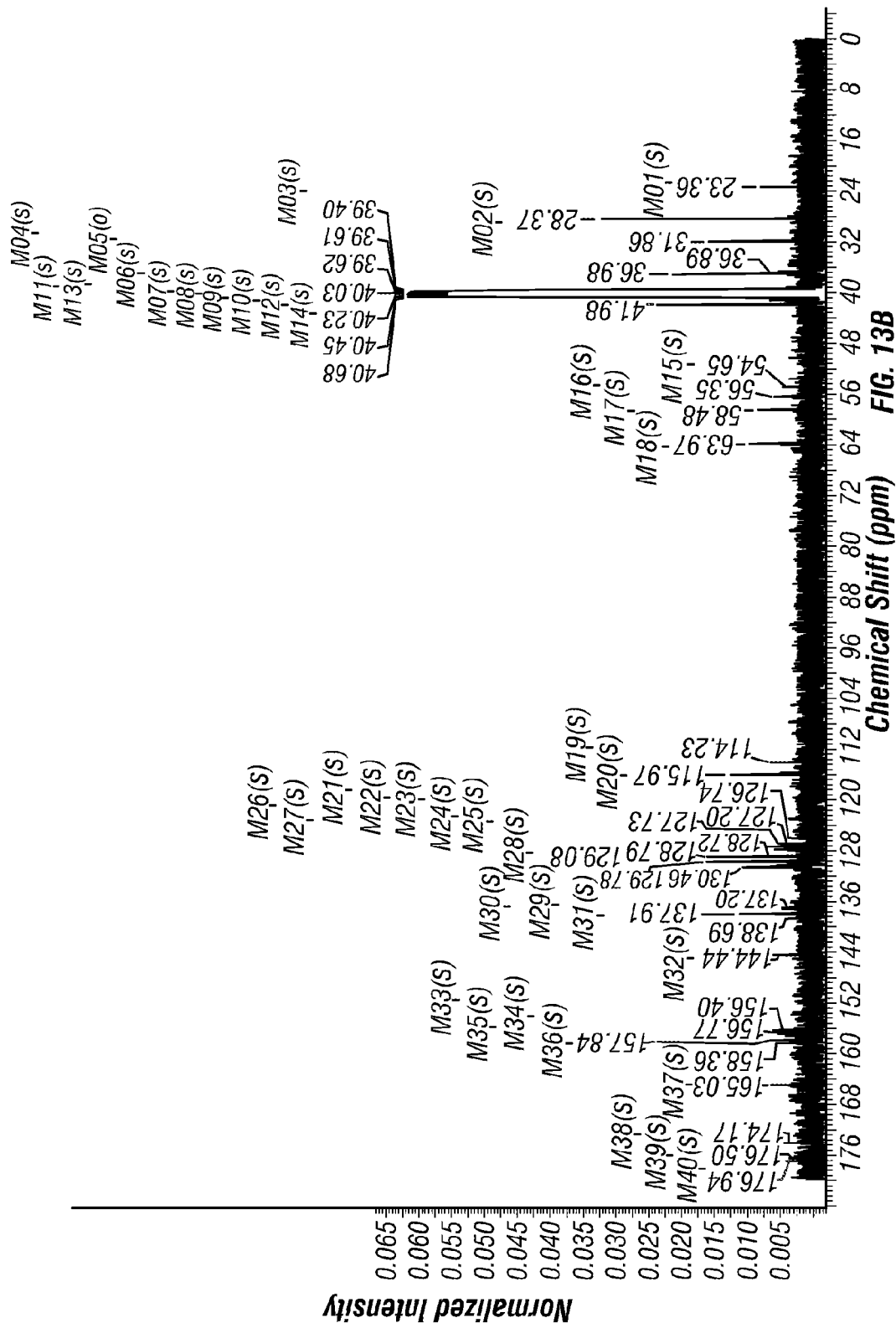

All reagents were commercially available and used without further purification. The final compounds (2155-14 and 2155-18) were purified using preparative HPLC with a dual pump Shimadzu LC-20AB system equipped with a Luna C18 preparative column (21.5×150 mm, 5 micron) at λ=214 nm, with a mobile phase of (A) $H_2O$ (+0.1% formic acid)/(B) acetonitrile (ACN) (+0.1% formic acid) at a flow rate of 13 mL/min; gradients varied by compound based on hydrophobicity. 1H NMR and 13C NMR (spectra were recorded in DMSO-d6 on a Bruker Ascend 400 MHz spectrometer at 400.14 and 100.62 MHz, respectively, and MALDI-TOF mass spectra were recorded using an Applied Biosystems Voyager DE-PRO Biospectrometry workstation. Compound 2155-14: FIG. 12A shows 1H NMR spectra and FIG. 12B shows 13C NMR spectra. Compound 2155-18: FIG. 13A shows 1H NMR spectra and FIG. 13B shows 13C NMR spectra. The purities of synthesized compounds were confirmed to be greater than 95% by liquid chromatography and mass spectrometry on a Shimadzu LCMS-2010 instrument with ESI Mass Spec and SPD-20A Liquid Chromatograph with a mobile phase of (A) $H_2O$ (+0.1% formic acid)/(B) ACN (+0.1% formic acid) (5-95% over 6 min with a 4 min rinse).

Results of NMR and LCMS Characterization of Lead Compounds 2155-14 and 2155-18

(S)-1((R)-1((S)-2-(((S)-6-benzyl-2,3-dioxopiperazin-1-yl)methyl)pyrrolidin-1-yl)-3-cyclohexylpropan-2-yl)-5-(4-hydroxybenzyl)-4-phenethylpiperazine-2,3-dione Using General Scheme (FIG. 1, scheme 1) for the synthesis of H compound 2155-14 was synthesized using the following reagents: Boc-DCyclohexylalanine-OH (R1), Boc-L-Tyrosine(2-Br—Z)—OH (R2), and Phenylacetic Acid (R3). The final crude product was purified using HPLC as described above, with a gradient of (B) 0/5, 2/5, 4/20, 40/55. 1HNMR (400 MHz, DMSO-d6) δ ppm 0.80-1.05 (m, 2H) 1.08-1.20 (m, 3H) 1.24 (br. s., 2H) 1.50-1.71 (m, 6H) 1.78-1.96 (m, 2H) 1.97-2.13 (m, 2H) 2.55-2.65 (m, 2H) 2.67-2.88 (m, 6H) 2.90-3.04 (m, 3H) 3.11 (d, J=12.96 Hz, 1H) 3.19-3.32 (m, 2H) 3.37 (br. s., 1H) 3.52 (dd, J=13.08, 3.30 Hz, 2H) 3.65 (d, J=10.03 Hz, 2H) 3.70-3.94 (m, 2H) 6.73 (m, J=8.07 Hz, 2H) 7.01 (m, J=8.07 Hz, 2H) 7.15-7.31 (m, 9H) 8.50 (d, J=5.01 Hz, 1H) 13C NMR (101 MHz, DMSO-d6) δ ppm 22.74 (s, 1C) 26.13 (s, 1C) 26.30 (s, 1C) 26.56 (s, 1C) 29.54 (s, 1C) 32.83 (s, 1C) 33.55 (s, 1C) 33.63 (s, 1C) 34.51 (s, 1C) 37.14 (s, 1C) 37.51 (s, 1C) 39.40 (s, 1C) 39.61 (s, 1C) 39.82 (s, 1C) 40.03 (s, 1C) 40.23 (s, 1C) 40.45 (s, 1C) 40.66 (s, 1C) 48.41 (s, 1C) 55.86 (s, 1C) 58.51 (s, 1C) 62.76 (s, 1C) 115.89 (s, 1C) 126.79 (s, 1C) 127.11 (s, 1C) 127.76 (s, 1C) 128.81 (s, 1C) 128.98 (s, 1C) 129.13 (s, 1C) 129.77 (s, 1C) 130.35 (s, 1C) 137.72 (s, 1C) 139.29 (s, 1C) 156.65 (s, 1C) 156.72 (s, 1C) 157.34 (s, 1C) 157.80 (s, 1C) 157.95 (s, 1C) m/z calcd C44H55N5O5[M+H]+ 734.4281, found 735.1890 (MALDI), 734.15 (MS) Purity LCMS: 98.6% (TIC), 97.0% (254 nm, peakheight) k'=4.412 min (S)-4-(2-(adamantan-1yl)ethyl)-1-((S)-1-((S)-2-(((S)-6-benzyl-2,3-dioxopiperazin-1-yl)methyl)pyrrolidin-1-yl)-3-phenylpropan-2-yl)-5-(4-hydroxybenzyl) piperazine-2,3-dione (2)

Using General Scheme (FIG. 1, scheme 1) for the synthesis of H compound 2155-18 was synthesized using the following reagents: Boc-L-Phenylalanine-OH (R1), Boc-L-Tyrosine(2-Br—Z)—OH (R2), and 1-Adamantaneacetic Acid (R3). The final crude product was purified using HPLC as described above, with a gradient of (B) 0/5, 2/5, 4/30, 40/65.111 NMR (400 MHz, DMSO-d6) δ ppm 1.06-1.32 (m, 2H) 1.38 (br. s., 5H) 1.48-1.60 (m, 3H) 1.61-1.73 (m, 4H) 1.74-1.86 (m, 1H) 1.86-2.02 (m, 3H) 2.25 (q, J=8.15 Hz, 1H)

2.38 (d, J=7.46 Hz, 2H) 2.61 (br.s., 2H) 2.75-3.02 (m, 6H) 3.12 (br. s., 1H) 3.22 (d, J=12.10 Hz, 2H) 3.29-3.42 (m, 7H) 3.42-3.63 (m, 4H) 3.66-3.83 (m, 2H) 3.88 (d, J=10.51 Hz, 1H) 6.76 (d, J=8.07 Hz, 2H) 7.02 (d, J=6.97 Hz, 3H) 7.09-7.34 (m, 6H) 8.54 (d, J=5.13 Hz, 1H) 13C NMR (101 MHz, DMSO-d6) δ ppm 23.36 (s, 1C) 28.37 (s, 1C) 31.86 (s, 1C) 36.89 (s, 1C) 36.98 (s, 1C) 39.40 (s, 1C) 39.61 (s, 1C) 39.82 (s, 1C) 40.03 (s, 1C) 40.23 (s, 1C) 40.45 (s, 1C) 40.66 (s, 1C) 41.13 (s, 1C) 41.96 (s, 1C) 54.85 (s, 1C) 56.35 (s, 1C) 58.48 (s, 1C) 63.97 (s, 1C) 114.23 (s, 1C) 115.97 (s, 1C) 126.74 (s, 1C) 127.20 (s, 1C) 127.73 (s, 1C) 128.72 (s, 1C) 128.79 (s, 1C) 129.08 (s, 1C) 129.78 (s, 1C) 130.46 (s, 1C) 137.20 (s, 1C) 137.91 (s, 1C) 138.69 (s, 1C) 144.44 (s, 1C) 156.40 (s, 1C) 156.77 (s, 1C) 157.84 (s, 1C) 158.36 (s, 1C) 165.03 (s, 1C) 174.17 (s, 1C) 176.50 (s, 1C) 176.94 (s, 1C) m/z calcd C48H59N5O5 [M+H]+ 786.4594, found 787.0037 (MALDI), 786.15 (MS) Purity LCMS: 97.1% (TIC), 98.0% (254 nm, peak height) k'=4.943 min Synthesis of Positional Scanning Library 1344.

Positional scanning library 1344 was synthesized as described in Scheme 2 (FIGS. 11A-H). Positional Scanning library 1344 utilized both individual and mixtures of amino acids (R1, R2, and R3) and carboxylic acids (R4). The synthetic technique and subsequent screening facilitates the generation of information regarding the likely activity of individual compounds contained in the library (Houghten, R. A.; Pinilla, C.; Giulianotti, M. A.; Appel, J. R.; Dooley, C. T.; Nefzi, A.; Ostresh, J. M.; Yu, Y.; Maggiora, G. M.; Medina-Franco, J. L.; Brunner, D.; Schneider, J. Strategies for the use of mixture-based synthetic combinatorial libraries: scaffold ranking, direct testing in vivo, and enhanced deconvolution by computational methods. *J Comb Chem* 2008, 10, 3-19; Reilley, K. J.; Giulianotti, M.; Dooley, C. T.; Nefzi, A.; McLaughlin, J. P.; Houghten, R. A. Identification of two novel, potent, low-liability antinociceptive compounds from the direct in vivo screening of a large mixture-based combinatorial library. *AAPS J* 2010, 12, 318-329; and Reilley, K. J.; Giulianotti, M.; Dooley, C. T.; Nefzi, A.; McLaughlin, J. P.; Houghten, R. A. Identification of two novel, potent, low-liability antinociceptive compounds from the direct in vivo screening of a large mixture-based combinatorial library. *AAPS J* 2010, 12, 318-329.

The equimolar isokinetic ratios utilized for the mixtures were previously determined and calculated for each of the amino acids and carboxylic acids (Acharya, A. N.; Ostresh, J. M.; Houghten, R. A. Determination of isokinetic ratios necessary for equimolar incorporation of carboxylic acids in the solid-phase synthesis of mixture-based combinatorial libraries. *Biopolymers* 2002, 65, 32-39 and Ostresh, J. M.; Winkle, J. H.; Hamashin, V. T.; Houghten, R. A. Peptide libraries: determination of relative reaction rates of protected amino acids in competitive couplings. *Biopolymers* 1994, 34, 1681-1689). Library 1344 has a total diversity of 738, 192 compounds (26×26×26×42=738,192). The R1, R2, and R3 positions as shown in Scheme 2 (FIG. 11H) each consisted of 26 amino acids and the R4 position contained 42 carboxylic acids. By way of example, sample 2 (FIGS. 3A-D) contains an equal molar amount of all 28,392 individual compounds in library 1344 that have S-benzyl fixed at the R1 position and likewise sample 28 contains an equal molar amount of all 28,392 individual compounds in library 1344 that have S-benzyl fixed at the R2 position.

Scaffold Ranking Library.

The scaffold ranking library contained one sample for each of the 37 positional scanning libraries tested. Each of these samples contained an approximate equal molar amount of each compound in that library. So, for example, scaffold ranking library 1344 contained 738,192 pyrollidine-bis-diketopiperazines in approximately equal molar amounts. Each of these 37 mixture samples can be prepared by mixing the cleaved products of the complete positional scanning library, as was the case for 1344, or they can be synthesized directly as a single mixture (Santos, R. G.; Appel, J. R.; Giulianotti, M. A.; Edwards, B. S.; Sklar, L. A.; Houghten, R. A.; Pinilla, C. The mathematics of a successful deconvolution: a quantitative assessment of mixture-based combinatorial libraries screened against two formylpeptide receptors. *Molecules* 2013, 18, 6408-6424).

TPIMS Mixture Library Screening.

Mixture libraries were solubilized in 3% DMSO/$H_2O$ and added to polypropylene 384 well plates (Greiner cat #781280). 1,250 CHO-K1, A549, or M14 cells were plated in 384-well plates in 5 μL of serum-free media (F12 for CHO-K1 and A549, DMEM for M14). Test compounds and gefitinib (pharmacological assay control) were prepared as 10-point, 1:3 serial dilutions starting at 300 then added to the cells (5 μL per well) using the Biomek $NX^P$. Plates were incubated for 72 h at 37° C., 5% $CO_2$ and 95% RH. After incubation, 5 μL of CellTiter-Glo® (Promega cat #: G7570) were added to each well, and incubated for 15 min at room temperature. Luminescence was recorded using a Biotek Synergy H4 multimode microplate reader. Viability was expressed as a percentage relative to wells containing media only (0%) and wells containing cells treated with 1% DMSO only (100%). Three parameters were calculated on a per-plate basis: (a) the signal-to-background ratio (SB); (b) the coefficient for variation [CV; CV=(standard deviation/mean)×100)] for all compound test wells; and (c) the Z'-factor (18). The $IC_{50}$ value of the pharmacological control (gefitinib, LC Laboratories #G-4408) was also calculated to ascertain the assay robustness. Time course viability assay was performed as described for library screening with luminescence measurements performed at 4, 24, 48, and 72 h.

Hexosaminidase Viability Assay.

Hexosaminidase assay was used to study the effects of 2155-14 and 2155-18 on cell viability or cell proliferation of both B16/F-10 and SKMEL-28 cells (Landegren, U. Measurement of cell numbers by means of the endogenous enzyme hexosaminidase. Applications to detection of lymphokines and cell surface antigens. *J Immunol Methods* 1984, 67, 379-388). In brief, cells were plated in 96 well plates, grown overnight and treated the next day with increasing concentrations of compounds (0-50 μM) for 48 h. After 48 h of treatment, media was discarded and cells were washed with PBS to remove residual media from wells. Hexosaminidase substrate (75 μL) (Sigma Aldrich; cat #N9376) was added to each well, incubated at 37° C. for 30 min followed by addition of 112.5 μL of developer into each well. Final absorbance was measured at λ=405 nm. Cell growth was calculated as percent viability=[(AB)×100], where A and B were the absorbance of treated and control cells, respectively.

Luciferase Counterscreen Assay.

Lead compounds were tested for inhibition of luciferase from the CellTiter-Glo® assay kit (Promega cat #: G7570). The ATP concentration in the luciferase assay was matched to the response produced by M14 cells. Test compounds were prepared as 10-point, 1:3 serial dilutions starting at 300 then added to the DMEM (5 μL per well) using the Biomek $NX^P$. Plates were incubated for 1 h at 37° C., 5% $CO_2$ and 95% RH. After incubation, 5 μL of CellTiter-Glo® (Promega cat #: G7570) was added to each well, and incubation continued for 15 min at room temperature. Luminescence was recorded using a Biotek Synergy H4 multimode microplate reader. Inhibition was expressed as a percentage relative to wells containing media only (0%) and wells containing CellTiter-Glo® (100%).

ApoTox-Glo™ Triplex Assay.

M14 #5 cells were plated in 384-well format at a density of 1,250 cells in 5 µL of serum-free DMEM media and incubated at 37° C. in 5% $CO_2$ for 4 h. Control and test compounds were serially diluted in a ratio of 1:3 and added to wells in 4 µL. Ionomycin, terfenadine, and panobinostat were used as controls of mechanism of cell death. Plates were incubated at 37° C. in 5% $CO_2$ for 4, 24, 48, and 72 h. At the end of each time point Viability/Cytotoxicity™ Reagent was prepared containing 400 µM glycylphenylalanyl-aminofluorocoumarin (GF-AFC) substrate (cleavable by live cell proteases) and 400 µM bis-alanylalanyl-phenylalanyl-rhodamine 110 (bis-AAF-R110) substrate (cleavable by dead cell proteases). 4 µL of the Viability/Cytotoxicity™ Reagent was used per well. The plate was incubated for 30 min at 37° C. Fluorescence was read at $\lambda_{Ex}$=400 nm and $\lambda_{Em}$=505 nm for GF-AFC and $\lambda_{Ex}$=485 nm and $\lambda_{Em}$=520 nm for bis-AAF-R110 on the BioTek Synergy™ 4 Multi-Mode Microplate Reader. Caspase-Glo® 3/7 Reagent was then added in 12 µL volume. The plate was incubated for 30 min at room temperature and luminescence was measured on the BioTek Synergy™ 4 Multi-Mode Microplate Reader.

Nuclear Proteins Induce Autophagy and Death of Melanoma Cells

Experimental Procedures and Results

Melanoma Cell Panel.

Lead compounds 2155-14 and 2155-18 were discovered as a result of a phenotypical screen of 3 cell lines (M14 melanoma, A549 lung cancer, and CHO-K1 non-malignant control) (Onwuha-Ekpete, L. et al. Novel pyrrolidine diketopiperazines selectively inhibit melanoma cells via induction of late-onset apoptosis. *Journal of medicinal chemistry* 57, 1599-1608, doi:10.1021/jm4019542 2014). Initial characterization demonstrated that these compounds caused late onset apoptosis. Before proceeding with studies of the target(s) and mechanism of action of the lead compounds, additional information was obtained that could aid in the formation of the hypothesis about the mechanism of action. Additional melanoma cell lines harboring different mutations and non-malignant cells (Table 5 shown in FIG. 14 and Table 6 shown in FIG. 15) were tested to determine whether 2155-14 and 2155-18 preferentially inhibit melanoma cells with a specific molecular background, which could provide additional clues about the mechanism of action (Table 6, FIG. 15). 2155-14 and 2155-18 did not exhibit significant preferences towards either of the tested melanoma cell lines (Table 6, FIG. 15). 2155-14 and 2155-18 exhibited potency towards melanoma cell lines comparable to Zelboraf (Table 6, FIG. 15 and Sondergaard, J. N. et al. Differential sensitivity of melanoma cell lines with BRAFV600E mutation to the specific Raf inhibitor PLX4032. *J Transl Med* 8, 39, doi:10.1186/1479-5876-8-39 2010 and Yadav, V. et al. Reactivation of mitogen-activated protein kinase (MAPK) pathway by FGF receptor 3 (FGFR3)/Ras mediates resistance to vemurafenib in human B-RAF V600E mutant melanoma. *J Biol Chem* 287, 28087-28098, doi:10.1074/jbc.M112.377218 2012). Also, similar to Zelboraf there was limited toxicity towards non-malignant cells (Table 6, FIG. 15). Compounds were not toxic to mouse embryonic fibroblasts (MEF) while killing murine melanoma cells (B16F10). Zelboraf was toxic to MEFs. Activity across several melanoma cell lines with different mutational background and disease stages similar to FDA-approved melanoma drug Zelboraf suggested that 2155-14 and 2155-18 could potentially be used for broad-based melanoma therapy.

Ras/Raf/MEK/ERK Pathway Analysis.

Melanoma proliferation and viability are mainly regulated by the Ras/Raf/MEK/ERK pathway. Most of the molecular alterations (i.e. mutations, deletions, amplifications) that drive melanoma are also concentrated in these pathways. (Cohen, C. et al. Mitogen-actived protein kinase activation is an early event in melanoma progression. *Clin Cancer Res* 8, 3728-3733 2002 and Davies, H. et al. Mutations of the BRAF gene in human cancer. *Nature* 417, 949-954, doi: 10.1038/nature00766 (2002).

Flow cytometry was used to determine whether 2155-14 and 2155-18 had an effect on these pathways (FIGS. 16A-B). At the 24 h time point none of the tested compounds exhibited any effect on phosphorylation of ERK 1/2 or Akt (FIG. 16A). At 48 h, cell treatment with 2155-14 resulted in approximately a 20% decrease of cell population with dual pathway activation as compared to the untreated control. Cells with single pathway activation were not significantly affected (FIG. 16B) while the amount of cells where both pathways were inactive increased by approximately 10%. Interestingly, 2155-18 had no effect on either cell population, suggesting that its mechanism of action might be different from 2155-14. Treatment with the combination of BRAF and MEK1/MEK2 inhibitors dabrafenib/trametinib (an FDA-approved melanoma therapy) strikingly decreased the population with dual pathway activation which inversely correlated with population with dual inactive pathways, but unlike 2155-14 the amount of PI3K-activated cells was increased. There is a significant cross-talk between PI3K and MAPK pathways, therefore, increased amount of PI3K-activated cells in response to MEK inhibition is not surprising and has been reported by others as a basis of acquired resistance to the BRAFi/MEKi therapy (Atefi, M. et al. Reversing melanoma cross-resistance to BRAF and MEK inhibitors by co-targeting the AKT/mTOR pathway. *PLoS One* 6, e28973, doi:10.1371/journal.pone.0028973 2011). Therefore, absence of PI3K activation in cells treated with 2155-14 could be beneficial for melanoma therapy. These data suggested that the potency of 2155-14 and 2155-18 against melanoma cell lines is likely not due to the inhibition of MAPK or NRAS pathways, which prompted further investigation of the mechanism of action.

Mechanism of Cell Death.

The mechanism by which 2155-14 and 2155-18 cause melanoma cell death was investigated. Caspases 3/7 activity at 0 and 4 h time points in M14. WM266-4 cells was not statistically different from untreated control (FIGS. 17A-E) even though both caspase 8 and 9 signal in cells treated with 2155-14 and 2155-18 was significantly different from untreated control cells at 0 and 4 h (FIGS. 17B and 17C). Typically, effector caspases (e.g., 3/7) increase activity very shortly after initiator caspases (e.g., 8) become active. The 24 h delay in caspase 3/7 activity increase suggested that activity of initiator caspases between 30 min and 4 h did not directly lead to the activity increase of caspases 3/7; therefore, activation of caspases 3/7 at 24 h is possibly due to an additional process initiated by 2155-14 and 2155-18. Viability of WM266-4 cells was impaired at 24 h after addition of 2155-14 and 2155-18, but was almost completely restored in case of 2155-14, but not 2155-18, by pre-incubation with 10 µM caspase 8 inhibitor Z-IETD-FMK and pan-caspase inhibitor Z-VAD-FMK. Interestingly, after 48 h of exposure, viability of WM266-4 cells was only ~25% in the case of 2155-14 even with caspase inhibitor pre-treatment. Loss of viability after 48 h in combination with caspase 3/7 activity spike at 24 h suggested that additional processes initiated by 2155-14 and 2155-18 are not dependent on initiator caspases.

To further investigate the mechanism of cell death caused by the lead compounds, we stained WM-266-4 cells treated with 2155-14 and 2155-18 for autophagy and mitochondrial potential at 1, 4, and 24 h after addition of the compounds were stained. At the 1 h time point no autophagy or other signs of cellular distress in either of conditions was observed (data not shown). At the 4 h time point unstained cells treated with 2155-14 and 2155-18 exhibited traits of apoptosis (FIG. 18A, top panel; note smaller cell size, rounded shape, membrane blebbing, and apoptotic bodies). At 24 h the apoptosis intensified leading to the extensive cell death in the case of 2155-14 treatment (FIG. 18A, mid lower panel). The effect of 2155-18 at 24 h was less pronounced than 2155-14. Interestingly, cells in the presence of 2155-14 stained positive for autophagy as early as 4 h after compound addition (FIG. 18B), while cells treated with 2155-18 did not stain positive for autophagy. At 24 h the intensity of autophagy staining increased in cells treated with 2155-14 (FIG. 18C), but not with 2155-18 suggesting that the compounds act via different mechanisms. Quantitation of the representative image of cells showed that 57% of cells treated with 2155-14 were undergoing autophagy, whereas untreated control cells showed no signs of autophagy (FIG. 18D).

Activation of caspase 9 as early as 30 min after compound addition suggested a possible impairment of mitochondrial function, and thus mitochondrial potential changes were tested. There was no significant effect 1 h after the addition of compounds. At 4 h, mitochondrial potential was decreased in the presence of 2155-14 (FIGS. 19A-E). Comparison of the effect of 2155-14 on mitochondrial potential and autophagy at 4 h after treatment showed dose dependent response in both assays (FIG. 19E). However, the effect on autophagy was more significant; therefore, the mechanism of autophagy was selected for further studies. Additionally, caspase 9 activity at 30 min and 4 h did not lead to activation of caspase 3/7, corroborating the evidence for mitochondrial impairment being a secondary event.

Autophagy by western blot of autophagy markers LC3-II (Barth, S., Glick, D. & Macleod, K. F. Autophagy: assays and artifacts. *J Pathol* 221, 117-124, doi:10.1002/path.2694 2010) and beclin-1 in both WM266-4 and M14 cells was confirmed (FIGS. 20A-C). Since autophagy staining at 4 h after treatment with 2155-14 was observed how soon after the compound treatment the levels of LC3-II increased was tested. At an early time point (30 min) autophagy potentiation as compared to the untreated control was not observed. 24 h after 2155-14 treatment a dose dependent increase of LC3-II, beclin-1 and autophagy staining in WM266-4 cells (FIGS. 20A and 20B) and M14 cells (FIG. 20C) was observed. Interestingly, 2155-18 showed a dose dependent inhibitory effect on basal autophagy (FIG. 20B), further suggesting a different mechanism of action compared with 2155-14.

Cleavage of lamin A/C is one of the hallmarks of apoptosis, therefore, the effect of 2155-14 on levels of cleaved lamin A/C as well as levels of LC3-II was monitored to determine whether autophagy results in apoptotic cell death. Western blot analysis of cells treated with 2155-14 showed that pretreatment with autophagy inhibitor LY294002 (a PI3K inhibitor) had a very limited effect on LC3-II and cleaved lamin A/C levels, while hydroxychloroquine (HCQ, a lysosomal lumen alkalizer) (Yang, Y. P. et al. Application and interpretation of current autophagy inhibitors and activators. *Acta Pharmacol Sin* 34, 625-635, doi:10.1038/aps.2013.5 2013) pretreatment increased levels of both LC3-II and cleaved lamin A/C (FIGS. 21A-E), explaining the failure to rescue viability of WM266-4 cells treated with 2155-14 (FIG. 21E). This suggested that 2155-14 is capable of overriding or bypassing PI3K inhibition and functioning by a mechanism different from PI3K-controlled autophagy.

Caspases have been shown to play an important role in the crosstalk between apoptosis and autophagy whereby caspase 8 activity is believed to inhibit autophagy and direct cell death to the apoptotic pathways, while the opposite is believed to be true for caspase 9 (Wu, H. et al. Caspases: a molecular switch node in the crosstalk between autophagy and apoptosis. *Int J Biol Sci* 10, 1072-1083, doi:10.7150/ijbs.9719 2014 and You, M. et al. TRAIL induces autophagic protein cleavage through caspase activation in melanoma cell lines under arginine deprivation. *Mol Cell Biochem* 374, 181-190, doi:10.1007/s11010-012-1518-1 2013). Knockdown of caspase 2 led to increased autophagy in mouse embryonic fibroblasts (Tiwari, M. et al. A nonapoptotic role for CASP2/caspase 2: modulation of autophagy. *Autophagy* 10, 1054-1070, doi:10.4161/auto.28528 2014 and Tiwari, M., Lopez-Cruzan, M., Morgan, W. W. & Herman, B. Loss of caspase-2-dependent apoptosis induces autophagy after mitochondrial oxidative stress in primary cultures of young adult cortical neurons. *J Biol Chem* 286, 8493-8506, doi:10.1074/jbc.M110.163824 2011). In light of the caspase inhibitors failure to rescue viability of WM266-4 cells, what effect the inhibition of caspases would have on autophagy progress was tested. The autophagy signal was strongest at 24 h in the staining experiment, therefore, this time point was selected. Initially, WM266-4 cells were pre-treated with 10 μM of caspase 8, caspase 6, and pan-caspase inhibitors for 3 h before adding 100 μM 2155-14. Only partial inhibition of lamin A/C cleavage was observed (FIGS. 22A-D) which explains why viability was not rescued by 10 μM caspase inhibitors (FIGS. 17D and 17E). Additionally, there was no significant difference in LC3-II levels between cells pre-treated with 10 μM caspase inhibitors and 2155-14 alone or pre-treated with caspase inhibitors and untreated control (FIGS. 22B and 22D). Therefore, WM266-4 cells were pre-treated with 50 μM of caspase 2, caspase 8, caspase 6, and pan-caspase inhibitors. Cleavage of lamin A/C was almost completely abrogated by 50 μM of caspase-8, caspase 6, and pan-caspase inhibitors, and, to the lesser extent, caspase 2 inhibitor (FIGS. 23A-D). However, there was no significant difference in LC3-II levels between cells pre-treated with caspase inhibitors and 2155-14 alone and a significant difference between cells pre-treated with caspase inhibitors and untreated control (FIGS. 23B and 23D). These results suggest that autophagy initiated by 2155-14 is caspase-independent, while apoptosis is caspase-dependent. Additionally, activation of caspase 3/7 at 24 h of exposure to 2155-14 in the absence of initiator caspase activity is suggestive of alternative mechanism by which caspase 3/7 is activated leading to autophagic cell death.

Caspases were shown to have functions in processes other than cell death (e.g. innate immune response to microbial invasion) (Yi, C. H. & Yuan, J. The Jekyll and Hyde functions of caspases. *Dev Cell* 16, 21-34, doi:10.1016/j.devcel.2008.12.012 2009), therefore, to ascertain that 2155-14-mediated increase of caspase activity leads to apoptosis flow cytometry-based annexin V assays was performed (FIG. 24A-C). Populations of viable, necrotic, early and late apoptotic cells were determined at 4, 24 and 48 h. At 4 h apoptosis was detected only in staurosporine-treated cells (FIG. 24A). At 24 h and 48 h, 18% and 32% of 2155-14-treated cells, respectively, were undergoing late apoptosis consistent with the published hypothesis of the instant inventors (FIGS. 24B and 24C). Early apoptotic and necrotic cells were less than 5% of total population suggesting that 2155-14 causes late apoptosis. In presence of pan-caspase inhibitor Z-VAD-FMK 29% of cells were undergoing late apoptosis at 48 has a result of 2155-14 application suggesting that pan-caspase inhibition did not rescue viability. This is consistent with CellTiter Glo® viability assay results whereby neither of caspase inhibitors was able to rescue viability of WM266-4 cells after treatment with 2155-14 (FIG. 17E). This suggests that despite the early (4 h) increase of activity of caspases 8 and 9 after 2155-14 treatment, they are not the primary drivers of apoptosis. (Note: 2155-14 appeared more potent in CellTiter Glo® viability assay than in Annexin V assay possibly due to the significantly smaller amount of cells used in CellTiter Glo® assay (1,250 cells vs 1,000,000 cells in CellTiter Glo® assay and Annexin V assay, respectively).

Calpains have been shown to activate caspase 3/7 in the absence of initiator caspase activity (Waterhouse, N. J. et al. Calpain activation is upstream of caspases in radiation-induced apoptosis. *Cell Death Differ* 5, 1051-1061, doi: 10.1038/sj.cdd.4400425 1998; Gafni, J., Cong, X., Chen, S. F., Gibson, B. W. & Ellerby, L. M. Calpain-1 cleaves and activates caspase-7. *J Biol Chem* 284, 25441-25449, doi: 10.1074/jbc.M109.038174 2009; and Ruiz-Vela, A., Gonzalez de Buitrago, G. & Martinez, A. C. Implication of calpain in caspase activation during B cell clonal deletion. *EMBO J* 18, 4988-4998, doi:10.1093/emboj/18.18.4988 1999); therefore, WM266-4 cells were tested for calpain activity in the presence of 2155-14 and 2155-18. Calpain activity at 30 min was at the baseline level in the presence of 2155-14, followed by a time-dependent increase of activity at 4 and 24 h (FIGS. 25A-D). This activity profile matches well with the caspase 3/7 activity profile in the presence of 2155-14, suggesting that 2155-14 induced calpain activity leading to the initiator caspase-independent caspase 3/7 activation at 24 h (FIG. 17A). Pre-treatment of WM266-4 cells with broad-spectrum calpain inhibitor III (MDL-28170) and relatively selective calpain-1 inhibitor PD151746 shut down calpain activity induced by 2155-14 at 30 min and 4 h but not at 24 h (FIG. 23A). Interestingly, the combination of 2155-14 and broad-spectrum calpain inhibitor III had an even more pronounced negative effect on viability of cells than either compound alone suggesting synergy (FIGS. 25A-B). In striking contrast, calpain-1 inhibitor PD151746 was able to restore cell viability to ~75% at 24 h and ~50% at 48 h, while at 72 h all cells were dead, which correlated with increased calpain activity (FIG. 25B). Calpain inhibitor III (MDL-28170) is also an inhibitor for cathepsin B, a lysosomal enzyme implicated in melanoma invasiveness, whereas PD151746 does not inhibit cathepsin B, suggesting that activity against cathepsin B could be affecting cell viability in the case of calpain inhibitor III. To test this hypothesis, cathepsin B inhibitor CA074 was used to determine its effect on cell viability and calpain activity in the presence of 2155-14. Application of CA074 resulted in a striking increase (~5-fold) of calpain activity as early as 30 min which persisted at 4 and 24 h (FIG. 25C). The effect on calpain activity correlated with the decrease of viability at 24 h to 25% and resembled the effect of 2155-14 (FIG. 24D) causing time-dependent loss of viability. This result suggested that cathepsin B activity is required to keep calpain activity at basal levels and the 2155-14 effect could be mediated in WM266-4 cells via inhibition of cathepsin B.

Target ID Studies.

To determine the molecular target of 2155-14, the DARTS approach (drug affinity responsive target stability) (Lomenick, B. et al. Target identification using drug affinity responsive target stability (DARTS). *Proc Natl Acad Sci USA* 106, 21984-21989, doi:10.1073/pnas.0910040106 2009 and Lomenick, B., Olsen, R. W. & Huang, J. Identification of direct protein targets of small molecules. *ACS Chem Biol* 6, 34-46, doi:10.1021/cb100294v 2011) was utilized, whereby cell lysates undergo limited digestion with a non-selective proteinase (e.g., pronase) in the presence of a lead compound. (FIG. 26A, DARTS workflow). Proteins that bind the lead present as bands of differential intensity on SDS-PAGE and are identified using proteomic techniques. One differentially hydrolyzed band (FIG. 26B, vertical arrows) was identified suggesting that binding of 2155-14 to the protein represented by the band made it less susceptible to pronase cleavage. Bands from non-treated control and sample treated with 2155-14 were excised, trypsinized, and run on LC/MS/MS. Lamin A/C was the protein with the highest score suggesting the possibility of being the target of 2155-14. In addition to lamin A/C, lamin B2, transketolase (TKT), and cytoskeleton-associated protein 4 (CKAP4) were also identified as possible targets (Table 7 shown in FIG. 27). The exclusive unique peptide counts were too close to make the identification of one over the other with confidence.

In order to confirm results of DARTS experiment, eight analogs of fluorescently-labeled 2155-14 were synthesized in 4 different positions to enable microscopy studies (Table 8 shown in FIGS. 28A-B). The potency of fluorescent analogs against WM266-4 melanoma cells varied from sub-micromolar to greater than 100 µM. The majority of analogs exhibited potency against WM266-4 cells comparable to or better than the parent compound 2155-14 with the exception of 2476-69.2 (FIGS. 29A-D) which did not affect the viability of WM266-4 cells up to 33.3 µM. Interestingly, substitutions in position 4 alone or in combination with position 3 (FIGS. 28A-B) had the most deleterious effect on activity of compounds against melanoma cells, while substitutions in position 3 either alone (FIGS. 28A-B) or in combination with substitution in position 1 and 2 (FIG. 29A, FIG. 28) produced the most potent compounds. Two compounds with substitution in position 3, but varied length of an aliphatic linker, exhibited 10-fold difference in potency (FIGS. 28A-B) suggesting that longer linkers can be explored in this position. The compound with dual substitution in positions 3 and 4 had the lowest activity against WM266-4 cells (FIGS. 28A-B) suggesting that position 4 should not be modified in future SAR studies, while positions 1-3 can tolerate modifications.

To determine whether fluorescently-labeled analogs of 2155-14 induced autophagy as well as the original compound, WM266-4 cells were incubated with the two most potent compounds (2476-67.2 and 2476-66.2, each at 5 µM) with the intention to harvest cells and perform western blotting for LC3. However, a routine trypsin harvesting procedure failed to dissociate cells from the bottom of the flasks (untreated cells dissociated easily in less than 1 min). The increased adherence of cells to the substrate was proposed to be a characteristic of autosis or autophagic cell death (Liu, Y. & Levine, B. Autosis and autophagic cell death: the dark side of autophagy. *Cell Death Differ* 22, 367-376, doi:10.1038/cdd.2014.143 2015 and Liu, Y. et al. Autosis is a Na+,K+-ATPase-regulated form of cell death triggered by autophagy-inducing peptides, starvation, and hypoxia-ischemia. *Proc Natl Acad Sci USA* 110, 20364-20371, doi:10.1073/pnas.1319661110 2013). This experiment was repeated, but instead of using trypsin the cells were scraped off the flasks and lysed. Lamin A/C and LC3 were detected following regular protocol. In contrast to 2155-14, application of 5 µM of both 2476-67.2 and 2476-66.2 lead to a complete degradation of lamin A and β-actin and partial degradation of Lamin C, which resulted in a striking increase of cleaved lamin A/C (FIG. 29B, left blot). Also in contrast to 2155-14, neither of LC3 isoforms nor actin were detected. This suggested that 2476-66.2 and 2476-67.2 cause autophagy much faster than the parent compound 2155-14, therefore, both compounds were re-tested at 2.5 µM. However, no cleavage of lamin A/C or increase of levels of LC3-II was detected (FIG. 29B, right blot and quantification graph) suggesting that the 2.5 µM dose was too low. To overcome this obstacle and to confirm that 2476-67.2 and 2476-66.2 cause autophagy, WM266-4 cells were stained with autophagosome-specific dye (Autophagy 2.0, Cat #ENZ-51031-0050). As can be seen in FIGS. 29C and 29D, application of 2476-67.2 resulted in an intensive green staining of WM266-4, which is statistically significant as compared to the untreated control. All eight fluorescent analogs were used to stain WM266-4 and M14 cells for up to 48 h. However, as early as after 1 h, strong staining of nuclear envelope was observed (FIGS. 30A-J for WM266-4 cells and I-N for M14 cells) suggesting a significant affinity of analogs to the nuclear envelope constituents. Additionally, all analogs stained bead-like intra-nuclear structures (FIG. 30B, red arrows). Diffuse staining of the cytoplasm by 2476-67.2 was also observed. However, 2476-69.2, which was inactive against melanoma cells, also stained the cytoplasm, but not the nuclear envelope (FIG. 30F), suggesting that anti-melanoma activity of 2476-67.2 and 2155-14 is due to the binding to the nuclear envelope and not the cytoplasm. Incubation up to 48 h did not result in a change of staining patterns.

Figure 30K:
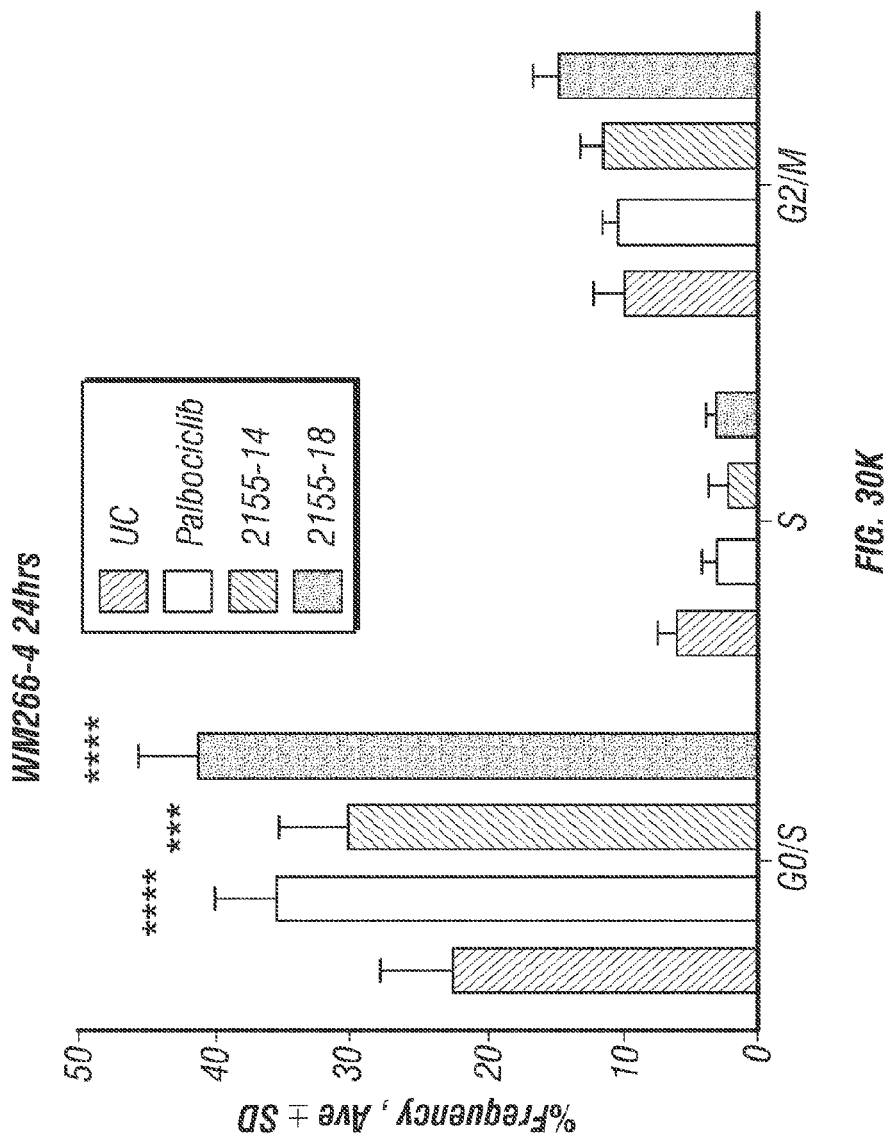

To further corroborate the evidence that the observed specific staining occurs in the nuclear envelope, WM266-4 (FIG. 30C) cells were stained using rabbit monoclonal anti-lamin A/C antibody conjugated to Alexa Fluor® 647 (Abcam ab205770). Cellular localization of anti-lamin A/C antibody staining approximates that of 2476-67.2 in WM266-4 cells (FIG. 30C). Additionally, M14 cells were counterstained with 2476-67.2 (FIGS. 30D-J). As can be seen in FIGS. 23A-D unlike in WM266-4 cells, 2476-67.2 preferentially stains one side of the nuclear membrane, whereas anti-lamin A/C antibody stain is equally distributed around the circumference similar to WM266-4 cells. This suggests differences between 2476-67.2 binding of WM266-4 and M14 cells, however, 2476-67.2 stains nuclear membrane in both WM266-4 and M14 cells suggesting binding of lamin A/C. Lamin A/C is an integral part of nuclear lamina that lines the inner membrane of the nuclear envelope and also forms sub-nuclear structures (Ostresh, J. M., Dorner, B. & Houghten, R. A. Peralkylation. "Libraries from libraries": chemical transformation of synthetic combinatorial libraries. *Methods in molecular biology* 87, 41-49 1998 and Manku, S., Laplante, C., Kopac, D., Chan, T. & Hall, D. G. A mild and general solid-phase method for the synthesis of chiral polyamines. Solution studies on the cleavage of borane-amine intermediates from the reduction of secondary amides. *The Journal of organic chemistry* 66, 874-885 2001), which is consistent with the observed staining pattern by 2476-67.2 suggesting that 2476-67.2 and 2155-14 indeed bind to lamin A/C in the nuclear envelope and in the nucleus. Lamins are important for formation of the mitotic spindle (Kuga, T. et al. Lamin B2 prevents chromosome instability by ensuring proper mitotic chromosome segregation. *Oncogenesis* 3, e94, doi:10.1038/oncsis.2014.6 2014), which could explain the effect of 2155-14 and 2155-18 on the cell cycle (FIG. 30K).

To confirm the results of the DARTS and staining experiments, compound 2155-14 (Table 8, FIG. 28: 2529-1) and analogs of 2155-14 (Table 8, FIG. 28: 2529-3, 2529-5, and 2529-7) biotinylated in positions 1-3 were re-synthesized to enable pulldown studies. Effects of 2155-14 and biotinylated analogs on melanoma cell viability and levels of LC3-II and lamin A/C cleavage were compared to ascertain biotinylation did not result in significance changes of the compounds' biological activities. 2529-1 (re-synthesis of 2155-14) and 2529-7 (analog of 2529-1 biotinylated in position 3, Table 8, FIG. 28) were as potent as 2155-14 in inhibiting the viability of WM266-4 cells ($IC_{50}$=1.5±0.2 µM versus 4±0.5 µM and 3.3±0.5 for 2529-1, 2155-14 and 2529-7, respectively). 100 µM of both 2529-1 and 2529-7 completely inhibited viability of WM266-4 cells after 72 h of treatment. For comparison, 2529-3 and 2529-5 were significantly less potent than 2529-1 and 2529-7 ($IC_{50}$>100 exhibiting maximal inhibition of cell viability of only 42% and 37% at 100 µM at 72 h, respectively. Western blot analysis revealed that biotinylated compounds 2529-3, 2529-5, and 2529-7 had no effect on cleavage of lamin A/C as opposed to non-biotinylated 2155-14/2529-1 (FIGS. 31A-E). Interestingly, only biotinylated 2529-7 demonstrated an effect on LC3-II levels similar to non-biotinylated 2155-14/2529-1 (FIGS. 31B and 31D). This suggested that 2529-7 induces autophagy but not apoptosis at 24 h after exposure, potentially binding targets relevant to induction of autophagy but not apoptosis. Additionally, this explains the significantly lower effect of 2529-3 and 2529-5 on WM266-4 cell viability.

Pulldown of whole cell lysates of WM266-4 and M14 cells was conducted using biotinylated analogs of 2155-14 complexed to the streptavidin agarose beads. Lysates were incubated with beads complexed to biotinylated analogs of 2155-14 for 1 and 24 h. Protein bands found in lanes representing beads complexed to biotinylated analogs of 2155-14 (2529-3, 2529-5, and 2529-7) were compared to control lanes (beads alone, lysate+beads, and non-biotinylated 2155-14/2529-1). Bands occurring in both control and sample lanes were not pursued any further. As evidenced by SDS-PAGE gels (FIGS. 32A-D), four specific bands (occurring only in 2529-3, 2529-5 and/or 2529-7 treatment lanes) were found in lysates of WM266-4 and M14 cells incubated for 24 h. Interestingly, bands 2-4 were also found in WM266-4 lysate incubated for 1 h with beads complexed to biotinylated analogs of 2155-14, while band 1 was absent suggesting slower binding. In addition to four specific bands found only in lanes for 2529-3, 2529-5, and 2529-7, treatment with non-biotinylated 2155-14/2529-1 resulted in two bands that were not found in any other lane (FIG. 32C, bands 5 and 6). However, bands 5 and 6 did not appear in the repeat of this experiment and were not further pursued (data not shown). The pulldown experiment was repeated for 24 h incubation of lysate and beads complexed to 2529-7. The same 4 specific bands were found (FIG. 32D).

Proteomic analysis of bands 1-4 revealed that top hits were ATP-dependent RNA helicase DDX1 (band 1, accession #Q92499), heterogeneous nuclear ribonucleoprotein H2 (band 2, hnRNP H2, accession #P55795), and heterogeneous nuclear ribonucleoprotein A2/B1 (bands 3 and 4, hnRNP A2/B1, accession #P22626) (Table 9, FIG. 33). Heterogeneous nuclear ribonucleoprotein A2 is a shorter isoform of canonical heterogeneous nuclear ribonucleoprotein B1 lacking residues 3-14 as compared to the canonical sequence. The lack of coverage in 3-14 amino acid region in band 4 as compared to band 3 further corroborates this hypothesis (FIG. 34A). This data suggested that band 3 (FIG. 32A) is the nuclear ribonucleoprotein B1, while band 4 is likely a heterogeneous nuclear ribonucleoprotein A2. Surprisingly, none of the potential targets was identified as lamin A/C, which could be attributable to the presence of biotin potentially blocking interaction between the biotinylated analog of 2155-14 and lamin A/C.

To confirm the identity of proteins from the proteomic experiments, western blot analysis of the pulldown SDS-PAGE gel was performed. The identity of DDX1 using a monoclonal antibody was confirmed (FIGS. 35A-F, top strip, predicted MW of 82 kDa) in case of 2529-7 treatment, but not 2529-3 treatment. Surprisingly, in the case of hnRNP H2, two bands in both 2529-3 and 2529-7 treatment lanes were detected (FIG. 35A, middle strip). Due to the lack of commercially available monoclonal antibodies for hnRNP H2, a polyclonal antibody raised to the region 311-340 of hnRNP H2 was utilized. This region is found in several proteins from hnRNP family, including hnRNP H1, which was the second highest scored protein after hnRNP H2 identified in band 2 of the proteomics experiment (Table 9, FIG. 33). ClustalW alignment showed that hnRNP H1 and H2 shared 96% amino acid identity based on the total sequence. Additionally, 29 out 30 amino acids in the antigen region (311-340) were identical indicating that the proteomics approach was not capable of resolving these proteins and 2155-14 could be interacting with both proteins. Interestingly, hnRNP H2 bands in the 2529-3 lane were much less abundant despite similar intensity in the input lanes suggesting that interactions between hnRNP H2 and 2529-3 are weaker than between hnRNP H2 and 2529-7. This could be the reason for lower activity of 2529-3 against melanoma cells compared with 2529-7. Application of hnRNP A1/B2 monoclonal antibody revealed three bands in the 2529-7 treatment lane, but no bands were found in the 2529-3 treatment lane suggesting a selective binding of 2529-7 to hnRNP A2/B1. As mentioned above, band 3 in the SDS-PAGE can be attributable to hnRNP B1, while band 4 is likely an hnRNP A2 isoform. An appearance of the third band is, therefore, unexpected and could be suggestive of binding of 2529-7 to a protein which was not detected by LC-MS/MS.

To determine if genomic modulation of DDX1, hnRNP H2, and hnRNP A2/B1 recapitulated the effects of administration of 2155-14, siRNA knockdown experiments were conducted. The concentration of siRNAs necessary to achieve complete knockdown was found to be 25 nM for DDX1 and hnRNP H2 and 50 nM for hnRNP A2/B1 (FIG. 36). WM266-4 cells were transfected with above mentioned siRNA concentrations (FIG. 35B) and the effect of knockdown on cell viability, LC3-II, and cleaved lamin A/C levels determined. After 24 h of transfection there was no significant effect on cell viability while at 48 and 72 h cells, in the presence of all three siRNAs and combinations thereof, were only ~25% viable as compared to untreated control cells (FIGS. 35C-E). This gradual loss of viability was reminiscent of a similar effect in the presence of 2155-14 (FIG. 35F) and thus siRNA treatment appeared to mimic the effects of administration of 2155-14. Surprisingly, only hnRNPH2 siRNA resulted in an increase of LC3-II levels (FIGS. 37A-F) suggesting that binding of 2155-14 to hnRNPH2, but not hnRNPA2/B1 or DDX1, leads to the potentiation of autophagy. Levels of cleaved lamin A/C were statistically significantly increased only in the presence of combination of all three siRNAs (FIGS. 37I and 37J), suggesting that binding to all three target proteins by 2155-14 results in the lamin A/C cleavage. Additionally, WM266-4 cells treated with hnRNPH2 siRNA stained positive at levels similar to 2155-14 when autophagosome dye was used confirming that hnRNPH2 modulation can potentially lead to autophagy induction (FIGS. 37K and 37L).

To address the lack of interaction between 2529-7 and lamin A/C, the DARTS experiment was repeated in which WM266-4 lysates were digested in the presence and absence of 2155-14 and probed with antibodies for lamin A/C, hnRNPH2, hnRNPA2/B1, and DDX1 (FIGS. 38A-F). Lamin A/C, hnRNPH2, hnRNPA2/B1, and DDX1 are present at higher concentrations in fractions of lysates treated with non-biotinylated 2155-14 (FIGS. 38B-D) indicating that 2155-14 protects these proteins from pronase proteolysis. This, in turn, confirms that 2155-14 interacts with all four proteins and the lack of lamin A/C interaction in the case of 2529-7 is indeed due to the presence of biotin.

Discussion

The experiments described herein identify lamin A/C, DDX1, hnRNP H2, and hnRNP A2/B1 as targets of an anti-melanoma compound 2155-14. hnRNP H2 and hnRNP A2/B1 are involved in mRNA splicing, export and stability (Geuens, T., Bouhy, D. & Timmerman, V. The hnRNP family: insights into their role in health and disease. *Hum Genet* 135, 851-867, doi:10.1007/s00439-016-1683-5 2016), while helicase DDX1 is involved in RNA unwinding (Chen, H. C., Lin, W. C., Tsay, Y. G., Lee, S. C. & Chang, C. J. An RNA helicase, DDX1, interacting with poly(A) RNA and heterogeneous nuclear ribonucleoprotein K. *J Biol Chem* 277, 40403-40409, doi:10.1074/jbc.M206981200 2002) and tRNA splicing (Popow, J., Jurkin, J., Schleiffer, A. & Martinez, J. Analysis of orthologous groups reveals archease and DDX1 as tRNA splicing factors. *Nature* 511, 104-107, doi:10.1038/nature13284 2014) and is known to interact with another ribonuclear protein, hnRNP K. DDX1, hnRNP H2, and hnRNP A2/B1 are known constituents of multi-protein spliceosomal complexes (Sharma, S., Kohlstaedt, L. A., Damianov, A., Rio, D. C. & Black, D. L. Polypyrimidine tract binding protein controls the transition from exon definition to an intron defined spliceosome. *Nat Struct Mol Biol* 15, 183-191, doi:10.1038/nsmb.1375 2008) suggesting that DDX1 and hnRNPA2/B1 could potentially form a complex with hnRNPH2 (as a precedence, hnRNPK is known to modulate autophagy[86] and interact with DDX1[87]), which explains co-precipitation of all 3 spliceosomal proteins with 2529-7. Binding of all 3 proteins is potentially needed to have an effect on autophagy which explains why individual knockdowns of DDX1 and hnRNPA2/B1 did not lead to autophagy and why binding of only hnRNPH2 by 2529-3 did not have the same effect. Lamin A/C is an integral part of nuclear lamina that lines inner membrane of the nuclear envelope and also forms sub-nuclear structures. Interestingly, lamin A/C was shown to interact with spliceosomal protein hnRNPE1 (Zhong, N., Radu, G., Ju, W. & Brown, W. T. Novel progerin-interactive partner proteins hnRNP E1, EGF, Mel 18, and UBC9 interact with lamin A/C. *Biochem Biophys Res Commun* 338, 855-861, doi:10.1016/j.bbrc.2005.10.020 2005) suggesting potential interaction between lamin A/C and DDX1, hnRNPH2 and hnRNPA2/B1 raising the possibility of 2155-14 interacting with all four proteins in the same location. No prior studies have connected the protein targets of 2155-14 to melanoma progression, suggesting they could be novel targets for melanoma drug discovery. Future studies will ascertain which targets or combination of targets can be engaged for drug discovery. Also, there has been no reports of small molecules that can bind to any of the proteins identified herein, therefore 2155-14 is a "first-in-class" compound. Based on these considerations, individual probes for each protein will need to be developed to assess the effects of binding to a single protein as opposed to binding to a tertiary (DDX1/hnRNPA2/B1/hnRNPH2) or quaternary (DDX1/hnRNPA2/B1/hnRNPH2/lamin A/C) complex. Knockdown of lamin A/C in MDA-MB-231 and MDA-MB-468 cells reduced nuclear rigidity and resistance to fluid shear stress (FSS) and lead to apoptosis (Mitchell, M. J. et al. Lamin A/C deficiency reduces circulating tumor cell resistance to fluid shear stress. *American journal of physiology. Cell physiology* 309, C736-746, doi:10.1152/ajpce11.00050.2015 2015).

In several prostate cancer cell lines lamin A/C was overexpressed and shRNA knockdown lead to inhibition of cell growth, colony formation, migration, and invasion (Kong, L. et al. Lamin A/C protein is overexpressed in tissue-invading prostate cancer and promotes prostate cancer cell growth, migration and invasion through the PI3K/AKT/PTEN pathway. *Carcinogenesis* 33, 751-759, doi:10.1093/carcin/bgs022 2012) suggesting that binding of 2155-14 to lamin A/C could be inducing cell death. hnRNP A2/B1 was shown to be present in G361 melanoma cells due to the reactivity to the patient's serum sample (Suzuki, A. et al. Identification of melanoma antigens using a Serological Proteome Approach (SERPA). *Cancer genomics & proteomics* 7, 17-23 2010) suggesting a presence of antibodies to hnRNP A2/B1. hnRNP A2/B1 mRNA was also overexpressed in G361 melanoma cells as compared to melanocytes. hnRNP H1/H2 was shown to be responsible for drug resistance to capecitabine due to aberrant splicing of thymidine phosphorylase mRNA in monocytic/macrophage leukemia cell lines THP-1 and U937 (Stark, M., Bram, E. E., Akerman, M., Mandel-Gutfreund, Y. & Assaraf, Y. G. Heterogeneous nuclear ribonucleoprotein H1/H2-dependent unsplicing of thymidine phosphorylase results in anticancer drug resistance. *J Biol Chem* 286, 3741-3754, doi:10.1074/jbc.M110.163444 2011).

All of the protein targets identified in the experiments described herein participate in multi-component complexes and, therefore, are involved in many processes. For example, numerous oncogenes were shown to be direct targets of hnRNPs, indicating their importance in cancer development (Jean-Philippe, J., Paz, S. & Caputi, M. hnRNP A1: the Swiss army knife of gene expression. *International journal of molecular sciences* 14, 18999-19024, doi:10.3390/ijms140918999 2013). At this stage it is not possible to ascertain the exact process affected by the binding of 2155-14 to these proteins. However, based on the autophagy-mediated death of WM266-4 and M14 cells it is likely that binding of 2155-14 results in interference with protein translation which is known to induce autophagy in melanoma (Chen, W. L., Pan, L., Kinghorn, A. D., Swanson, S. M. & Burdette, J. E. Silvestrol induces early autophagy and apoptosis in human melanoma cells. *BMC cancer* 16, 17, doi:10.1186/s12885-015-1988-0 2016). hnRNP K, a known binding partner of DDX1, was shown to regulate autophagy and was upregulated in acute myeloid leukemia cells derived from non-remission patients (Zhang, J. et al. HnRNP K contributes to drug resistance in acute myeloid leukemia through the regulation of autophagy. *Experimental hematology* 44, 850-856, doi:10.1016/j.exphem.2016.04.014 2016). In this context, an increase of LC3-II levels as a result of genomic modulation of hnRNPH2 is certainly very interesting. hnRNP H2 has never been shown to regulate autophagy; therefore, future studies of its connection to autophagy and potential to drive cell death could lead to a novel approach to melanoma drug discovery. Mechanistically, binding of quercetin to hnRNP A1 was shown to prevent its shuttling between the nucleus and cytoplasm leading to apoptotic cell death of PC-3 cells with 100 μM $IC_{50}$ (Nara, H. et al. Thieno[2,3-d]pyrimidine-2-carboxamides bearing a carboxybenzene group at 5-position: Highly potent, selective, and orally available MMP-13 inhibitors interacting with the S1" binding site. *Bioorg. Med. Chem.*, in press 2014).

A nanoparticle-conjugated aptamer specific to hnRNP A2/B1 was able to inhibit proliferation of multiple cancer cell lines (Li, H. et al. Nanoparticle-conjugated aptamer targeting hnRNP A2/B1 can recognize multiple tumor cells and inhibit their proliferation. *Biomaterials* 63, 168-176, doi:10.1016/j.biomaterials.2015.06.013 2015). This evidence in combination with our results suggests 2155-14 represents a lead for future optimization studies targeting lamin A/C, DDX1, hnRNP H2, and hnRNP A2/B1 binding.

Both siRNA and 2155-14 treatment resulted in a gradual time-dependent loss of viability consistent with late onset activation of caspase 3/7 at 24 h after 2155-14 addition. Modulation of nuclear proteins could generally lead to slower cell death, as compared to fast apoptosis-inducing drugs, which could allow for autophagy to take its course resulting in degradation of intracellular proteins and organelles. This, in turn, could lead to smaller amounts of intracellular proteins being released into the patients' bloodstream upon cell death resulting in fewer immunogenic effects. Despite binding to multiple molecular targets, the described probe exhibited selectivity for melanoma cell lines while sparing multiple other cancer and non-malignant cell lines. Interestingly, binding of hnRNP A2/B1 and HSP90 by natural product phenanthrene-based tylophorine derivative-1 (PBT-1) had potent activity against lung cancer and no overt toxicity (Chen, C. Y. et al. The antitumor agent PBT-1 directly targets HSP90 and hnRNP A2/B1 and inhibits lung adenocarcinoma growth and metastasis. *Journal of medicinal chemistry* 57, 677-685, doi:10.1021/jm401686b 2014) suggesting that binding of multiple targets in cancer cells can be well tolerated. Moreover, it was proposed that polypharmacology of anti-cancer agents can be advantageous in preventing of drug resistance (Medina-Franco, J. L., Giulianotti, M. A., Welmaker, G. S. & Houghten, R. A. Shifting from the single to the multitarget paradigm in drug discovery. *Drug Discov Today* 18, 495-501, doi:10.1016/j.drudis.2013.01.008 2013 and Paolini, G. V., Shapland, R. H., van Hoorn, W. P., Mason, J. S. & Hopkins, A. L. Global mapping of pharmacological space. *Nat Biotechnol* 24, 805-815,10.1038/nbt1228 2006) common for single or even dual target melanoma drugs. The mechanisms of mRNA processing and nuclear envelope composition are believed to be well-conserved between different cell types and it is not immediately clear why 2155-14 does not inhibit viability of non-melanoma cancer cells or non-malignant cells. One possible explanation is that 2155-14 binds to a different set of targets in other cell types as compared to melanoma. This hypothesis is supported by the data demonstrating that binding of 2529-3 to just hnRNP H2 does not affect melanoma cell viability as much as binding of 2529-7 to three different targets. Further investigation of the molecular basis of this selectivity can improve understanding of melanoma cell biology and lead to the drugs with decreased toxicity as compared to the existing therapies.

Mechanistic investigation showed that probe 2155-14 potentiates basal autophagy leading to melanoma cell death in BRAF and NRAS mutated melanoma cells indicating that this can be a novel approach to a much needed broad-spectrum melanoma therapy. The precise mechanism by which increased autophagy progresses to the cell death has not been investigated in melanoma. Both autophagy and caspase inhibitors failed to prevent loss of viability of WM266-4 cells, and therefore it is not clear whether cells treated with 2155-14 die via apoptotic or autophagic pathway. Caspase inhibitors were able to completely inhibit cleavage of lamin A/C, but not the increase of LC3-II and they did not rescue cell viability suggesting that caspase activity might not be necessary to drive 2155-14-mediated cell death. Interestingly, a biotinylated analog of 2155-14, 2529-7, did not induce cleavage of lamin A/C, but increased levels of LC3-II leading to the WM266-4 cell death with potency similar to 2155-14 ($IC_{50}$=4±0.5 μM and 3.3±0.5 μM for 2155-14 and 2529-7, respectively) supporting the hypothesis that both apoptotic and autophagic cell death mechanisms are inacted. Cell viability loss was only slowed down by calpain μ-selective inhibitor PD151746 suggesting its role in the regulation of autophagy-driven cell death. Colunga et al. (Colunga, A., Bollino, D., Schech, A. & Aurelian, L. Calpain-dependent clearance of the autophagy protein p62/SQSTM1 is a contributor to DeltaPK oncolytic activity in melanoma. *Gene therapy* 21, 371-378, doi: 10.1038/gt.2014.6 2014) showed that calpain activation in melanoma 3D culture can lead to inhibition of growth which was restored by calpain-specific inhibitor PD150606 but not by pan-caspase inhibitor Z-VAD-FMK, which is in agreement with the described data. Interestingly, PD150606 also restored expression of p62, a marker of autophagy, suggesting a complex role of calpain in regulation of autophagy in melanoma. Additionally, calpains were shown to affect mitochondrial membrane potential (Wales, S. Q., Laing, J. M., Chen, L. & Aurelian, L. ICP10PK inhibits calpain-dependent release of apoptosis-inducing factor and programmed cell death in response to the toxin MPP+. *Gene therapy* 15, 1397-1409, doi:10.1038/gt.2008.88 2008), which could explain the effect of 2155-14 on mitochondrial potential. Inhibition of calpain μ activity was overcome after 24 h of co-application with 2155-14, which lead to the time-dependent loss of viability. This could be due to either a dose-limiting effect of calpain μ inhibitor PD150606 or its inability to completely block the processes initiated by 2155-14. Overall, it appears that apoptosis caused by 2155-14 and 2155-18 is initiated by calpain I (i.e. calpain μ) and executed by caspase 3/7, however, inability of calpain inhibitors to prevent cell death suggests that apoptosis is not the only cause of loss of cell viability.

Inability of autophagy, caspase, and calpain inhibitors to prevent cell death after exposure to 2155-14 suggests a contribution of another type of cell death different from autophagy-driven caspase-dependent apoptosis, for example, an autosis. An actual autophagic cell death due to excessive uncontrollable autophagy (sometimes referred to as autosis (Munoz-Pinedo, C. & Martin, S. J. Autosis: a new addition to the cell death Tower of Babel. *Cell death &disease* 5, e1319, doi:10.1038/cddis.2014.246 2014), which has no known morphological or molecular markers, is a poorly studied controversial subject (Lin, L. & Baehrecke, E. H. Autophagy, cell death, and cancer. *Molecular &cellular oncology* 2, e985913, doi:10.4161/23723556.2014.985913 2015). However, it cannot be completely discarded at this stage; therefore, further studies are needed to understand the type of cell death caused by 2155-14 and its molecular underpinnings. Data presented herein shows that the biotinylated analog of 2155-14, 2529-7, induces autophagy and causes cell death in the absence of cleavage of lamin A/C and supports this hypothesis.

Based on the findings described herein and literature evidence, it is hypothesized that binding of spliceosome by 2155-14 leads to the cell death occurring by two independent mechanisms: apoptosis and autosis (FIG. 39).

Proposed mechanism of action of 2155-14 (FIG. 39) (1) Binding of spliceosome leads to the increase of activity of caspase 8 and 9 as early as 30 min after addition of 2155-14 (FIGS. 17A-E2); (2) Caspase 6 is activated by caspase 8 (Mintzer, R. et al. A whole cell assay to measure caspase-6 activity by detecting cleavage of lamin A/C. *PLoS One* 7, e30376, doi:10.1371/journal.pone.0030376 2012); (3) Caspase 6 cleaves lamin A/C (FIGS. 22A-D, caspase 6, 8 and pan-caspase inhibitors shut down lamin A/C cleavage). Lamin A/C cleavage is both marker and a committed step of apoptosis; (4) Calpain I/II activity increases 4-24 hours after 2155-14 addition (FIGS. 24A-C) leading to (5) activation of caspase 3/7 at 24 hours after 2155-14 addition (FIG. 17A) and (6) apoptosis (Annexin V, FIGS. 23A-D), and a collateral loss of activity of caspases 8 and 9 (FIGS. 17A-E), with possible contributions to the potentiation of basal autophagy and decrease of mitochondrial potential (FIGS. 19A-E). (7) Calpain inhibitors could not fully rescue viability suggesting their tangential involvement into the control of the autophagy process induced by 2155-14. Alternative pathway of (8) autophagy induction can be hypothesized to be based on the pleiotropic effects of interference with mRNA maturation and protein translation as the result of spliceosome binding leading to uncontrollable cell death via (9) autosis (based on inability of trypsin to detach dansyl analog-treated WM266-4 cells from TC flask combined with ability of dansyl analog to induce autophagy, FIG. 26).

Experimental Procedures

Synthetic Protocols

General synthesis procedure for pyrrolidine-bis-diketopiperazines and tagged analogs (FIGS. 40, 41 dansyl tag, and 42 biotin tag). All compounds were synthesized via solid-phase methodology on 4-methylbenzhydrylamine hydroch oride resin (MBHA) (1.2 mmol/g, 100-200 mesh) using the "tea-bag" approach (Houghten, R. A. General method for the rapid solid-phase synthesis of large numbers of peptides: specificity of antigen-antibody interaction at the level of individual amino acids. *Proc Natl Acad Sci USA* 82, 5131-5135 1985) with some modifications to the method previously described elsewhere (Pinilla, C. et al. Selective agonists and antagonists of formylpeptide receptors: duplex flow cytometry and mixture-based positional scanning libraries. *Mol Pharmacol* 84, 314-324, doi:10.1124/mol.113.086595 2013). Boc- and Fmoc-amino acids were coupled utilizing standard coupling procedures (6 equiv) with hydroxybenzotriazole hydrate (HOBt, 6 equiv), and N,N'-diisopropylcarbodiimide (DIC, 6 equiv) in dimethylformamide (DMF, 0.1 M) for 120 min. Boc protecting groups were removed with 55% trifluoroacetic acid (TFA)/45% dichloromethane (DCM) (1×, 30 min) and subsequently neutralized with 5% diisopropylethylamine (DIEA)/95% DCM (3×, 2 min). Fmoc protecting groups were removed with 20% piperidine/80% DMF (2×, 30 min). Carboxylic acids were coupled utilizing standard coupling procedures (10 equiv) with HOBt (10 equiv) and DIC (10 equiv) in DMF (0.1 M) for 120 min. Trityl protection was carried out by neutralizing bags with 5% DIEA/95% DCM (3×, 2 min), treating bags with triphenylmethyl chloride (Trt-Cl, 5 equiv) and DIEA (10 equiv) in 10% DMF/90% DCM (0.1 M) for 2 h, neutralizing bags again (3×, 2 min), and repeating Trt-Cl treatment (18 h). The trityl group was removed by washing with a solution of 2% TFA/5% triisopropylsilane (TIS)/93% DCM (3×, 2 min). Biotin was coupled utilizing standard coupling procedures (10 equiv) with DIC (10 equiv) in DMF (0.1 M) for 120 min. Dansyl chloride was coupled utilizing (10 equiv) with DIEA (10 equiv) in DMF (0.1 M) for 120 min. Completion of all couplings was monitored with a ninhydrin test. Compounds were reduced to polyamines using a 40× excess of borane (1.0 M in tetrahydrofuran (THF)) over each amide bond in a glass vessel under nitrogen at 65° C. for 72 h. The solution was then poured off, the reaction was quenched with methanol (MeOH), and the bags were washed with THF (1×, 1 min) and MeOH (4×, 1 min) and allowed to air dry. Once dry, the bags were treated with piperidine overnight at 65° C. in a glass vessel. The solution was poured off, and the bags were washed with DMF (2×, 1 min), DCM (2×, 1 min), MeOH (1×, 1 min), DMF (2×, 1 min), DCM (2×, 1 min), and MeOH (1×, 1 min), and allowed to air dry. Completion of reduction was checked by cleaving a control sample and analyzing using LC-MS. As previously reported by the inventor's group and others the reduction of polyamides with borane is free of racemization (Nefzi, A. O., J. M.; Houghten, R. A. Parallel solid phase synthesis of tetrasubstituted diethylenetriamines via selective amide alkylation and exhaustive reduction of N-acylated dipeptides. *Tetrahedron* 55, 335-344 1999). Diketopiperazine cyclization was performed under anhydrous conditions (<22% humidity). The dry bags were washed with anhydrous DMF (2×, 1 min), then added to a solution of 1,1'-oxalyldiimidazole (5 fold excess for each cyclization site) in anhydrous DMF (0.1 M) and shaken at room temperature overnight. The solution was poured off and the bags were rinsed with DMF (3×, 1 min) and DCM (3×, 1 min). Completion of cyclization was checked by cleaving a control sample and analyzing by LC-MS. The compounds were then cleaved from the resin with hydrofluoric acid (HF) in the presence of anisole in an ice bath at 0° C. for 90 min and extracted using 95% acetic acid (AcOH)/5% $H_2O$ (2×, 5 mL). Final crude products were purified using HPLC as described below. All chirality was generated from the corresponding amino acids.

Compound Purification and Characterization.

The final compounds were purified using preparative HPLC with a dual pump Shimadzu LC-20AB system equipped with a Luna C18 preparative column (21.5×150 mm, 5 micron) at λ=214 nm, with a mobile phase of (A) $H_2O$ (+0.1% formic acid)/(B) acetonitrile (ACN) (+0.1% formic acid) at a flow rate of 13 mL/min; gradients varied by compound based on hydrophobicity. $^1$H NMR and $^{13}$C NMR spectra were recorded in DMSO-d6 on a Bruker Ascend 400 MHz spectrometer at 400.14 and 100.62 MHz, respectively, and MALDI-TOF mass spectra were recorded using an Applied Biosystems Voyager DE-PRO Biospectrometry workstation. The purities of synthesized compounds were confirmed to be greater than 95% by liquid chromatography and mass spectrometry on a Shimadzu LCMS-2010 instrument with ESI Mass Spec and SPD-20A Liquid Chromatograph with a mobile phase of (A) $H_2O$ (+0.1% formic acid)/(B) ACN (+0.1% formic acid) (5-95% over 6 min with a 4 min rinse).

FIGS. 43A-B (S)-1 ((R)-1 ((S)-2-(((S)-6-benzyl-2,3-dioxopiperazin-1-yl)methyl)pyrrolidin-1-yl)-3-cyclohexylpropan-2-yl)-5-(4-hydroxybenzyl)-4-phenethylpiperazine-2,3-dione Using General Scheme: FIG. 40 for the synthesis of bis-cyclic diketopiperazines compounds 2155-14 and 2529-1 were synthesized using the following reagents: (2 g) MBHA resin starting material, Boc-L-Phenylalanine-OH ($R_1$), Boc-D-Cyclohexylalanine-OH ($R_2$), Boc-L-Tyrosine (2-Br—Z)—OH ($R_3$), and Phenylacetic Acid ($R_4$). The final crude product was purified using HPLC as described above, with a gradient of (B) 0/5, 2/5, 4/20, 40/55. Isolated Mass 504.2 mg, % yield 28.62%.

$^1$H NMR (400 MHz, DMSO-d6) δ ppm 0.80-1.05 (m, 2H) 1.08-1.20 (m, 3H) 1.24 (br. s., 2H) 1.50-1.71 (m, 6H) 1.78-1.96 (m, 2H) 1.97-2.13 (m, 2H) 2.55-2.65 (m, 2H) 2.67-2.88 (m, 6H) 2.90-3.04 (m, 3H) 3.11 (d, J=12.96 Hz, 1H) 3.19-3.32 (m, 2H) 3.37 (br. s., 1H) 3.52 (dd, J=13.08, 3.30 Hz, 2H) 3.65 (d, J=10.03 Hz, 2H) 3.70-3.94 (m, 2H) 6.73 (m, J=8.07 Hz, 2H) 7.01 (m, J=8.07 Hz, 2H) 7.15-7.31 (m, 9H) 8.50 (d, J=5.01 Hz, 1H) $^{13}$C NMR (101 MHz, DMSO-d6) δ ppm 22.74 (s, 1C) 26.13 (s, 1C) 26.30 (s, 1C) 26.56 (s, 1C) 29.54 (s, 1C) 32.83 (s, 1C) 33.55 (s, 1C) 33.63 (s, 1C) 34.51 (s, 1C) 37.14 (s, 1C) 37.51 (s, 1C) 39.40 (s, 1C) 39.61 (s, 1C) 39.82 (s, 1C) 40.03 (s, 1C) 40.23 (s, 1C) 40.45 (s, 1C) 40.66 (s, 1C) 48.41 (s, 1C) 55.86 (s, 1C) 58.51 (s, 1C) 62.76 (s, 1C) 115.89 (s, 1C) 126.79 (s, 1C) 127.11 (s, 1C) 127.76 (s, 1C) 128.81 (s, 1C) 128.98 (s, 1C) 129.13 (s, 1C) 129.77 (s, 1C) 130.35 (s, 1C) 137.72 (s, 1C) 139.29 (s, 1C) 156.65 (s, 1C) 156.72 (s, 1C) 157.34 (s, 1C) 157.80 (s, 1C) 157.95 (s, 1C) m/z calcd $C_{44}H_{55}N_5O_5$ $[M+H]^+$ 734.42, found 734.15 (MALDI), 734.15 (MS ESI) Purity LCMS: 99.0% (254 nm, peak height).

FIGS. 44A-C

N-(4-((S)-1-(((S)-1-((R)-3-cyclohexyl-2-((S)-5-(4-hydroxybenzyl)-2,3-dioxo-4-phenethylpiperazin-1-yl)propyl)pyrrolidin-2-yl)methyl)-5,6-dioxopiperazin-2-yl)butyl)-5-(dimethylamino)naphthalene-1-sulfonamide Using the scheme of FIG. 41 for the synthesis of Dansyl tagged pyrrollidine-bis-diketopiperazines compound 2476-66 was synthesized using the following reagents: (100 mg) MBHA resin starting material, Boc-L-Lysine(Fmoc)-OH ($R_1$), Boc-D-Cyclohexylalanine-OH ($R_2$), Boc-L-Tyrosine (2-Br—Z)—OH ($R_3$), and Phenylacetic Acid ($R_4$). The final crude product was purified using HPLC as described above, with a gradient of (B) 0/5, 2/5, 4/20, 40/55. Isolated Mass 1.5 mg % yield 1.31%

$^1$H NMR (400 MHz, DMSO-d6) δ ppm 8.46 (br. s., 2H) 8.30 (d, J=9.17 Hz, 1H) 7.58 (br. s., 1H) 7.22 (br. s., 2H) 7.08-7.18 (m, 2H) 6.96 (d, J=9.29 Hz, 2H) 6.77 (br. s., 2H) 6.71 (br. s., 2H) 3.73 (br. s., 2H) 3.67 (d, J=11.25 Hz, 1H) 3.59 (br. s., 1H) 3.49 (s, 3H) 3.52 (s, 2H) 3.11 (s, 3H) 3.14 (s, 4H) 3.05 (br. s., 1H) 2.97 (br. s., 1H) 2.79-2.91 (m, 5H) 2.75 (br. s., 3H) 2.67 (br. s., 6H) 2.33 (br. s., 1H) 1.97-2.21 (m, 2H) 1.89 (d, J=12.72 Hz, 1H) 1.81 (br. s., 1H) 1.63 (d, J=13.33 Hz, 4H) 1.51 (br. s., 1H) 1.43 (br. s., 2H) 1.29 (br. s., 3H) 1.16 (br. s., 4H) 0.91 (d, J=19.68 Hz, 2H) m/z calcd C53H69N707S $[M+H]^+$ 948.50, found 474.80 (MS ESI) Purity LCMS: 96.0% (254 nm, peak height).

FIGS. 45A-B

N—((S)-6-((S)-2-(((S)-6-benzyl-2,3-dioxopiperazin-1-yl)methyl)pyrrolidin-1-yl)-5-((S)-5-(4-hydroxybenzyl)-2,3-dioxo-4-phenethylpiperazin-1-yl)hexyl)-5-(dimethylamino)naphthalene-1-sulfonamide Using the scheme shown in FIG. 41 for the synthesis of Dansyl tagged pyrrollidine-bis-diketopiperazines compound 2476-66.2 was synthesized using the following reagents: (100 mg) MBHA resin starting material, Boc-L-Phenylalanine-OH ($R_1$), Boc-L-Lysine(Fmoc)-OH ($R_2$), Boc-L-Tyrosine(2-Br—Z)—OH ($R_3$), and Phenylacetic Acid ($R_4$). The final crude product was purified using HPLC as described above, with a gradient of (B) 0/5, 2/5, 4/20, 40/55. Isolated Mass 1.6 mg % yield 1.41%

$^1$H NMR (400 MHz, DMSO-d6) δ ppm 8.42-8.56 (m, 2H) 8.31 (d, J=8.80 Hz, 1H) 7.55-7.64 (m, 1H) 7.22 (s, 2H) 7.26 (s, 2H) 7.16 (br. s., 3H) 6.98 (s, 2H) 7.01 (s, 1H) 6.88 (br. s., 1H) 6.74 (d, J=5.01 Hz, 2H) 4.26 (br. s., 1H) 3.67-3.91 (m, 2H) 3.58 (br. s., 2H) 3.42 (br. s., 4H) 2.96 (br. s., 2H) 2.88 (br. s., 3H) 2.82 (br. s., 6H) 2.52-2.78 (m, 12H) 2.12 (br. s., 2H) 1.74 (br. s., 1H) 1.64 (br. s., 1H) 1.54 (br. s., 2H) 1.25 (br. s., 1H) 1.16 (br. s., 1H) 1.09 (br. s., 1H) 0.91 (br. s., 2H) m/z calcd $C_{53}H_{63}N_7O_7S$ [M+H]$^+$ 942.46, found 471.75 (MS ESI) Purity LCMS: 99.0% (254 nm, peak height).

FIGS. 46A-B

N-(4-((S)-4-((R)-1-((S)-2-(((S)-6-benzyl-2,3-dioxopiperazin-1-yl)methyl)pyrrolidin-1-yl)-3-cyclohexylpropan-2-yl)-5,6-dioxo-1-phenethylpiperazin-2-yl)butyl)-5-(dimethylamino)naphthalene-1-sulfonamide Using the scheme shown in FIG. 41 for the synthesis of Dansyl tagged pyrrolidine-bis-diketopiperazines compound 2476-67 was synthesized using the following reagents: (100 mg) MBHA resin starting material, Boc-L-Phenylalanine-OH ($R_1$), Boc-D-Cyclohexylalanine-OH ($R_2$), Boc-L-Lysine(Fmoc)-OH ($R_3$), and Phenylacetic Acid ($R_4$). The final crude product was purified using HPLC as described above, with a gradient of (B) 0/5, 2/5, 4/20, 40/55. Isolated Mass 8.4 mg % yield 7.51%

$^1$H NMR (400 MHz, DMSO-d6) δ ppm 8.42-8.53 (m, 2H) 8.29-8.40 (m, 1H) 8.10 (d, J=6.48 Hz, 1H) 7.87 (br. s., 1H) 7.59 (q, J=9.37 Hz, 2H) 7.18-7.35 (m, 10H) 4.59 (br. s., 1H) 3.84 (br. s., 1H) 3.65-3.79 (m, 2H) 3.54 (d, J=13.08 Hz, 3H) 3.07-3.25 (m, 5H) 2.90-3.04 (m, 3H) 2.83 (br. s., 10H) 2.58 (br. s., 3H) 1.95-2.11 (m, 2H) 1.85 (d, J=9.90 Hz, 2H) 1.60 (br. s., 3H) 1.53 (br. s., 3H) 1.39 (br. s., 2H) 1.30 (br. s., 3H) 1.15 (br. s., 2H) 1.10 (br. s., 1H) 1.05 (br. s., 3H) 0.69-0.94 (m, 2H) m/z calcd $C_{53}H_{69}N_7O_6S$ [M+H]$^+$ 932.51, found 466.85 (MS ESI) Purity LCMS: 99.0% (254 nm, peak height).

FIGS. 47A-B

N-(2-((S)-4-((R)-1-((S)-2-(((S)-6-benzyl-2,3-dioxopiperazin-1-yl)methyl)pyrrolidin-1-yl)-3-cyclohexylpropan-2-yl)-6-(4-hydroxybenzyl)-2,3-dioxopiperazin-1-yl)ethyl)-5-(dimethylamino)naphthalene-1-sulfonamide Using the scheme shown in FIG. 41 for the synthesis of Dansyl tagged pyrrolidine-bis-diketopiperazines compound 2476-67.2 was synthesized using the following reagents: (100 mg) MBHA resin starting material, Boc-L-Phenylalanine-OH ($R_1$), Boc-D-Cyclohexylalanine-OH ($R_2$), Boc-L-Tyrosine(2-Br—Z)—OH ($R_3$), and Boc-Glycine-OH ($R_4$). The final crude product was purified using HPLC as described above, with a gradient of (B) 0/5, 2/5, 4/20, 40/55. Isolated Mass 0.9 mg % yield 0.83%

$^1$H NMR (400 MHz, DMSO-d6) δ ppm 8.48 (br. s., 2H) 8.24-8.31 (d, J=7.59 Hz, 1H) 8.08 (m, 1H) 7.79 (br. s., 1H) 7.58 (br. s., 1H) 7.25-7.33 (br. s., 3H) 7.05-7.11 (m, 2H) 6.97 (d, J=8.99 Hz, 2H) 6.82 (br. s., 2H) 6.74 (br. s., 2H) 3.02 (br. s., 2H) 2.99 (br. s., 1H) 2.87 (m, 1H) 2.78-2.83 (m, 5H) 2.76 (br. s., 3H) 2.69 (br. s., 6H) 2.32-2.35 (d, J=5.78 Hz, 2H) 1.99-2.16 (m, 2H) 1.91 (d, J=12.72 Hz, 1H) 1.86 (br. s., 1H) 1.63 (d, J=11.97 Hz, 5H) 1.51 (m, 1H) 1.43 (br. s., 2H) 1.29 (br. s., 4H) 1.16 (br. s., 3H) 0.94 (br. s., 2H) m/z calcd $C_{50}H_{63}N_7O_7S$ [M+H]$^+$ 906.46, found 453.65 (MS ESI) Purity LCMS: 95.0% (254 nm, peak height).

FIGS. 48A-B

N-(4-((S)-1-(((S)-1-((R)-3-cyclohexyl-2-((S)-5-(4-hydroxybenzyl)-2,3-dioxo-4-phenethylpiperazin-1-yl)propyl)pyrrolidin-2-yl)methyl)-5,6-dioxopiperazin-2-yl)butyl)-5-((3aS,4S,6aR)-2-oxohexahydro-1H-thieno[3,4-d]imidazol-4-yl)pentanamide Using the scheme shown in FIG. 42 for the synthesis of Biotin tagged pyrrollidine-bis-diketopiperazines compound was synthesized using the following reagents: (100 mg) MBHA resin starting material, Fmoc-L-Lysine(Boc)-OH ($R_1$), Fmoc-D-Cyclohexylalanine-OH ($R_2$), Fmoc-L-Tyrosine(2-Br—Z)—OH ($R_3$), and Phenylacetic Acid ($R_4$). The final crude product was purified using HPLC as described above, with a gradient of (B) 0/5, 2/5, 4/20, 40/55. Isolated Mass 4.9 mg % yield 4.33%

$^1$H NMR (400 MHz, DMSO-d6) δ ppm 8.56 (br. s., 1H) 7.81 (br. s., 1H) 7.29 (br. s., 1H) 7.24 (br. s., 2H) 7.01 (br. s., 1H) 6.72 (br. s., 1H) 6.40 (d, J=15.89 Hz, 1H) 4.90 (br. s., 1H) 4.31 (br. s., 1H) 3.93-4.17 (m, 1H) 3.63-3.87 (m, 4H) 3.60 (br. s., 1H) 3.53 (br. s., 2H) 3.44 (br. s., 14H) 3.31 (br. s., 2H) 3.20 (br. s., 2H) 3.09 (br. s., 1H) 3.04 (br. s., 1H) 2.83 (d, J=11.49 Hz, 3H) 2.74 (br. s., 1H) 2.59 (d, J=12.72 Hz, 4H) 2.28 (br. s., 1H) 2.04 (br. s., 3H) 1.89 (br. s., 1H) 1.81 (d, J=9.41 Hz, 1H) 1.69 (br. s., 2H) 1.63 (br. s., 3H) 1.48 (br. s., 2H) 1.42 (br. s., 2H) 1.29 (br. s., 4H) 1.19 (br. s., 2H) 0.96 (br. s., 2H) m/z calcd $C_{51}H_{72}N_8O_7S$ [M+H]$^+$ 941.53, found 471.15 (MS ESI) Purity LCMS: 99.0% (254 nm, peak height).

FIGS. 49A-B

N—((S)-6-((S)-2-(((S)-6-benzyl-2,3-dioxopiperazin-1-yl)methyl)pyrrolidin-1-yl)-5-((S)-5-(4-hydroxybenzyl)-2,3-dioxo-4-phenethylpiperazin-1-yl)hexyl)-5-((3aS,4S,6aR)-2-oxohexahydro-1H-thieno[3,4-d]imidazol-4-yl)pentanamide Using the scheme shown in FIG. 42 for the synthesis of Biotin tagged pyrrollidine-bis-diketopiperazines compound was synthesized using the following reagents: (100 mg) MBHA resin starting material, Fmoc-L-Phenylalanine-OH ($R_1$), Fmoc-L-Lysine(Boc)-OH ($R_2$), Fmoc-L-Tyrosine(2-Br—Z)—OH ($R_3$), and Phenylacetic Acid ($R_4$). The final crude product was purified using HPLC as described above, with a gradient of (B) 0/5, 2/5, 4/20, 40/55. Isolated Mass 6.4 mg % yield 5.70%

$^1$H NMR (400 MHz, DMSO-d6) δ ppm 9.53 (br. s., 1H) 9.35 (br. s., 1H) 8.62 (br. s., 1H) 7.82 (br. s., 1H) 7.25-7.35 (m, 6H) 7.22 (br. s., 1H) 7.01 (br. s., 2H) 6.72 (br. s., 1H) 6.30-6.46 (m, 1H) 4.76 (br. s., 1H) 4.30 (br. s., 1H) 4.12 (br. s., 1H) 4.02 (d, J=12.47 Hz, 1H) 3.78 (br. s., 2H) 3.56-3.69 (m, 4H) 3.51 (br. s., 10H) 3.33 (br. s., 2H) 3.16 (d, J=11.62 Hz, 2H) 2.92-3.11 (m, 4H) 2.76-2.92 (m, 4H) 2.70 (br. s., 1H) 2.57 (d, J=12.10 Hz, 1H) 2.26 (br. s., 1H) 2.02 (br. s., 3H) 1.84 (br. s., 1H) 1.59 (br. s., 1H) 1.43 (br. s., 5H) 1.29

(br. s., 2H) m/z calcd $C_{51}H_{66}N_8O_7S$ [M+H]$^+$ 935.48, found 468.45 (MS ESI) Purity LCMS: 99.0% (254 nm, peak height).

FIG. 50

N-(4-((S)-4-((R)-1-((S)-2-(((S)-6-benzyl-2,3-di-oxopiperazin-1-yl)methyl)pyrrolidin-1-yl)-3-cyclo-hexylpropan-2-yl)-5,6-dioxo-1-phenethylpiperazin-2-yl)butyl)-5-((3aR,4R,6aS)-2-oxohexahydro-1H-thieno[3,4-d]imidazol-4-yl)pentanamide Using the scheme shown in FIG. 42 for the synthesis of Biotin tagged pyrrollidine-bis-diketopiperazines compound was synthesized using the following reagents: (100 mg) MBHA resin starting material, Fmoc-L-Phenylalanine-OH ($R_1$), Fmoc-D-Cyclohexylalanine-OH ($R_2$), Fmoc-L-Lysine (Boc)-OH ($R_3$), and Phenylacetic Acid ($R_4$). The final crude product was purified using HPLC as described above, with a gradient of (B) 0/5, 2/5, 4/20, 40/55. Isolated Mass 16.1 mg % yield 14.50%

$^1$H NMR (400 MHz, DMSO-d6) δ ppm 9.39 (br. s., 1H) 8.65 (br. s., 1H) 7.78 (br. s., 1H) 7.33 (br. s., 5H) 7.28 (br. s., 3H) 6.29-6.47 (m, 1H) 4.86 (br. s., 1H) 4.21-4.36 (m, 1H) 4.12 (br. s., 1H) 4.03 (d, J=12.72 Hz, 2H) 3.79 (br. s., 4H) 3.59-3.75 (m, 7H) 3.52 (d, J=18.58 Hz, 3H) 3.25-3.43 (m, 2H) 3.18 (br. s., 2H) 2.97-3.10 (m, 4H) 2.92 (br. s., 2H) 2.70-2.87 (m, 1H) 2.57 (d, J=11.62 Hz, 1H) 2.29 (br. s., 1H) 2.04 (br. s., 2H) 1.99 (br. s., 1H) 1.85 (br. s., 2H) 1.65 (br. s., 2H) 1.60 (br. s., 3H) 1.48 (br. s., 2H) 1.33-1.44 (m, 3H) 1.29 (br. s., 4H) 1.13 (br. s., 3H) 0.72-0.96 (m, 2H) m/z calcd $C_{51}H_{72}N_8O_6S$ [M+H]$^+$ 925.53, found 463.20 (MS ESI) Purity LCMS: 95.0% (254 nm, peak height).

Methods

Cell Viability Assays.

Cells were plated in 384-well plates in 8 μL of media. Test compounds and dabrafenib (pharmacological assay control) were prepared as 10-point, 1:3 serial dilutions starting at 300 μM, then added to the cells (4 μL per well) using the Biomek Plates were incubated for 72 h at 37° C., 5% $CO_2$ and 95% relative humidity. After incubation, 4 μL of CellTiter-Glo® (Promega cat #: G7570) were added to each well, and incubated for 15 min at room temperature. Luminescence was recorded using a Biotek Synergy H4 multimode microplate reader. Viability was expressed as a percentage relative to wells containing media only (0%) and wells containing cells treated with DMSO only (100%). Three parameters were calculated on a per-plate basis: (a) the signal-to-background ratio (SB); (b) the coefficient for variation [CV; CV=(standard deviation/mean)×100)] for all compound test wells; and (c) the Z'-factor (18). The IC$_{50}$ value of the pharmacological control (dabrafenib, LC Laboratories #G-4408) was also calculated to ascertain the assay robustness. In case of viability rescue assays, cells were pre-treated with caspase, calpain, and autophagy inhibitors for 1-3 h before addition of test compounds. Time course viability assay was done with luminescence measurements performed at 4, 24, 48, and 72 h.

Luciferase Counterscreen Assay.

Lead compounds and various inhibitors used in present study were tested for inhibition of luciferase from the CellTiter-Glo® assay kit (Promega cat #: G7570). The ATP concentration in the luciferase assay was matched to the response produced by WM266-4 cells. Test compounds were prepared as 10-point, 1:3 serial dilutions starting at 300 μM, then added to the DMEM (5 μL per well) using the Biomek NC$^P$. Plates were incubated for 1 h at 37° C., 5% $CO_2$ and 95% relative humidity. After incubation, 5 μL of CellTiter-Glo® (Promega cat #: G7570) was added to each well, and incubation continued for 15 min at room temperature. Luminescence was recorded using a Biotek Synergy H4 multimode microplate reader. Inhibition was expressed as a percentage relative to wells containing media only (0%) and wells containing CellTiter-Glo® (100%).

MAPK-Akt Flow Cytometry Assay.

WM266-4 cells were seeded at 250,000 cells/well in E-MEM medium supplemented with 10% FBS and 1% penicillin/streptomycin in 6 well plates (Greiner Bio-One CellStar cat #655180) and allowed to adhere overnight. After incubation cells were treated with control (25 μM dabrafenib+25 μM trametinib), and 25 μM 2155-14 and 18 for 24 and 48 hours. Manufacturer's instructions for Muse™ PI3K/MAPK Dual Pathway Activation kit (EMD Millipore MCH200108) were followed. Cells were harvested, washed with PBS, and re-suspended in 1× assay buffer supplemented with fixation buffer and incubated on ice for 10 min. Cells were permeabilized with permeablization buffer supplied with the kit and incubated with an antibody cocktail (5 μL of Anti-Akt/PKB+5 μL of Anti-phospho-Akt). Cells were analyzed on Muse flow cytometer (EMD Millipore) using PI3K/MAPK Dual Pathway sub-routine.

Annexin V Flow Cytometry Assay.

WM266-4 cells were seeded at 1,000,000 cells/flask in EMEM medium supplemented with 10% FBS and 1% penicillin/streptomycin in T25 flasks (Nunc cat #75008384) and allowed to adhere overnight. 24 hours after plating, the cells were pre-treated with pan-caspase inhibitor Z-VAD-FMK at 10 μM for 2 hrs. After pre-treatment, the cells were treated with 2155-14 (100 μM) and staurosporine (1 μM) for 4, 24 and 48 hrs. After 4, 24 and 48 hrs of compound exposure the adherent and floating cells were combined and stained using the TACS Annexin V-FITC Apoptosis detection kit (Trevigen Inc, Gaithersburg, Md., USA) using manufacturer's protocol. Viable, necrotic, early and late apoptotic cells were counted using Accuri flow cytometer as per the manufacturer instructions.

Cell Staining for Autophagy.

WM266-4 cells were seeded at 10,000 cells/well in 0.1 mL of E-MEM medium supplemented with 10% FBS and 1% penicillin/streptomycin in 96 well plates (Greiner Bio-One CellStar cat #655180) and allowed to adhere overnight. After overnight incubation 100 μM 2155-14, 2155-18, 50 nM hnRNPH2 siRNA or 25 μM 2476-67.2 were added and incubated for various length of time. Cells were rinsed with warm PBS and stained with CYTO-ID® 1.0 Autophagy reagent (Enzo ENZ-51031-0050) and counterstained with DAPI. Cells were imaged using Cytation 5 imager (Biotek Inc, Winooski, Vt.) using GFP and DAPI filter sets. For % autophagic cells calculations cell counts were conducted using DAPI-stained nuclei and Object Sum Area value was obtained from at least 1,000 cells/well using DAPI channels. To obtain number of cells undergoing autophagy the cell count was conducted using GFP channel. Both GFP and DAPI cell counts were conducted using optimized algorithm in automatic mode. 8 replicate wells were used. % autophagic cells was calculated using Equation 1:% autophagic cells=100%*(number of cells, GFP channennumber of cells, DAPI channel)

To calculate staining intensity, the Object Sum Area value from GFP channel was obtained and divided by number of cells using DAPI channel. Both GFP and DAPI cell counts were conducted using optimized algorithm in automatic mode. 3 replicate wells were used.

Mitochondrial Potential Assay.

5,000 WM266-4 cells were seeded in 100 µL of EMEM medium supplemented with 10% FBS in 24-well plate. The cells were treated with carbonyl cyanide m-chlorophenyl hydrazone (CCCP, 25-50 µM) as a pharmacological control and 1-100 µM of 2155-14. After 1, 4, and 24 h, the cells were stained with 200 nM of Mito-Tracker dye (ThermoFisher cat #M22425) and DAPI for 1 h. Finally, the cells were washed with PBS and media was added. The cells were imaged and analyzed using Cytation 5 imager using Cy5 and DAPI filter sets (Biotek Inc, Winoosky, Vt.). To calculate staining intensity, the Object Sum Area value from Cy5 channel was obtained and divided by number of cells using DAPI channel. Both Cy5 and DAPI cell counts were conducted using optimized algorithm in automatic mode. 3 replicate wells were used.

Cell Staining with Dansylated Derivatives of 2155-14.

WM266-4 cells were seeded at 10,000 cells/well in 0.1 mL of E-MEM medium supplemented with 10% FBS and 1% penicillin/streptomycin in 96 well plates (Greiner Bio-One CellStar cat #655180) and allowed to adhere overnight. After overnight incubation cells were stained with 100 µM of fluorescent analogs of 2155-14 for various length of time, and rinsed with warm PBS. Cells were imaged using Cytation 5 imager (Biotek Inc, Winooski, Vt.) using custom filter set: $\lambda_{excitation}$=377/50 and $\lambda_{emission}$=542/27 nm.

Cell Staining for Lamin A/C.

WM266-4 cells were seeded at 10,000 cells/well in 0.1 mL of E-MEM medium supplemented with 10% FBS and 1% penicillin/streptomycin in 96 well plates (Greiner Bio-One CellStar cat #655180) and allowed to adhere overnight. After overnight incubation cells were fixed with ice cold methanol for 5 min, rinsed 3 times with PBS and permeabilized with 0.1% Triton X-100 for 5 minutes, and blocked with 1% BSA/0.3 M glycine in 0.1% PBS-Tween for 1 h. After blocking cells were incubated overnight at +4° C. with rabbit monoclonal Anti-Lamin A/C (ab205770) at 1 µg/mL in 1% BSA in PBST. After incubation, cells were counterstained with DAPI and rinsed with PBS. Cells were imaged using Cytation 5 imager.

Western Blotting for LC3.

$1 \times 10^6$ of WM266-4 or M14 cells were seeded in 3 mL of E-MEM or RPMI-1640 medium supplemented with 10% FBS and 1% penicillin/streptomycin in 6 cm plates. After 24 h, the cells were pretreated with caspase inhibitors (2 µM Z-IETD-FMK, 2 Z-VEID-FMK, 10 µM Z-VAD-FMK) for 3 h. After pretreatment with caspase or autophagy inhibitors, the cells were treated with autophagy control (rapamycin (10 µM) and chloroquine (5 µM)) and apoptosis control (1 µM staurosporine) and 2155-14 and 2155-18 at various concentrations and length of time either with or without caspas or autophagy inhibitors. The cells were trypsinized (except for cells treated with fluorescent analogs of 2155-14, 2476-66.2 and 2476.67.2, which were scraped off the flasks) and collected in 15 mL tubes followed by lysis, SDS-PAGE, and western blot analysis of LC3 using polyclonal LC3 AB antibody (Cell Signaling Cat #4108, RP: 1:1000; 2% BSA) and actin using monoclonal β-actin antibody (Sigma-Aldrich A5441). After washing with TBST, the membranes were treated with chemilumiscent horseradish peroxidase detection reagent (Thermo Scientific, Cat #32209) and exposed to autoradiography film (Denville Scientific, Inc., Metuchen, N.J., USA, cat #E3018). ImageJ software (NIH, Bethesda, Md.) was used to quantify the intensity of proteins bands. The protein bands were normalized against loading controls (β-actin) and expressed as a fold of an untreated control.

Western Blotting for Lamin A/C.

$1 \times 10^6$ of WM266-4 or M14 cells were seeded in 3 mL of E-MEM or RPMI-1640 medium supplemented with 10% FBS and 1% penicillin/streptomycin in 6 cm plates. After 24 h, the cells were pretreated with caspase inhibitors (2 µM Z-IETD-FMK, 2 µM Z-VEID-FMK, 10 µM Z-VAD-FMK) for 3 h or autophagy inhibitors (10 µM LY294002 and 1 µM hydroxychloroquine) for 1 h. After pretreatment with caspase or autophagy inhibitors, the cells were treated with apoptosis control (1 µM staurosporine) or autophagy inducer (10 µM rapamycin+5 µM chloroquine) and 2155-14 at various concentration and length of time either together or without caspase or autophagy inhibitors. The cells were trypsinized (except for cells treated with fluorescent analogs of 2155-14, 2476-66.2 and 2476.67.2, which were scraped off the flasks) and collected in 15 mL tubes followed by lysis, SDS-PAGE, and western blot analysis of Lamin A/C using polyclonal Lamin A/C antibody (Cell Signaling Cat #2032, RP: 1:1000; 2% BSA) and actin using monoclonal β-actin antibody. After washing with TBST, the membranes were treated with chemilumiscent horseradish peroxidase detection reagent (Thermo Scientific, Cat #32209) and exposed to autoradiography film (Denville Scientific, Inc., Metuchen, N.J., USA, cat #E3018). ImageJ software (NIH, Bethesda, Md.) was used to quantify the intensity of proteins bands. The protein bands were normalized against loading controls.

DARTS-LC-MS/MS.

WM266-4 melanoma cell lysates were prepared using a routine protocol with commercially available M-PER buffer supplemented with protease and phosphatase inhibitors. Lysates were split into control and compound test portions, and DMSO and 2155-14 were added to the respective lysate portions and incubated at RT for 1 h to allow for 2155-14 binding to its target(s). Pronase dilutions (1:100. 1:300, 1:1000. 1:3000 and 1:10000, Roche #10165921001) were prepared from 10 mg/mL stock. Lysates were split into 5 aliquots, and pronase dilutions were added to lysate aliquots and incubated at RT for 30 min. After 30 min, digestion was stopped by adding SDS loading buffer, and samples were heated up to 95° C. for 5 min and run on SDS-PAGE. After staining, one differentially hydrolyzed band was observed (FIG. 18B, vertical arrows (in color show as red)) suggesting that binding of 2155-14 to the protein represented by the band made it less susceptible to the cleavage by pronase. Two gel bands were cut below the 75 kDa marker in the 1:1000 pronase dilution samples (indicated below by the arrow) from the gels, in-gel treated with 10 mM DTT followed by 50 mM iodoacetamide, and subjected to trypsin digestion. Prior to mass spectrometry analysis, the peptide pools were acidified, desalted through Zip-Tip C18 tip columns and dried down. Each sample was reconstituted in 23 µL of 0.1% formic acid and 13 µL were utilized for MS analysis.

Each sample was analyzed by liquid-chromatography-tandem MS (LC-MS/MS) using an EASY-nLC 1000 system coupled to a Q Exactive mass spectrometer (Thermo Fisher Scientific). Peptides were concentrated and desalted on an RP pre-column (0.1×20 mm EASY-column, Thermo Fisher Scientific) and on-line eluted on an analytical RP column (0.075×100 mm EASY-column, Thermo Fisher Scientific), operating at 300 nL/min using the following gradient: starting at 5% B, 10% B for 3 min, 40-80% B in 60:00 min, 80% B in 6 min, and 5% B for 20 min [solvent A: 0.1% formic acid (v/v); solvent B: 0.1% formic acid (v/v), 80% ACN (v/v) (Fisher Scientific)]. Protein identification was carried out using Mascot algorithms, allowing optional modifications (Met oxidation), carbamidomethylation of Cys as a fixed modification, two missed cleavages, and a mass tolerance of 10 and 20 PPM for precursor and fragment ions, respectively. MS/MS raw files were searched against human proteins. Lamin A/C, DDX1, hnRNP H2, and hnRNP A2/B1 were additionally probed by western blot using methods described elsewhere in this section.

Pull-Down with Biotinylated Analogs of 2155-14.

WM-266-4 and M14 cells were sonicated in RIPA lysis buffer containing added protease inhibitors. Affinity beads were prepared by addition of the 0.3 mg biotinylated probes to the 50 μL of streptavidin agarose resin, which was washed three times with the lysis buffer. Following incubation at 4° C. for 1 h, the obtained affinity beads complexed with biotinylated compounds were washed three times with lysis buffer to remove any unbound materials. The cell lysates (1 mg protein content) were then added to the probe-bound beads, and samples were incubated at 4° C. for 1 h and overnight on a rotator. Following 5 washes with lysis buffer, the samples were subjected to SDS-PAGE. The gels were stained overnight with colloidal blue (Invitrogen). Gel bands of interest were excised, reduced, carbidomethylated, dehydrated, and digested with Trypsin Gold (Promega) as per manufacturers' instructions. Following digestion, peptides were extracted, all fractions were combined, and the volume was reduced in a SpeedVac to near dryness, and re-suspended to 20 μL using 95% $ddH_2O$/5% ACN/0.1% formic acid (FA) prior to analysis by 1D reversed-phase LC-nESI-MS2 (as outlined below) (Ludwig, M. R. et al. Surveying the serologic proteome in a tissue-specific kras(G12D) knockin mouse model of pancreatic cancer. *Proteomics* 16, 516-531, doi:10.1002/pmic.201500133 2016).

Mass Spectrometry of Pulldown Bands.

Peptide digests (8 μL each) were injected onto a 1260 Infinity nHPLC stack (Agilent) and separated using a 75 micron I.D.×15 cm pulled tip C-18 column (Jupiter C-18 300 Å, 5 micron, Phenomenex). This system runs in-line with a Thermo Orbitrap Velos Pro hybrid mass spectrometer, equipped with a nano-electrospray source (Thermo Fisher Scientific), and all data were collected in CID mode. The nHPLC was configured with binary mobile phases that included solvent A (0.1% FA in $ddH_2O$), and solvent B (0.1% FA in 15% $ddH_2O$/85% ACN), programmed as follows; 10 min @ 0% B (2 μL/min, load), 90 min @ 0%-40% B (0.5 nL/min, analyze), 15 min @ 0% B (2 μL/min, equilibrate). Following each parent ion scan (350-1200 m/z @ 60 k resolution), fragmentation data (MS2) was collected on the top most intense 15 ions. For data dependent scans, charge state screening and dynamic exclusion were enabled with a repeat count of 2, repeat duration of 30 s, and exclusion duration of 90 s.

MS Data Conversion and Searches.

The XCalibur RAW files were collected in profile mode, centroided, and converted to MzXML using ReAdW v. 3.5.1. The mgf files were then created using MzXML2Search (included in TPP v. 3.5) for all scans. The data was searched using SEQUEST, which was set for two maximum missed cleavages, a precursor mass window of 20 ppm, trypsin digestion, variable modification C at 57.0293, and M at 15.9949. Searches were performed with a species specific subset of the UniRef100 database.

Peptide Filtering, Grouping, and Quantification.

The list of peptide IDs generated based on SEQUEST search results were filtered using Scaffold (Protein Sciences, Portland Oreg.). Scaffold filters and groups all peptides to generate and retain only high confidence IDs while also generating normalized spectral counts (N-SC's) across all samples for the purpose of relative quantification. The filter cut-off values were set with minimum peptide length of >5 AA's, with no MH+1 charge states, with peptide probabilities of >80% C.I., and with the number of peptides per protein ≥2. The protein probabilities were then set to a >99.0% C.I., and an FDR<1.0. Scaffold incorporates the two most common methods for statistical validation of large proteome datasets, the false discovery rate (FDR) and protein probability (Keller, A., Nesvizhskii, A. I., Kolker, E. & Aebersold, R. Empirical statistical model to estimate the accuracy of peptide identifications made by MS/MS and database search. *Analytical chemistry* 74, 5383-5392 2002; Nesvizhskii, A. I., Keller, A., Kolker, E. & Aebersold, R. A statistical model for identifying proteins by tandem mass spectrometry. *Analytical chemistry* 75, 4646-4658 2003; and Weatherly, D. B. et al. A Heuristic method for assigning a false-discovery rate for protein identifications from Mascot database search results. *Molecular & cellular proteomics: MCP* 4, 762-772, doi:10.1074/mcp.M400215-MCP200 2005). Relative quantification across experiments was then performed via spectral counting (Liu, H., Sadygov, R. G. & Yates, J. R., 3rd. A model for random sampling and estimation of relative protein abundance in shotgun proteomics. *Analytical chemistry* 76, 4193-4201, doi:10.1021/ac0498563 2004 and Old, W. M. et al. Comparison of label-free methods for quantifying human proteins by shotgun proteomics. *Molecular & cellular proteomics: MCP* 4, 1487-1502, doi:10.1074/mcp.M500084-MCP200 2005), and when relevant, spectral count abundances were then normalized between samples (Beissbarth, T. et al. Statistical modeling of sequencing errors in SAGE libraries. *Bioinformatics* 20 Suppl 1, i31-39, doi:10.1093/bioinformatics/bth924 2004).

Western Blotting for hnRNP H2, DDXJ, and hnRNP BJ/A2.

WM-266-4 cells were sonicated in RIPA lysis buffer containing protease inhibitors. Affinity beads were prepared by addition of the biotinylated probes (0.3 mg) to the streptavidin agarose resin (50 μL), which was first washed three times with the lysis buffer. Following incubation at 4° C. for 5 h, the obtained affinity beads were washed 3 times with lysis buffer to remove any unbound materials. The protein extract (1 mg) was then added to the probe-bound beads, and samples were incubated at 4° C. overnight. Following 5 washes with lysis buffer, the protein isolates were subjected to SDS-PAGE followed by transfer to nitrocellulose membrane. hnRNP H2 was detected using rabbit polyclonal antibody (Abgent #: AP13497b; 1:3,000, in 2% milk overnight), DDX1 monoclonal antibody (Santa Cruz #sc-271393, 1:1,000 in 2% BSA overnight), or hnRNP B1/A2 monoclonal antibody (Santa Cruz #SC-32316, 1:1,000 in 2% BSA overnight). After washing with TBST, the membranes were treated with chemilumiscent horseradish peroxidase detection reagent (Thermo Scientific, Cat #32209) and exposed to autoradiography film (Denville Scientific, Inc., Metuchen, N.J., USA, cat #E3018). ImageJ software (NIH, Bethesda, Md.) was used to quantify the intensity of proteins bands. The protein bands were normalized against loading controls.

siRNA Knockdown of hnRNP H2, DDXJ, and hnRNP B1/A2.

WM-266-4 cells ($0.7 \times 10^6$ cells in 500 μL) were seeded in 60 mm dish. For each well to be transfected, RNAi duplex-Lipofectamine™ RNAiMAX complexes were prepared as follows. 10 μM RNAi duplex in 100 μL Opti-MEM® I was added in reduced Serum Medium without serum. The solution was mixed gently and incubated for 5 min. After incubation, 10 µL of Lipofectamine™ RNAiMAX was added to the mixture and mixed gently and then incubated for 30 min at RT. After incubation, RNAi duplex-Lipofectamine™ RNAiMAX complexes were added to each plate and incubated for 48 h at 37° C., 95% RH, 5% $CO_2$. The medium was changed after 12-14 h. After 48 h, the cells were trypsinized and collected in 15 mL tubes followed by lysis and western blot analysis of hnRNP H2, hnRNP B1/A2, DDX1, and actin as shown in the previous section. Cell viability, LC3, and lamin A/C levels were assessed post knockdown using above mentioned methods.

Cell Cycle Arrest Assay.

$3 \times 10^6$ cells seeded in 5 mL of E-MEM medium supplemented with 10% FBS and 1% penicillin/streptomycin in 10 cm plates. After 24 h, the cells were harvested in 15 mL tubes, $2 \times 10^6$ cells were fixed with 70% ice cold ethanol and stained using cell cycle reagent (Life Technologies #F10797). The cell cycle analysis was performed using Accuri flow cytometer (Biorad).

Caspase 3/7, Caspase 8, and Caspase 9 Activity Assays.

WM266-4 and M14 cells were plated in 384-well plates in 5 µL of complete media (EMEM and RPMI-1640, respectively). 5 µL of 200 µM 2155-14 and 2155-18 were added to the cells. Plates were incubated at 37° C., 5% $CO_2$ and 95% relative humidity for various lengths of time. After incubation, 5 µL of caspase 3/7, caspase 8, and caspase 9 Glo® reagent (Promega cat #: G7570) were added to each well, and incubated for 15 min at room temperature. Luminescence was recorded using a Biotek Synergy H4 multimode microplate reader.

Calpain Activity Assays.

The Calpain-Glo Protease Assay (Promega cat #) was used to measure the calpain enzyme activity in live cells, according to the manufacturer's instructions. 1,250 of WM-266-4 cells were plated in 384-well white TC-treated plates in 5 µL of serum-free EMEM media. The cells were incubated overnight at 37° C., 5% $CO_2$ and 95% relative humidity and 5 µL of test compounds 2155-14, (100 µM), calpain inhibitor III and PD151746 (25 µM) were added alone or in combination and incubated at 37° C., 5% $CO_2$, and 95% relative humidity for 0.5, 4, and 24 h. After incubation, 10 µL, of a freshly prepared dilution of the Calpain-Glo Reagent stock solution (consisting of Suc-LLVY-Glo™ substrate, Calpain-Glo™ buffer, Luciferin Detection Reagent, and $CaCl_2$) was added to cells at above mentioned times and luminescence was recorded with a Neo 2 microplate reader (Biotek Inc). All experiments were performed in triplicate and the values provided are the calculated average of at least three independent experiments.

CONCLUSION

With identification of lamin A/C, ATP-dependent RNA helicase DDX1 (DDX1), heterogeneous nuclear ribonuclear protein H1/H2 (hnRNP H2), and heterogeneous nuclear ribonuclear protein A2/B1 (hnRNP A2/B1) as targets of selective anti-melanoma compound 2155-14, the instant invention has satisfied the need for innovative approaches and targets for melanoma drug discovery leading to novel therapies.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not intended to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The drug targets, methods, procedures, and techniques described herein are presently representative of the preferred embodiments, are intended to be exemplary and are not intended as limitations on the scope. Changes therein and other uses will occur to those skilled in the art which are encompassed within the spirit of the invention. Although the invention has been described in connection with specific, preferred embodiments, it should be understood that the invention as ultimately claimed should not be unduly limited to such specific embodiments. Indeed various modifications of the described modes for carrying out the invention which are obvious to those skilled in the art are intended to be within the scope of the invention.

What is claimed is:

1. A method for treating metastatic melanoma in a subject in need thereof, the method comprising:
providing a composition including a pharmaceutically acceptable carrier and a therapeutically-effective amount of a compound that interacts with a cellular protein selected from the group consisting of lamin A/C, ATP-dependent RNA helicase DDX1 (DDX1), heterogeneous nuclear ribonuclear protein H1/H2 (hnRNP H2), and heterogeneous nuclear ribonuclear protein A2/B1 (hnRNP A2/B1), the compound having a formula:

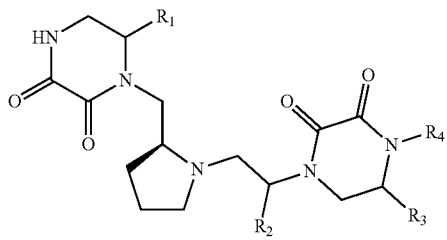

in which the $R_1$, $R_2$, and $R_3$ positions of the compound is a single amino acid or a mixture of amino acids and the $R_4$ position of the compound is a single carboxylic acid or a mixture of carboxylic acids; and
administering the composition to the subject.

2. The method according to claim 1, wherein the subject is a human or an animal.

3. The method according to claim 1, wherein the compound that interacts with the cellular protein inhibits the cellular protein.

4. The method according to claim 1, wherein the compound is an antagonist of at least one of lamin A/C, DDX1, hnRNP H2, and hnRNP A2/B1.

5. The method according to claim 1, wherein the compound is substituted at the $R_3$ position.

6. The method according to claim 1, wherein the pharmaceutically acceptable carrier is at least one of a diluent, a binder, a disintegrant, a flavoring, a filler, and a lubricant.

7. The method according to claim 1, wherein the metastatic melanoma has a mutation in at least one of a BRAF genetic pathway and a NRAS genetic pathway.

8. A method for inhibiting metastatic melanoma cells in a subject in need thereof, the method comprising:
providing a composition including a pharmaceutically acceptable carrier and a therapeutically-effective amount of a compound that inhibits a cellular protein selected from the group consisting of lamin A/C, ATP-dependent RNA helicase DDX1 (DDX1), heterogeneous nuclear ribonuclear protein H1/H2 (hnRNP H2), and heterogeneous nuclear ribonuclear protein A2/B1 (hnRNP A2/B1), the compound having a formula:

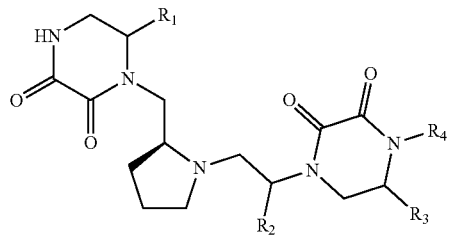

wherein the $R_1$, $R_2$, and $R_3$ positions of the compound is a single amino acid or a mixture of amino acids and the $R_4$ position of the compound is a single carboxylic acid or a mixture of carboxylic acids; and
administering the composition to the subject.

9. The method according to claim 8, wherein the metastatic melanoma cells have a mutation in at least one of a BRAF genetic pathway and a NRAS genetic pathway.

10. The method according to claim 8, wherein the subject is a human or an animal.

11. The method according to claim 8, wherein the compound is an antagonist of at least one of lamin A/C, DDX1, hnRNP H2, and hnRNP A2/B1.

12. The method according to claim 8, wherein the compound is substituted at the $R_3$ position.

13. The method according to claim 8, wherein the pharmaceutically acceptable carrier is at least one of a diluent, a binder, a disintegrant, a flavoring, a filler, and a lubricant.

14. The method according to claim 7, wherein, when the compound is administered to the subject, the compound potentiates basal autophagy and perturbs mitochondrial potential in the metastatic melanoma cells having a mutation in at least one of a BRAF genetic pathway and a NRAS genetic pathway.

15. The method according to claim 9, wherein, when the compound is administered to the subject, the compound potentiates basal autophagy and perturbs mitochondrial potential in the metastatic melanoma cells having a mutation in at least one of a BRAF genetic pathway and a NRAS genetic pathway.

* * * * *